(12) United States Patent
Ahn et al.

(10) Patent No.: US 12,415,939 B2
(45) Date of Patent: Sep. 16, 2025

(54) NANO-ADHESIVE AND SURFACE PRIMER COMPOUND AND USE THEREOF

(71) Applicant: The Regents of the University of California, Oakland, CA (US)

(72) Inventors: Kollbe B. Ahn, Goleta, CA (US); Herbert J. Waite, Goleta, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 761 days.

(21) Appl. No.: 15/764,467

(22) PCT Filed: Sep. 29, 2016

(86) PCT No.: PCT/US2016/054418
§ 371 (c)(1),
(2) Date: Feb. 26, 2019

(87) PCT Pub. No.: WO2017/059057
PCT Pub. Date: Apr. 6, 2017

(65) Prior Publication Data
US 2020/0181455 A1    Jun. 11, 2020

Related U.S. Application Data

(60) Provisional application No. 62/248,846, filed on Oct. 30, 2015, provisional application No. 62/235,243, filed on Sep. 30, 2015.

(51) Int. Cl.
*C09J 4/00*     (2006.01)
*A61L 24/06*    (2006.01)
(Continued)

(52) U.S. Cl.
CPC ............. *C09J 4/00* (2013.01); *A61L 24/06* (2013.01); *A61L 27/34* (2013.01); *C07C 57/42* (2013.01);
(Continued)

(58) Field of Classification Search
None
See application file for complete search history.

(56) References Cited

U.S. PATENT DOCUMENTS 3,349,032 A * 10/1967 Krieg ............... C09K 8/607
166/275
10,280,342 B2 * 5/2019 Waite .................. C07F 7/1804
(Continued)

FOREIGN PATENT DOCUMENTS

CN    101870650 A  * 10/2010
KR    101458058 B1 * 11/2014 ............. C09D 5/002

OTHER PUBLICATIONS

Machine Translation of CN-101870650-A (Year: 2010).*
(Continued)

*Primary Examiner* — Shamim Ahmed
*Assistant Examiner* — Bradford M Gates
(74) *Attorney, Agent, or Firm* — GATES & COOPER LLP

(57) ABSTRACT

A compound for self-assembly onto a mineral and/or metal oxides substrate, the compound comprising a catechol group attached to an end group through a spacer group. The compound include a structure of Formula (I):

(Continued)

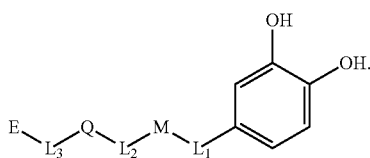

Formula (I)

29 Claims, 78 Drawing Sheets

(51) Int. Cl.
    *A61L 27/34*      (2006.01)
    *C07C 57/42*      (2006.01)
    *C07F 9/12*      (2006.01)
    *C09J 5/00*      (2006.01)
    *H10K 10/46*      (2023.01)

(52) U.S. Cl.
    CPC    *C07F 9/12* (2013.01); *C09J 5/00* (2013.01); *H10K 10/466* (2023.02); *H10K 10/476* (2023.02); *A61L 2400/12* (2013.01)

(56) References Cited

U.S. PATENT DOCUMENTS

| | | | | |
|---|---|---|---|---|
| 2004/0115107 | A1* | 6/2004 | Singh | C22B 3/288 |
| | | | | 423/22 |
| 2005/0288398 | A1* | 12/2005 | Messersmith | C09J 201/06 |
| | | | | 524/17 |
| 2009/0215925 | A1 | 8/2009 | Urban et al. | |
| 2011/0230556 | A1* | 9/2011 | Sadar | A61K 31/09 |
| | | | | 435/375 |
| 2012/0116424 | A1* | 5/2012 | Lee | A61L 24/0005 |
| | | | | 606/151 |
| 2014/0155299 | A1* | 6/2014 | Hardy | C09K 8/52 |
| | | | | 507/90 |
| 2015/0148311 | A1* | 5/2015 | Lewis | A61P 11/06 |
| | | | | 514/249 |

OTHER PUBLICATIONS

Albrecht, "Dicatechol ligands: novel building-blocks for metallo-supramolecular chemistry", Chemical Society Reviews, vol. 27, pp. 281-287 (Year: 1998).*

Machine Translation of KR 101458058 B1 (Year: 2014).*

Luo et al., "Corrosion inhibition of mild steel in simulated seawater solution by a green eco-friendly mixture of glucomannan (GL) and bisquaternary ammonium salt (BQAS)", 2017, Corrosion Science, 125, pp. 139-151 (Year: 2017).*

Ahn, B.K., et al., "High-performance mussel-inspired adhesives of reduced complexity", Nature Communications, 2015, pp. 1-7, vol. 6, No. 8663.

Seo, S., et al., "Microphase Behavior and Enhanced Wet-Cohesion of Synthetic Copolyampholytes Inspired by a Mussel Foot Protein", J. Am. Chem. Soc., 2015, pp. 9214-9217, vol. 137.

Ahn, B.K., et al., "Surface-initiated self-healing of polymers in aqueous media", Nature Materials, Sep. 2014, pp. 867-872, vol. 13.

PCT International Search Report & Written Opinion dated Jan. 13, 2017 for PCT Application No. PCT/US2016/054418.

Das, S. et al., "Molecularly smooth self-assembled monolayer for high-mobility organic field-effect transistors", Nano Lett., Sep. 27, 2016, vol. 16, No. 10, pp. 6709-6715.

* cited by examiner

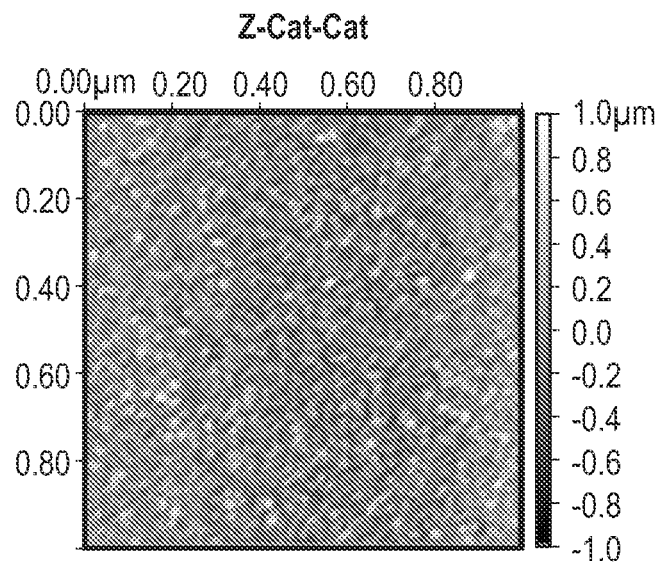
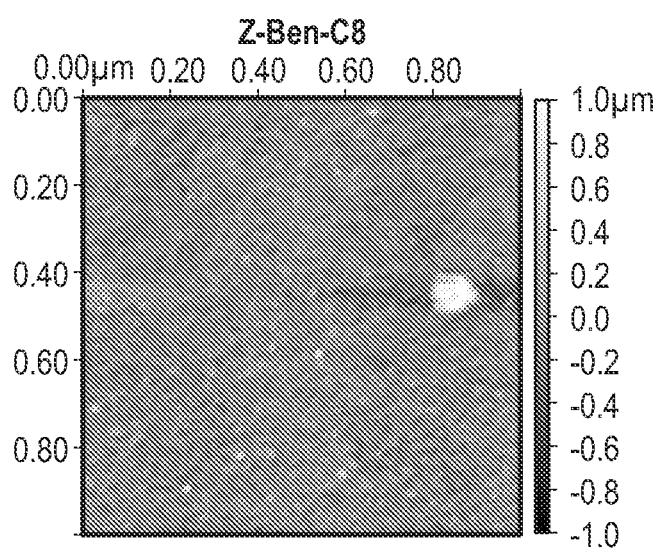
FIG. 4(Cont...)

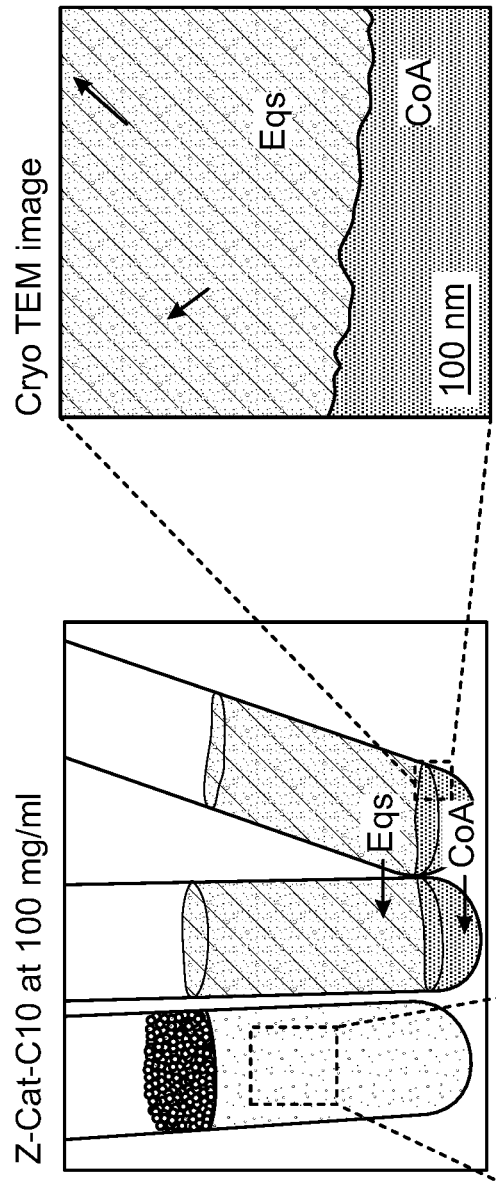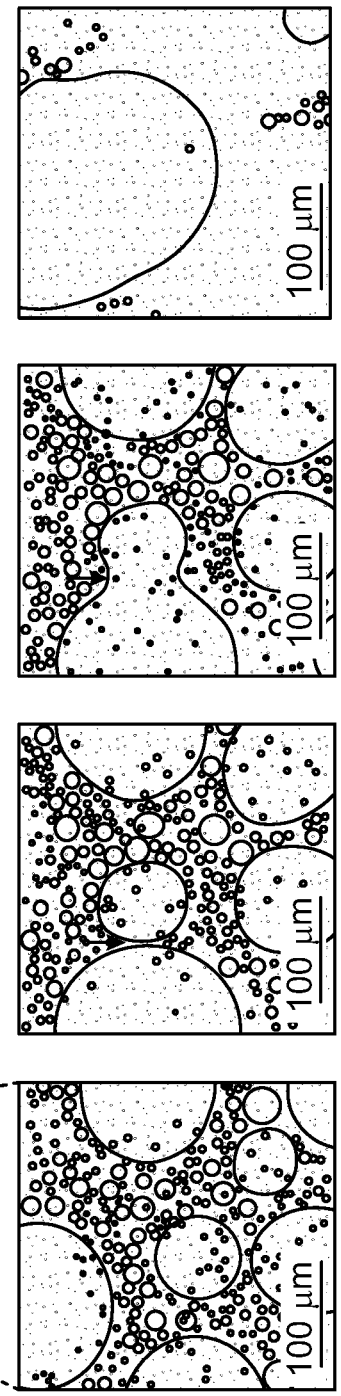
FIG. 10C
FIG. 10A
FIG. 10B

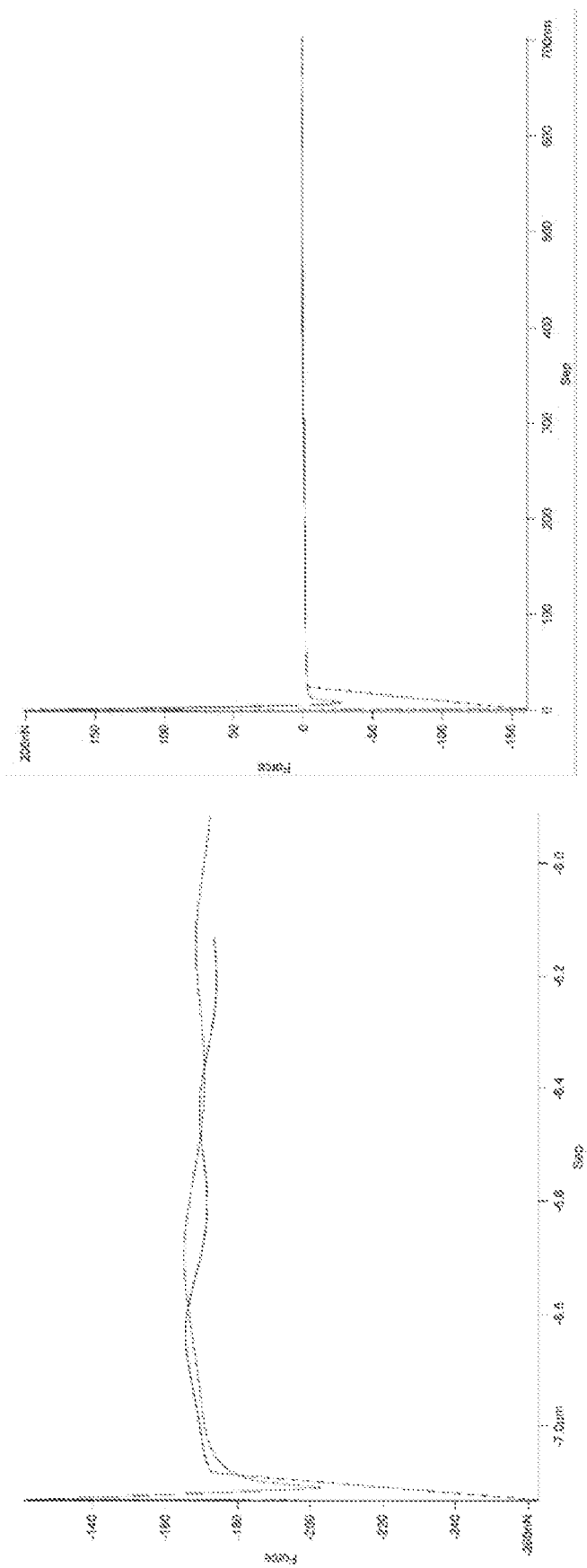

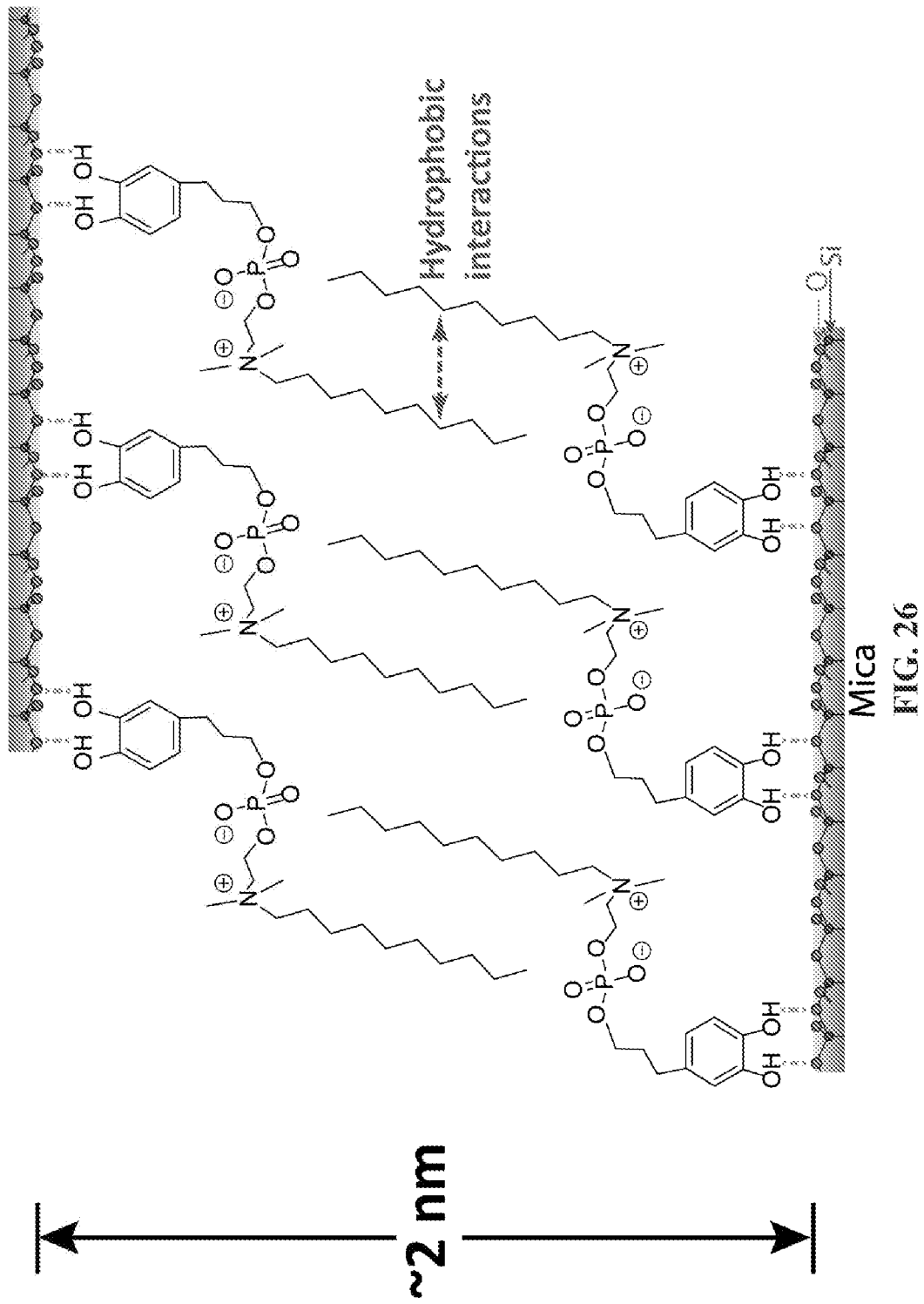

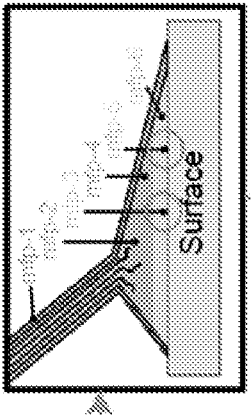
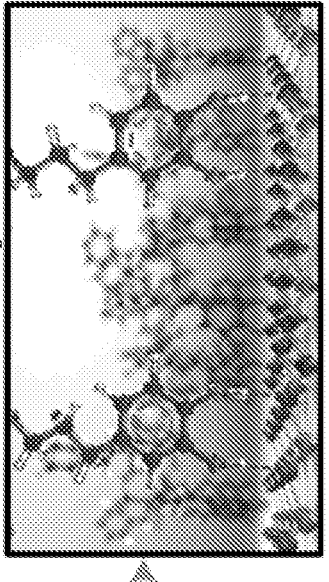
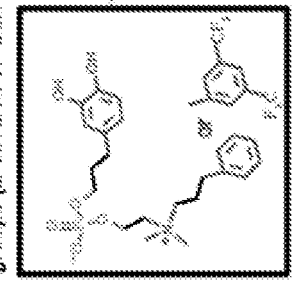
FIG. 31

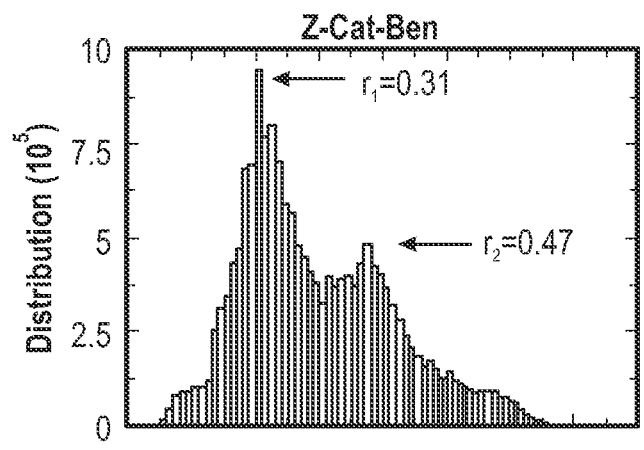
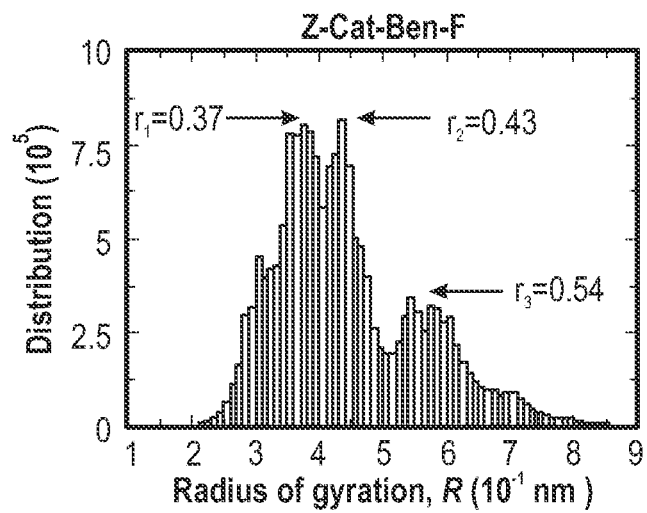
FIG. 35D

G  Model: Z-Cat-Ben assembly on silica- 3D

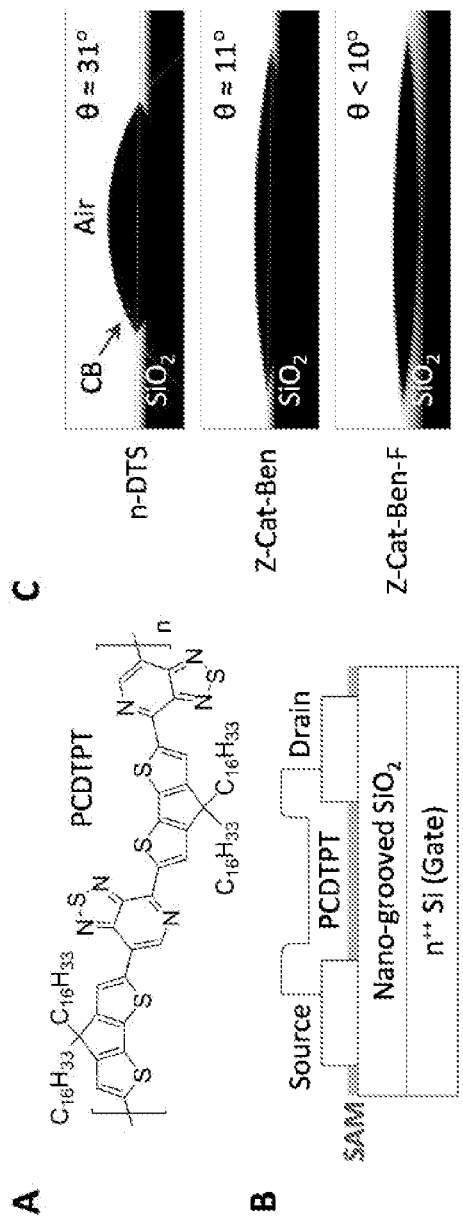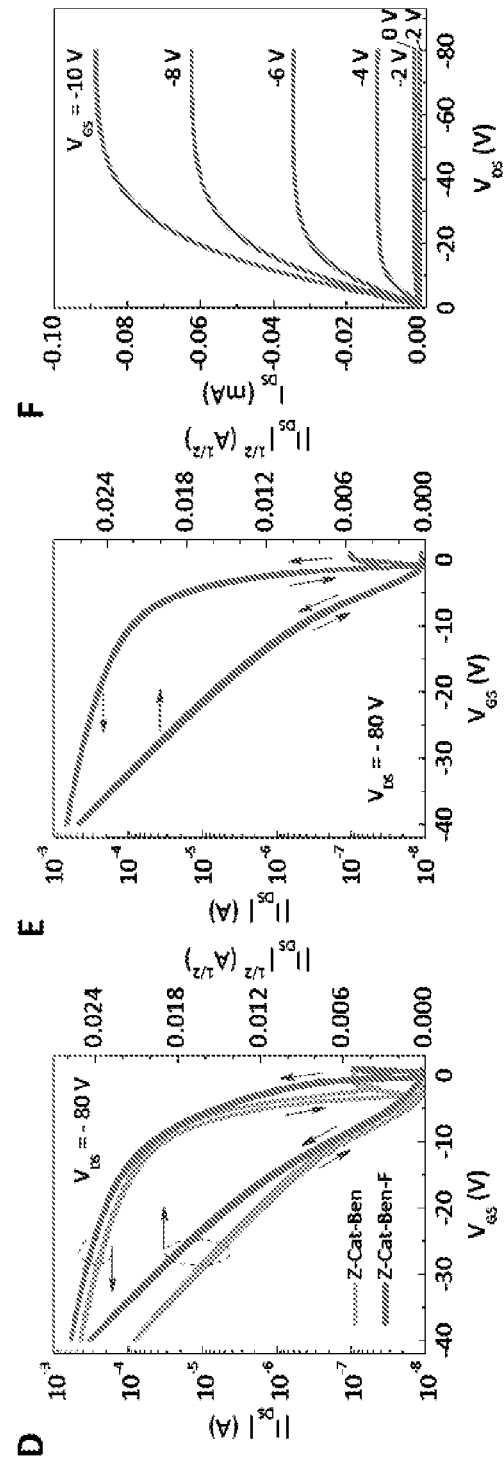
FIGS. 43A-43F

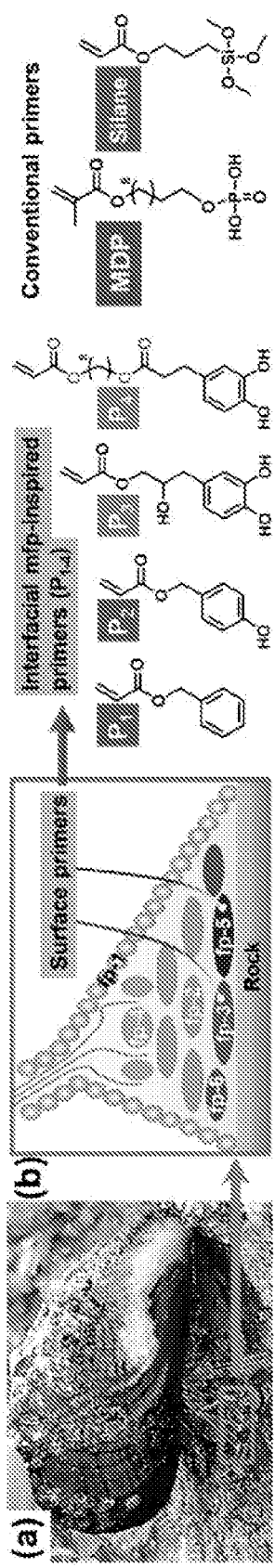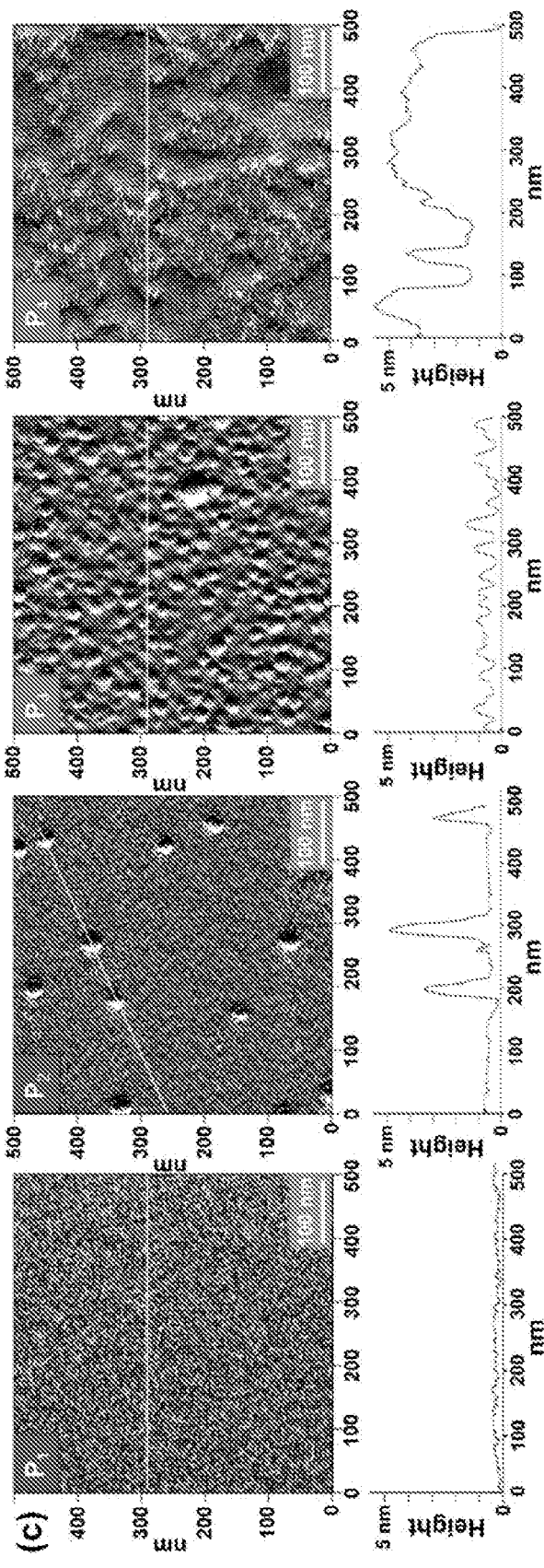
FIGS. 48A-48C

NANO-ADHESIVE AND SURFACE PRIMER COMPOUND AND USE THEREOF

CROSS-REFERENCE OF RELATED APPLICATION

This application claims priority to U.S. Provisional Application No. 62/235,243, filed Sep. 30, 2015; and U.S. Provisional Application No. 62/248,846, filed Oct. 30, 2015, the contents of which are hereby incorporated by reference in the entirety.

STATEMENT REGARDING FEDERALLY SPONSORED RESEARCH

This invention was made with Government support under Grant N00014-13-1-0867, awarded by the Office of Naval Research; Grant RO1 DE018468, awarded by the National Institute of Health; Award Nos. DMR-0856060, DMR-1436263, DMR-1121053, DMR-1410985, CNS-0960316, MCB-1158577, MSN-1059108, and ACI-1053575, awarded by the National Science Foundation. The Government has certain rights in the invention.

BACKGROUND

1. Technical Field

The field of the currently claimed embodiments of this invention relates to adhesives. More specifically, the present invention relates to self-assembly nano adhesives.

2. Discussion of Related Art

Adhesive proteins of marine mussels have attracted considerable interest because of their superior adhesion properties, including rapidity, strength, and versatility, under dry or wet conditions. One of the common structural elements contributing to the adhesive properties of these marine organisms is the incorporation of the catecholic amino acid 3,4-dihydroxy-L-phenylalanine (DOPA) into the adhesive proteins. Catecholic moieties (or DOPA) form strong hydrogen and chealating bondings to mineral and metal oxides surfaces in bedentate fashion with combination of hydrophobic or electrostacic interactions. These moities are unusually rich in interfacial proteins (e.g., mfp-3 and -5), and mussels use these moieties as surface primers.

The surface primer of the present invention is a thin coating (or primary layer) that adheres to the mineral and metal oxide surfaces and generates secondary surfaces to interact (or crosslink) with bulk adhesives to enhance performance of bonding or adsorption of secondary layers or materials (conventional adhesives, cements, proteins, and so forth). Surprisingly and unexpectedly, the inventors of the present invention discovered that the priming concept of mussels can be used in small molecules (molecular weight <2 kDa) for the applications for surface priming, nano-thin adhesives, and coatings to great advantages.

SUMMARY

A compound according to an embodiment of the current invention includes a catechol group attached to an end group through a spacer group, wherein the catechol group, the end group and the spacer group satisfy Formula (I):

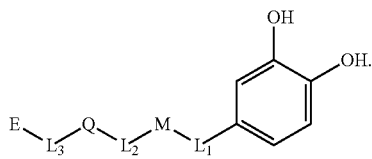

In an embodiment, the catechol group may be

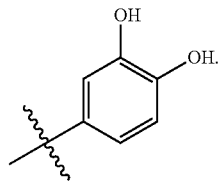 [SMILES: *c1ccc(O)c(O)c1]

In an embodiment, the spacer group may be $L_3$-Q-$L_2$-M-$L_1$. In an embodiment, the end group may be E. In an embodiment, the spacer group may be selected from the group consisting of alkyl, non-polar, zwitterionic, cationic, anionic, and non-charged polar moiety. In an embodiment, each of $L_2$ and $L_3$ may be $C_1$-$C_{15}$ alkyl, or optionally substituted $C_2$-$C_{15}$ alkenyl. In an embodiment, $L_3$, when present, may be a bond, $C_1$-$C_{15}$ alkyl, or optionally substituted $C_2$-$C_{15}$ alkenyl. In an embodiment, M and Q, when present, may be each selected from —($CO_2$)—, NRR', —RCOH or $PO_4$, wherein R and R' are each selected from a group consisting of H or $C_1$-$C_5$ alkyl. In an embodiment, E may be selected from the group consisting of acrylate, methacrylate, epoxy, amine, substituted phenyl, unsubstituted phenyl, catechol, alkyl, alkylenyl, cationic, anionic, non-charged polar, and non-polar moiety. In an embodiment, E may be selected from a group consisting of $C_2$-$C_6$ alkenyl, $C_1$-$C_6$ alkyl, and optionally substituted or unsubstituted phenyl. In an embodiment, the substituted phenyl may be an aromatic moiety selected from a group consisting of dihydroxyphenyl, catechol, and di(trifluoromethyl)phenyl.

A compound according to an embodiment of the current invention, wherein the catechol group, the end group and spacer group satisfy Formula (II):

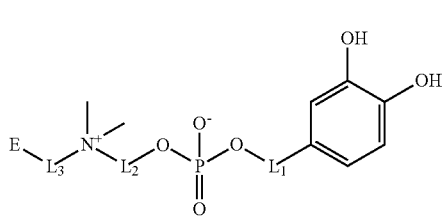

wherein: each of $L_1$ and $L_2$ may be $C_2$-$C_6$ alkyl; $L_3$ may be a bond or $C_2$-$C_{15}$ alkyl; E may be selected from a group consisting of $C_4$-$C_{12}$ alkyl, phenyl, dihydroxyphenyl, catechol, and 3,5-di(trifluoromethyl)phenyl.

In an embodiment according to the current invention, the compound may be selected from a group consisting of

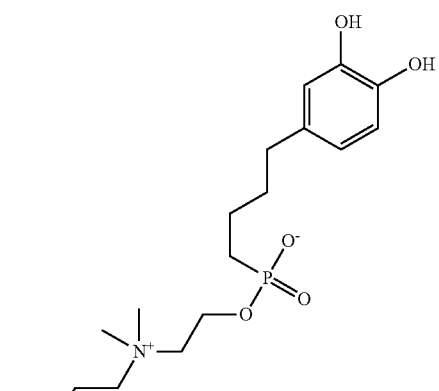
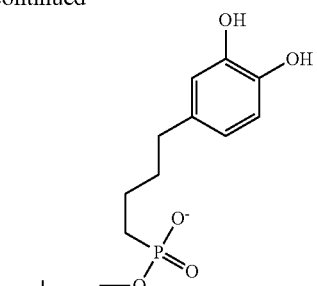
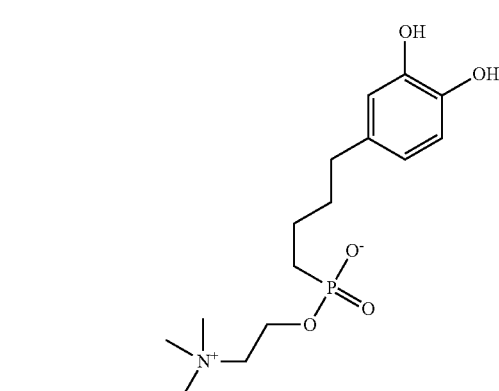
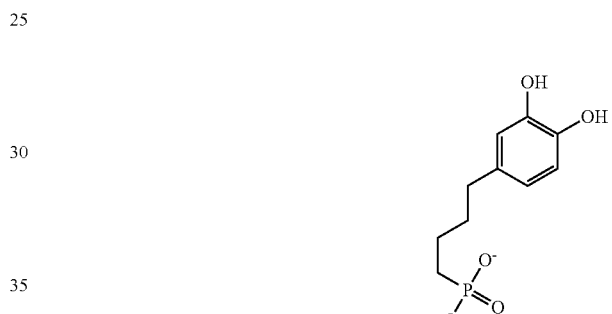
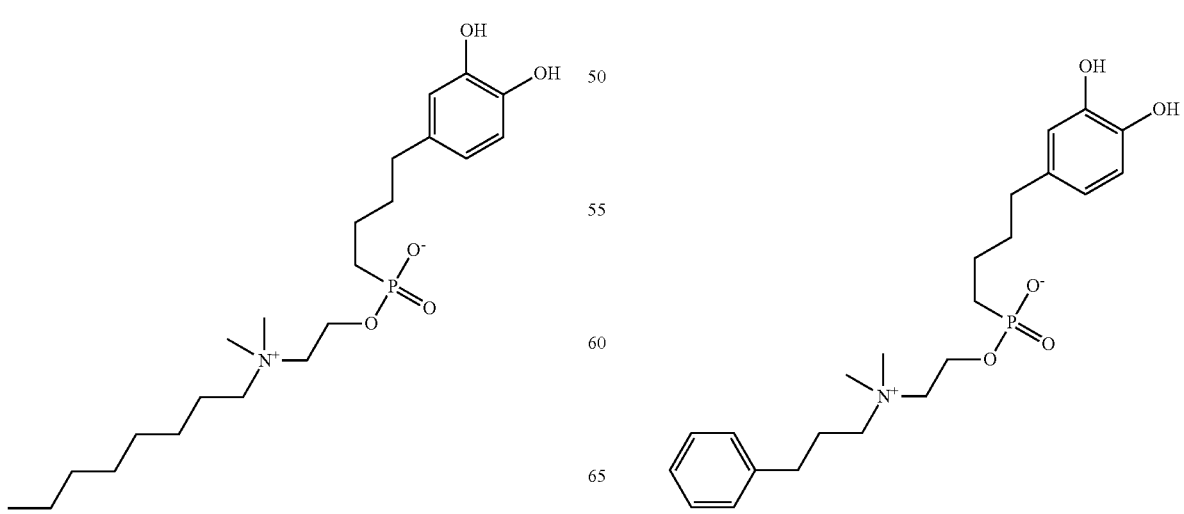

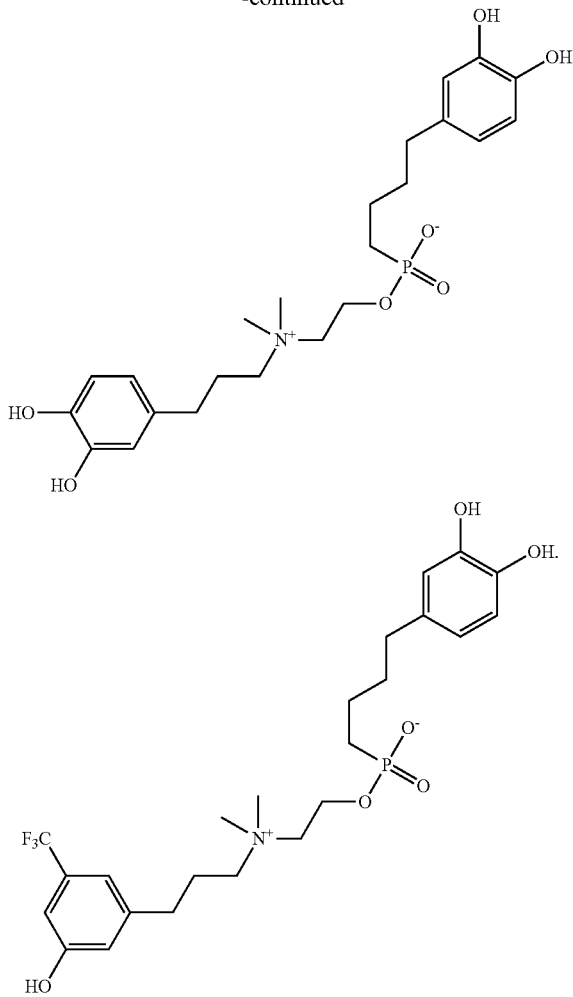

A compound according to an embodiment of the current invention, wherein the catechol group, the end group and spacer group satisfy Formula (III):

Formula (III)

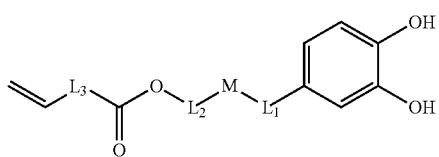

wherein: each of $L_1$ and $L_2$ is $C_1$-$C_{10}$ alkyl; $L_3$ is a bond; and M is —COH— or —CO$_2$—.

In an embodiment according to the current invention, the compound may be selected from a group consisting of

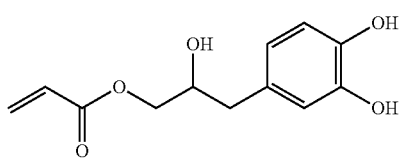

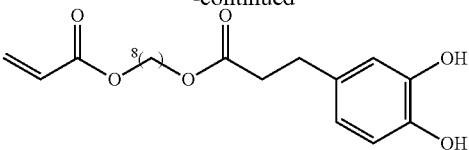

A nano-adhesive and surface primer includes a compound according to the present invention.

A method of using a compound according to an embodiment of the present invention including a catechol group attached to an end group through a spacer group. The method according to an embodiment of the present invention includes providing a first oxide and/or metal containing surface; applying a layer of the compound onto the surface, wherein the compound self-assembly by attaching the catechol group onto the surface; and generating a first secondary surface layer with the end group of the compound.

In an embodiment, the first surface may be an oxide containing surface and the catechol group of the compound forms H-bond with the oxide containing surface. In an embodiment, the first surface may be a metal containing surface and the catechol group of the compound forms chelating-bond with the metal containing surface. In an embodiment, the oxide containing surface may be selected from the group consisting of mica, silica, kaolin, zirconia, aluminum, copper, chrome, chrome-cobalt, silicon, calcium, aluminum oxide, copper oxide, titanium oxide, zinc oxide, calcium oxide, tin oxide, indium-tin oxide, steal, and hydroxylapatite. In an embodiment, the layer may have a thickness between 0.1 to 10 nm. In an embodiment, the compound may be treated with an oxidizing agent. In an embodiment, the oxidizing agent may be periodate. In an embodiment, the compound may be used as a dental/bone adhesive, surface primers for dental/medical implants, surface primers for polymer composites including dental and bone cements, or for battery anodes/binders, electro circuits, semiconductors, nanosensing devices, organic solar cells, opto-electronic devices, hetero-junctions, and electron tunneling junctions.

In an embodiment, the method further includes affixing a second oxide and/or metal containing surface onto the first secondary surface layer. In an embodiment, the method further includes applying a layer of the compound onto the second oxide and/or metal containing surface thereby forming a second secondary surface layer with the end group of the compound. In an embodiment, the end group of the compound of the first secondary surface layer may interact with the end group of the compound of the second secondary surface layer. In an embodiment, the interaction between the first secondary surface layer and the second secondary surface layer may include hydrophobic interactionor π-π stacking. In an embodiment, a third and a fourth layer of the compound may be applied onto the first secondary surface layer and the second secondary surface layer, wherein the compound self-assembles onto the first secondary surface layer and the second secondary surface layer creating a third and a fourth secondary surface layer with the catechol group of the compound. In an embodiment, the catechol group of the third secondary surface layer may interact with the fourth secondary surface layers. In an embodiment, the interaction may be crosslinking or H-bonding.

BRIEF DESCRIPTION OF FIGURES

FIG. 1A shows a California mussel anchored by byssal threads and plaques to a rock in the intertidal zone. FIG. 1B shows a schematic of the distribution of different mussel foot proteins (mfp) in a plaque. FIG. 1C shows the primary sequence of mfp-5, "S" denotes phosphoserine. Pie chart in FIG. 1D shows key functionalities in mfp-5. FIG. 1E shows Mfp-mimetic small molecule, Z-Cat-C10 of a zwitterionic surfactant, was inspired by mfp-5. Light micrograph image of liquid-phase separated Z-Cat-C10 at 100 mg/ml concentration was provided in FIG. 1F.

FIG. 2A shows a summary of the engineered homologs with various alkyl chain length, aromatic substitution, with/without catechol. FIG. 2B shows critical aggregation concentration (CAC) of each homolog is deduced from the final inflection point in the plot of log concentration vs. surface tension as measured by the Wilhelmy plate technique. FIG. 2C shows a schematic of the multiple beam interferometry (MBI) technique used in the surface forces apparatus (SFA), showing the fringes of equal chromatic order (FECO) used to measure the hard-wall thickness and interfacial energy of interaction between the zwitterionic films. FIG. 2D shows a representative force vs. distance plots between mica surfaces coated with thin zwitterionic films adsorbed from 5 mM aqueous dispersions of Z-Cat-C10, Z-Cat-C8, Z-Cat-C6, Z-Cat-C4, and Z-Cat-Cat. The work of cohesion, $W_c$ (minimum potential well of W vs. D, y-axis, right), is synonymous with the interaction energy of the zwitterions, and did not change for contact times ($t_c$) ranging from 2 min to 12 h. Surface forces were measured during approach and separation of the surfaces, respectively. FIG. 2E is a plot of the homolog interaction energies vs. CAC of the homologs. FIG. 2F is a plot of the homolog hard-wall thickness vs. CAC. Trend dashed-lines were added as a visual aid in FIGS. 2E and 2F. The error bars indicate standard deviations (n=5, independent experiments).

FIGS. 10A-10C show fluid-fluid phase separation of mfp-mimetic zwitterions by complex coacervation and the effect of oxidative crosslinking in macro-scale adhesion. FIG. 10A shows phase separation of Z-Cat-C10 (100 mg/ml) in 4 mm diameter glass test tubes. Shown are the turbid dispersion of coacervate microdroplets (left) and the bulk-separated phases with the denser coalesced coacervate phase on the bottom (middle) and tilted to emphasize the fluidity of both phases (right). FIG. 10B show optical micrographs showing the time course of coacervate coalescence in Z-Cat-C10 at 0-24 min. The 16 min 4 s image shows coalescence of two micro-droplets. FIG. 10C shows a Cryo-TEM image of the dense phase; the image of turbid dispersion is similar. White arrows indicate same small aggregations in both equilibrium solution (EqS) and coacervate phase (CoA), an area of a large aggregate of those smaller aggregates in the lower part of the field of view.

FIGS. 13A and 13B show representative force vs. distance plots of symmetric (a) and asymmetric (b) periodate oxidized Z-Cat-C10 films on mica. Prior to periodate, the work of adhesion W, did not change for contact times ($t_c$) from 2 min to 12 h. After oxidation with periodate (250 pmoles), $t_c \leq 10$ min, $t_c$=60 min, and $t_c$=12 h. Filled and open circles represent the forces measured during approach and separation of the surfaces, respectively. FIG. 13C is a cartoon of the two self-assemble nano-glue layers (upper and lower, respectively) and the interface. FIG. 13D is a AFM image of atomically smooth adhesive layer formed from 5 mM Z-Cat-C10 on mica (the layer on $SiO_2$ and $CuO_2/Cu(OH)_2$ shown in FIG. 5 and FIG. 6, respectively). FIG. 13E is a graph showing Adhesion Energey ($W_a = F_a/1.5\pi R$) of the nano-glue from Z-Cat-C10 measured on silicon wafer and copper plate, where adhesion force, $F_a$, (minimum of the potential well of the F vs. D curves obtained from AFM measurements) and R (radius of silicon dioxide probe). FIG. 13F shows SEM image of underwater glued nano silica beads ($\phi$=100 nm) on silicon wafer by the nano-glue from 5 mM Z-Cat-C10.

(FIG. 14A) a plane $SiO_2$ surface (RMS~1 nm), (FIG. 14B) a $SiO_2$ surface coated with Z-Cat-C10 (RMS~1 nm): subsequently after spreading the 5 mM Z-Cat-C10, waiting for 2 min, rinsing thoroughly, and drying for ~5 min.

(FIG. 15A) a plane $CuO_2/Cu(OH)_2$ surface (RMS~2 nm), (FIG. 15B) a $CuO_2/Cu(OH)_2$ surface coated with Z-Cat-C10 (RMS~2 nm): subsequently after spreading the 5 mM Z-Cat-C10, waiting for 2 min, rinsing thoroughly, and drying for ~5 min.

FIG. 16 is an AFM force run on copper plate in ambient condition using $\phi$=5 μm silica tip after drying the substrate for ~5 min. Cantilever spring constant (K) was 1.8 N m$^{-1}$. Force measured in red when approaching and in blue when separating.

FIG. 17 is an AFM force run on silicon wafer in ambient condition using $\phi$=1 μm silica tip after drying the substrate for ~5 min. Cantilever spring constant (K) was 6 N m$^{-1}$. Force measured in red when approaching and in blue when separating.

FIG. 24A shows the phase-separated fluid at the bottom was collected with a syringe and injected on to a top of steal plated underwater (FIG. 24B), then glued onto the other plate (FIG. 24C).
FIGS. 24D, 24E and 24F show the lab adhesion test after 12 h.
FIG. 24G is a demonstration of lap joint fracture test (apparent cross section=2.54×2.54 cm).
FIG. 24H is a demonstration of standard 3 point bending peel test (apparent cross section=1.27×2.54 cm).

(FIG. 25A) 0.001 mM (below its CAC), (FIG. 25B) 0.05 mM (above CAC) and (FIG. 25C) 5 mM.

FIG. 26 is a chemical configuration of Z-Cat-C10 on mica at low concentrations.

FIG. 31 illustrates the key features of interfacial mfps and the mfp-mimetic molecules.

FIG. 33A is a schematic of the multiple beam interferometry (MBI: the distance between the surfaces, shape of the interface and the refractive index of the media between the surfaces can be accurately determined by MBI technique) technique used in the surface forces apparatus (SFA), showing the fringes of equal chromatic order (FECO) used to measure the hard-wall thickness and interfacial energy of interaction between the zwitterionic films; FIG. 33B is a graph showing Representative force vs. distance plots between mica surfaces coated with thin zwitterionic films adsorbed from aqueous dispersions (concentration, C) of Z-Cat-Ben (C=0.5 mM and C=5 mM) and Z-Cat-Ben-F (C=5 mM). The cohesion energy, $W_c$ (minimum potential well of the interaction energy, W vs. Distance, D on the right y-axis), did not change for contact times ($t_c$) ranging from 2 min to 12 h. Surface forces were measured during approach (solid circles) and separation (open circles) of the surfaces, respectively. FIG. 33C is an AFM image of atomically smooth monolayer formed from 5 mM dispersion in aqueous media on mica. FIG. 33D is a Schematic of the two self-assembled monomolecular layers (upper and lower, respectively) and the interface showing π-π stacking of the benzene rings.

FIGS. 35A-35G show Surface orientation of the SAM. FIG. 35A is a 1D plot of GIWAXS data—generated by averaging over azimuthal range 0-180 degrees. FIG. 35B is a 2D GIWAXS data collected on a custom built 2D SAXS/WAXS instrument by stitching together 9 exposures in a 3×3 grid. Effective exposure time is ~3.5 hrs. FIG. 35C is a graph showing average distance between the plane formed by the Si atoms of the mineral surface and the center of mass of the aromatic rings (Ben) for Z-Cat-Ben and Z-Cat-Ben-F as a function of time. The shaded gray area corresponds to the equilibration period, which took ca. 500 ns. FIG. 35D is a distribution of radii of gyration for all Z-Cat-Ben and Z-Cat-Ben-F molecules, averaged over the last 200-ns of simulation. FIG. 35E Density of Z-Cat-Ben and Z-Cat-Ben-F along the perpendicular axis to the mineral (silica) surface, averaged over the last 200-ns of simulation. Curves represent the average densities as a function of distance D from the silica surface for each group (Cat and Ben represent the cathecol and aromatic rings, while P, N and $O_{water}$ represent the phosphorous, nitrogen and water oxygen atoms, respectively. The position of the mineral (silica) surface in the graphs is shown by a representation of silica as CPK molecular model. FIG. 35F is a graph showing Radial distribution functions between the center of mass of cathecol-cathecol (Cat-Cat), aromatic-aromatic (Ben-Ben) and cathecol-aromatic (Cat-Ben) rings for Z-Cat-Ben and Z-Cat-Ben-F molecules, as a function of time, averaged over the last 200-ns of simulation. Radial distribution functions represent a histogram from the calculated distances between all pairs. Graphs are normalized to the number density (ρ) of each system multiplied by the volume of the spherical shell, which is given by $g(r)=4\pi r^2\rho dr$. Therefore, peaks correspond to the relative intensity of interacting groups at their interacting distances. FIG. 35G is a schematic of the self-assembled monomolecular layer on silica surface from the simulation studies.

FIGS. 43A-43F show Transistor characteristics of the SAM. FIG. 43A shows Molecular structure of PCDTPT. FIG. 43B shows a device structure of OFETs. FIG. 43C shows contact angle images of chlorobenzene (CB) droplets on nano-grooved $SiO_2$ substrates modified with n-DTS, Z-Cat-Ben, and Z-Cat-Ben-F SAMs. The θ denotes contact angle between the CB droplet and SiO$_2$ substrate. FIG. 43D is a chart showing transfer curves of the devices with Z-Cat-Ben (orange) and Z-Cat-Ben-F (blue) SAMs on Au electrodes patterned nano-grooved SiO$_2$ dielectrics. FIGS. 43E (Transfer) and 43F (Output) are graphs showing curves of the device with the Z-Cat-Ben-F SAM on Ni electrode patterned nano-grooved SiO$_2$ dielectric. The drain current ($I_{DS}$) was taken at a drain-source voltage ($V_{DS}$) of −80 V with forward and reverses weeping of gate-source voltages ($V_{GS}$). Channel width/length is 1000/200 µm for the devices used in this study.

FIGS. 48A-48C show surface priming by mussel-inspired primers. FIG. 48A shows a mussel attached to a rock surface using its byssus (Goleta Pier, California); FIG. 48B is a schematics showing the location of interfacial mfps within a plaque, and the chemical structures of the mussel-inspired primers and conventional primers; Figure AFM images and height profiles of the mussel-inspired adsorbed primers on mica.

FIG. 50A shows density profiles of primers along the perpendicular axis to the mineral surfaces. All three primers were simulated on the silica surfaces, and only P$_3$ was simulated on mica to confirm the universal mineral adsorption. Curves represent the average densities as a function of distance D from the oxygen atoms on mineral surface to each P primer molecule. The position of the mineral (silica and mica) surfaces in the graphs are shown as CPK model. FIG. 50B are two graphs showing radial distribution functions between the aromatic rings for each primer type and mineral surface oxygen atoms over time. The radial distribution function is given by g(r)=4πr$^2$ρ dr, which represents a normalized histogram constructed from the calculated radial distances r between all molecular pairs of a given number density p. FIG. 50C is a graph showing radial distribution functions between the center of mass of primer molecules and aromatic groups represented as CG (catechol group) carbon atoms over time. FIG. 50D are graphs of radial distribution function between the oxygen atoms from mineral surface and hydroxyl groups of P$_2$ and P$_3$. A representative snapshot of the preferred adsorption configuration is shown as an inset in each case following the CPK molecular model and each hydroxyl group labelled. FIG. 50E shows two graphs of modeling of molecular adsorption of the inventive molecules on silica and mica surfaces, respectively, using molecular dynamic simulations. FIG. 50F is a histogram of the average minimum distance between the plane formed by the 0 atoms of the mineral surface and the C6 carbon atom. All analyses were performed using the last 50-ns time interval of each simulation.

FIG. 54A is a schematic of experimental procedures in lap shear test. FIGS. 54B and 54C are schematic drawing of (b) Silane-grafted and (c) catechol-primed silicate mineral surfaces. FIGS. 54D-54F are graphs showing lap shear strengths of cured PMA on (d) mica, (e) glass and (f) tooth enamel (IRB No. S-D20 160003) surfaces treated with different primers (MDP, Silane, P$_1$, P$_2$, P$_3$, and P$_4$). In each case, the RMS surface roughness R (measured in AFM) is shown. (g) Schematic showing the experimental procedures used in the SFA measurements. (h) Adhesion force (left axis) and pressure (right axis) between 2 identical primer-treated mica surfaces. Inset: an example of the measured normal force signal during loading and adhesion force measurement. P-value was calculated using the Student's t-test (*p<0.01; **p<0.001).

FIG. 57A is a schematic showing the experimental procedure used in the compressive failure test, and schematic drawing and SEM image of a primer-treated glass filled composite. FIG. 57B are graphs showing a representative stress-train curve of the mineral-PMA composite. FIG. 57B' is a zoom in of the stress-strain curve (x-axis: 0.2-0.42, y-axis: 225-320 MPa) emphasizing the jagged stress decrease during failure of the P3-treated sampled (red circle). FIG. 57 C are graphs showing elastic modulus, ultimate strength, strain at failure, and toughness of the composites. P-value was calculated using the Student's t-test (*p<0.05; **p<0.001).

DETAILED DESCRIPTION

Figures 1A, 1B, 1C, 1D, 1E, 1F:
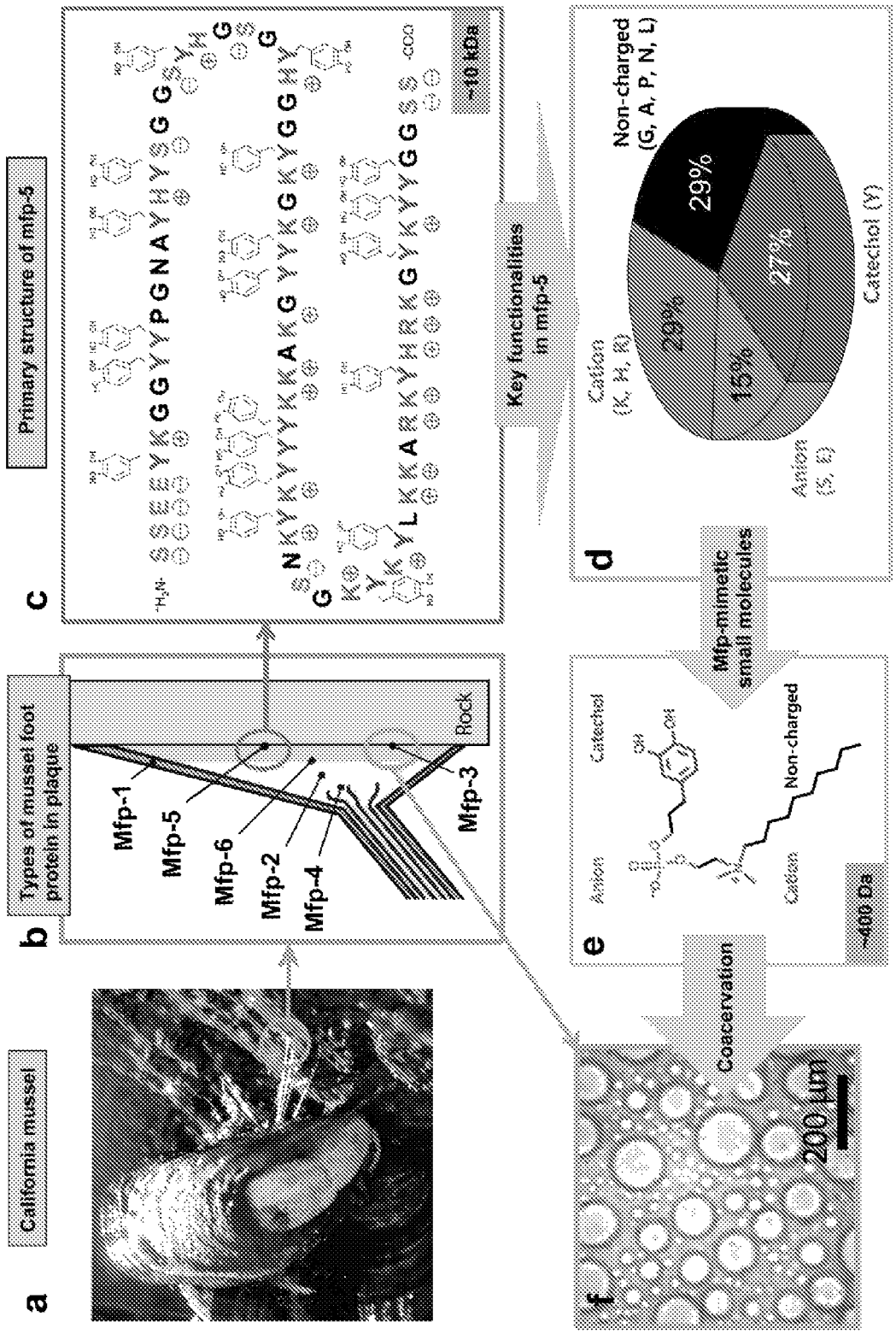
FIGS. 1A-1F show key features of natural and translated mussel adhesion.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background, Detailed Description sections and Examples, are incorporated by reference into this disclosure as if each had been individually incorporated.

Some embodiments of the current invention are directed to an inventive catechol containing nano-adhesive and surface primer. The inventive nano-adhesive and surface primer contain a catechol group. The inventive compound comprises a catechol group attached to anend group through a spacer group. The inventive compound can self-assemble onto metal and mineral oxide substrates. When applied to an oxide containing surface, the catechol group of the inventive compound can self-assembly and canform not only an H-bond with the oxide containing surface, but chelating bond with metal containing surface. The end group of the inventive compound can form a secondary surface layer to interact with bulk materials chemically or physically via cross-linking, H-bonding, or hydrophobic interaction. A secondary surface can optionally be applied onto the nano-adhesive. In other words, a secondary layer is tunable by modifying the end group of the catecholic molecule [catechol-spacer (zwitterionic or alky)-end (acrylate, epoxy, alkyl, benzyl, catechol, and so forth)].

In some embodiments, the inventive compound comprises a compound of Formula I:

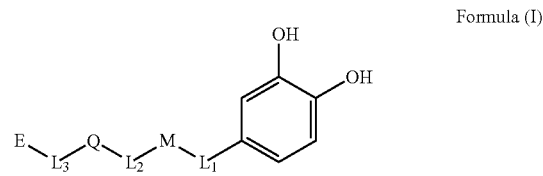

Formula (I)

In some embodiments, the catechol group may be

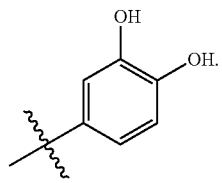 [SMILES: *c1ccc(O)c(O)c1]

In some embodiments, the spacer group may be $L_3$-Q-$L_2$-M-$L_1$. In some embodiments, the end group may be E. In some embodiments, the spacer group may be selected from the group consisting of alkyl, non-polar, zwitterionic, cationic, anionic, and non-charged polar moiety. In some embodiments, each of $L_2$ and $L_3$ may be $C_1$-$C_{15}$ alkyl, or optionally substituted $C_2$-$C_{15}$ alkenyl. In an embodiment, $L_3$, when present, may be a bond, $C_1$-$C_{15}$ alkyl, or optionally substituted $C_2$-$C_{15}$ alkenyl. In some embodiments, M and Q, when present, may be each selected from —(CO$_2$)—, NRR', —RCOH or PO$_4$, wherein R and R' are each selected from a group consisting of H or $C_1$-$C_5$ alkyl. In some embodiments, E may be selected from the group consisting of acrylate, methacrylate, epoxy, amine, substituted phenyl, unsubstituted phenyl, catechol, alkyl, alkylenyl, cationic, anionic, non-charged polar, and non-polar moiety. In some embodiments, E may be selected from a group consisting of $C_2$-$C_6$ alkenyl, $C_1$-$C_6$ alkyl, and optionally substituted or unsubstituted phenyl. In some embodiments, the substituted phenyl may be an aromatic moiety selected from a group consisting of dihydroxyphenyl, catechol, and di(trifluoromethyl)phenyl.

In some embodiments, the compound of Formula (I) has the formula:

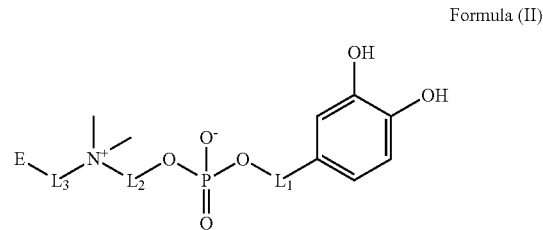

Formula (II)

wherein: each of $L_1$ and $L_2$ may be $C_2$-$C_6$ alkyl; $L_3$ may be a bond or $C_2$-$C_{15}$ alkyl; E may be selected from a group consisting of $C_4$-$C_{12}$ alkyl, phenyl, dihydroxyphenyl, catechol, and 3,5-di(trifluoromethyl)phenyl.

In some embodiments, the compound of Formula (II) is selected from:

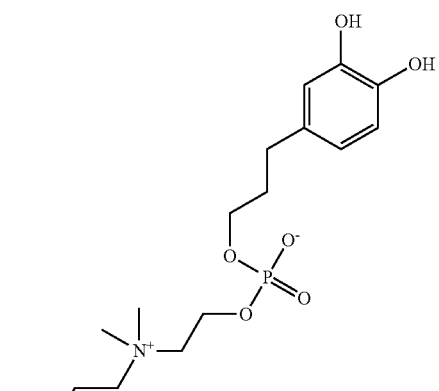
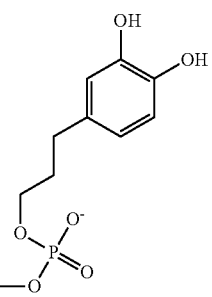
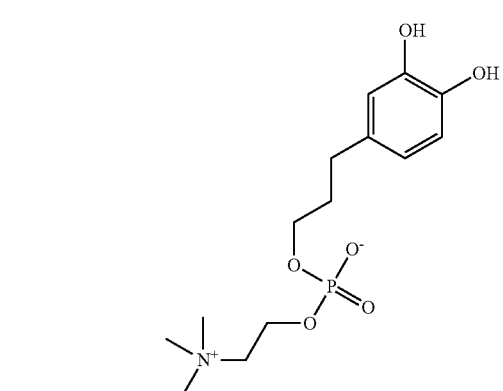
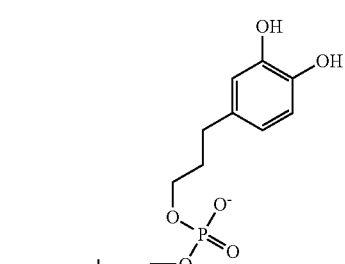
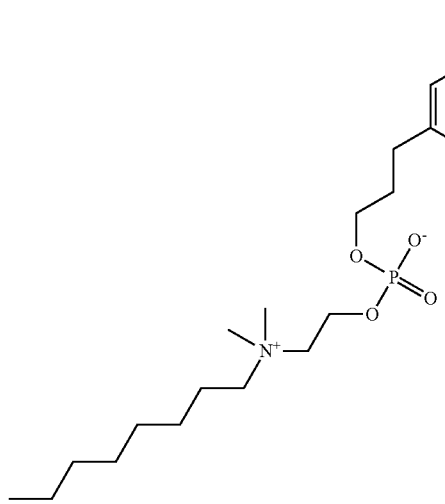
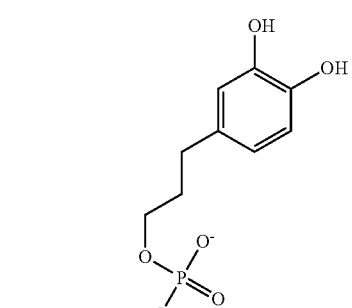

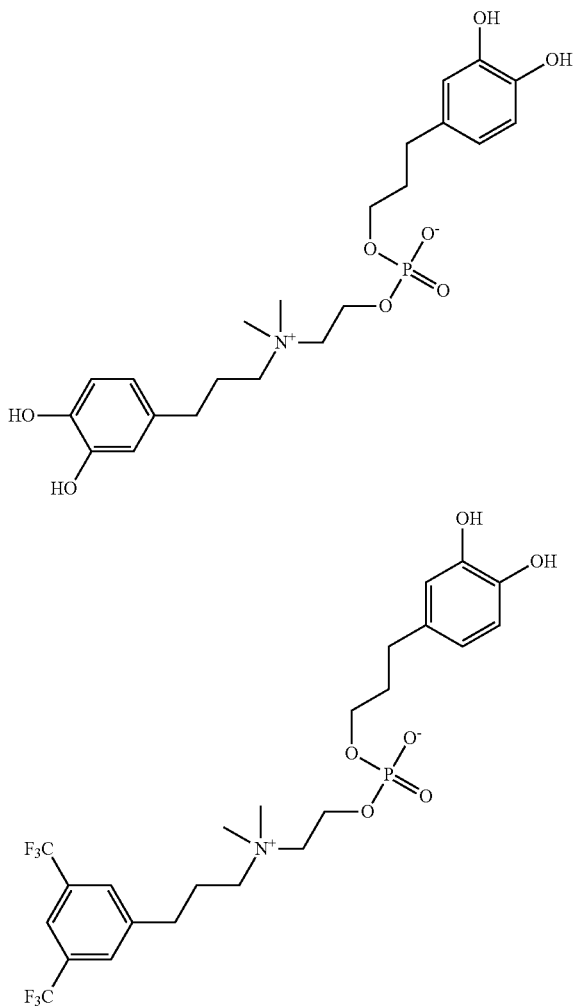

In some embodiments, the compound of Formula (I) has the formula:

Formula (III)

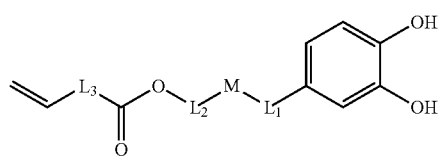

wherein: each of $L_1$ and $L_2$ is $C_1$-$C_{10}$ alkyl; $L_3$ is a bond; and M is —COH— or —CO$_2$—.

In some embodiments, the compound of Formula (II) is selected from:

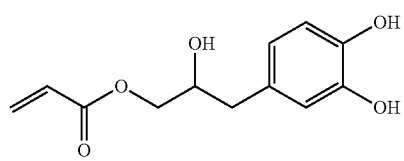

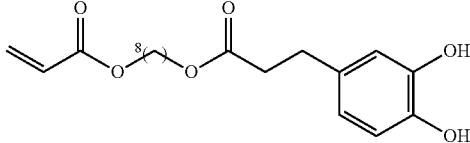

In some embodiments, the compound of Formula (I) can be used as an adhesive, a primer or a coating. The inventive compound of Formula (I) has strong adhesion (~50 mJ m$^{-2}$) and retains the ability to coacervate. This inventive compound may adhere to diverse surfaces and self-assembles into a molecularly smooth, thin, and strong glue layer.

In some embodiments, the method of using the compound of Formula (I) includes providing an oxide and/or metal containing surface. The method includes applying a layer of the compound onto the oxide containing surface, wherein the catechol group of the compound forms an H-bond with the oxide containing surface and generates a secondary surface layer with the end group.

In some embodiments, the method includes applying a layer of the compound onto the metal containing surface, wherein the catechol group of the compound forms a chelating-bond with the metal containing surface and generating a secondary surface layer with the end group.

In some embodiments, the adhesive layer has a thickness from between 0.1 to 10 nm, between 0.5 to 10 nm, between 1 to 10 nm, between 1 to 5 nm, or between 5 to 10 nm.

In some embodiments, the compound of Formula (I) can be applied onto mineral or metal oxide surfaces, such as mica, silicon wafer, glass, bone, enamel surfaces, silica, kaolin, zirconia, aluminum, copper, chrome, chrome-cobalt, calcium, aluminum oxide, copper oxide, silica oxide, titanium oxide, zinc oxide, calcium oxide, tin oxide, indium-tin oxide, or hydroxylapatite.

In some embodiments, the compound of Formula (I) can be treated with an oxidizing agent, such as periodate to form a quinone derivative.

In some embodiments, the compound of Formula (I) can be used as a dental/bone adhesive, surface primers for dental/medical implants, surface primers for polymer composites including dental and bone cements, or for battery anodes/binders, electro circuits, semiconductors, nanosensing devices, organic solar cells, opto-electronic devices, hetero-junctions, and electron tunneling junctions.

In some embodiments, a second oxide and/or metal containing surface may be affixed onto the first secondary surface layer. In some embodiments, the method further includes applying a layer of the compound of Formula (I) onto the second oxide and/or metal containing surface thereby forming a second secondary surface layer with the end group of the compound. In some embodiments, the end group of the compound of the first secondary surface layer may interact with the end group of the compound of the second secondary surface layer. In some embodiments, the interaction between the first secondary surface layer and the second secondary surface layer may include a hydrophobic interaction or a π-π stacking. In some embodiments, a third and a fourth layer of the compound may be applied onto the first secondary surface layer and the second secondary surface layer, wherein the compound self-assembles onto the first secondary surface layer and the second secondary surface layer creating a third and a fourth secondary surface layer with the catechol group of the compound. In some embodiments, the catechol group of the third secondary surface layer may interact with the fourth secondary surface layers. In some embodiments, the interaction may be cross-linking or H-bonding.

The following examples describe some further concepts of the invention with reference to particular examples. The general concepts of the current invention are not limited to the particular examples.

High Performance Mussel-Inspired Adhesives of Reduced Complexity:

Despite the recent progress in and demand for wet-adhesives, practical underwater adhesion remains limited or nonexistent for diverse applications. Translation of mussel-inspired wet adhesion typically entails catechol-functionalization of polymers and/or polyelectrolytes, and solution processing of many complex components and steps that require optimization and stabilization. Here, the complexity of a wet adhesive primer to synthetic low molecular weight catecholic zwitterionic surfactants was reduced to show very strong adhesion (~50 mJ m$^{-2}$) and retain the ability to coacervate. This catecholic zwitterion adheres to diverse surfaces and self-assembles into a molecularly smooth, thin (<4 nm), and strong glue layer. The catecholic zwitterion holds particular promise as an adhesive for nanofabrication. This example significantly simplifies bio-inspired themes for wet adhesion by combining catechol with hydrophobic and electrostatic functional groups in a small molecule.

Marine mussels attach to rocks by way of thread-like tethers on wind- and wave-swept seashores where wave velocities can reach 25 m s$^{-1}$. Mussel attachment tenacity is enabled by adaptations at multiple length scales, and the nanometer scale corresponds most closely to the chemistry of the interface. Interfacial mussel foot proteins (mfps), especially mfp-3 and mfp-5, are rich in the catecholic amino acid, 3, 4-dihydroxyphenylalanine (Dopa), which has been adopted for functionalizing diverse synthetic polymers. Although the role of Dopa in wet adhesion is under increasing scrutiny, its introduction into polymers often endows them with strong underwater adhesion and self-healing capabilities. Other common amino acids, e.g., lysine, phosphoserine, histidine, are also relevant to mfp adhesion and merit translation to synthetic systems. Mfps are protein polyelectrolytes with high charge densities, and lend themselves to complex coacervation, which appears to be critical for the lossless fluidic delivery of mfps to target surfaces underwater. Lysine and phosphoserine have been adopted to enhance adsorption, but also to drive charge-dependent complexation needed for the dense fluid phase-separation (coacervation) of adhesive polyelectrolytes from the equilibrium solution. Of particular interest here, mfp-5 and -3 function as adhesive primers at the plaque-substratum interface. Despite recent progress in the science of wet-adhesion, practical underwater adhesion remains limited or nonexistent for a variety of potential applications. Biomimetic synthetic initiatives have aspired to remedy this by mimicking specific attributes of the bioadhesive model systems of mussels and sandcastle worms. These attributes include macromolecular adsorption to surfaces, fluid-fluid phase-separation (coacervation), and curing by oxidative catechol-based cross-linking, and involve many complex components and steps requiring optimization and stabilization.

In this example, both the strong wet-adhesion of mfp-5 films and the coacervation of mfp-3 were translated into a smaller and simpler zwitterionic platform. Several motifs borrowed from the interfacial adhesive mfps (including catechol, positive and negative charges, and nonpolar moieties) were simplified and combined into a single, low molecular weight, one-component adhesive system. By taking a previously reported gemini zwitterionic surfactant with charged quaternary amine and phosphate groups and two alkyl tails, one of the tails was replaced with a catechol, and the other tail was varied to create a family of mfp-mimetic zwitterionic adhesive homologs (mass <500 Da). These homologs exhibited very strong and spontaneous catechol-mediated binding to surfaces, stable phase-separation as one-component coacervates or bilayer films, and periodate-mediated curing. The measured adhesion energy ($W_{ad}$~50 mJ m$^{-2}$) is the highest reported to date for a nm-thick film formed underwater, and 2-3 times greater than mfp-5 or engineered recombinant mfp-amyloid fusion protein. Zwitterion-mediated adhesion is likely to stimulate applications at multiple length-scales including nanofabrications that require molecularly smooth and thin (<4 nm) adhesive layers, e.g., in electronic, lithographic and biomedical applications.

Results

Zwitterionic Adhesives Design Inspiration

The phosphate, amine, catechol, and hydrophobic (alkyl or benzyl) functionalities in the zwitterions were adopted from the following mole percents of amino acid residues in mfp-5, e.g., anionic residues (~15 mol %), cationic residues (~29 mol %), Dopa (~27 mol %), and assorted non-charged (~29 mol %) (FIG. 1). Accordingly, the chemical complexity of mfps was reduced, and adhesion and coacervation were recapitulated by a strategic combination of functionalities in the zwitterionic platform (FIG. 1E-1F). Various homologs were designed by replacing one or both alkyl chains with mfp-mimetic functionalities (FIG. 2A) and their interfacial and adhesive properties were investigated. These homologs includes Z-Cat-Cat, Z-Ben-C8, Z-Cat-C8, Z-Cat-C4, Z-Cat-C6, and Z-Cat-Z10.

Interfacial Properties and Redox Stability

Figures 2A, 2B, 2C, 2D, 2E, 2F:
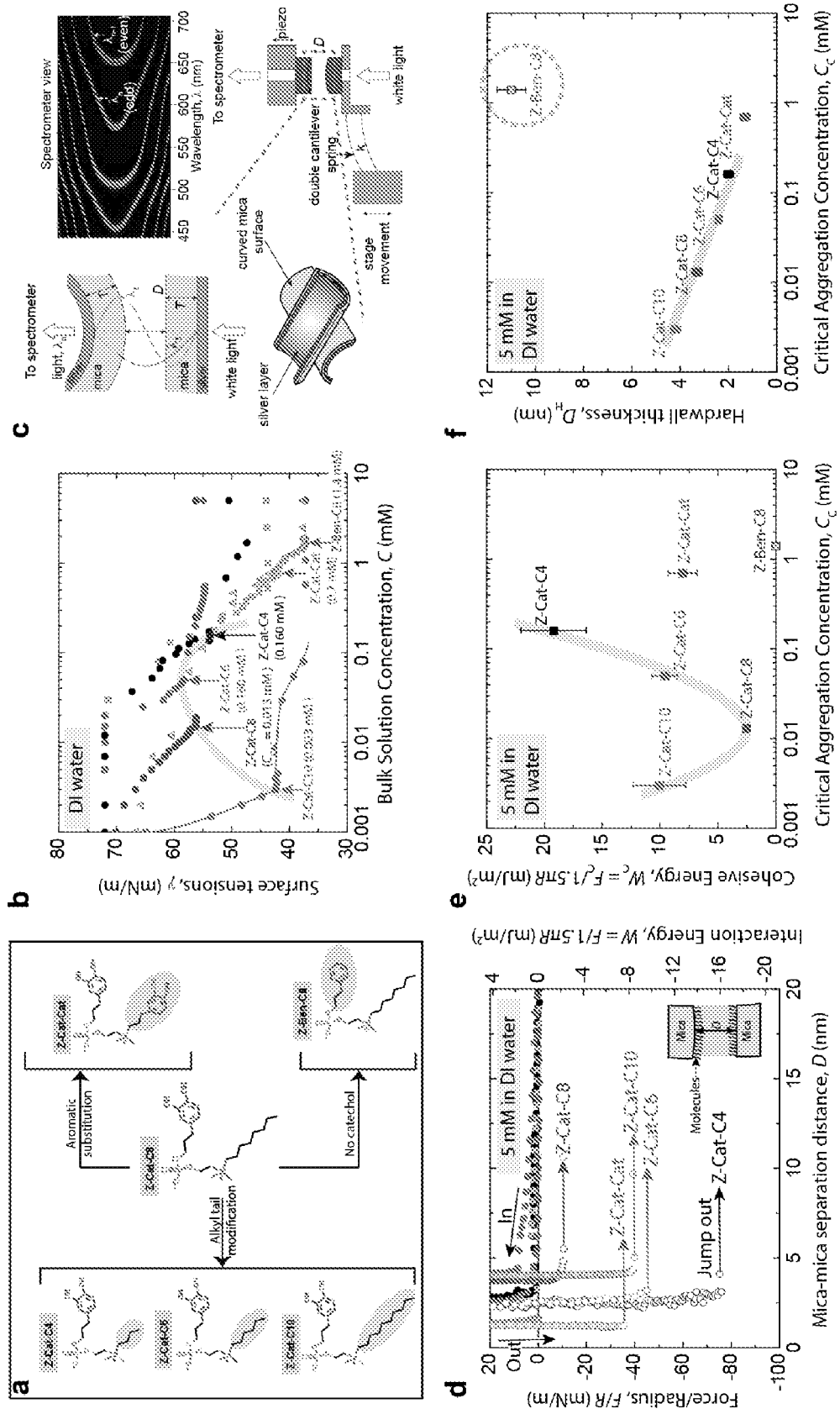
FIGS. 2A-2F show Mfp-mimetic zwitterionic surfactants, their aggregation behaviors, and surface forces of mfp-mimetic zwitterion films on freshly cleaved mica.
Figure 3:
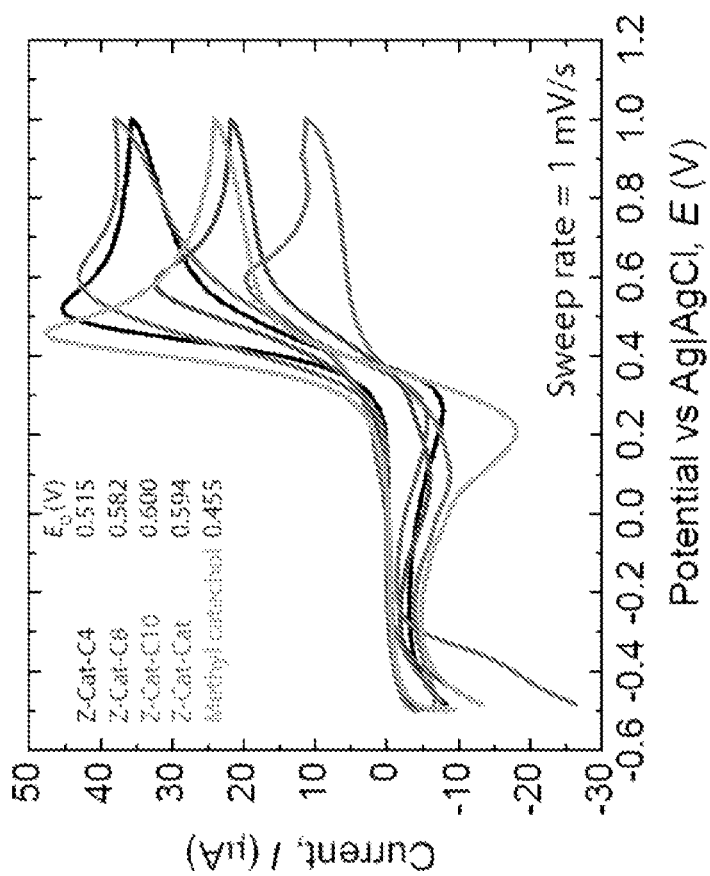
FIG. 3 is a graph showing cyclic voltammetry measurements for 5 mM solution of the small molecules in DI water.

The aggregation tendency of each homolog in water was assessed by the critical aggregation concentration (CAC). The CAC is the concentration at which further addition of solute molecules to a solvent makes them go into finite sized aggregates while the monomer concentration remains unchanged. The CAC was determined from the solution surface tension of varying homolog concentrations in deionized (DI) water (n.b. the line of Z-Cat-C10 in FIG. 2B) by Wilhelmy plate tensiometry. FIG. 2B shows that decreasing alkyl tail length increases the CAC gradually from Z-Cat-C10 to -C8, -C6, and -C4 (parabolic dashed-line from Z-Cat-C10 to -C4), consistent with thermodynamic predictions. Conversely, aromatic substitution (FIG. 2A) increased CAC significantly. The substitution of the catechol of Z-Cat-C8 by a benzene (FIG. 2A) also increased CAC. Based on cyclic voltammetry combined with UV-Vis spectroscopy, the oxidative stability of catechol functionalities in all zwitterionic homologs (e.g., $E_{1/2}$ of Z-Cat-C10~+0.25 V at 1 mV s$^1$) was significantly increased by comparison with 4-methylcatechol (completely solvent accessible, $\Delta E_{1/2}$~+0.12 V in DI water at 1 mV s$^{-1}$), suggesting a highly stabilizing environment in the dispersion (FIG. 3).

Surface Force Measurements and Interfacial Interaction Study

Figure 4:
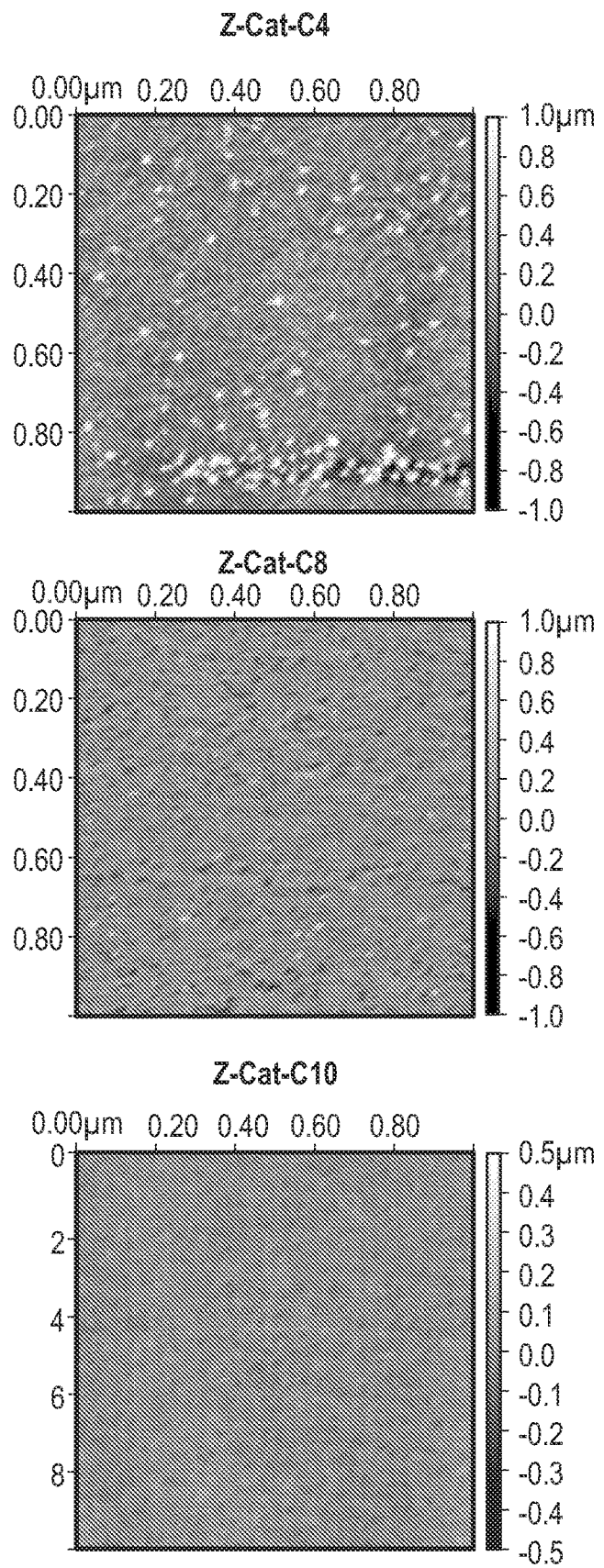
FIG. 4 shows AFM images of the small molecules absorbed on mica surfaces.
Figure 5:
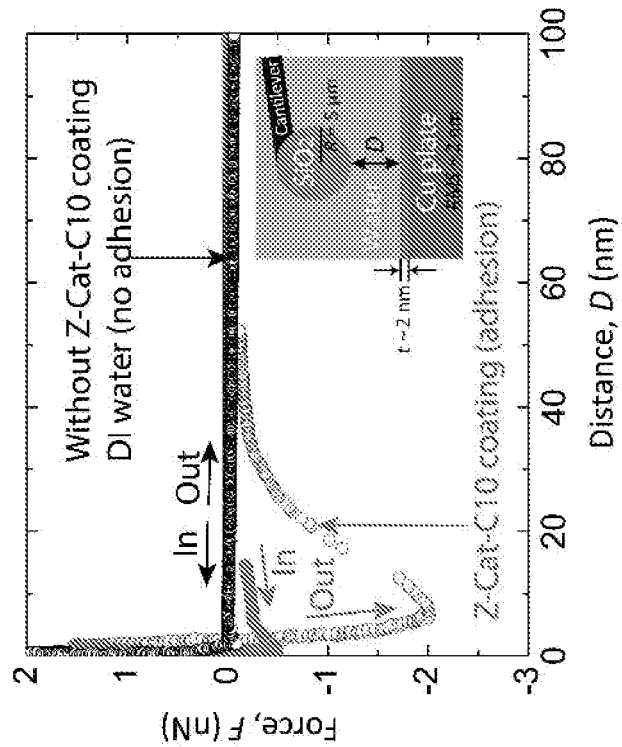
FIG. 5 shows AFM force run on copper plate underwater using $\phi$=10 m silica tip. Cantilever spring constant (K) was 0.1 N m−1.
Figure 7A:
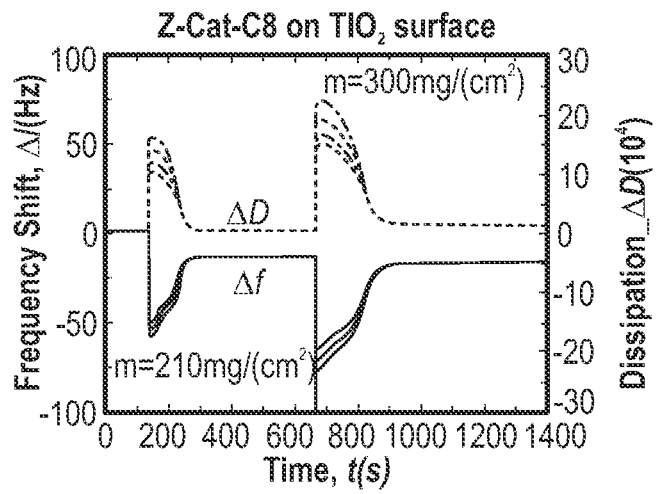
FIGS. 7A-7E are QCM-D experiments showing the adsorption of all molecules onto a TiO2 surface.
Figure 7B:
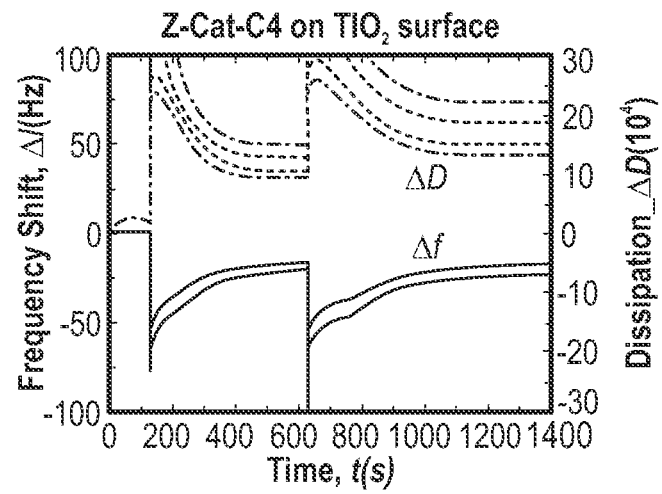
Figure 7C:
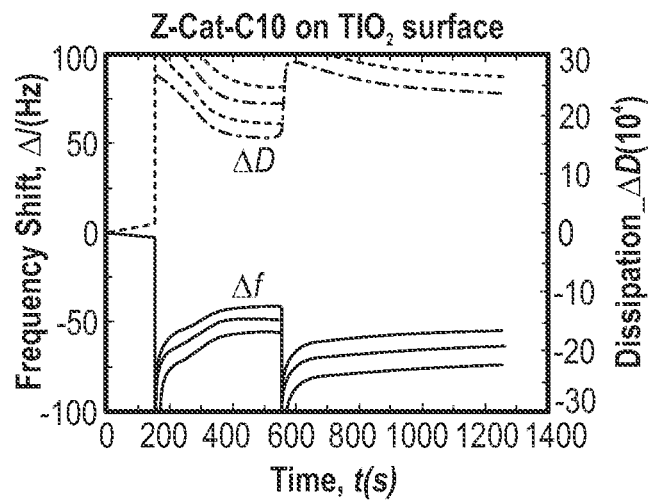
Figure 7D:
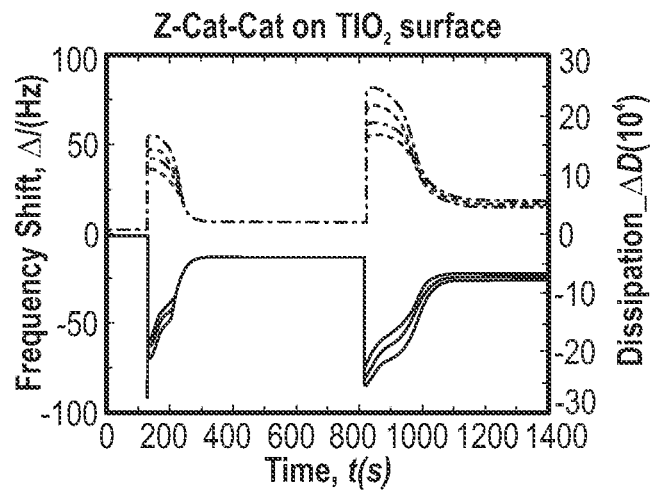
Figure 7E:
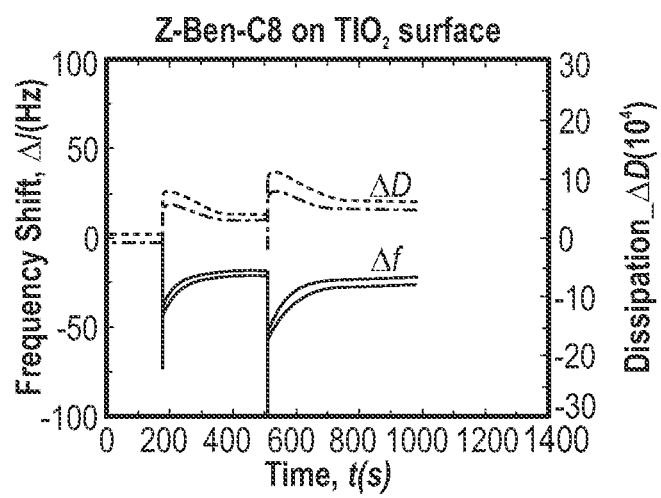
Figure 8A:
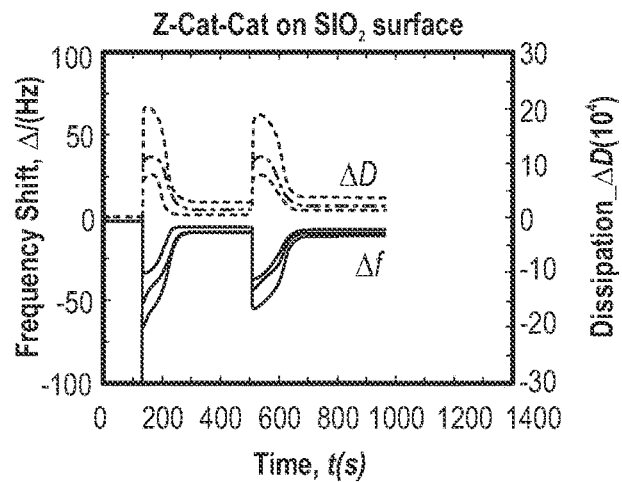
FIGS. 8A-8E are QCM-D experiments showing the adsorption of all molecules onto a SiO2 surface.
Figure 8B:
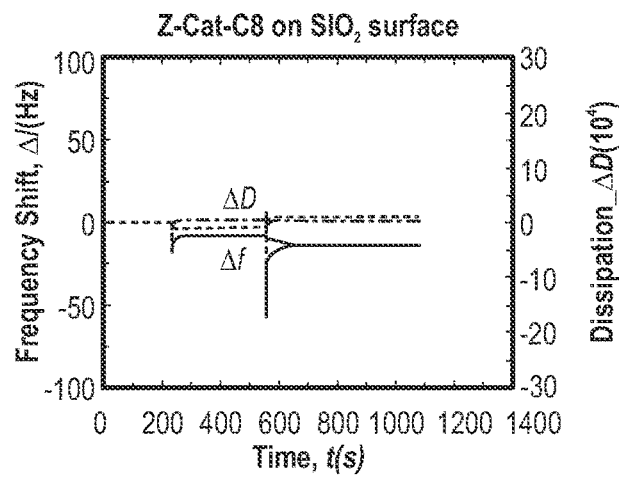
Figure 8C:
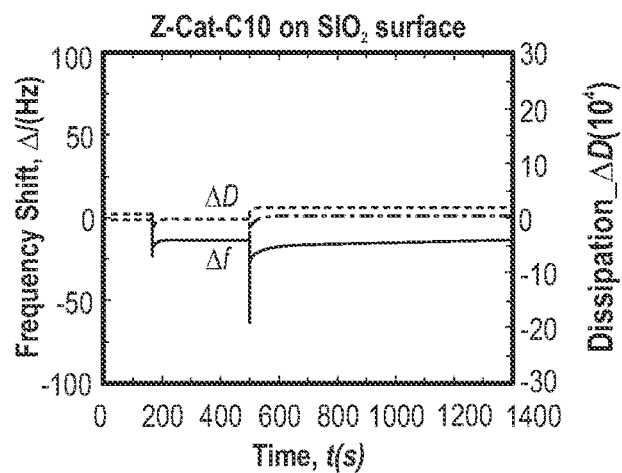
Figure 8D:
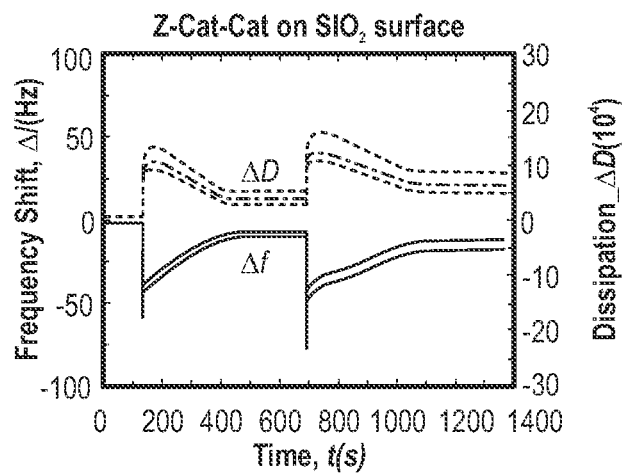
Figure 8E:
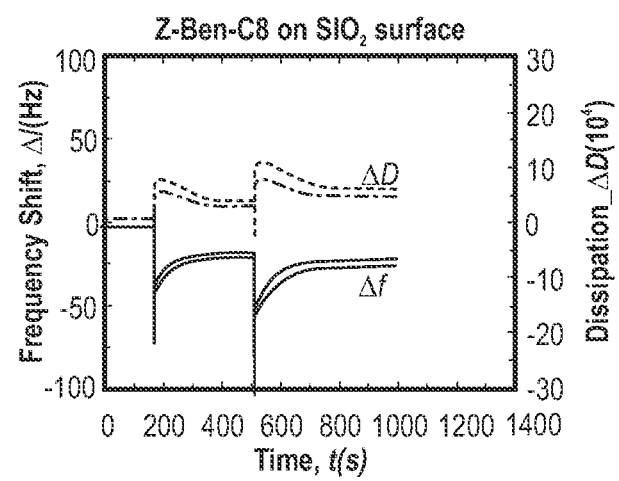
Figure 9:
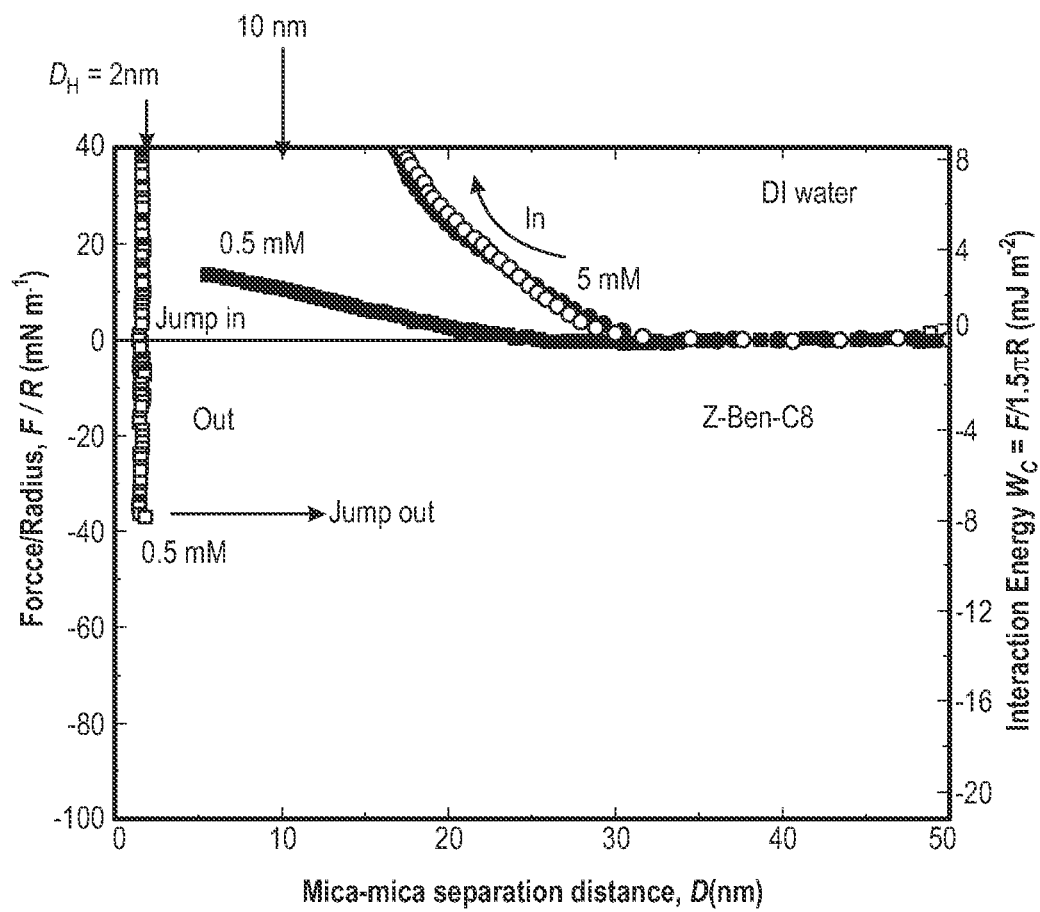
FIG. 9 is a graph showing the representative force vs. distance plots between mica surfaces of 0.5 mM and 5 mM aqueous dispersions of Z-Ben-C8.

Thin films of the zwitterionic homologs were deposited on mica surfaces by adsorption from 5 mM solution (>CAC for all homologs), and investigated by the surface forces apparatus (SFA) (FIG. 2C), atomic force microscopy (AFM) (FIGS. 4, 5 and 6), and quartz crystal microbalance with dissipation (QCM-D) (FIGS. 7A-7E and FIGS. 8A-8E). FIGS. 7A-7E shows that frequency and dissipation change upon addition of (5 mM) of each single molecule solution to a titania surface. In this two-step adsorption, each molecule was deposited (50 μL) onto a titania surface in DI $H_2O$ using a static cell. FIGS. 8A-8E shows that frequency and dissipation change upon addition of (5 mM) of each single molecule solution to a silica surface. In this two-step adsorption, each molecule was deposited (50 μL) onto a silica surface in DI $H_2O$ using a static cell. Surface forces measurements between symmetric thin films on mica were investigated in the SFA. Upon approach of the two surfaces, Z-Ben-C8 films showed regular bilayer repulsion and jump-in instabilities typical for surfactant layers (FIG. 9), whereas the catecholic homologs showed only slight or no repulsion (FIG. 2D). Z-Cat-C4 (19.2±2.4 mJ $m^{-2}$) exhibited the greatest cohesion (or adhesion) energies in DI water, followed by Z-Cat-C10 (10.1±2.3 mJ $m^{-2}$), Z-Cat-C6 (9.6±1.1 mJ $m^{-2}$), Z-Cat-Cat (8.1±1.3 mJ $m^{-2}$), and Z-Cat-C8 (2.5±0.3 mJ $m^{-2}$) (FIG. 2E). Notably, the interaction energies of Z-Cat-C10, -C8, -C6, and -C4 were closely correlated with the CAC (see, parabola drawn in the plot in FIG. 2E as in FIG. 2B).

The hard-wall thickness (the limiting distance between the mica surfaces during the approach run in the SFA) of each homolog was measured and correlated with the CAC (FIG. 2F) corresponding to the catechol-containing zwitterions, which formed strongly cohesive ($W_c$=2.2-21.6 mJ $m^{-2}$) bilayers (0.5-2.0 nm). In contrast, the non-catecholic Z-Ben-$C_8$ formed multilayered films (~5 nm) without cohesive tendencies. In the catechol-containing homologs with alkyl tails (FIG. 2a), e.g. Z-Cat-C10, -C8, -C6 and -C4, the hard-wall thickness and CAC were both correlated with alkyl tail length (line in FIG. 2F).

Figure 11:
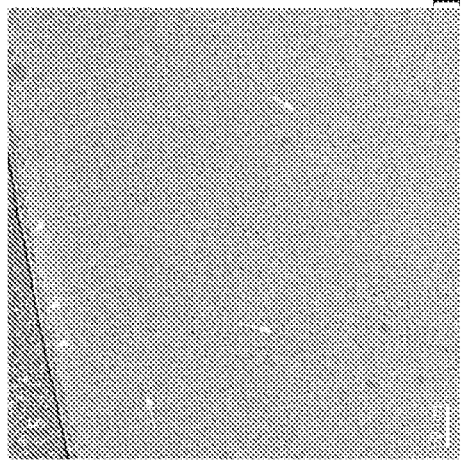
FIG. 11 is a Cryo-TEM image shows mostly small aggregates (arrows) and some individual aggregates (arrowheads) attached to the support film (S).
Figure 12:
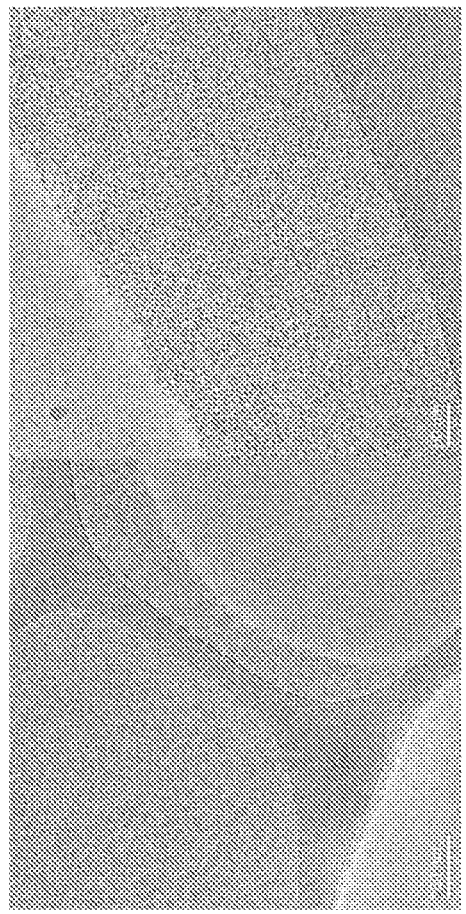
FIG. 12 show Cryo-TEM images show large domains of packed aggregates attached to the carbon support film.

Z-Cat-C10, which exhibited the lowest CAC among the homologs and readily phase-separated into dense visible coacervates and equilibrium solution at high concentrations (100 mg $ml^{-1}$), was chosen for further scrutiny. Coalescence of the coacervate microdroplets in bulk solution was observed by microscopy (FIGS. 10A and 10B), and spreading of coacervates over a glass substrate was recorded on an inverted microscope. Cryogenic transmission electron microscopy (cryo-TEM) images (FIG. 11 and FIG. 12) showed small micelle-like aggregates in both equilibrium solution and coacervate phases.

Figure 13A:
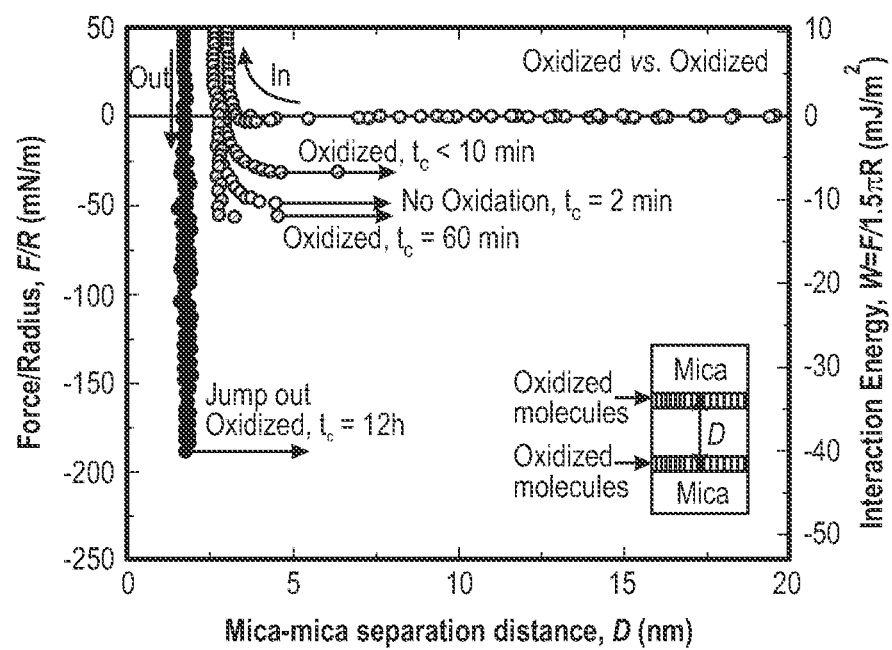
FIGS. 13A-13F area series of figures showing atomically smooth, thin, strong nano-adhesive from mfp-mimetic zwitterion, i.e., Z-Cat-C10, and the effect of oxidative crosslinking.
Figure 13B:
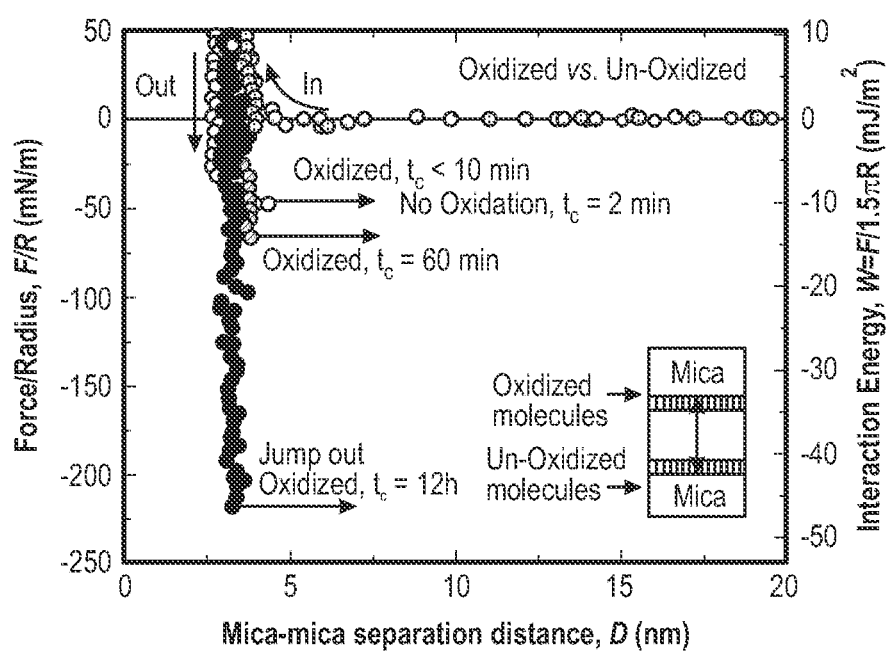
Figure 13C:
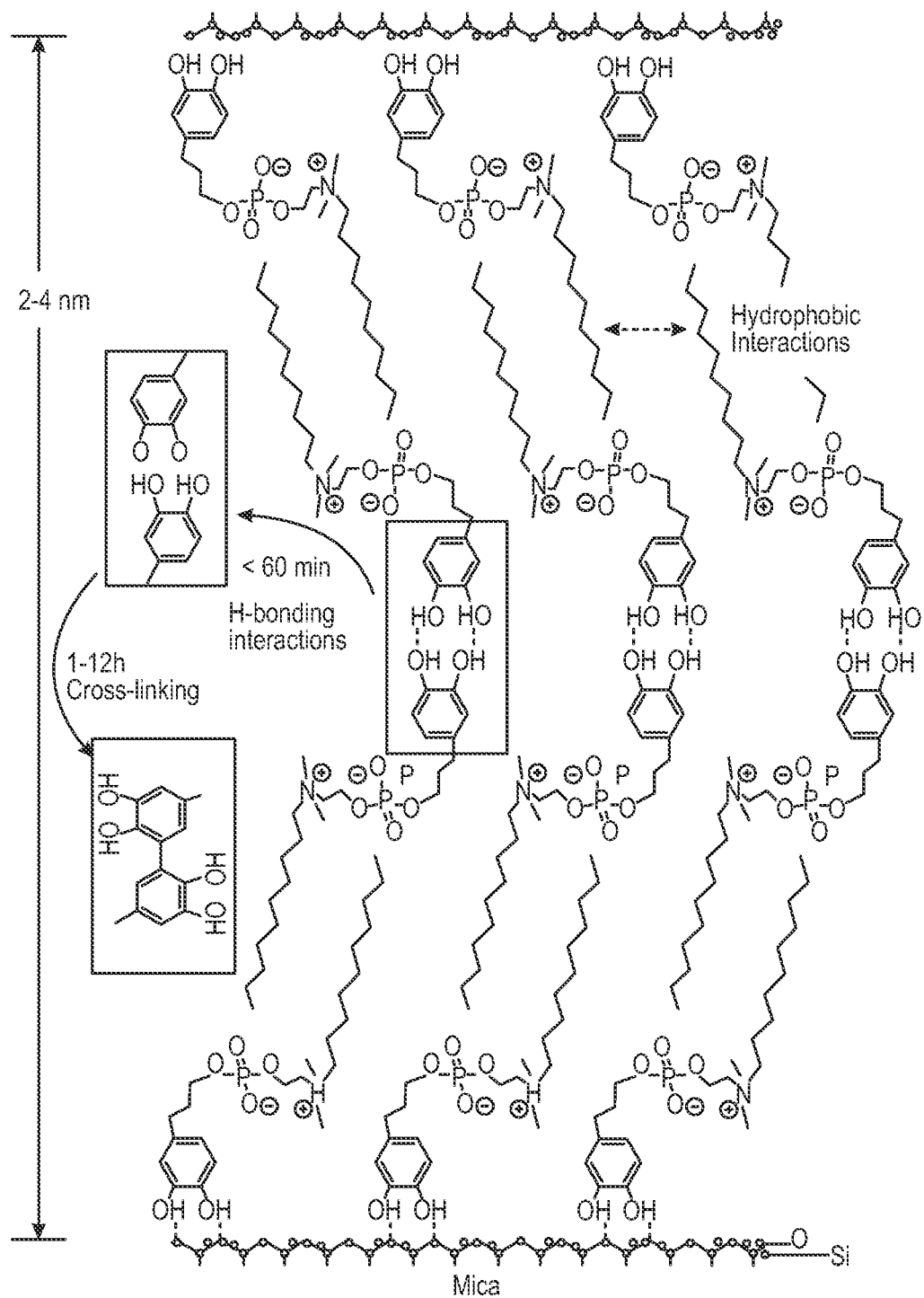

Mussels rely on quinone-mediated protein cross-linking to increase plaque cohesion. o-Quinones are produced by the 2-electron oxidation of targeted Dopa residues. Accordingly, the catechol in Z-Cat-C10 was oxidized with sodium periodate resulting in a stoichiometric −2$H^+$ and −2$e^-$ oxidation to o-quinone. Given the nano Newton precision of the SFA, the adhesion of monomolecular layers of Z-Cat-C10 on mica was measured. SFA force-distance profiles between surfaces allow the measurement of adhesion forces that can be translated into adhesion energies ($W_{ad}$) by the Johnson-Kendall-Roberts (JKR) theory for soft deformable surfaces. Analysis by SFA showed that the observed cohesion or adhesion energy correlated well with the symmetric or asymmetric oxidation of catechol by periodate. After symmetric periodate oxidation (FIG. 13a), cohesion initially decreased by 50% for contact times of ≤$t_c$=10 min, but then rebounded after $t_c$=60 min contact times. Conversely, asymmetric oxidation, i.e. all catechol on one side and all quinone on the other (FIG. 13B), maintained the initial adhesion for contact times of ≤$t_c$=10 min, followed by a 50% increase in adhesion after a $t_c$=60 min contact time. The loss and subsequent recovery of adhesion, respectively, following oxidation were previously explained as the loss of H-bonding interactions because quinones are exclusively H-bond acceptors (short-term), followed by the quinone-mediated formation of covalent crosslinks (long-term). The high adhesion ($W_{ad}$~50 mJ $m^{-2}$) obtained after $t_c$=12 h of compressive contact, contrasts with ≤$t_c$=10 min and $t_c$=1 h contacts. According to the post-oxidation analyses, covalent crosslinks formed within and between the thin films (~2-4 nm) (FIG. 13C).

Figure 6:
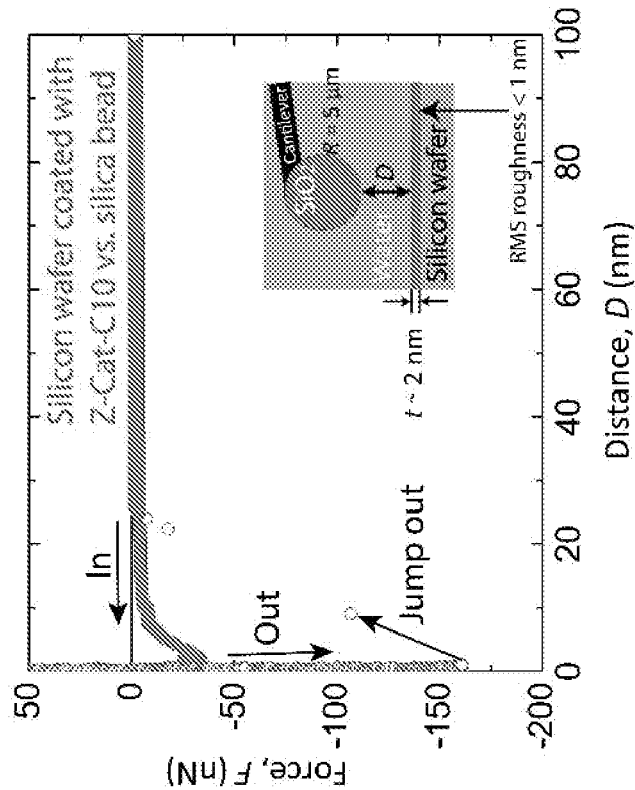
FIG. 6 shows AFM force run on silicon wafer underwater using $\phi$=10 μm silica tip. Cantilever spring constant (K) was 0.1 N m-1.
Figure 13E:
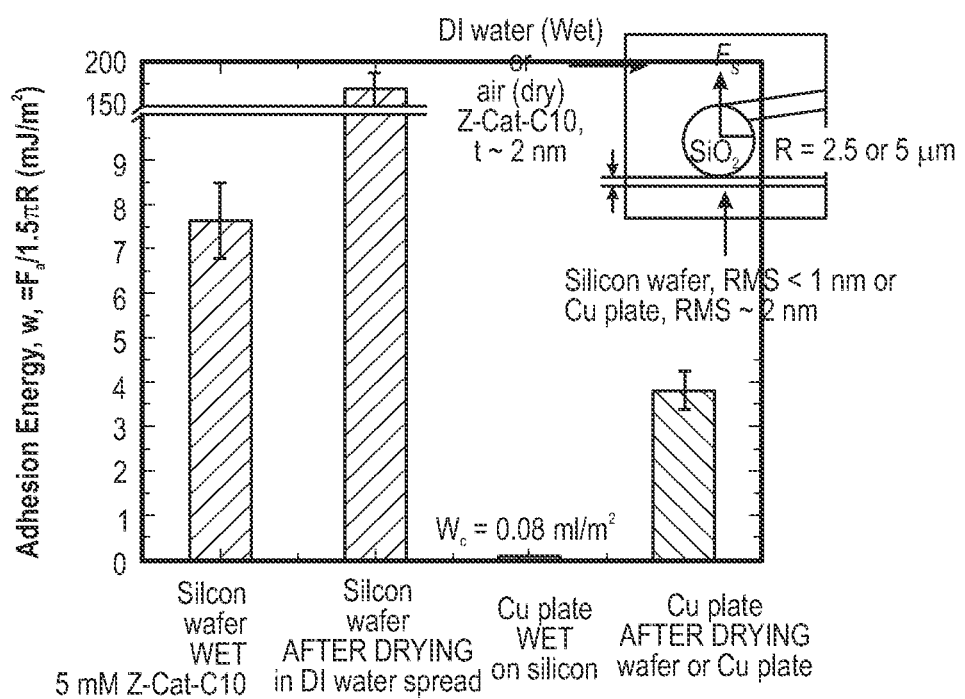
Figure 14A:
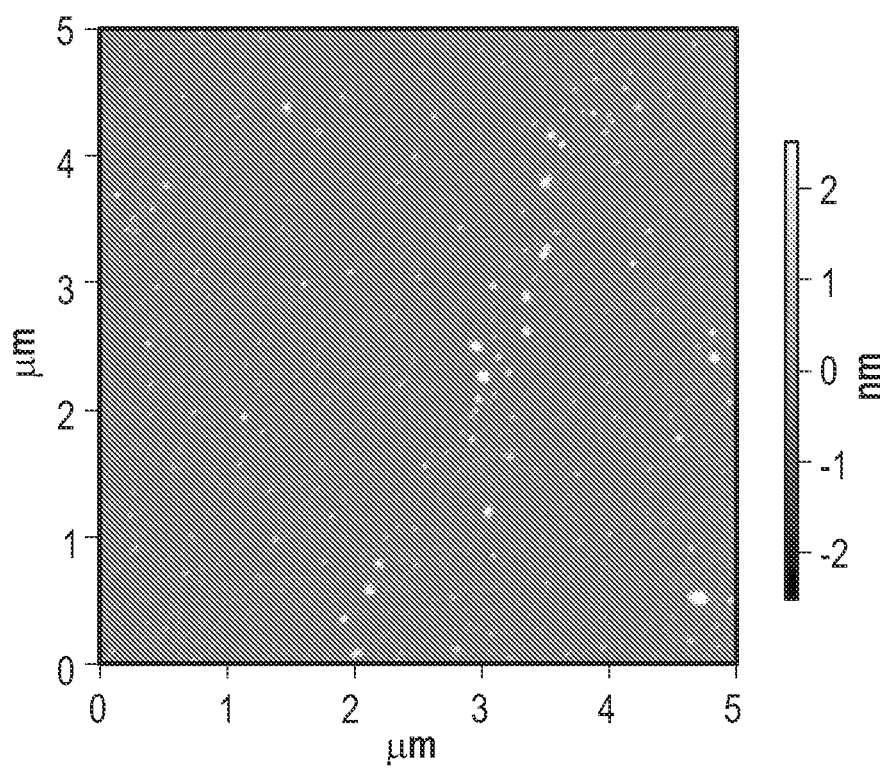
FIGS. 14A-14B are AFM images of a silicon wafer.
Figure 14B:
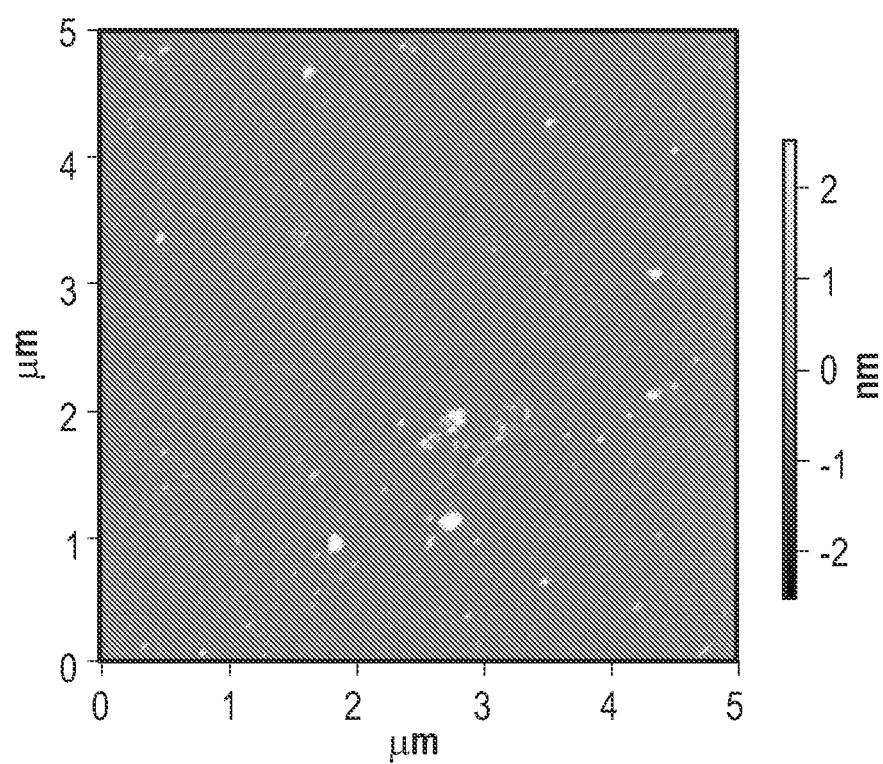
Figure 15A:
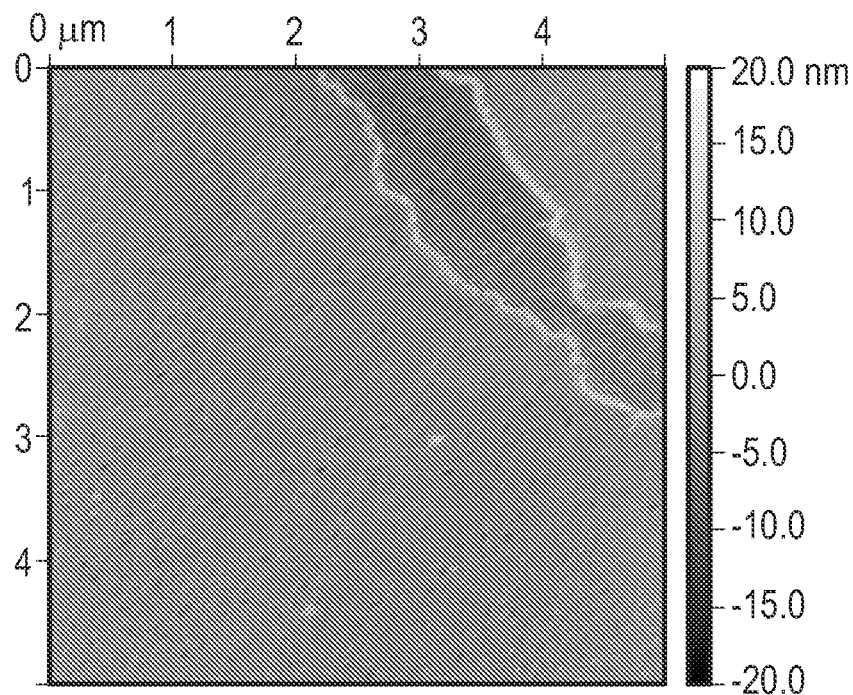
FIGS. 15A-15B are AFM images of a copper plate.
Figure 15B:
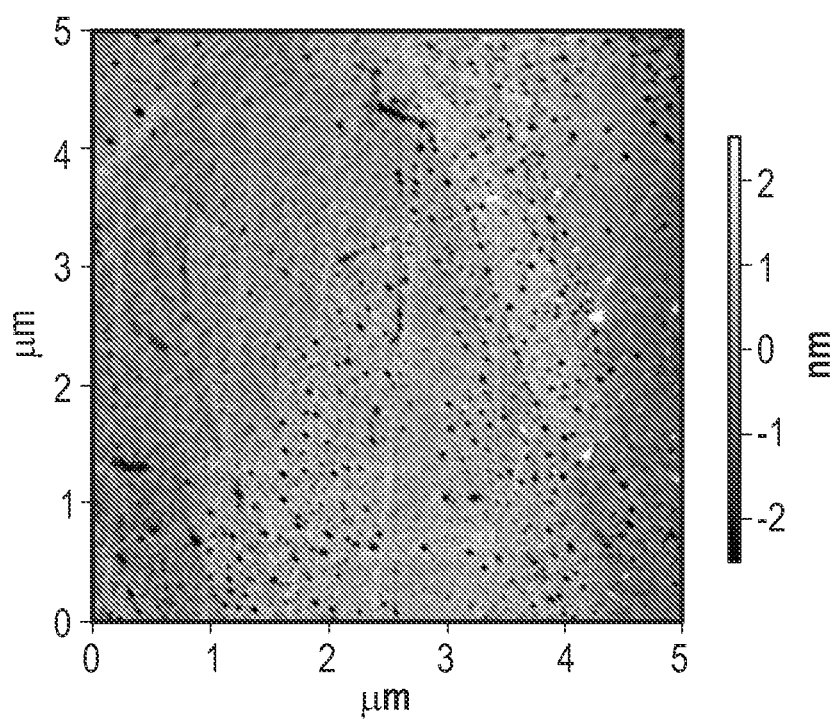
Figure 19:
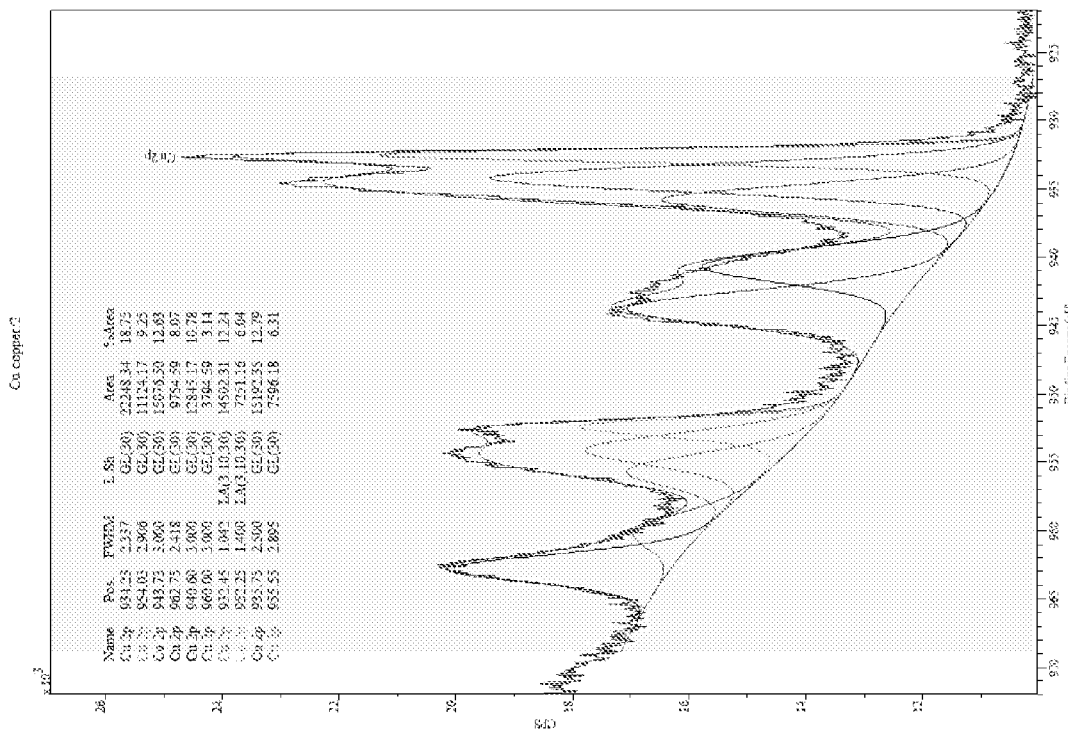
FIG. 19 is an XPS of copper plate, high resolution Cu 2p.
Figure 18:
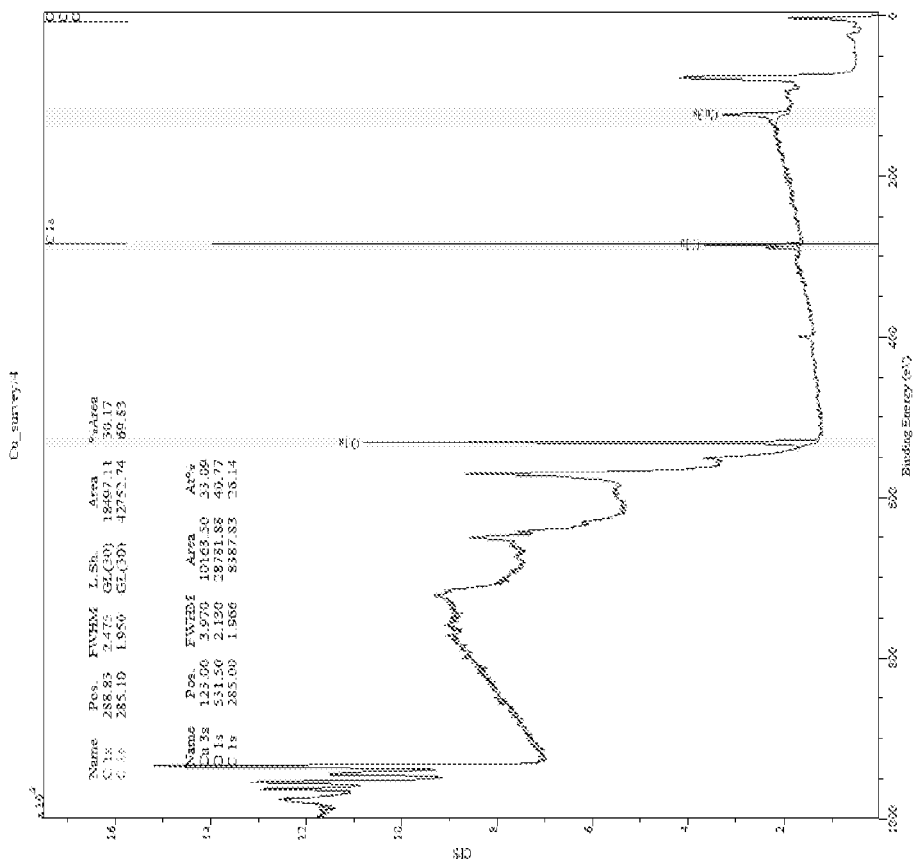
FIG. 18 is an XPS of copper plate survey.
Figure 21:
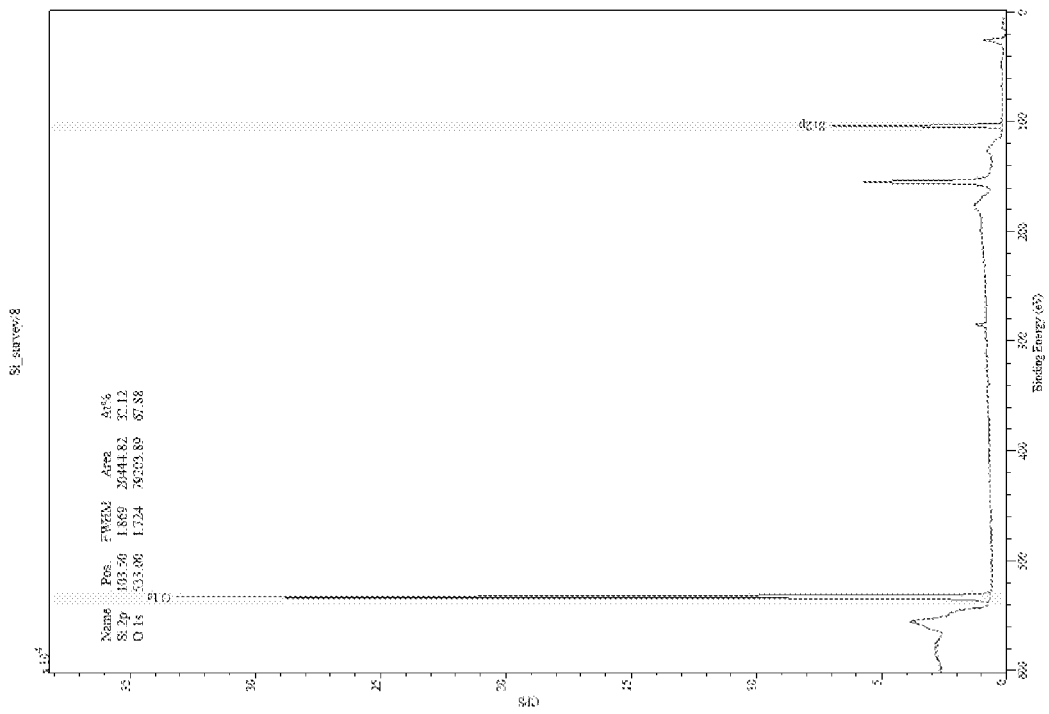
FIG. 21 is an XPS of silicon wafer survey.
Figure 20:
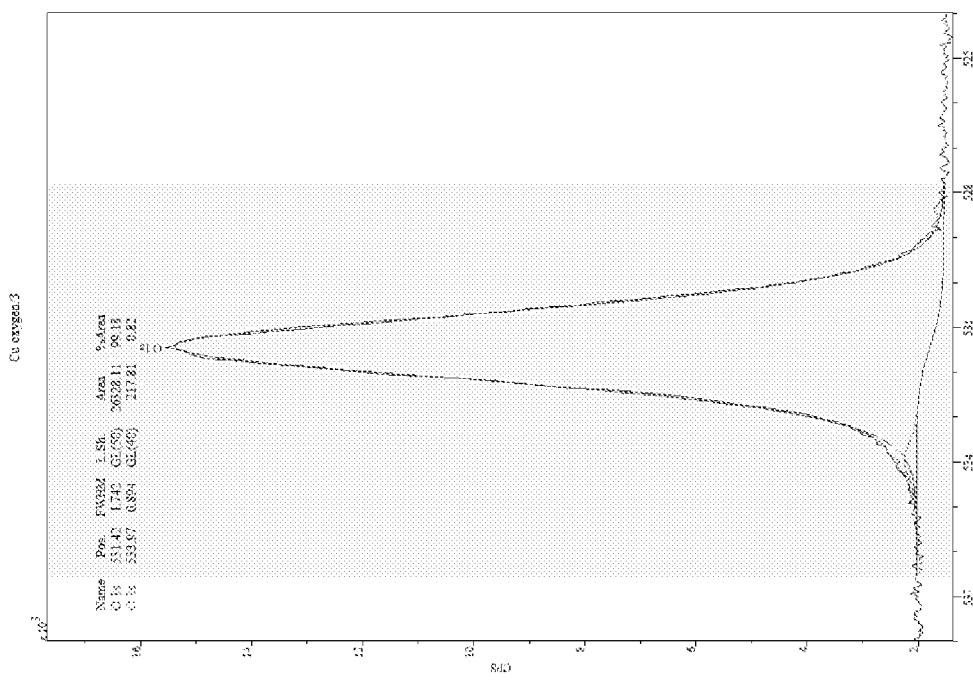
FIG. 20 is an XPS of copper plate, high resolution O1s.
Figure 23:
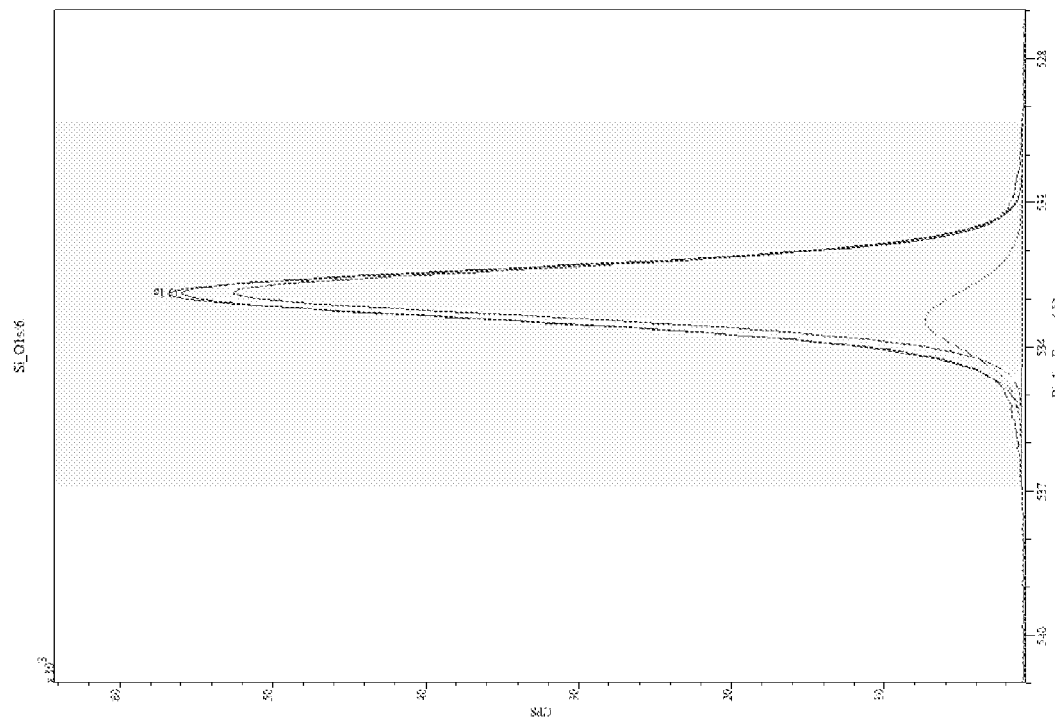
FIG. 23 is an XPS of silicon wafer, high resolution O 1s.
Figure 22:
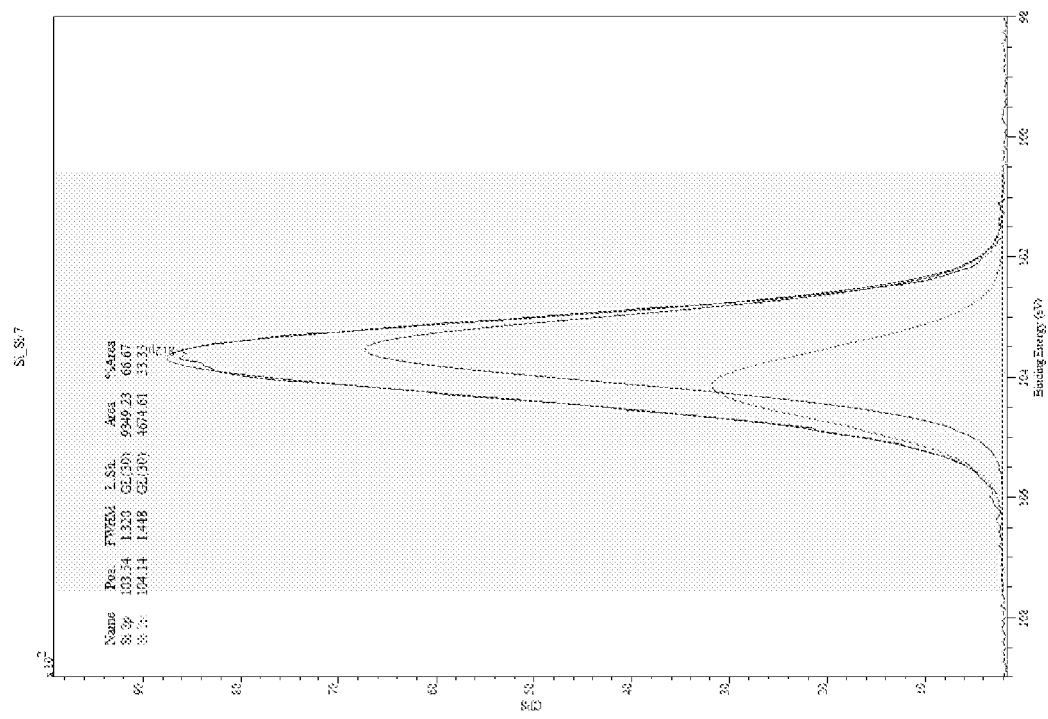
FIG. 22 is an XPS of silicon wafer, high resolution Si 2p.
Figures 24A, 24B, 24C, 24D, 24E, 24F:
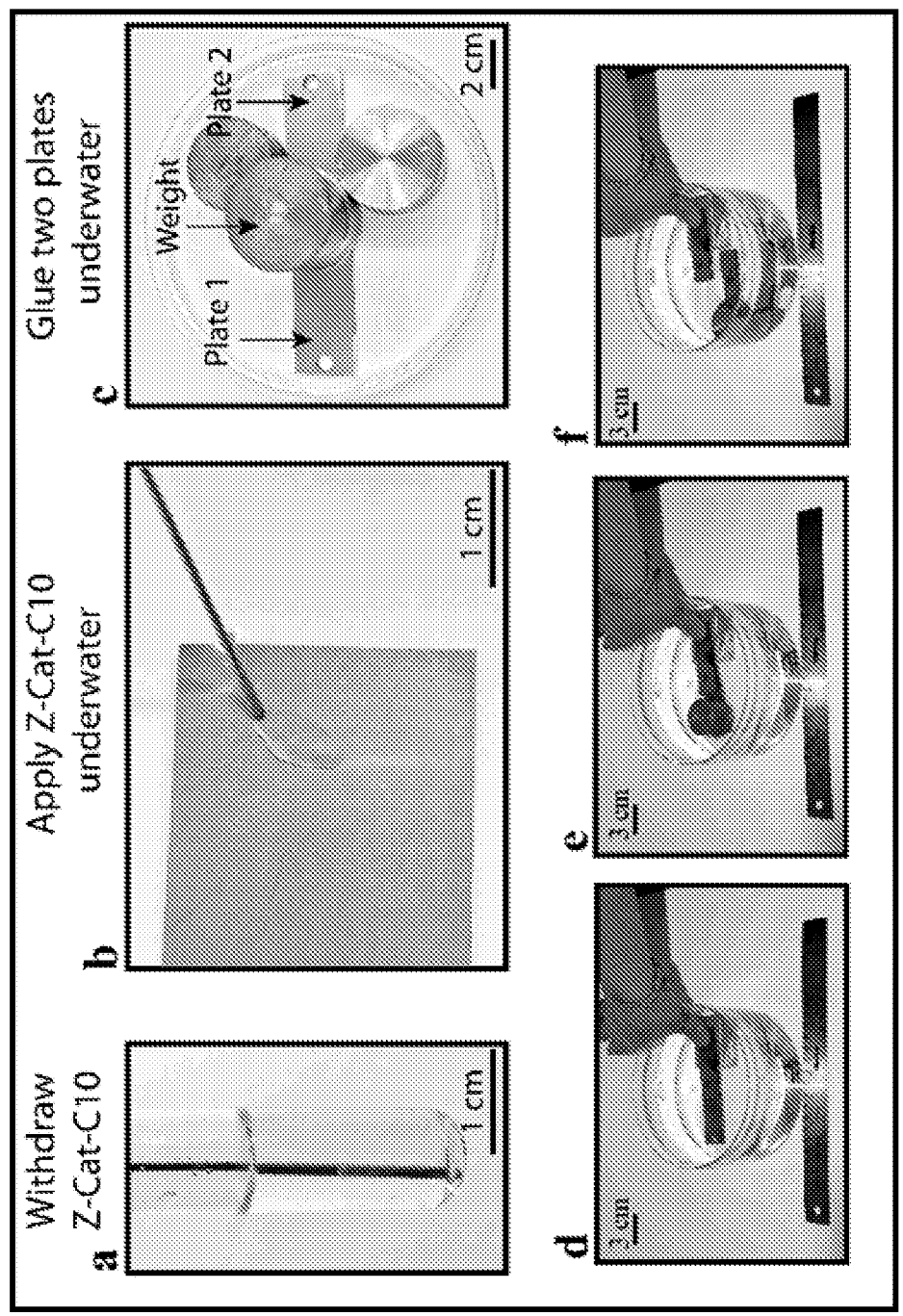
FIGS. 24A-24H show a macro-scale lab adhesion test.
Figure 24G:
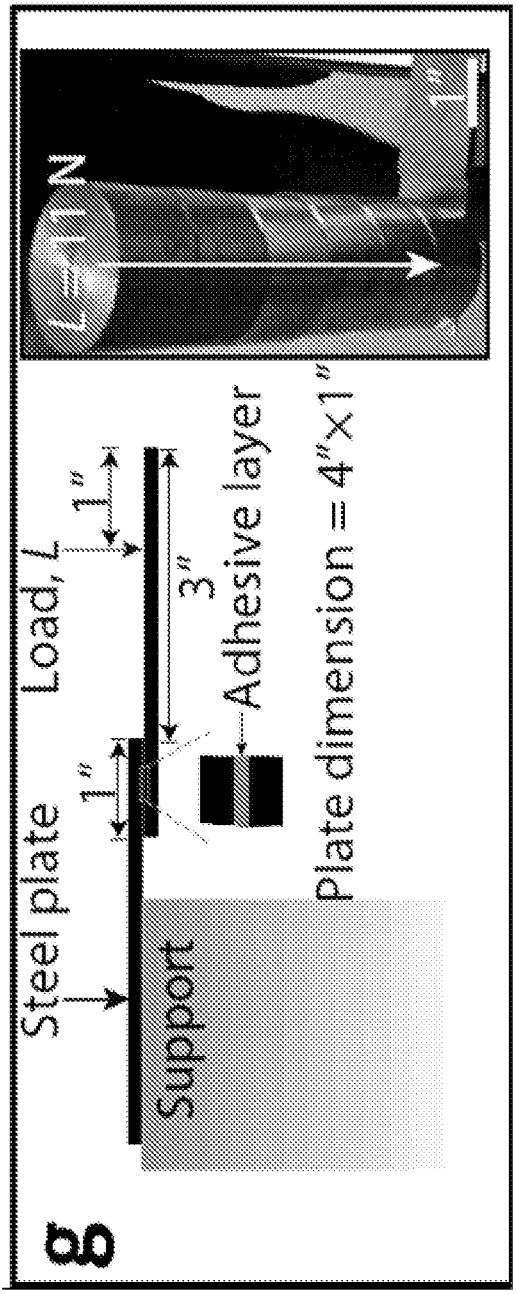
Figure 24H:
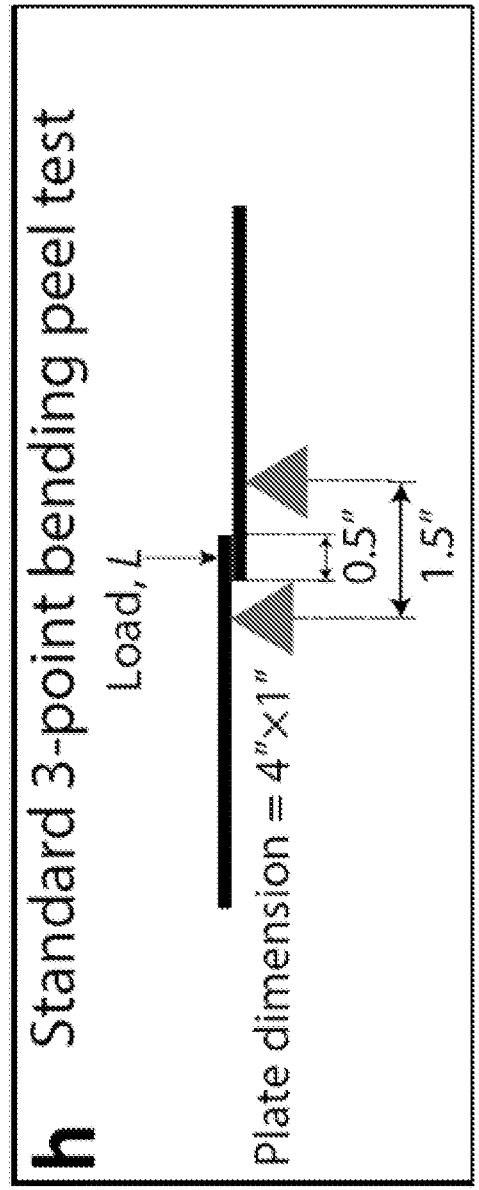

Not limited to mica, 5 mM Z-Cat-C10 formed thin, molecularly smooth (~2 nm) films on silicon wafers (FIGS. 14A-14B) and copper (FIG. 15A-15B). The wet- and dry-adhesion of these films (FIGS. 5, 6 and 16, 17) on silicon wafers ($SiO_2$, RMS surface roughness <1 nm) and copper ($CuO_2/Cu(OH)_2$, RMS surface roughness ~2 nm) surfaces, was measured using silica ($SiO_2$) probes in the AFM (FIG. 13E). FIG. 13E shows adhesion Energey ($W_a$=$F_a$/1.5πR) of the nano-glue from Z-Cat-C10 measured on silicon wafer and copper plate, where adhesion force, $F_a$, (minimum of the potential well of the F vs. D curves obtained from AFM measurements) and R (radius of silicon dioxide probe). FIG. 6 shows SEM image of underwater glued nano silica beads (φ=100 nm) on silicon wafer by the nano-glue from 5 mM Z-Cat-C10. The error bars indicate standard deviations (n=5, independent experiments). The surfaces were prepared by spreading 5 mM Z-Cat-C10 over the surfaces, followed by thorough rinsing and adhesive testing. The wet work of adhesion ($W_{ad}$=$F_{ad}$ 1.5$^{-1}$ $π^{-1}$ $R^{-1}$), ~7.7 mJ $m^{-2}$ for the $SiO_2$ and $SiO_2$ interface, resembled $W_{ad}$~7.0 mJ $m^{-2}$ reported for catechol-functionalized polysiloxanes and $SiO_2$ interface, and ~0.1 mJ $m^{-2}$ for adhesion between the $CuO_2/Cu(OH)_2$ and $SiO_2$ surfaces. After air-drying the surfaces for ~5 min, the adhesion ($W_{ad}$) between $CuO_2/Cu(OH)_2$ and $SiO_2$ surfaces increased significantly to ~4 mJ $m^{-2}$ and to ~175 mJ $m^{-2}$ between $SiO_2$ and $SiO_2$ surfaces, which, in the latter case, is 50-fold greater than the $W_{ad}$ (~3.5 mJ $m^{-2}$) for catecholic polysiloxane adhesion to $SiO_2$ as calculated from the $F_{ad}$ (83 nN) measured using silica probes (φ=5 m) in AFM. Comparatively weaker adhesion to the copper plate is tentatively attributed to higher RMS and hydroxides on its surface measured by AFM and X-ray photoelectron spectroscopy (XPS), respectively (FIGS. 18-23). A suspension of silica beads (φ=100 nm) in DI water was prepared, and spread over a silicon wafer previously coated with 5 mM Z-Cat-C10. The silica beads remained glued to the film, even after rinsing with pulsed jets of running tap water (0.24 MPa).

Discussion

Catechol-functionalized zwitterionic surfactants are clearly more than detergents, and show the following favorable attributes as adhesive primers: (1) they aggregate in water as dense fluidic coacervates at concentrations above the CAC; (2) the coacervates spread uniformly over surfaces; (3) in confinement in the SFA, the coacervates rearrange as paired bilayers (~2.5 nm thickness) with the catecholic head groups facing the mica surface on one side and bulk solvent on the other; (4) the coacervate environment stabilizes catechols by ~+0.1 V against oxidation, and (5) following periodate treatment, adhesion of thin films of Z-Cat-$C_{10}$ on mica approaches $W_{ad}$~50 mJ $m^{-2}$—a new high for catechol-mediated adhesion.

Surprisingly and unexpectedly, the results reveal Z-Cat-C10 adhesion on mica to be 2-3-fold greater than mfp-5 (14 mJ $m^{-2}$) and the new mfp-amyloid recombinant fusion protein (21 mJ $m^{-2}$). Results obtained before and after periodate oxidation of Z-Cat-C10 suggest the following failure modes: before periodate, the work of adhesion averaged ~20 mJ m$^{-2}$. Because the hydrophobic bilayer and catechol-to-mica contacts are strong, the weaker inter-catechol H-bonding between the two bilayers (FIG. 13C) unzips during separation. After covalent aryl-aryl coupling with periodate, the adhesion failed at ~50 mJ m$^{-2}$, which is commensurate with the energy required to separate the two halves of a lipid bilayer leaflet, thus suggesting that adhesion to the mica surface is stronger than ~50 mJ m$^{-2}$.

Because the SFA-based work of adhesion (units J m$^{-2}$) is difficult to relate to reported bulk adhesion properties (J m$^3$), it was compared to peel fracture energy. With native mussel plaques deposited onto silica, peel fracture energy[1] was 100 J m$^{-2}$, which resembles the energy of high performance adhesive PS/PVP blends on silicon. The magnitude of disparity between the work of adhesion and peel fracture energy is striking but plausible. In tests of symmetrically deposited Z-Cat-C10, the paired bilayer structure (FIG. 13C) offers little opportunity for energy dissipation via sacrificial bonds and hidden lengths, whereas in the plaque, molecular scaffolds of different length scales exist. The relationships between the adhesive surface primers and their overlying molecular scaffolds remain to be explored. Although the catechol-functionalized zwitterionic surfactants were designed to be adhesive primers, some bulk tests in lap shear or a 3-point bending peel mode on stainless steel (SS304) (FIGS. 24A-24H) showed unexpected gap-filling capabilities and strengths of ~MPa or ~20 N cm$^{-1}$, suggesting that stacked bilayers as shown in FIG. 13C may not be limited to 2 layers.

For Concentrations below CAC: For the macro-scale test, Z-Cat-C10 was dissolved at 0.1 mg ml$^{-1}$ concentration in DI water (clear sample), then Z-Cat-C10 coacervate (phase-separated liquid) was injected into artificial sea water, periodate (Sigma Aldrich) solution (1M), DI for CV and UV-Vis. In CV for the sample in DI water, its oxidation peak at 530 mV and a reduction peak at 316 mV appeared indicating catechol functionality. Moreover, an absorbance peak at 280 nm in the UV-Vis spectrum supported the presence of the catecholic structure. In artificial sea water, alkaline pH and saturated oxygen conditions are an appropriate environment for catechol oxidation.

Figure 25A:
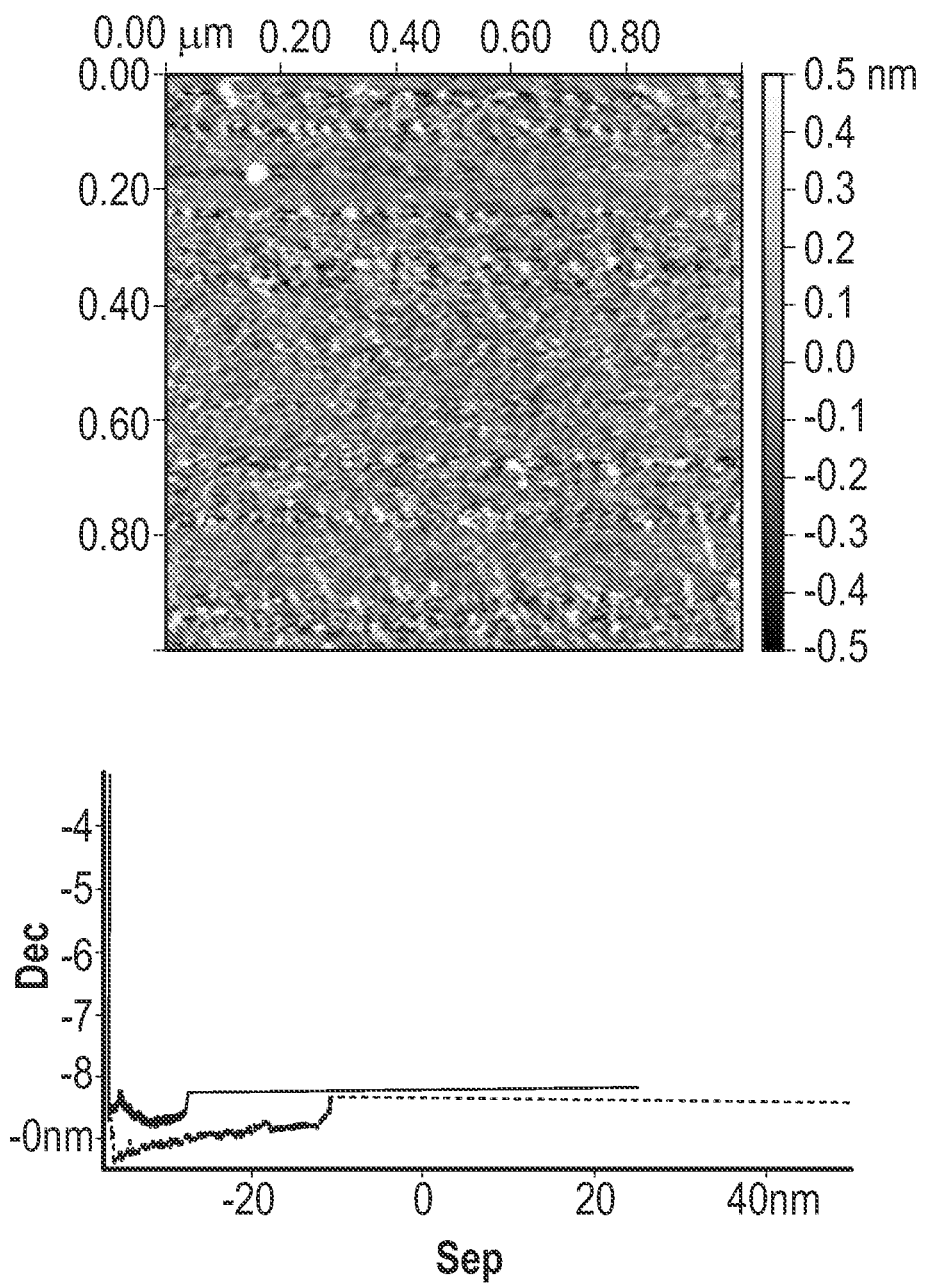
FIGS. 25A-25C are AFM images of Z-Cat-C10 at different concentration.
Figure 25B:
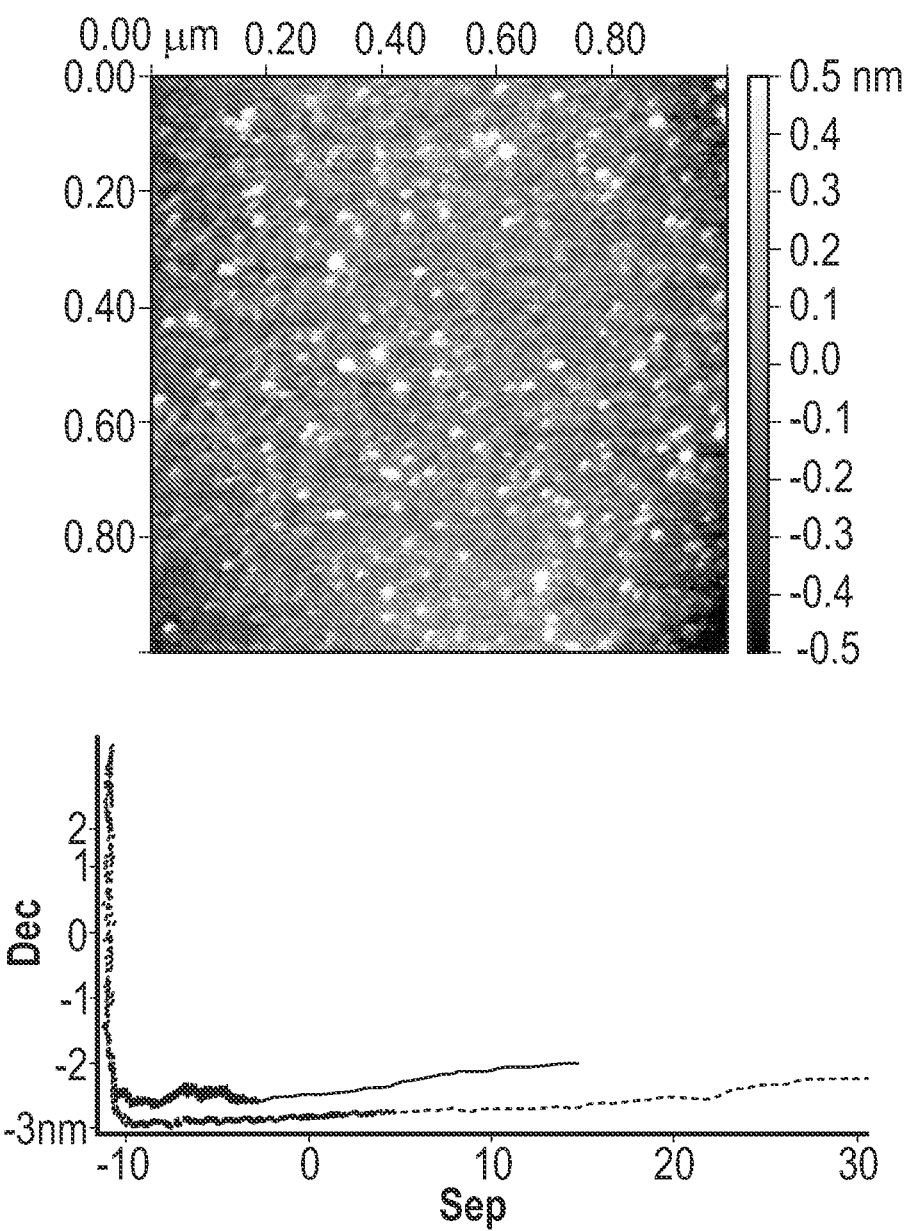
Figure 25C:
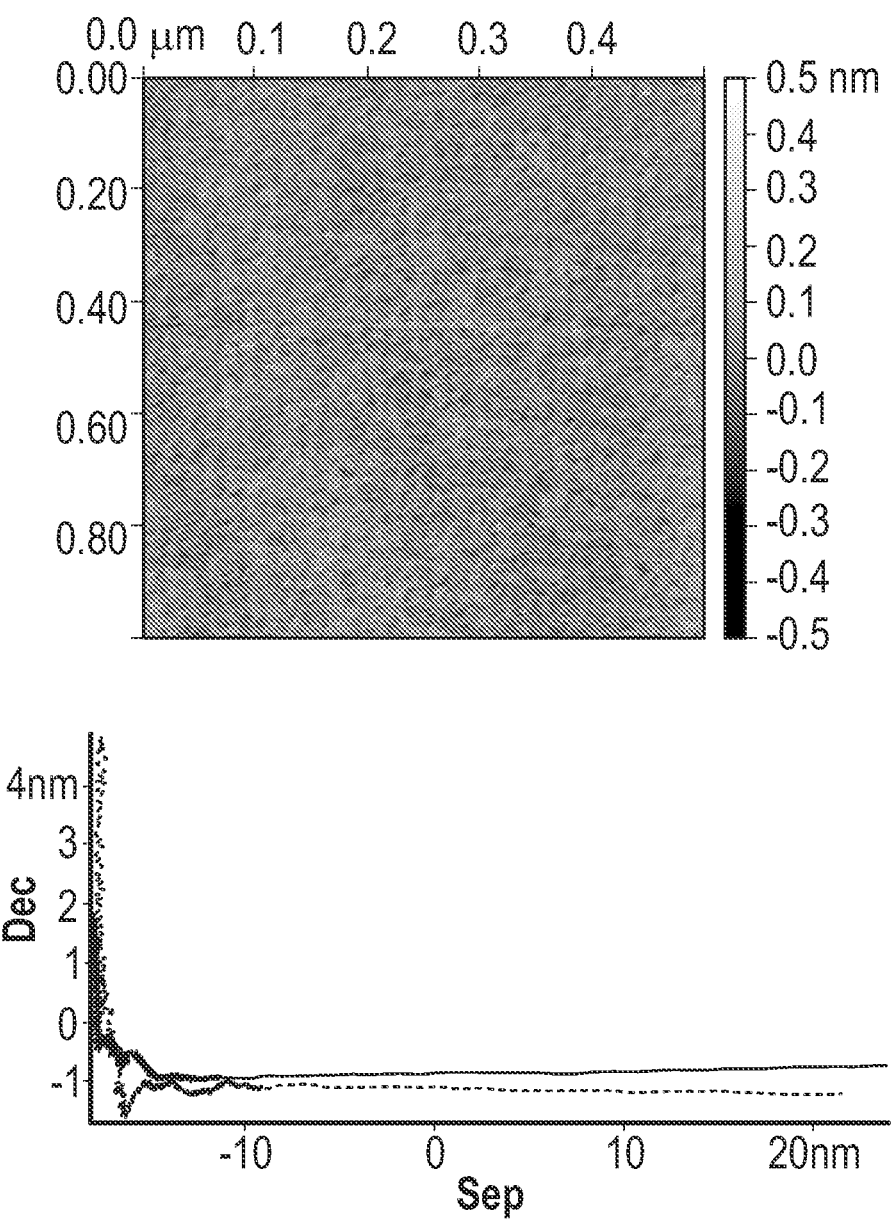

AFM images of Z-Cat-C10 at different concentrations: 0.001 mM (below its CAC), 0.05 mM (above CAC) and 5 mM, are shown in FIGS. 25A-25C. The 5 mM concentration shows molecularly smooth surface and its chemical configuration is suggested in FIG. 13D.

The cartoon of its chemical configuration at low concentrations is suggested in FIG. 26. As shown, two layers of mica are coated with Z-Cat-10. The catechol end of the Z-Cat-10 self-assembled onto the mica. This self-assembly creates secondary layers with the C10 end of Z-Cat-C10 on each of the mica. The two secondary layers of the two mica interacts and form hydrophobic interaction.

Figure 13D:
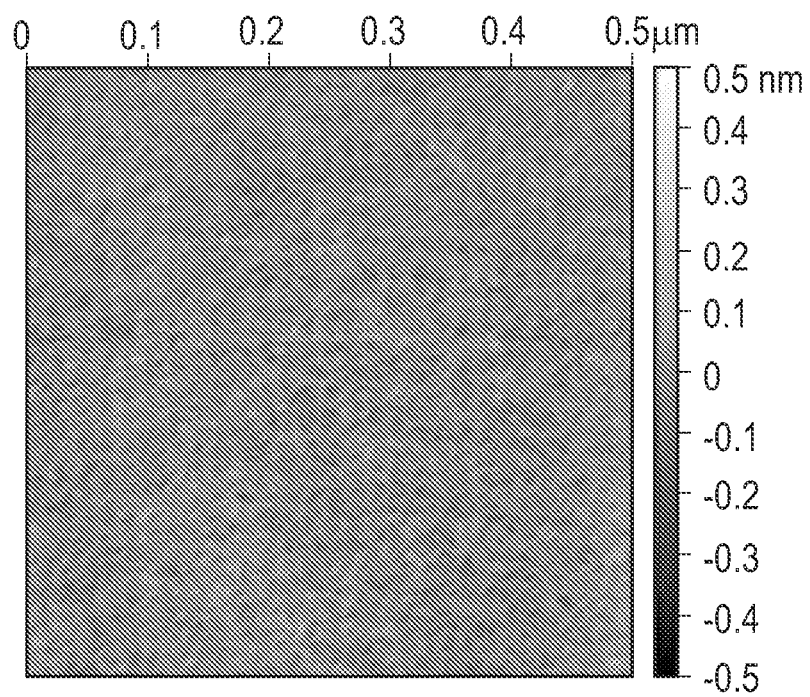

Coacervates formed from 5 mM Z-Cat-C10 effectively coat mica surfaces as atomically smooth bilayers (the schematic of the bilayer shown in FIGS. 13C, and the surface image shown in FIG. 13D). The catecholic functionalities interact with mica by H-bonding and, between two bilayers, by intercatecholic H-bonding and aryl coupling following oxidative crosslinking (FIGS. 13A-13C). In the absence of coacervation, at 0.001 mM Z-Cat-C10, which is below the CAC at 0.05 mM solution, Z-Cat-C10 forms monolayers that exhibit only weak adhesion and no cross-linking (FIGS. 25A-25C and 26).

Figures 27A, 27B:
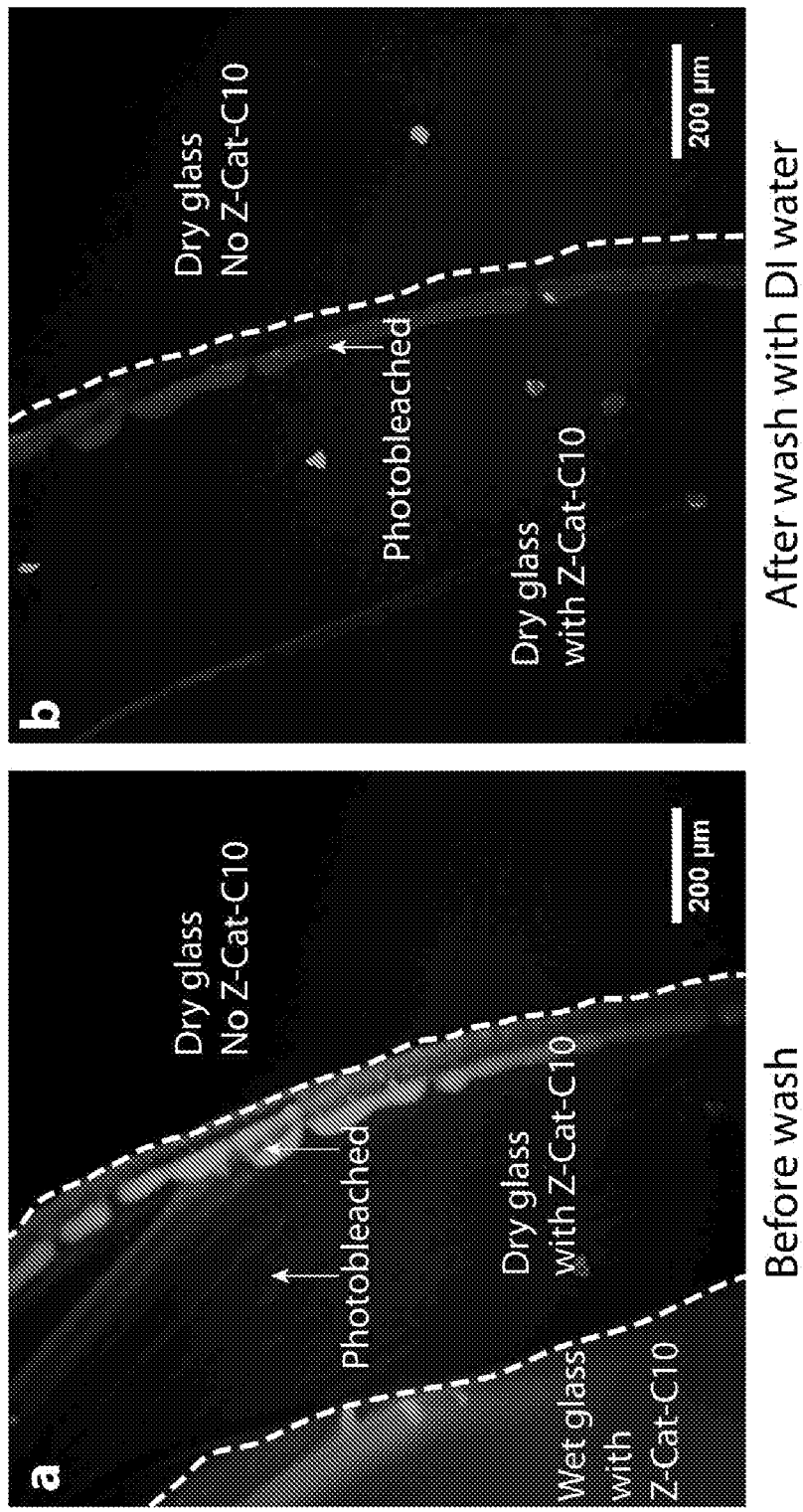
FIGS. 27A-27B are a fluorescence imaging of a silica surface coated with a 5 mM solution of Z-Cat-C10 (in DI water) before and after rinsing the surface with DI water.

Quartz Crystal Microbalance (QCM): Adsorption of the molecules on different surfaces such as silica, SiO$_2$, (FIGS. 7A-7E) and titania, TiO$_2$, (FIGS. 8A-8E) was also explored by the quartz crystal microbalance (QCM) and confocal fluorescence microscopy after rhodamine staining (FIG. 27A-27B). Quartz crystal microbalance with dissipation (QCM-D): A "static cell" (often called "Open Model") QCM-D (Q-Sense, Biolin Scientific) was employed to qualitatively show the adsorption of the zwitterionic molecules onto mineral and metal oxide surfaces. 50 µl of 5 mM zwitterionic solution was deposited onto TiO$_2$ and SiO$_2$ surface, respectively, in DI H$_2$O (100 µl) using a static cell via two-step adsorption. In this two-step adsorption, all the zwitterionic molecules adsorb onto both TiO$_2$ and SiO$_2$ (using quartz sensors with the corresponding top-layer. See FIGS. 7A-E and 8A-E). Frequency and dissipation change upon addition of 5 mM solution of each zwitterionic molecule to TiO$_2$ and SiO$_2$ surface, respectively (See FIGS. 7A-E and 8A-E). The results are in contrast to all the studied mussel foot proteins, which adsorb onto TiO$_2$ but not to SiO$_2$ according to previous QCM-D experiments (less than 10 ng cm$^{-2}$). The results emphasize qualitatively that all the zwitterionic molecules adsorb onto both TiO$_2$ and SiO$_2$, which is in agreement with the SFA and AFM results. However, a quantitative discussion regarding the adsorbed mass (frequency shift) and the viscoelastic properties (dissipation) of the adsorbed "soft" layers is challenging because the mass of the zwitterionic molecules cannot be separated from the mass of adsorbed water.

Z-Ben-C8 in the SFA: The catechol-containing homologs behaved differently from the noncatecholic control (Z-Ben-C8). Z-Ben-C8 shows regular bilayer repulsion and jump-in patterns of a general surfactant when two surfaces were approached (see approach and separation patterns in FIG. 9), whereas catechol-containing molecules did not show a significant repulsion or no repulsion at all (see approach and separation patterns of the molecules in FIG. 10B). Z-Ben-C8 had a CAC similar to that of Z-Cat-Cat (and $W_c$=8.1±1.3 mJ m$^{-2}$); however, the latter never formed more than a monolayer on mica.

Figure 30:
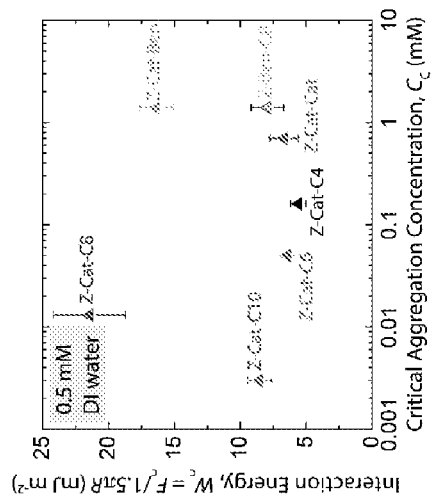
FIG. 30 is a plot of the adhesive interaction energy vs. the CAC.
Figure 29:
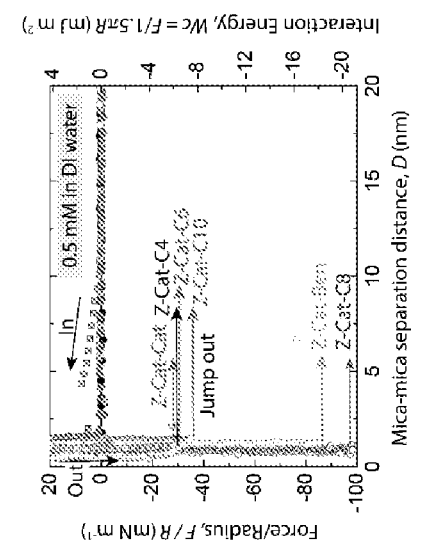
FIG. 29 is a graph of representative force vs. distance plots between mica surfaces of 0.5 mM aqueous dispersions of Z-Cat-C10, -C8, -C6, -C4, and -Cat-Cat.
Figure 28:
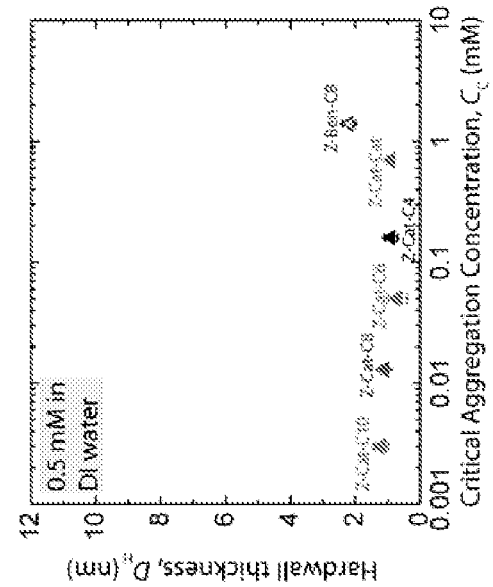
FIG. 28 is a plot of the hardwall thickness in 0.5 mM concentration vs. CAC of Z-Cat-C10, -C8, -C6, -C4, and -Cat-Cat.

SFA measurements were performed on molecules deposited at 0.5 mM concentration in DI water to test the effect of concentration on the interfacial cohesive forces between the thin films. Z-Ben-C8 (no catechol) solution (below its CAC) formed bilayer (2 nm) whereas the catechol-carrying small molecules formed monolayer (1 nm) (FIG. 28). The representative force vs. distance plots between mica surfaces of 0.5 mM aqueous dispersions of Z-Cat-C10, -C8, -C6, -C4, and -Cat-Cat (FIG. 29). Notice that error bars indicate standard deviation (n=5 independent experiment). The cohesive interaction energy, $W_c$, of all molecules did not change for contact times, $t_c$ from 2 min to 12 h. Filled and open circles represent the forces measured during approach and separation of the surfaces respectively. The interaction energy of Z-Cat-C8 (~22 mJ m$^{-2}$) was very high at 0.5 mM concentration (FIG. 30). Notice that error bars indicate standard deviation (n=5 independent experiment).

The hard-wall thickness (approximately, the sum of the hydrodynamic diameters of the films on the upper and lower mica surfaces in SFA) of each homolog was also measured as the limiting distance between the mica surfaces during the approach run in the SFA. SFA experiments were performed for Z-Cat-C8 and Z-Cat-C10 at C=0.001 and 0.005 mM, respectively, to test the effect of deposition concentrations below the critical aggregation concentration (CAC) on the measured interaction (adhesive and cohesive) forces. It should be noted that in SFA measurements, $W_{ad}$ or $W_c$→−$E_{ad}$ or −$E_c$ respectively, where E is the energy of interaction between the surfaces. The reason for following this convention is because the measured adhesive or cohesive forces between the surfaces are attractive. The interaction between two asymmetric surfaces is referred to as adhesion and the interaction between two symmetric surfaces is referred to as cohesion.

Atomic Force Microscopy (AFM) scans of a mica surface adsorbed with the small molecules from a solution in DI water of varying concentrations (5 mM). Z-Cat-C10 forms a defect free atomically smooth bilayer on mica. On the other hand, Z-Cat-C4, Z-Cat-C8, Z-Cat-10 and Z-Cat-Cat form small aggregates on the surface, and Z-Ben-C8 formed thick multilayer.

AFM force runs were measured with and without Z-Cat-C10 on silicon wafer and copper plate, respectively, vs. silicon dioxide probe. Underwater force run was conducted for the surface prepared subsequently after spreading the 5 mM Z-Cat-C10, waiting for 2 min, rinsing thoroughly with degassed DI water thoroughly for 3 times. Dry force run was performed after ~5 min dry of the surface prepared as for the underwater force run. Because adhesive force increased significantly after the glue layer dried for ~5 min using a gas duster gently, the $\phi$=10 μm probe stuck to $CuO_2/Cu(OH)_2$ surface, and the both $\phi$=10 and 5 μm probe stuck to $SiO_2$ surface. Cantilever spring constant (K) for #=10 μm silica tip on silicon wafer and copper plate with Z-Cat-C10, was 0.1 N m$^{-1}$.

Adhesion force, $F_a$) measured with $\phi$=10 μm probe was ~2 nN at $S_{iO2}$ and $C_{uO2}/Cu(O_H)_2$ interface and ~167 nN at $S_{iO2}$ and $S_{iO2}$ interface, respectively. The underwater adhesive force was measured with $\phi$=10 μm probe at $C_{uO2}/Cu(O_H)_2$ and $S_{iO2}$ interface; $_{Fa}$~2 nN, and 1 μm probe at $S_{iO2}$ and $S_{iO2}$ interface; $_{Fa}$~170 nN, respectively. Dry adhesive force increased significantly, thus measured with $\phi$=5 μm probe at $C_{uO2}/Cu(O_H)_2$ and $S_{iO2}$ interface; $_{Fa}$~260 nN, and 1 μm probe at $S_{iO2}$ and $S_{iO2}$ interface; $_{Fa}$~150 nN, respectively.

The measured adhesion, Fa, force (minimum of the potential well of the F vs. D curves obtained from AFM measurements) is related to the adhesion energy per unit area by Wa=Fa/2πR for rigid surfaces with weak adhesive interactions, and by Wa=Fa/1.5πR (used in this study) for soft deformable surfaces with strong adhesion or cohesion. Since copper surface (RMS~2 nm) is rougher than silicon wafer (RMS<1 nm), the Wa on copper surface was comparatively weaker than the $W_a$ of silicon wafer. Hydroxide/oxide on copper surface also weakens the adhesion to copper plate compared to just oxide on silicon wafer (see FIGS. 18-23). This strong and defectless nano-glue layer hold particular promise for electronic devices to obviate the interfacial failure causes fatal multifunction.

Adhesion test: In the context of adhesion, adhesion energies and adhesion forces (or strengths) are very different; the first is unchangeable for a given system, whereas the latter can vary greatly just by slightly changing test parameters. The two are related by $W_{ad}=\int \vec{F}_{ad}d\vec{x}$, where $W_{ad}$ is the adhesion energy, $F_{ad}$ is the force, and x is the displacement of the two surfaces as they are separated. Note that $F_{ad}$ and x are vectors, i.e. the angle at which the two surfaces are separated also affects the force for separation. As a result, different paths for surfaces to separate yield very different adhesion forces, $F_{ad}$, but involve the same net changes in energy, i.e., adhesion energies, $W_{ad}$. Therefore, adhesion forces, $F_{ad}$, measured in different configurations, e.g., the lap joint rupture (force), three point bending peel strength (force per width), and shear strength (force per area), and/or measured on different surfaces, e.g., type of materials and surface roughness (determining actual contact area), are not interchangeable nor comparable to one another. For example, $F_{ad}$ of peeling can be orders of magnitude less than $F_{ad}$ of planner separation, whereas $W_{ad}$ in both cases is same. Therefore, rather than comparing $F_{ad}$ measured and reported in different configurations and/or on different surfaces, $W_{ad}$ reported in this study was compared to previously published $W_{ad}$ using the similar techniques, i.e., SFA and AFM, based on Johnson-Kendall-Roberts (JKR) theory between atomically smooth mica surfaces or between silica surfaces with RMS roughness <1 nm.

The lap joint bending peel test showed that Z-Cat-C10 prevented the rupture of the bonding between the steel plates for a load up to 0.3 kg underwater and 1.1 kg under dry ambient conditions when the joint prepared in artificial sea water and aqueous periodate solution, respectively. As a control, the joint made from 3M double sided Scotch® tape under dry ambient conditions held only up to 0.3 kg under dry ambient conditions.

In summary, it has been shown that a synthetic low molecular weight catecholic zwitterionic surfactant mimics the strong adhesive priming and self-coacervating properties of mfps. The high wet-cohesion (or -adhesion) energies ranged from ~20 to ~50 mJ m$^{-2}$ for uncross-linked and cross-linked films, respectively. This example underscores the importance of catechols and of maintaining a balance between hydrophobic and electrostatic interactions for tuning or optimizing both coacervation and adhesion. These catecholic zwitterions are adaptable as coatings or adhesive primers for diverse surfaces and, given their uniformly thin (<4 nm) and strong glue-layers, hold particular promise as a new tool for nanofabrication.

Methods

Synthesis of the Molecules

All synthetic manipulations were carried out under an atmosphere of Argon unless otherwise noted, and no attempt was made to optimize reaction yields. TLC plates (UV 254 indicator, glass backed, thickness 200 mm) and silica gel (standard grade, 230-400 mesh) were purchased from Merck. Bonded C2 reverse phase silica was prepared as previously described or purchased from Analtech (Catalog number 08010). Normal phase flash chromatography was performed manually in glass columns. Reverse phase flash chromatography was performed with bonded C2 reverse phase silica hand packed in plastic columns and performed on a Biotage SP4 chromatography system. Diethyl ether, THF, ethyl acetate, and hexanes were purchased from Fisher Scientific. Diethyl ether and THF was taken from Innovative Technologies Solvent Purification System (SPS) and used immediately. Dimethylformamide (DMF) and Acetonitrile (MeCN) were purchased pre-dried from Spectrum and stored over activated 4 Å or 3 Å molecular sieves respectively after opening. Et$_3$N was distilled and stored on activated 4 Å molecular sieves under argon. NMR solvents were purchased from Cambridge Isotopes Laboratories. NMR spectra were recorded at 23° C. on Varian Unity INOVA (500 and/or 600 MHz) spectrometers. NMR spectra were processed using the MestreNova software package and processed with automatic phase correction, and automatic baseline correction using Bernstein Polynomial fitting. Reported chemical shifts are referenced to residual solvent peaks. Reported chemical shifts for multiplets are reported corresponding to the most downfield peak of the multiplet, where s=singlet, d=doublet, t=triplet, q=quartet, p=pentet, sex=sextet, sept=septet, m=multiplet, br=broad. IR spectra were acquired on a FTIR Perkin Elmer Spectrum Two:

UATR Two spectrometer using 1 cm$^{-1}$ resolution. High resolution mass analyses were obtained using a 5975C Mass Selective Detector, coupled with a 7890A Gas Chromatograph (Agilent Technologies) as capillary column a HP-5MS cross-linked 5% phenylmethyl-polysiloxanediphenyl column (30 m×0.250 mm, 0.25 micron, Agilent Technologies) was employed. Helium was used as carrier gas at a constant flow of 1 ml min$^{-1}$.

Synthesis of Small-Molecule Zwitteronic Adhesives:

formed with the largest possible football shaped stir bar that can fit into the flask. If stirring is observed to cease during the procedure due to caking of the base, one septa can be briefly removed while under positive Argon flow, and the solidified mass of K$_2$CO$_3$ at the bottom of the flask broken up gently with a dry metal spatula until stirring resumes, whereupon a fresh septa is added to the flask and the vessel stirred until completion on the reaction.

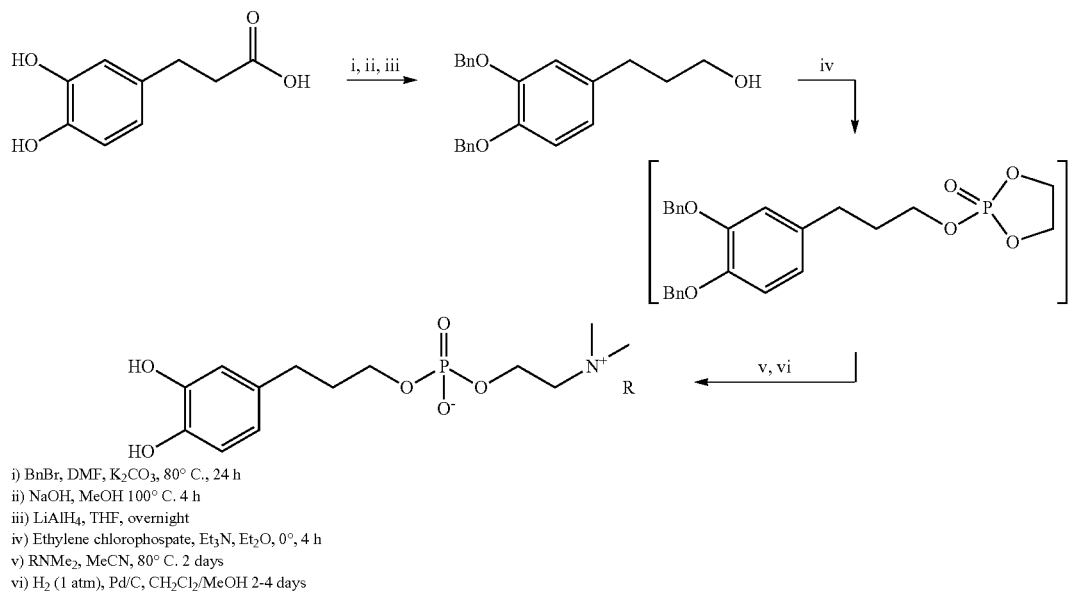

i) BnBr, DMF, K$_2$CO$_3$, 80° C., 24 h
ii) NaOH, MeOH 100° C. 4 h
iii) LiAlH$_4$, THF, overnight
iv) Ethylene chlorophospate, Et$_3$N, Et$_2$O, 0°, 4 h
v) RNMe$_2$, MeCN, 80° C. 2 days
vi) H$_2$ (1 atm), Pd/C, CH$_2$Cl$_2$/MeOH 2-4 days Synthesis of Starting Materials Benzyl 3-(3,4-bis(benzyloxy)phenyl)propanoate (2)

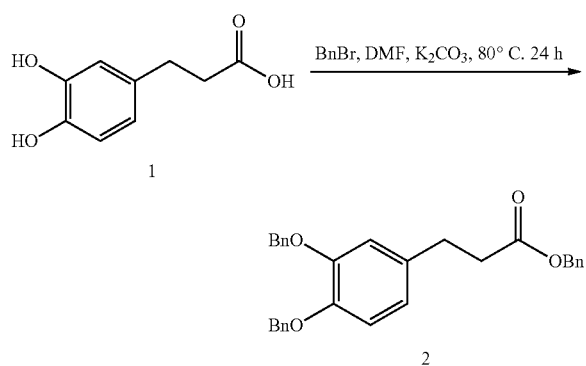

Benzyl 3-(3,4-bis(benzyloxy)phenyl)propanoate 2 was synthesized from 3-(3,4-dihydroxyphenyl)propanoic acid 1, purchased from Alfa Aesar, according to a previously described procedure with slight modifications. As the carboxylic acid contains potentially air sensitive catechol moieties, after opening, the bottle of carboxylic acid was purged with argon, and the cap tightly wrapped with parafilm until subsequent use. While the previously published procedure was observed to work well on scales <5 grams, adequate stirring became problematic on the scales required for this work, and it is recommended that the procedure be per- A flame dried 500 ml 3-necked round bottom flask was fitted with rubber septa and a large football shaped stir-bar and allowed to cool to ambient temperature under positive argon flow. Subsequently, 20 grams (1 equiv., 109.8 mmol) of 3-(3,4-dihydroxyphenyl)propanoic acid was added, followed by 200 ml of anhydrous DMF with stirring. Once dissolved, 90.9 grams of anhydrous K$_2$CO$_3$ (6 equiv., 658.7 mmol) was added with stirring. Then, 58.678 ml of fresh benzyl bromide (4.5 equiv., 494 mmol) was added via syringe. The solution was placed in an oil bath set to 80° C. and stirred for 1 day at this temperature. After this time, no further reaction was observed by TLC, which also indicated the reaction was incomplete, and contained in addition to the desired product, a mixture of mono- and di-benzylated products. The reaction vessel was allowed to cool to room temperature. The reaction mixture was then poured through a large fritted glass funnel into a 2 L round bottom flask to remove solids, and the reaction vessel was rinsed 3×300 ml EtOAc through the frit. The solvent was then removed under reduced pressure with a rotary evaporator. To assist subsequent extraction, residual DMF was removed by 4 cycles of evaporation with toluene (500 ml). The crude residue was then redissolved in 1.5 L of Et$_2$O and washed 5×100 ml ice cold water, 1×500 ml Brine, dried over Na$_2$SO$_4$, and concentrated under reduced pressure. The crude residue was then dry-loaded onto silica gel and purified by flash chromatography gradient elution 10-40% Et$_2$O/hexanes in a large (18 inch tall) glass column. Fractions containing the only desired product were identified by TLC at R$_f$=0.31 (20:80 Et$_2$O:Hexanes, Stain=UV/Seebach's stain), pooled, and concentrated under reduced pressure to yield 17.42 grams of desired product. Fractions containing the two regioisomeric dibenzylated products, in which the carboxylic acid and either the 3- or 4-hydroxyl was benzylated, were identified by TLC at $R_f$=0.15 and 0.19 (20:80 Et$_2$O: Hexanes Stain=UV/Seebach's stain), pooled, concentrated under reduced pressure, and then resubjected to the reaction conditions to give an additional 20.56 grams of product, bringing the total amount of product to 37.98 grams in 76% isolated yield. The material was quickly checked for purity by $^1$H-NMR and then carried on immediately to the next step. If the yield of the initial reaction is not deemed objectionable, after removal of solvent, rather than collecting partially benzylated material and resubjecting it to the reaction conditions, the product can be more rapidly purified by 2 successive filtrations over a 6-8 inch tall pad of basic Al$_2$O$_3$ (Acros, 50-200 μm) eluting with 20% Et$_2$O/Hexanes.
$^1$H NMR (500 MHz, CDCl$_3$) δ (ppm): 7.45-7.41 (m, 4H) 7.38-7.27 (m, 11H), 6.85 (d, J=8.5 Hz, 1H), 6.80 (d, J=2 Hz, 1H), 6.70 (dd, J=2, 8.5 Hz, 1H) 5.12 (s, 2H), 5.10 (s, 2H), 5.09 (s, 2H), 2.88 (t, J=7.5 Hz, 2H), 2.63 (t, J=7.5 Hz, 2H)

3-(3,4-bis(benzyloxy)phenyl)propanoic acid (3)

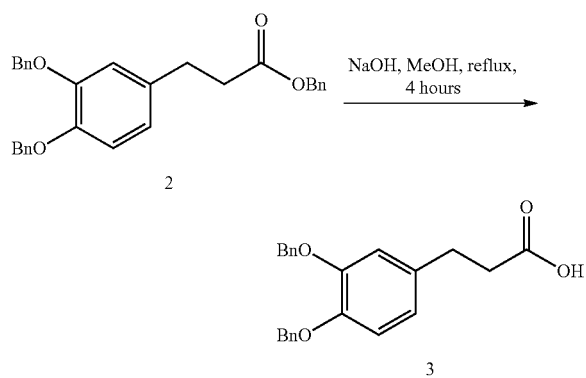

3-(3,4-bis(benzyloxy)phenyl)propanoic acid 3 was synthesized in 88% isolated yield by saponification of 2 as previously described. Spectral data matches that of previously reported.
$^1$H NMR (500 MHz, CDCl$_3$) δ (ppm): 9.19 (s, 1H), 7.46-7.41 (m, 4H), 7.38-7.33 (m, 4H), 7.32-7.27 (m, 2H), 6.87 (d, J=8.5 Hz, 1H), 6.80 (d, J=2 Hz, 1H), 6.73 (dd, J=2, 8 Hz, 1H), 5.14, (s, 2H), 5.13 (s, 2H), 2.87 (t, J=7.5 Hz, 2H), 2.62 (t, J=7.5 Hz)

3-(3,4-bis(benzyloxy)phenyl)propan-1-ol (4)

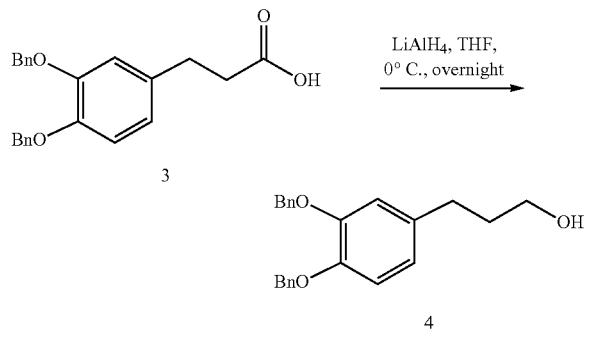

3-(3,4-bis(benzyloxy)phenyl)propan-1-ol 4 was synthesized from 3 in 89% isolated yield by reduction with LiAlH$_4$. 7.24 grams of acid 3 (20 mmol, 1 equiv.) were dissolved in 100 ml of anhydrous THF and cooled to 0° C. in an ice bath. 3.04 grams of LiAlH$_4$ (80 mmol, 4 equiv.) was then added carefully in 4 portions. The reaction was left to stir overnight under argon while warming to ambient temperature. The reaction was then quenched cautiously according to the Feiser workup, diluted with 100 ml of Et$_2$O and the aluminum solids were filtered off. The solution was then transferred to a separatory funnel, washed once with saturated NaHCO$_3$, dried over Na$_2$SO$_4$, filtered, and evaporated under reduced pressure to afford crude material. The crude material was subsequently purified on a pad of silica eluting with Et$_2$O. The compound was isolated as a clear viscous oil which gradually solidified over one week under high vacuum to a white wax. Over time, a slight pink coloration developed on the surface of the wax but this did not adversely purity as determined by $^1$H-NMR or negatively affect subsequent steps. Attempts to prepare this compound directly from the reduction of the corresponding benzyl ester led to unsatisfactory levels of purity, as benzyl alcohol co eluted with product in flash chromatography, while bulb to bulb distillation was inefficient and took extended times to reach a satisfactory level of purity. Spectral data matches that of previously reported.
$^1$H NMR (600 MHz, CDCl$_3$) δ (ppm): 7.47-7.42 (m, 4H), 7.40-7.33 (m, 4H), 7.32-7.28 (m, 2H), 6.87 (d, J=7.8 Hz, 1H), 6.79 (d, J=1.8 Hz, 1H), 6.71 (dd, J=1.5, 8.1 Hz, 1H), 5.15 (s, 2H), 5.13 (s, 2H), 3.62 (q, J=6 Hz, 2H), 2.62 (t, J=7.5 Hz, 2H), 1.84 (p, J=7.2 Hz, 2H), 1.18 (t, J=5.7 Hz, 1H).

Procedure for Preparation of Dimethylamide (5)

Dimethylamide 5 was conveniently prepared with 1-1' carbonyldiimidazole as peptide coupling reagent. A flame dried flask was fitted with a PTFE coated stir bar, rubber septa, and let cool to ambient temperature under positive argon flow. 1 equiv. of the corresponding carboxylic acid, 4 equiv. of anhydrous Et$_3$N, and anhydrous CH$_2$Cl$_2$ [0.5M] were added to the flask successively. The flask was cooled to 0° C. in an ice bath and stirred briefly, whereupon 1-1' carbonyldiimidazole (1.1 equiv.) was added portionwise, (gas evolution) the cooling bath was then removed, and the solution was stirred for an additional 30 minutes while warming to ambient temperature. Finally Dimethylamine as the hydrochloride salt, (2 equiv.), was added in one portion and the solution was stirred until TLC indicated completion. Upon completion the contents of the reaction vessel were transferred to a separatory funnel, diluted with CH$_2$Cl$_2$, and the organic layer was washed 2×1N HCl, 2×sat. NaHCO$_3$, and dried over Na$_2$SO$_4$. The organic layer was filtered, evaporated under reduced pressure, and the crude residue was filtered once over a pad of basic Al$_2$O$_3$ eluting with EtOAc, evaporated again, and purified by flash chromatography gradient elution with 50-100% EtOAc/Hexanes. Dimethylamide 5 was obtained in high purity as determined by TLC, and not fully characterized at this stage as it was carried immediately on to the next step. Yield was not optimized.

3-(3,4-bis(benzyloxy)phenyl)-N,N-dimethylpropanamide (5)

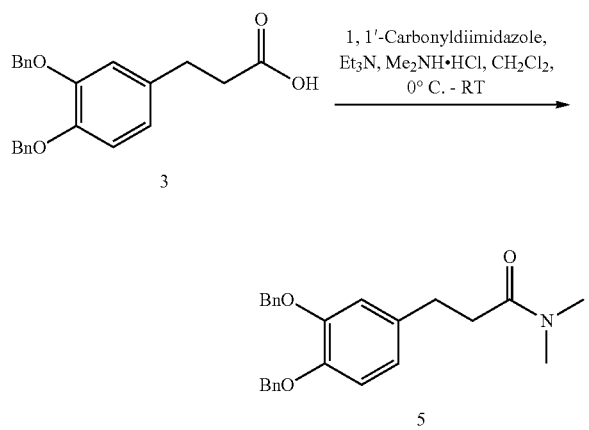

Prepared according to the procedure given above in 76% isolated yield, and carried immediately on to the next step.

$^1$H NMR (600 MHz, CDCl$_3$) δ (ppm): 7.46-7.44 (t, J=7.2 Hz, 4H), 7.37-7.34 (dd, J=3, 7.2 Hz, 4H), 7.32-7.29 (m, 2H), 6.87 (d, J=8.4 Hz, 1H), 6.83 (d, J=1.8 Hz, 1H), 6.74 (dd, J=1.8, 8.4 Hz, 1H), 5.15 (s, 2H), 5.14 (s, 2H), 2.93 (s, 3H), 2.88 (m, 5H), 2.54 (t, J=8.4 Hz, 2H)

3-(3,4-bis(benzyloxy)phenyl)-N,N-dimethylpropan-1-amine (6)

Prepared according to the general procedure in 87% isolated yield.

$^1$H NMR (600 MHz, CDCl$_3$) δ (ppm): 5.15 (s, 2H), 5.13 (s, 2H), 2.54 (t, J=7.8 Hz, 2H), 2.25 (t, J=7.2 Hz, 2H), 2.20 (s, 6H), 1.74 (p, J=7.8 Hz, 2H) $^{13}$C NMR (125 MHz, CDCl$_3$) δ (ppm): 148.96, 147.67, 137.37, 137.20, 132.55, 128.46, 128.45, 127.82, 127.81, 127.40, 127.35, 121.29, 115.49, 115.42, 71.41, 71.27, 68.53, 62.04, 49.43, 31.50, 24.13 FTIR (cm$^{-1}$): 3088, 3058, 3031, 2939, 2857, 2814, 2763, 1605, 1588, 1509, 1454, 1423, 1379, 1261, 1221, 1158, 1134, 1067, 1016, 907, 847, 731, 694, 624, 605, 463 ESI-HRMS: Calculated for C$_{25}$H$_{30}$NO$_2^+$: 376.2271. Found: 376.2266 (M+H)$^+$

General Procedure for the Synthesis of Benzyl-Protected Molecules by the Chabrier Reaction 7-13.

Benzyl-protected zwitterionic coacervates were prepared via the Chabrier-Reaction, according to a previously described procedure, with certain modifications, and no attempt was made to optimize yields. Ethylene chlorophosphonate was purchased from Aesar, stored in a freezer, and used as received. In a typical procedure, a flame-dried flask was fitted with a PTFE coated stir bar, rubber septa, and cooled under positive argon flow. Freshly prepared alcohol was added to the flask followed by anhydrous Et$_2$O [0.4 M], 1.15 equiv. Et$_3$N, and stirred under argon in an ice bath. 1.15 equiv. ethylene chlorophosphonate was then added semi-dropwise via syringe whereupon precipitation of the amine hydrochloride salt was observed to begin, and the flask was stirred for 10 minutes at 0° C. The ice bath was then removed and the flask was allowed to warm to ambient temperature with stirring for 4 hours. Hexanes equal to the volume of Et$_2$O in the flask, was then added to assist in precipitation of the amine hydrochloride salt, and the contents of the flask were filtered quickly over a pad of basic celite into a fresh round bottom flask. The contents of the reaction vessel was then rinsed once with hexanes, and once with Et$_2$O through the pad of basic celite, and volatiles were then removed under reduced pressure, and stored briefly in the round bottom flask under high vacuum while a second reaction vessel was prepared.

A schlenk-bomb type flask was fitted with a PTFE-coated stir bar, flame dried, fitted with two rubber septa, and allowed to cool to ambient temperature under positive argon flow. While the schlenk flask was cooling, the flask containing the phosphonate ester was back-filled with argon, removed from the vacuum manifold, fitted with a rubber septa, and an argon needle was inserted into the septum. The appropriate amount of anhydrous MeCN (2-4 ml per mmol alcohol) was then added to this flask via syringe, and swirled gently by hand until completely dissolved. At this point, the MeCN solution containing the phosphonate ester was transferred via syringe into the schlenk flask, and the round bottom was rinsed once with a minimal amount of MeCN into the schlenk flask. 2-4 equiv. of the appropriate amine was then added to the schlenk flask, and the rubber septa was replaced with a schlenk valve coated with high-vacuum grease. The schlenk valve was closed, whereupon the second rubber septa containing an argon needle was replaced with a glass adaptor connected to the high vacuum manifold and placed under high vacuum. The schlenk valve was then cautiously opened and atmosphere was removed from the flask for 10 seconds to remove atmosphere from the flask, the schlenk valve was then closed tightly, and the flask was refluxed under vacuum with stirring for 2-4 days at 80° C. in an oil bath.

Although in general the unoptimized yields were satisfactory for the purposes of this work, if yield is an important parameter, the following can occasionally assist in improving the overall efficiency. For relatively volatile amines such as n-$C_4H_9NMe_2$, the yield of the reaction was observed to depend on the headspace in the flask during reflux. As the reaction is performed in a sealed flask under vacuum, greater head space in the flask presumably lead to condensation of the amine above the level of solvent and gave decreased yield. Furthermore a high quality schlenk valve is essential, as the vacuum manifold is active during the reaction even though the schlenk valve is closed, and a faulty valve will lead to evaporation of solvent and amine over the course of the reaction. When volatile amines are used as nucleophiles in this reaction the following steps must be taken to ensure adequate yield. 1. The use of additional MeCN as solvent to reduce headspace. 2. Increasing amine equivalents from 2 to 4. 3. Applying vacuum to the flask very briefly before re-sealing to avoid evaporation of amine. 4. Increasing reaction time from 2 to 4 days.

When the indicated time had been reached the flask was removed from the oil bath and allowed to cool to ambient temperature. The flask was then backfilled with argon, removed from the vacuum manifold and the schlenk valve was removed. As the inside neck of the flask contained residual vacuum grease from the schlenk valve, to avoid contamination with this potential impurity, rather than pouring, the reaction mixture was transferred via syringe into a round bottom flask and the reaction vessel was washed twice with $CH_2Cl_2$ into the round bottom flask. Volatiles were removed under reduced pressure and traces of solvents were removed by several rounds of evaporation with pentanes to give the crude, protected coacervates. The residue was then dissolved in a minimum amount of $CH_2Cl_2$ and loaded on top of a plastic column packed with bonded C2 reverse phase silica. The column containing the crude residue was then capped and purified on a Biotage SP4 column chromatography system with gradient elution from 0-35% MeOH/$CH_2Cl_2$ collecting the set of UV active fractions (254 nm, 10 mAu threshold) eluting last. Concentration of these fractions afforded pure benzyl protected coacervates which were characterized by HRMS, FTIR, $^1H$—, and $^{13}C$-NMR prior to de-protection.

Although Menger's procedure documents the use of washing, and recrystallization to purify these compounds, the present recrystallization under the reported conditions led to only modest increases in purity, gave diminished yields and was highly dependent on the molecule being purified. As the last step of the synthesis (catalytic hydrogenolysis) was chosen to avoid the necessity of additional purification and introduction of additional impurities, and considering that catechols in their unprotected state are highly polar, and prone to oxidation/polymerization, an additional purification step following catechol-de-protection was deemed undesirable and considerably more difficult. Key to the success of this work was ensuring a high level of purity prior to de-protection of the catechols and thus it is recommended that purification of benzylated catechol intermediates be performed with C2-bonded reverse phase silica gel.

"Reverse phase" C2 silica is technically a misnomer in this case as compounds of low polarity displayed low retention times eluting first, and compounds of high polarity displayed high retention times, eluting last. Gradient elution was performed starting with 0% MeOH/100% $CH_2Cl_2$ and the % of MeOH was increased over 10-25CV's to 35% MeOH/65% $CH_2Cl_2$. If cost of the reverse phase silica gel is of consideration, then C2 silica could be prepared readily by reacting the appropriate amount of ethyltrichlorosilane with standard grade silica gel (230-400 mesh) according to a previously described procedure. However, C2 silica prepared by this route was considerably more polar than the commercial material obtained from Analtech, and required longer and larger, 0-100% MeOH/$CH_2Cl_2$ gradients to allow the desired product to elute. Both sources of C2 silica gel were used in this work and no substantial difference in the purity was observed with material purified with either source of C2 silica. To further reduce cost, the C2 silica from either source could be reused several times after use by flushing with 10-20 volumes of MeOH and storing the sealed columns wet with MeOH in a refrigerator. Before reuse, the columns were then flushed with 5-10 volumes of $CH_2Cl_2$ prior to loading crude compound. Without exception, in all cases the desired product was observed to elute last on the column, although on occasion the first few fractions of those that contained desired material also contained unidentified yellow-colored impurities, and these fractions were either discarded or separated, concentrated, and repurified according to the procedure.

Phospholane Intermediate

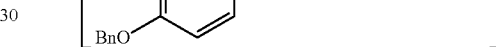

The cyclic phospholane intermediate in all cases was used immediately after preparation without further purification. However $^1H$-NMR shifts of this crude material are included here for reference purposes and completeness of the supplementary information.

$^1H$ NMR (500 MHz, $CDCl_3$) δ (ppm): 7.46-7.42 (m, 4H) 7.38-7.33 (m, 4H), 7.32-7.28 (m, 2H), 6.87 (d, J=6.5 Hz, 1H), 6.79 (d, J=1.5 Hz, 1H), 6.70 (dd, J=1.5, 6.5 Hz, 1H), 5.15 (s, 2H), 5.13 (s, 2H), 4.47 (m, 2H), 4.35 (m, 2H), 4.13 (dt, J=2, 5 Hz, 2H), 2.63 (t, J=6.5 Hz, 2H), 1.97 (p, J=6 Hz, 2H)

Z-Cat-$C_4$-Bn (7)

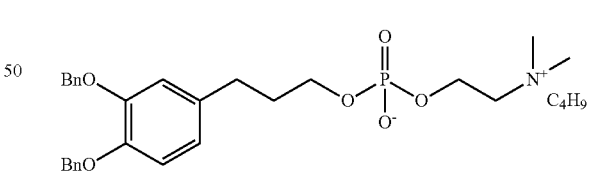

7

91% isolated yield.

$^1H$ NMR (600 MHz, $CDCl_3$) δ (ppm): 7.47-7.42 (m, 4H), 7.37-7.33 (m, 4H), 7.32-7.28 (m, 2H), 6.87-6.84 (m, 2H), 6.72 (dd, J=7.8 Hz, 1H), 5.12 (s, 2H), 5.10 (s, 2H), 4.26 (m, 2H), 3.88 (q, J=7.2 Hz, 2H), 3.71 (m, 2H), 3.44 (m, 2H), 3.26 (s, 6H), 2.62 (t, J=9 Hz, 2H), 1.91 (p, J=9 Hz, 2H), 1.66 (m, 2H), 1.38 (sex, J=9 Hz, 2H), 0.95 (t, J=9 Hz, 3H); $^{13}C$ NMR (150 MHz, $CDCl_3$) δ (ppm): 148.91, 147.24, 137.55, 137.44, 135.70, 128.49, 128.48, 127.84, 127.79, 127.55, 127.41, 121.44, 116.05, 115.46, 71.58, 65.44, 64.71, 64.04, 58.93, 51.67, 32.75, 32.66, 31.70, 24.68, 19.67, 13.74; FTIR ($cm^{-1}$): 3031, 2937, 2875, 1588, 1510, 1454, 1424, 1380, 1247, 1158, 1135, 1087, 1064, 1042, 982, 937, 806, 731, 695, 623, 536, 486 HRMS: Calculated for $C_{31}H_{42}NaNO_6P^+$: 578.2642 Found: 578.2637 (M+Na)$^+$ Z-Cat-C$_6$-Bn (8)

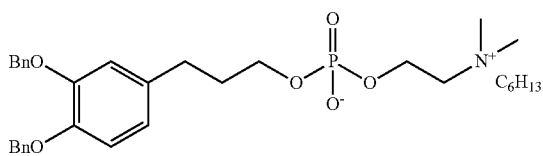

46% isolated yield.

$^1$H NMR (600 MHz, CDCl$_3$) δ (ppm): 7.44-7.40 (m, 4H), 7.35-7.26 (m, 6H), 6.84-6.83 (m, 2H), 6.70-6.68 (m, 1H), 4.24 (m, 2H), 3.85 (q, J=6 Hz, 2H), 3.69 (m, 2H), 3.39 (m, 2H), 3.24 (s, 6H), 2.60 (t, J=7.8 Hz, 2H), 1.88 (p, J=7.2 Hz, 2H), 1.63 (m, 2H), 1.35-1.22 (m, 8H), 0.87 (t, J=7.2 Hz, 3H); $^{13}$C NMR (150 MHz, CDCl$_3$) δ (ppm): 148.97, 147.31, 137.61, 137.51, 135.77, 128.54, 128.53, 127.88, 127.84, 127.60, 127.46, 121.50, 116.14, 115.53, 71.69, 71.64, 65.86, 64.26, 58.92, 53.20, 51.77, 50.46, 32.78, 31.75, 26.03, 22.84, 22.50, 14.01; FTIR (cm$^{-1}$): 3039, 2955, 2931, 2259, 2200, 1588, 1510, 1454, 1425, 1379, 1250, 1136, 1088, 1046, 967, 906, 807, 722, 696, 640, 599, 538, 487; HRMS: Calculated for $C_{33}H_{46}NaNO_6P^+$: 606.2955 Found: 606.2949 (M+Na)

Z-Cat-C$_8$-Bn (9)

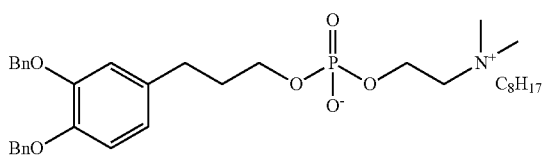

83% isolated yield.

$^1$H NMR (600 MHz, CDCl$_3$) δ (ppm): 7.47-7.38 (m, 4H), 7.35-7.26 (m, 6H), 6.86-6.81 (m, 2H), 6.70 (dd, J=1.8, 7.8 Hz, 1H), 5.10 (s, 2H), 5.09 (s, 2H), 4.25 (m, 2H), 3.86 (q, J=6 Hz, 2H), 3.69 (m, 2H), 3.38 (m, 2H), 3.24 (s, 6H), 2.61 (t, J=7.8 Hz, 2H), 1.89 (p, J=7.2 Hz, 2H), 1.62 (m, 2H), 1.33-1.17 (m, 12H), 0.86 (t, J=7.2 Hz, 3H); $^{13}$C NMR (150 MHz, CDCl$_3$) δ (ppm): 148.98, 147.32, 137.63, 137.53, 135.80, 128.55, 128.54, 127.88, 127.84, 127.60, 127.46, 121.51, 116.16, 115.53, 71.70, 71.65, 65.90, 64.84, 64.80, 58.91, 51.79, 32.78, 32.73, 31.76, 29.29, 29.16, 26.40, 22.91, 22.69, 14.18; FTIR (cm$^{-1}$): 3071, 3034, 2926, 2856, 1651, 1589, 1511, 1455, 1425, 1379, 1221, 1159, 1136, 1081, 1039, 972, 733, 695, 539, 491 ESI-HRMS: Calculated for $C_{35}H_{50}NNaO_6P^+$: 634.3268 Found: 634.3243 (M+Na)$^+$ Z-Cat-C$_{10}$-Bn (10)

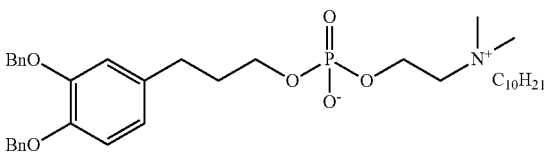

81% isolated yield.

$^1$H NMR (600 MHz, CDCl$_3$) δ (ppm): 7.47-7.38 (m, 4H), 7.37-7.24 (m, 6H), 6.86-6.81 (m, 2H), 6.70 (dd, J=1.8, 8.4 Hz, 1H), 5.10 (s, 2H), 5.08 (s, 2H), 4.25 (m, 2H), 3.86 (q, J=6 Hz, 2H), 3.70 (m, 2H), 3.38 (m, 2H), 3.24 (s, 6H), 2.61 (t, J=7.8 Hz, 2H), 1.88 (p, J=7.2 Hz, 2H), 1.62, (m, 2H), 1.35-1.17 (m, 14H), 0.87 (t, J=7.2 Hz, 3H); $^{13}$C NMR (150 MHz, CDCl$_3$) δ (ppm): 148.98, 147.32, 137.63, 137.53, 128.54, 128.53, 127.88, 127.83, 127.60, 127.45, 121.51, 116.15, 115.53, 71.69, 71.64, 65.88, 65.86, 64.85, 64.81, 58.98, 58.95, 51.77, 32.77, 32.71, 31.95, 31.75, 29.55, 29.51, 29.35, 22.92, 22.77, 14.18; FTIR (cm$^{-1}$): 3071, 3031, 2924, 2854, 1657, 1589, 1511, 1454, 1425, 1379, 1243, 1159, 1137, 1081, 1040, 1026, 967, 805, 789, 732, 695, 539, 489; ESI-HRMS: Calculated for $C_{37}H_{54}NNaO_6P^+$: 662.3581. Found: 662.3586 (M+Na)$^+$ Z-Cat-C$_{12}$-Bn (11)

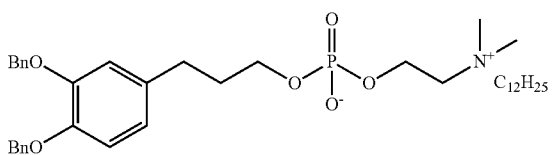

45% isolated yield.

$^1$H NMR (600 MHz, CDCl$_3$) δ (ppm): 7.40-7.32 (m, 4H), 7.29-7.24 (m, 4H), 7.23-7.19 (m, 2H), 6.78-6.75 (m, 2H), 6.63 (dd, J=1.2, 8.4 Hz, 1H) 5.04 (s, 2H), 5.02 (s, 21H), 4.18 (m, 2H), 3.84 (m, 2H), 3.68 (m, 2H), 3.31 (m, 2H), 3.17 (s, 6H), 2.53 (t, J=7.8 Hz, 2H), 1.81 (p, J=7.2 Hz, 2H), 1.61 (m, 2H), 1.29-1.06 (m, 16H), 0.81 (t, J=7.2 Hz, 3H); $^{13}$C NMR (150 MHz, CDCl$_3$) δ (ppm): 148.98, 147.30, 137.61, 137.51, 135.76, 128.52, 128.51, 127.81, 127.58, 127.43, 121.47, 116.11, 115.52, 71.67, 71.61, 65.78, 64.81, 64.77, 64.25, 58.91, 51.74, 32.78, 32.73, 32.00, 31.75, 29.71, 29.62, 29.53, 29.43, 29.37, 26.41, 22.91, 22.78, 14.22; FTIR (cm): 3071, 3028, 2923, 2853, 1589, 1512, 1455, 1425, 1378, 1227, 1137, 1084, 1040, 1026, 971, 721, 694, 492; ESI-HRMS: Calculated For $C_{39}H_{58}NNaO_6P^+$: 690.3894. Found: 690.3884 (M+Na)$^+$ Z-Cat-Cat-Bn (12)

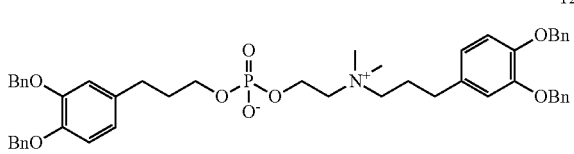

72% isolated yield. Samples of 12 were observed to degrade over time, and immediately after purification it was carried on to the next step.

$^1$H NMR (600 MHz, CDCl$_3$) δ (ppm): 7.47-7.37 (m, 8H), 7.35-7.23 (m, 12H), 6.87-6.74 (m, 4H), 6.71-6.63 (m, 2H), 5.17-5.03 (m, 8H), 3.89 (s, 1H), 3.58 (m, 2H), 3.29 (m, 2H), 3.09-2.95 (m, 3H), 2.90-2.72 (m, 6H), 2.30-2.16 (m, 4H), 1.69-1.47 (m, 4H); FTIR (cm$^{-1}$): 3031, 2941, 1588, 1510, 1454, 1425, 1380, 1259, 1218, 1159, 1136, 1078, 1011, 968, 848, 807, 733, 695, 466; HRMS: Calculated for $C_{50}H_{56}NNaO_8P^+$: 842.3636 Found: 852.3635 (M+Na)$^+$ Z-Ben-C$_8$ (13)

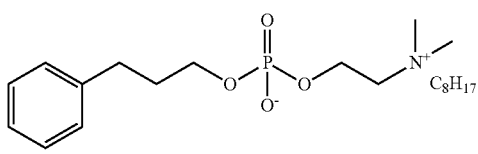

64% isolated yield.

¹H NMR (600 MHz, CDCl₃) δ (ppm): 7.18-7.14 (m, 2H), 7.10-7.04 (m, 3H), 4.17 (m, 2H), 3.79 (q, J=6.6 Hz, 2H), 3.38 (m, 2H), 3.21 (s, 6H), 2.60 (t, J=7.8 Hz, 2H), 1.85 (p, J=7.2 Hz, 2H), 1.65-1.52 (m, 2H), 1.29-1.06 (m, 10H), 0.79 (t, J=6.3 Hz, 3H); ¹³C NMR (150 MHz, CDCl₃) δ (ppm): 141.83, 128.32, 128.23, 125.66, 65.37, 64.65, 63.97, 63.90, 58.77, 52.86, 52.52, 32.57, 32.53, 32.07, 31.57, 29.15, 28.99, 26.26, 22.75, 22.47, 13.97 FTIR (cm⁻¹): 3029, 2924, 2854, 1604, 1496, 1468, 1453, 1378, 1246, 1093, 1063, 1034, 979, 947, 905, 826, 795, 752, 743, 699, 594, 540, 498, 485. ESI-HRMS: Calculated for $C_{21}H_{38}NNaO_4P^+$: 422.2431. Found: 422.2430 (M+Na)⁺

General Procedure for De-Protection of Catechols by Hydrogenolysis 14-19

The oxidative stability of each of the zwitterionic coacervates containing unprotected catechols, either in the solid state, a solution in $D_6$-DMSO, or as a colloidal dispersion in water, was not known prior to undertaking this study and thus every effort was made to exclude atmospheric oxygen during all manipulations at all points after the catechols had been deprotected. Likewise, as purification of unprotected catechols was envisaged to be difficult and require application of purification techniques under inert atmosphere, every effort was made to increase the purity of the intermediates immediately preceding the de-protection step and the final products were all obtained in satisfactory purity as determined by FTIR, ¹H—, and ¹³C-NMR Spectroscopy.

In a typical procedure, A Schlenk-bomb type flask was fitted with a PTFE coated stir bar, flame dried, fitted with two rubber septa and allowed to cool to ambient temperature under positive argon flow. One septa was briefly removed, 10-20 wt % of Pd/C (5% Pd, Type 87L, dry, Aesar) relative to mass of substrate was added to the flask and the septa was resealed. A small quantity of $CH_2Cl_2$ (4-8 ml) was added via syringe through the septa to rinse residual Pd on the sides of the flask to the bottom. A separate round bottom flask containing the desired amount of substrate was fitted with a rubber septa and argon needle, and vented briefly to purge air out. The vent needle was then removed, and the appropriate volume of a 1:1 v/v mixture of $CH_2Cl_2$/MeOH was added through the septa via syringe. The flask was then swirled by hand until the benzyl-protected coacervate had dissolved, and this solution containing the substrate was transferred via syringe to the schlenk flask. The interior of the round bottom flask was then rinsed with a small quantity of MeOH (4-8 ml), and transferred via syringe to the schlenk flask. The first septa over the threaded part of the flask was quickly removed and replaced with a schlenk valve coated with vacuum grease. The schlenk valve was closed, whereupon the second rubber septa was replaced with a glass adaptor connected to the high vacuum manifold and placed under high vacuum, which placed the antechamber before the schlenk valve under vacuum, and the flask was stirred gently. The schlenk valve was then cautiously opened placing the contents of the flask under vacuum and the atmosphere was removed under vacuum for 2-3 minutes. Once this time had elapsed the schlenk valve was closed, the antechamber before the valve was backfilled with argon and the glass adaptor connecting the flask to the vacuum manifold was quickly replaced with a rubber septa. A hydrogen balloon (double ballooned) connected to a needle was placed through the septa and then a vent needle was placed though the septa to purge argon from the antechamber for 30 seconds whereupon it was subsequently removed. Then the schlenk valve was opened slowly to allow hydrogen into the reaction vessel. Stirring was continued for 2-4 days, with periodic replacement of the hydrogen balloon (fresh balloons were used with every replacement).

As the high polarity of the products precluded the use of TLC or GC to monitor the progress of the reaction, reaction progress was monitored at 24 h intervals by removal of a 0.5-1.0 ml aliquot of the reaction mixture, which was worked up by filtration according to the procedure and analyzed by NMR to determine completion of the reaction. In general, most reactions were incomplete after one day, and showed full conversion after two full days, although on occasion, up to 4 days were necessary for certain substrates.

Once the indicated time had elapsed the schlenk valve was closed, and the remaining septa was replaced with a vacuum adaptor connected to a vacuum manifold and the antechamber before the schlenk valve was placed under vacuum. The schlenk valve was then cautiously opened placing the contents of the flask under vacuum and hydrogen gas was removed from the system in this manner for 5-10 minutes with stirring, whereupon there was concomitant bubbling and cooling of the flask due to slight solvent evaporation (Caution: opening the schlenk valve too quickly in this step will lead to solvent "bumping" into the vacuum manifold). During this time a separate round bottom flask was flame dried, fitted with a rubber septa, tared, and allowed to cool to ambient temperature under positive argon flow. The schlenk flask was then backfilled with argon, and while under positive argon flow the schlenk valve was removed and quickly replaced with a rubber septa. A 30 ml, luer lock, PTFE coated syringe was fitted with a long metal needle, and the syringe was filled and purged with argon 3×, whereupon it was inserted through the septa of the reaction vessel.

The Pd/C was then separated from the reaction mixture. This procedure was devised on the basis of the expected high polarity of the products, which would preclude removal of Pd/C, by the usual filtration over celite, silica, or alumina, and thus a relatively inert and nonpolar PTFE filter was chosen to remove the Pd/C. The choice of the benzyl protecting group for catechols in this context is particularly noteworthy, as the only byproduct is toluene which can be removed by simple evaporation. Use of an acetonide or silicon based protecting group for the catechol, and subsequent removal with acid or fluoride respectively, was deliberately avoided, as they would introduce other organic, or highly polar water-soluble impurities, which would be difficult to remove from the desired product with conventional techniques. However this procedure gave variable (39-93%) isolated yields, presumably due to adsorption of the products onto the charcoal surface, and no attempt was made to optimize yields, although on occasion, additional washing of the reaction flask and PTFE filter with degassed MeOH was performed to assist in product recovery.

With the outlet of the syringe facing down, 25 ml of the reaction mixture was pulled slowly up into the syringe, whereupon the needle was gently bent and the syringe was inverted so that the outlet of the syringe was now facing up. The needle was pulled above the level of solvent in the reaction mixture and a 5 ml blanket of argon pulled into the syringe. Then, very quickly, the needle was removed from the flask with the syringe still inverted, and the metal needle was removed from the luer lock and quickly replaced with an Acrodisc 0.45 μm PTFE membrane filter fitted with a fresh 18 gauge needle at the outlet. The empty round bottom flask, still fitted with septa and argon needle, was then inverted so that the neck of the flask was facing downward, and the needle attached to the membrane filter and syringe was placed though the septa of the inverted flask. The whole apparatus was inverted once more, so that the outlet of the syringe was facing down and the neck of the flask was facing up, and the solution was gently forced through the filter into the flask, removing the Pd/C from the solution. If more than 25 ml of solution were present in the schlenk flask, then the procedure was repeated with fresh syringes, needles, and filters, until no more liquid remained in the flask. The septa was then quickly removed from round bottom flask containing product, and immediately placed on a rotavap to remove volatiles. Several subsequent rounds of evaporation first with $CH_2Cl_2$, then with pentanes helped to remove trace solvents from the products, and the flask was immediately placed under high vacuum afforded pure de-protected coacervates. Pure coacervates were both stored in round bottom flasks under high vacuum, or in vials under an argon atmosphere and tightly wrapped with several layers of parafilm, until further study. Unfortunately the final products were not sufficiently stable under conditions of EI- or ESI-MS for accurate mass determination. However they were all characterized by $^1$H-NMR, $^{13}$C-NMR, and IR spectroscopy, which confirmed that the anticipated products had been produced in satisfactory purity. The benzyl-protected coacervates were all sufficiently stable for ESI-HRMS (QTOF2 Tandem Mass Spectrometer) and were fully characterized including this descriptor prior to hydrogenolysis. Additionally, MALDI-MS (Operational settings on a model DE-VoyagerPerseptive Biosystems mass spectrometer were 25,000V (accelerating voltage), 93% (grid voltage), guide wire voltage (0.3%), 500 ns (delay time) and a relative laser power of 1000.), although not sensitive enough for an accurate mass determination, was performed successfully for Z-Cat-C8, which showed the anticipated molecular ion.

Although azeotropic removal with pentanes, and gentle heating under high vacuum were successful at removing the majority of trace solvents from the pure coacervates, NMR spectra invariably contained some slight traces of solvents owing to the high propensity of the product molecules to self aggregate, trapping some residual solvents in the material.

Z-Cat-C$_4$ (14)

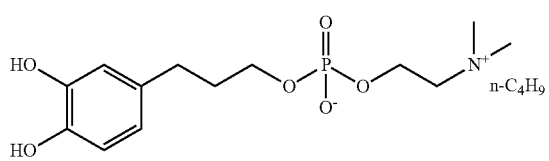

14

Reaction time=2 days (48 hours) 88% isolated yield.
$^1$H NMR (500 MHz, D$_6$-DMSO) δ (ppm): 9.67-8.74 (s, 1H), 9.67-8.74 (s, 1H) (overlapping), 6.76-6.58 (m, 2H), 6.46-6.37 (m, 1H), 4.06 (m, 2H), 3.68 (m, 2H), 3.51 (m, 2H), 3.35 (m, 2H), 3.07 (s, 6H), 2.44 (t, J=7.5 Hz, 2H), 1.77-1.58 (m, 4H), 1.32-1.20 (m, 2H), 0.92 (t, J=7.5 Hz, 3H); $^{13}$C NMR (125 MHz, D$_6$-DMSO) δ (ppm): 145.17, 143.29, 132.31, 118.63, 115.81, 115.51, 63.95, 63.83, 63.02, 58.19, 58.15, 50.74, 30.91, 23.76, 19.17, 13.50; FTIR (cm$^{-1}$): 3029, 2959, 1599, 1513, 1468, 1382, 1286, 1202, 1079, 1059, 1035, 977, 813, 768, 733, 634, 588, 535, 492

Z-Cat-C$_6$ (15)

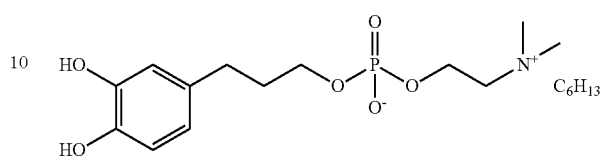

15

Reaction time=2 days (48 hours) 74% isolated yield.
$^1$H NMR (600 MHz, D$_6$-DMSO) δ (ppm): 9.79-8.80 (br, s, 1H), 9.79-8.80 (br, s, 1H) (overlapping), 6.69-6.58 (m, 2H), 6.44-6.33 (m, 1H), 4.04 (m, 2H), 3.69-3.60 (m, 2H), 3.51 (m, 2H), 3.32 (m, 2H), 3.06 (s, 6H), 2.42 (t, J=7.2 Hz, 2H), 1.77-1.56 (m, 4H), 1.33-1.16 (m, 8H), 0.90-0.78 (m, 3H); $^{13}$C NMR (150 MHz, D$_6$-DMSO) δ (ppm): 145.26, 143.38, 132.18, 118.50, 115.86, 115.57, 64.11, 63.88, 62.89, 58.25, 50.68, 32.45, 30.94, 30.68, 25.42, 21.98, 21.74, 13.83; FTIR (cm$^{-1}$): 3030, 2952, 1599, 1512, 1467, 1380, 1286, 1204, 1036, 966, 811, 765, 633, 537, 492

Z-Cat-C$_8$ (16)

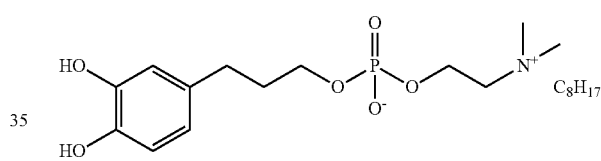

16

Reaction time=2 days (48 hours) 93% isolated yield.
$^1$H NMR (500 MHz, D$_6$-DMSO) δ (ppm): 9.14-8.43 (s, 1H), 9.14-8.43 (s, 1H) (overlapping), 6.45-6.40 (m, 2H), (dd, J=2, 8 Hz, 1H), 3.85 (m, 2H), 3.48 (q, J=6.5 Hz, 2H), 3.32 (m, 2H), 3.17 (m, 2H), 2.89 (s, 6H), 2.34 (m, 2H), 2.26 (t, J=8 Hz, 2H), 1.58-1.42 (m, 4H), 1.15-1.01 (m, 12H), 0.70 (t, J=7 Hz, 3H); $^{13}$C NMR (125 MHz, D$_6$-DMSO) δ (ppm): 145.12, 143.23, 132.37, 118.58, 115.75, 115.44, 64.13, 63.65, 63.60, 63.08, 58.05, 58.01, 50.71, 31.16, 30.96, 28.48, 25.78, 22.03, 21.76, 13.93; FTIR (cm$^{-1}$): 3029, 2925, 2855, 1599, 1512, 1467, 1378, 1285, 1201, 1061, 1034, 973, 812, 769, 633, 590, 537, 494; MALDI-MS (aCHCA matrix, Low-Res): Calculated for $C_{21}H_{38}NO_6P$: 431.244 Found: 431.308

Z-Cat-C$_{10}$ (17)

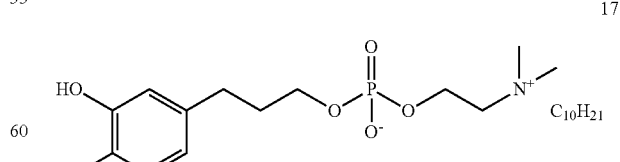

17

Reaction time=2 days (48 hours) 79% isolated yield.
$^1$H NMR (500 MHz, D$_6$-DMSO) δ (ppm): 9.83-8.55 (br, s, 1H), 9.83-8.55 (br, s, 11H) (overlapping), 6.64 (m, 2H), 6.39 (m, 1H), 4.07 (m, 2H), 3.70 (q, J=6.5 Hz, 2H), 3.52 (m, 211), 3.36 (m, 2H), 3.06 (s, 6H), 2.43 (t, J=8 Hz, 2H), 1.76 (p, J=7.5 Hz, 2H), 1.67 (m, 2H), 1.32-1.15 (m, 14H), 0.86 (t, J=7 Hz, 3H); $^{13}$C NMR (125 MHz, D$_6$-DMSO) δ (ppm): 141.24, 139.38, 128.12, 114.49, 111.86, 111.57, 60.15, 59.92, 58.89, 54.25, 46.66, 28.44, 27.28, 26.90, 24.93, 24.87, 24.68, 24.56, 21.79, 18.09, 17.81, 9.93; FTIR (cm$^{-1}$): 3031, 2923, 2854, 1599, 1512, 1467, 1378, 1286, 1204, 1154, 1079, 1037, 967, 812, 770, 634, 591, 538, 492

Z-Cat-C$_{12}$ (18)

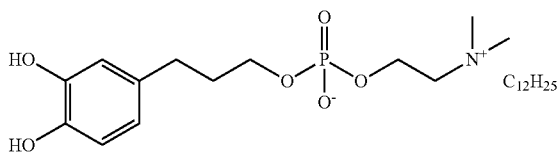

18

Reaction time=2.5 days (60 hours) 77% isolated yield.

$^1$H NMR (600 MHz, D$_6$-DMSO) δ (ppm): 9.12-8.27 (br, s, 1H), 9.12-8.27 (br, s, 1H) (overlapping), 6.48-6.36 (m, 2H), 6.22 (dd, J=1.8, 7.8 Hz, 1H), 3.87 (m, 2H), 3.46 (q, J=6 Hz, 2H), 3.31 (m, 2H), 3.15 (m, 2H), 2.87 (s, 6H), 2.32 (m, 4H), 2.24 (t, J=7.2 Hz, 2H), 1.56-1.37 (m, 4H), 1.14-0.99 (m, 16H), 0.68 (t, J=7.2 Hz, 3H); FTIR (cm$^{-1}$): 3034, 2922, 2852, 1696, 1599, 1512, 1466, 1444, 1378, 1286, 1202, 1079, 1036, 972, 812, 789, 634, 538, 495

Z-Cat-Cat (19)

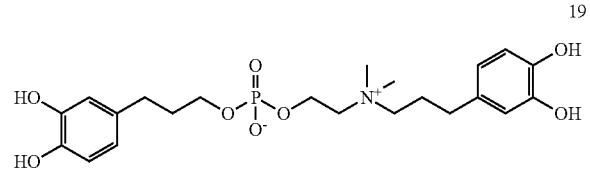 [SMILES: C[N+](C)(CCCc1ccc(O)c(O)c1)CCOP(=O)([O-])OCCCc1ccc(O)c(O)c1]

19

Hydrogenolysis of the Z-Cat-Cat-Bn (18) was accomplished with a slightly higher catalyst loading (20 wt % of Pd/C relative to mass of starting material) and extended reaction time (4 days) for complete de-protection, affording Z-Cat-Cat in 69% isolated yield. $^1$H-NMR of the product compared to that of starting material showed complete debenzylation. Like it's precursor, Z-Cat-Cat was observed to be highly susceptible to degradation over time, and several unidentified impurities, albeit in low concentration relative to product, were apparent by $^1$H—and $^{13}$C-NMR even when the sample was analyzed within <30 minutes of isolation. Attempts to increase the level of purity by either recrystallization or HPLC were unsuccessful and the compound was used "as is" for further study. It is recommended that extra care is taken to ensure that this compound be protected from atmospheric oxygen, and be used and analyzed immediately after isolation. Considering that the presence of trace impurities in this case did not give rise to improved or otherwise unexpected performance in adhesive tests or other false positives and that all other zwitterionic adhesives were obtained in higher purity, and several displayed higher adhesion, their presence in this case was not seen as problematic as it did not fundamentally affect the interpretation of the data or the broader conclusions of this work. Reaction time=4 days (96 hours) 69% isolated yield.

$^1$H NMR (500 MHz, D$_6$-DMSO) δ (ppm): 10.44-8.23 (br, m, 4H), 6.81-6.54 (m, 4H), 6.49-6.34 (m, 2H), 4.04 (m, 1H), 3.75-3.62 (m, 2H), 3.56-3.46 (m, 2H), 3.42-3.36 (m, 1H), 3.35-3.21 (m, 2H), 3.03 (s, 6H), 2.47-2.36 (m, 4H), 1.98-1.86 (m, 2H), 1.77-1.67 (m, 2H).

$^{13}$C NMR (125 MHz, D$_6$-DMSO) δ (ppm): 145.59, 145.34, 145.10, 143.79, 143.74, 143.24, 132.37, 130.74, 130.22, 118.69, 115.84, 115.78, 115.64, 115.52, 115.37, 65.12, 63.88, 63.32, 58.28, 52.15, 50.79, 30.89, 24.12, 22.95; FTIR (cm$^{-1}$): 3045, 2954, 1600, 1522, 1473, 1375, 1286, 1196, 1081, 1040, 962, 877, 816, 790

Interfacial and Redox Characterizations

Aqueous colloidal dispersions of each homolog were prepared in deoxygenated deionized (DI) water. The critical aggregation concentration (CAC) was determined from the solution surface tension of varying homolog concentrations in deionized (DI) water (e.g., see the red line of Z-Cat-C10 in FIG. 2B) by Wilhelmy plate tensiometry and has been described elsewhere. Use of the CAC instead of CMC here is a hedge to accommodate the uncertainty about whether micelles or other soluble aggregates were forming.

Cyclic voltammetry was performed on a Versastat 3 potentiostat from Ametek Co. These analyses were carried out using a three-electrode cell: a Pt wire as the counter electrode, an Ag/AgCl reference electrode, and a Carbon paste electrode (CPE) served as the working electrode. CPE is the best choice for adhesive materials because of its ability to be completely polished before each experiment. Catechol auto-oxidation was avoided by performing all electrochemical experiments with degassed deionized water in a glove bag under argon. Scan rate 1 mV s-1 was used for all experiments. CV of 5 mM synthesized polymers and 5 mM methyl catechol, a simple catechol-containing compound, were compared. Oxidation of Catechol carrying molecules occurred at more positive potentials than methyl catechol, indicating the unique structure of the dispersions provide shielding effects that stabilized catechol groups (FIG. 3).

Quartz Crystal Microbalance with Dissipation

The general interpretation of the QCM-D data is explained to demonstrate the adsorption of the zwitterionic molecules onto both titania and silica surfaces. Quartz crystal microbalance (QCM) is a surface sensitive technique that measures the change in resonant frequency of a vibrating quartz crystal upon adsorption of material to a surface. The quartz crystal is vibrated by applying a periodic voltage signal across it at its resonant frequency. The resonant frequency of the crystal decreases when the mass of the chip increases (due to adsorption of molecules on its surface), which can be converted to adsorbed mass Δm using the Sauerbrey equation:

$$\Delta m = -\frac{A_c \Delta f \sqrt{\rho_q \mu_q}}{2 f_0^2} \quad (1)$$

where $A_c$ is the area of the crystal, $\Delta f$ is the change in frequency, $\rho q$ is the density of quartz (2.648 g cm$^{-3}$), $\mu_q$ is the shear modulus of quartz (2.947×1011 g cm$^{-1}$ s$^2$) and $f_0$ is the resonant frequency of the crystal. The Sauerbrey equation assumes the adsorbed mass is rigid, uniformly distributed across the crystal and the frequency shift is less than 2% of the resonant frequency. Quartz crystal microbalance with dissipation (QCM-D) is an extension to the QCM technique developed by Q-Sense® and can be used to determine the rigidity/softness and the viscoelastic properties of the adsorbed material. The QCM quartz crystal was coated with different rigid materials (e.g., metals, polymers, dielectrics) and the adsorption kinetics can be monitored on these materials in liquid environment. Modeling of the $\Delta f$ and $\Delta D$ at different overtones also allows for the calculation of thin film viscosities, shear modulus, thicknesses, hydrations etc. of the adsorbed layers. Molecule adsorption experiments in a Quartz Crystal Microbalance with Dissipation (QCM-D) indicate that all molecules adsorbed ($\Delta F$) to $TiO_2$ and $SiO_2$ surfaces in DI $H_2O$. The change in dissipation ($\Delta D$) of the adsorbed film shows the degree viscoelasticity for each film.

Confocal Microscopy

Figure 13F:
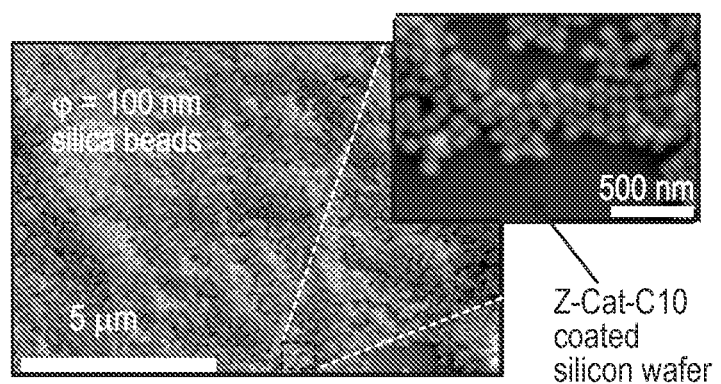

An Olympus Fluoview 1000S laser scanning confocal on an inverted microscope stand was used to monitor the intensity change of a polymer tagged with Rhodamine. An uncoated MatTek dish with a #1.5 thick cover-glass bottom was filled with DI water. A 30× silicon objective lens (NA 1.05) and the transmitted light detector were used to focus upon the inner surface of the coverglass surface. Once the polymer was added to the dish, a 559 laser at 4.8% was used to excite the tagged molecules and the confocal PMT detector was used (800×800 pixel, 2 μs pixel$^{-1}$). A 5 mM solution of Z-Cat-C10 was tagged with ~1 mol % Rhodamine dye and applied to a silica surface. The silica surface was then imaged before and after rinsing the surface with DI water. FIG. 13F shows that the molecules stay adheres to the surface and is not washed off unlike the mussel foot proteins that do not spontaneously adhere onto silica surface without a pressure. This shows that the molecules not only adsorb to the silica surface as demonstrated by QCM-D measurements, but also attaches strongly to the surface. Although the dye could perhaps interfere with the adsorption, it is non-polar, hence the data seem to corroborate the strong adsorption of the zwitterions to silica observed by the SFA, AFM, QCM-D and SEM techniques.

Measuring Normal Forces in the Surface Forces Apparatus

The interaction between two surfaces can be measured with nano-Newton level force resolution and Angstrom level resolution in the separation distance between the surfaces. The details of the SFA techniques have been describe in a work by Israelachvili et al. In a typical SFA experiment (FIG. 2C), the distance and the force between the surfaces are measured simultaneously. To begin with, the instrument is calibrated at large separation distances. When the two surfaces are not interacting, i.e., they are separated by large distances, the change in the separation between them is equal to the distance through which the motor moves the lower surface towards or away from the upper surface (or the upper surface driven by the piezo-tube moves towards the lower surface). However, once the surfaces are close enough to start interacting with each other, the measured separation distance deviates from the expected separation calibrated when there is no force between the surfaces. This deviation is due to the deflection of the double cantilever spring and is directly proportional to the force acting normally between the two opposing surfaces. Thus the normal force can be measured using Hooke's law, $F=k\Delta x$, where k is the spring constant of the double-cantilever spring and $\Delta x=D_{actual}-D_{applied}$ is the deflection of the spring, determined by taking the difference between the applied change in position of one of the surfaces $D_{applied}$ and the actual change in distance measured between the surfaces $D_{actual}$. The actual distance, $D_{actual}$, between the surfaces can be measured by multiple beam interferometry (MBI) and will be discussed below.

Measuring Distance in the SFA by Multiple Beam Interferometry

The distance between the surfaces, shape of the interface and the refractive index of the media between the surfaces can be accurately determined by Multiple Beam Interferometry (MBI) technique. In this technique, white light is directed through two back-silvered mica surfaces (or uniform and same thickness). As a white light passes between the mica surfaces, it undergoes interference due to the optical trap set up by the back silver on each of these surfaces giving rise to discrete wavelengths of light (FIG. 2C). These wavelengths of light are resolved in a spectrometer creating interference fringes known as 'fringes of equal chromatic order' (FECO). Since mica is birefringent, the FECO appears as doublets and termed as β and γ. Alternate fringes are termed as odd and even fringes with odd fringes having nodes at the center and even fringes with anti-nodes in the center. The FECO is then recorded on a camera and analyzed to determine the distance between the surfaces using the following equations:

$$\tan\left(\frac{2\pi\mu_2 D}{\lambda_n^D}\right) = \frac{2\bar{\mu}\sin\left(\frac{1-\lambda_n^0/\lambda_n^D}{1-\lambda_n^0/\lambda_{n-1}^0}\pi\right)}{(1+\bar{\mu}^2)\cos\left(\frac{1-\lambda_n^0/\lambda_n^D}{1-\lambda_n^0/\lambda_{n-1}^0}\pi\right) \pm (\bar{\mu}^2 - 1)} \quad (2)$$

$$T = n\lambda_n^0/4\mu_1 \quad (3)$$

$$n = \frac{\lambda_{n-1}^0}{F_n(\lambda_{n-1}^0 - \lambda_n^0)} \quad (4)$$

where D is the separation distance between the surfaces, n is the fringe order (n=1, 2, 3, ...) $\lambda_n^0$ is the wavelength of the $n^{th}$ order fringe (0 refers to the distance between the mica, D=0, or mica-mica contact reference), T is the thickness of each of the mica surfaces, $\mu_1$ is the refractive index of mica, $\mu_2$ is the refractive index of the medium, $\bar{\mu}=\mu_1/\mu_2$, and the − is used for odd fringes and the + is used for the even fringes, $F_n$ is a correction factor that depends on the phase changes at the mica-silver interface and dispersion effects that can be estimated as $F_n\sim 1.024+1/n$ for odd fringes measured near $\lambda\sim 550$ nm.

For small separation distance (D<30 nm) between the surfaces, eq. 2 can be approximated as $$D = \frac{\lambda_{n-1}^0(\lambda_n^D - \lambda_n^0)}{2\mu_1(\lambda_{n-1}^0 - \lambda_n^0)}, \text{ for } n \text{ odd} \quad (5)$$

$$D = \frac{\mu_1\lambda_{n-1}^0(\lambda_n^D - \lambda_n^0)}{2\mu_2^2(\lambda_{n-1}^0 - \lambda_n^0)}, \text{ for } n \text{ even} \quad (6)$$

It should be noted that the distance calculated with the equation for the odd fringes (eq. 5) is independent of the refractive index between the two surfaces whereas that calculated with even (eq. 6) is not. This allows for simultaneous measurement of refractive index along with the force and separation distance between the surfaces.

Lap Joint Bending Peel Test

The adhesive strength of the synthetic molecules at the macro-scale was demonstrated by gluing two steel plates under water (FIGS. 24A-24H). Below are the detailed methods following in sequential order in time:

1) The aqueous Z-Cat-C10 solution was prepared at 100 mg ml$^{-1}$ concentration (very turbid solution at room temperature) (FIG. 10A test-tube on the left).
2) The solution was centrifuged at 3000 rpm (805×g) for 5 min to expedite the process of liquid-liquid phase separation (FIG. 10A test-tubes in the middle and the right). 3) The lower dense coacervate phase was collected in a syringe (FIG. 24A) and injected (spread, ~10 µl) over a steel plate immersed in water i.e., artificial sea water, aqueous periodate solution, and DI water, respectively (FIG. 24B).
4) Another steel plate glued onto the steel plate with coacervates on as a lap joint (cross-sectional area 2.54 cm×2.54 cm.
5) The each lap joint was loaded (250 g) for 12 h of compressive setting (FIG. 24C).
6) The lap joint bending peel test was conducted underwater for each lap joint prepared in artificial seawater, aqueous periodate solution, and DI water, respectively (FIGS. 24D-24F).
7) The lap joint bending peel test was conducted dry ambient condition for the lap joint prepared in the periodate solution after 12 h drying in ambient condition Standard Three Point Bending Peel Test Samples were prepared as described above in "Lap Joint Bending Peel Test" underwater, i.e., aqueous periodate solution, then dried 12 h and 24 h, respectively, in ambient condition. In this standard three point bending peel test, the cross section area was 2.54 cm×1.27 cm.

The standard three point bending peel test (FIG. 24F) was conducted with a Bionix 200 tensile tester (MTS Systems) in ambient conditions. All tests were conducted with a test speed of 5 mm min-1.

The catecholic zwitterions were inspired by interfacial proteins (mfp-3 and -5) that function as adhesive primers, but not as bulk adhesives. To determine whether Z-Cat-C10 is limited to surface binding or develops measurable bulk cohesion (thickness <10 m), bulk rupture tests were done using a peeling-by-bending test to better mimic the role that interfacial proteins play in resisting plaque detachment as well as lap-shear bonding test. Lap joints were prepared by gluing two steel plates (SS304) immersed in water using the lower dense coacervate (~10 µl) (FIGS. 24A-24H). The lap joint (cross-sectional area=2.54 cm×2.54 cm) prepared in artificial seawater or periodate solution, respectively, held a load up to 3 N underwater. On the other hand, the lap joint prepared in DI water held only 1 N, suggesting that oxidative cross-linking of catechols is necessary to obtain high adhesion as shown in the SFA study described below. After 12 h ambient drying, the joint prepared in 1 M periodate solution held much higher load, 11 N: Standard three point bending peel strength of the lap joint (cross-sectional area=2.54 cm×1.27 cm) was measured under ambient dry conditions after drying 12 h. The peel strength and the lap shear bonding strength of the joint made with Z-Cat-C10 in the periodate solution exhibited 20.5 N $cm^{-1}$ (standard deviation=0.9, n=4)—stronger than the joint with 3M double sided Scotch Tape®, 12.0 N $cm^{-1}$ (standard deviation=0.1, n=4), prepared under ambient dry conditions. Shear bonding strength of the lap joint (cross-sectional area=2.54 cm×2.54 cm) was also measured, 1.1 MPa (standard deviation=0.3, n=4)—similar to Dopa-functionalized polypeptide prepared under ambient dry conditions, 0.9 MPa. The bulk test results shown here did not overwhelm the previously reported bulk adhesives, but it was expected because the small molecular surface primer is not a bulk adhesives. Nevertheless, the results present that the zwitterionic surfactants were capable of micro-gap-filling as well as nano-gap-filling shown in AFM and SFA, and indicate that they are more versatile than surface primers. The results also attest to the self-assembling ability of Z-Cat-C10 (FIGS. 13A-13C, double bilayer structure).

X-Ray Photon Spectroscopy (XPS)

Kratos Axis Ultra (Kratos Analytical, Manchester UK), was conducted with survey scans at a pass energy of 160 eV, and high-resolution scans at a pass energy of 40 eV. XPS of copper plate (FIGS. 18-20) showed the copper surface contains ~60:40 oxide:hydroxide. However, silicon wafer (FIGS. 21-23) has only oxide. The hydroxide is thought to weaken the adhesion to copper plate in AFM compared to silicon wafer in addition to its higher RMS roughness.

Nano Layer Adhesion to Silica Surface

Silica beads (diameter φ=100 nm) dispersion (10 mg $ml^{-1}$ in DI water) was spread on a silicon wafer coated with Z-Cat-C10 described above. The glued beads were, then, rinsed thoroughly with DI water. The resulting surface was then imaged with SEM to determine if the beads adhered to the Z-Cat-C10 coated silicon wafer surface. The beads were maintained to adhere onto the silicon wafer surface (FIG. 13E) whereas there is no silica bead on the bare silicon wafer surface. The strength of adhesion and film dimensions of catechol hold particular promise for nano-length scale tailoring that obviate current thicker adhesion promoters, e.g., high performance nanometer thin adhesives to enhance the power delivery and energy storage capacity of Li-ion batteries with high density of silicon nanoparticles by replacing the thick polymer adhesive binders currently used in Li-ion battery anodes.

Critical Aggregation Concentration (CAC)

Aqueous colloidal dispersions of each homolog were prepared in deoxygenated deionized (DI) water. The critical aggregation concentration (CAC) was determined from the solution surface tension of varying homolog concentrations in deionized (DI) water (e.g., see the line of Z-Cat-C10 in FIG. 2B) by Wilhelmy plate tensiometry and has been described elsewhere. Use of the CAC instead of CMC here is a hedge to accommodate the uncertainty about whether micelles or other soluble aggregates were forming.

Cyclic Voltammetry

Cyclic voltammetry was performed on a Versastat 3 potentiostat from Ametek Co. (Berwyn, PA). These analyses were carried out using a three-electrode cell: a Pt wire as the counter electrode, an Ag/AgCl reference electrode, and a Carbon paste electrode (CPE) served as the working electrode. CPE is the best choice for adhesive materials because of its ability to be completely polished before each experiment.

Measuring Adhesive and Cohesion Energies

The adhesion/cohesion energy of the synthetic zwitterionic molecules was investigated in SFA (SurForce LLC, Santa Barbara, CA). Two molecularly smooth freshly cleaved back silvered mica surfaces glued on cylindrical silica discs of radius of curvature, R~2 cm, were mounted in the SFA and 50 µL of a colloidal dispersion of the synthetic molecules in DI water were injected between the surfaces at different concentrations (C=0.5-5 mM) and the forces between the thin films of the molecules were measured by Multiple Beam Interferometry (MBI). The adhesion forces between Z-Cat-C10 molecules on various surfaces, e.g., silica and copper, were also measured by AFM (MFP-3D, Asylum research, Goleta, CA) in DI water and ambient conditions, respectively, at room temperature. AFM probes with a silicon dioxide particle (10, 5, and 1 µm, respectively) on a silicon nitride (SN) cantilever-0.6 N $m^{-1}$ were purchased from Novascan Technologies, Inc (Ames, IA). Cantilever spring constants were measured for each force run. Images of Z-Cat-C10 coating on silicon wafer and copper plates were visualized in an AFM.

Cryo-TEM

Cryo-TEM vitrified specimens were prepared in a controlled environment vitrification system (CEVS) at 25° C. and 100% relative humidity. The procedure is described in detail elsewhere. About 3 μL of the sample was applied onto a perforated ("lacey") carbon film-coated 200 mesh copper TEM grid. Excess liquid was blotted with filter paper, and the specimen was immediately plunged into liquid ethane at its freezing point (−183° C.). The vitrified specimens were transferred to a 626 Gatan cryo-holder, using it transfer station, and imaged at 120 kV acceleration voltage in an FEI Tecnai T12 $G^2$ TEM, using low-dose imaging to minimize electron-beam radiation-damage. Typical electron exposures were 10 to 15 $e^- Å^{-2}$. The specimens were kept in the TEM at about −175° C. Images were digitally recorded with a Gatan US1000 high-resolution (2 k×2 k pixels) cooled CCD camera, using the Digital Micrograph software.

QCM-D

A "static cell" (often called "Open Model") QCM-D (Q-Sense, Biolin Scientific, Linthicum Heights, MD) was employed to qualitatively show the adsorption of the zwitterionic molecules onto mineral and metal oxide surfaces.

XPS

XPS (Kratos Axis Ultra, Kratos Analytical, Manchester UK), was conducted with survey scans at a pass energy of 160 eV, and high-resolution scans at a pass energy of 40 eV. Nano layer adhesion to silica surface was imaged with SEM after rinsing silica beads (diameter φ=100 nm) dispersion (10 mg $ml^{-1}$ in DI water) spread on a silicon wafer coated with Z-Cat-C10 thoroughly with DI water.

Perfect Self-Assembled Monolayers on Dielectric Surfaces

Despite the need for molecularly smooth self-assembled monolayers (SAM) on silicon dioxide surfaces (the most common dielectric surface), current techniques are limited to non-ideal silane grafting. Here, it is demonstrated that the formation of a molecularly smooth (defect-free) SAM on various dielectric surfaces including silicon dioxides using a bio-inspired zwitterionic molecule [catechol-$(CH_2)_3$-phosphate-$(CH_2)_2$-quaternary ammonium-$(CH_2)_3$-benzene or -benzene-$(CF_3)_2$]. A combination of experimental and computational techniques confirms uniform thickness (~0.5 or ~1 nm) and orientation (all catechol head groups facing to the oxide surface) of the "monomolecular" layers. This defect-free (molecularly smooth), robust (strong bidentate binding of catechol to oxide surfaces), rapid (processing time <1 min), and green (using only water at room temperature) SAM represents a quantum leap towards the next generation of nanofabrication (e.g., SAM fabrication in organic field-effect transistors) compared to the current non-uniform and inconsistent polysiloxane-based SAM involving toxic chemicals, long (>10 h) processing time, and/or heat (>80° C.).

Self-assembled monolayers (SAMs) refer to spontaneous formation of organic assemblies on surfaces by physicochemical adsorption of molecules from a liquid or vapor phase through synergistic intermolecular interactions. SAMs provide a convenient and flexible platform to tailor the physicochemical properties of substrates, and have gained significant attention over the past decade in the area of lithography, electronic materials, molecular recognition, non-wetting surfaces and biomimetic systems. However, current SAM fabrication techniques are still far from ideal or practical because (a) organosulfur-based SAMs require oxide-free surfaces, (b) organosilane-based grafting do not form a smooth nor uniformly thin SAMs because the silanes polymerize internally to form siloxane linkages and only 10-20% of the chains bond to the surface, and (c) catecholic grafting on titanium oxide, phosphonic grafting on silicon dioxide or aluminum oxide or carboxylic grafting on zinc oxide is yet to be well-defined to form a reproducible defect-free "monomolecular" layer on a surface. The uniformness (defect-free) of SAM is critical for nano-electronic fabrication. Defects in SAMs generated from non-uniform adsorptions can cause catastrophic failure of electronic devices through change in the charge transfer properties of the underlying substrate due to penetration of impurities or damage of a bilayer through polymer penetration rendering them unreliable for desired applications. The present application shows molecularly smooth, uniformly thin, defect-free SAMs via a robust water-mediated process that overcomes the difficulties associated with existing technologies. Furthermore, there is a need in nanotechnology for flawless SAMs on various oxides substrates formed via an industrially and environmentally viable process inspired by biological self-assemblies of interfacial mussel foot proteins (mfp-3 and -5) (FIG. 31). FIG. 31 shows a mussel anchored by byssal threads and plaques to a surface; schematics of the mussel plaque showing the location of the mussel foot proteins (mfps); primary sequence of mfp-3s, mfp-3f and mfp-5; Z-Cat-Ben, a zwitterionic surfactant inspired by mfp-5; and a cartoon of the self-assembly of the Z-Cat-Ben molecules on a mineral surface. By modifying the alkyl tail group of a previously reported catecholic zwitterionic surfactant to a benzene ring. The adhesive "bilayer" was transformed to a self-assembled "monolayer" (SAM). To meet the current demand for manufacturing nano-electronic devices, a stable, molecularly smooth, defect-free SAM on dielectric surfaces is urgently required and is reported in this work.

Figure 32:
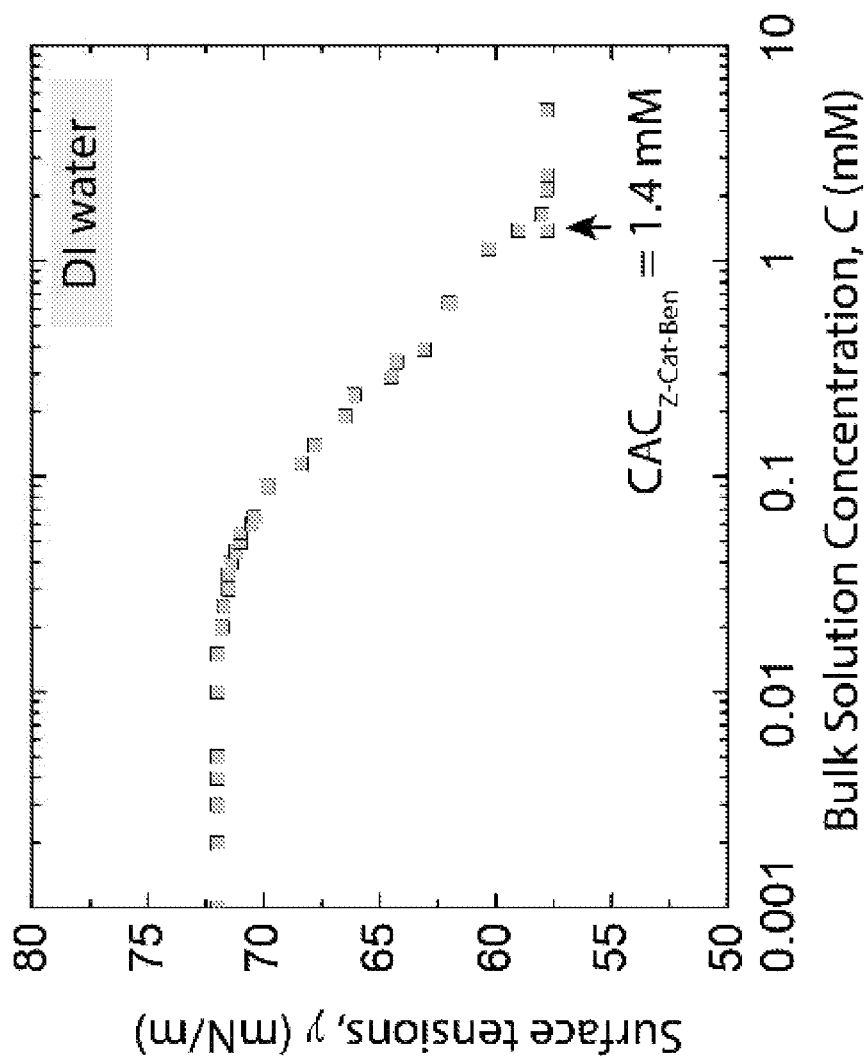
FIG. 32 is a graph showing Surface tension vs. Bulk concentration for Z-Cat-Ben as measured in a Langmuir Blodgett trough.
Figure 33A:
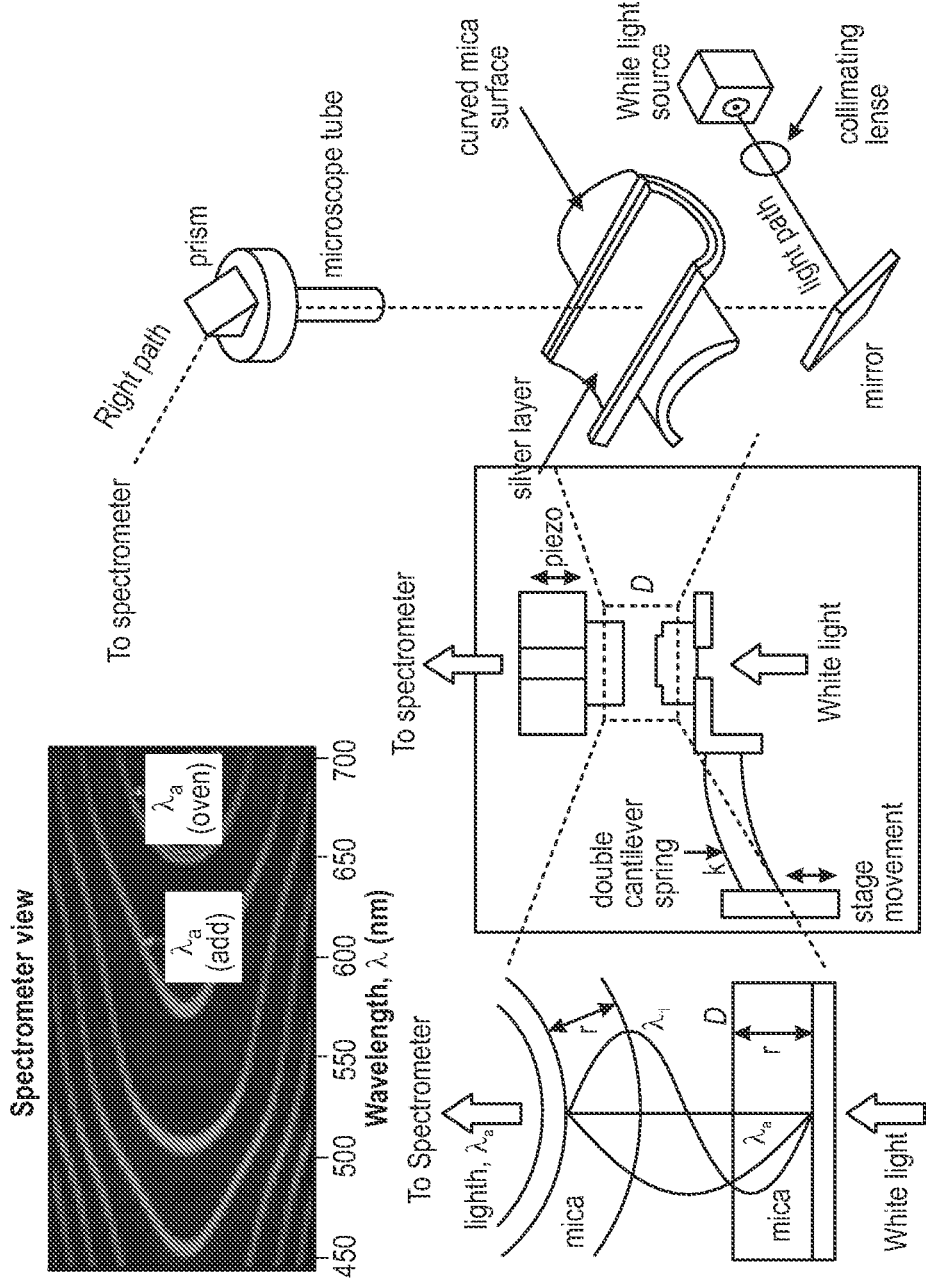
FIGS. 33A-33D) area Surface force and profile of the SAM.

The aqueous solution (bulk concentration 5 mM>critical aggregation concentration (CAC), see FIG. 32) of newly designed catecholic zwitterionic molecules (FIG. 31) formed a SAM in less than 1 min after simple drop-casting onto various mineral and metal oxide surfaces including mica, silica, copper oxides/hydroxides, zinc oxides, titanium oxides, and indium-tin oxides. The surface profile, interfacial force, layer-thickness, chemical configuration and the molecular orientation of the SAMs were confirmed by Atomic Force Microscope (AFM), Surface Force Apparatus (SFA) (FIGS. 33A and 33B), X-ray scattering, and Molecular Dynamics (MD) simulations. Surface profiling of the SAMs on mica, silica and copper oxides/hydroxides showed that the molecules rapidly (t<1 min) self-assemble onto the substrates forming molecularly smooth and uniformly thin monomolecular layers (FIG. 33C) unlike organosilane-based polymer layers. The cross section (below) showing the surface roughness of the deposited SAM film.

Figure 33B:
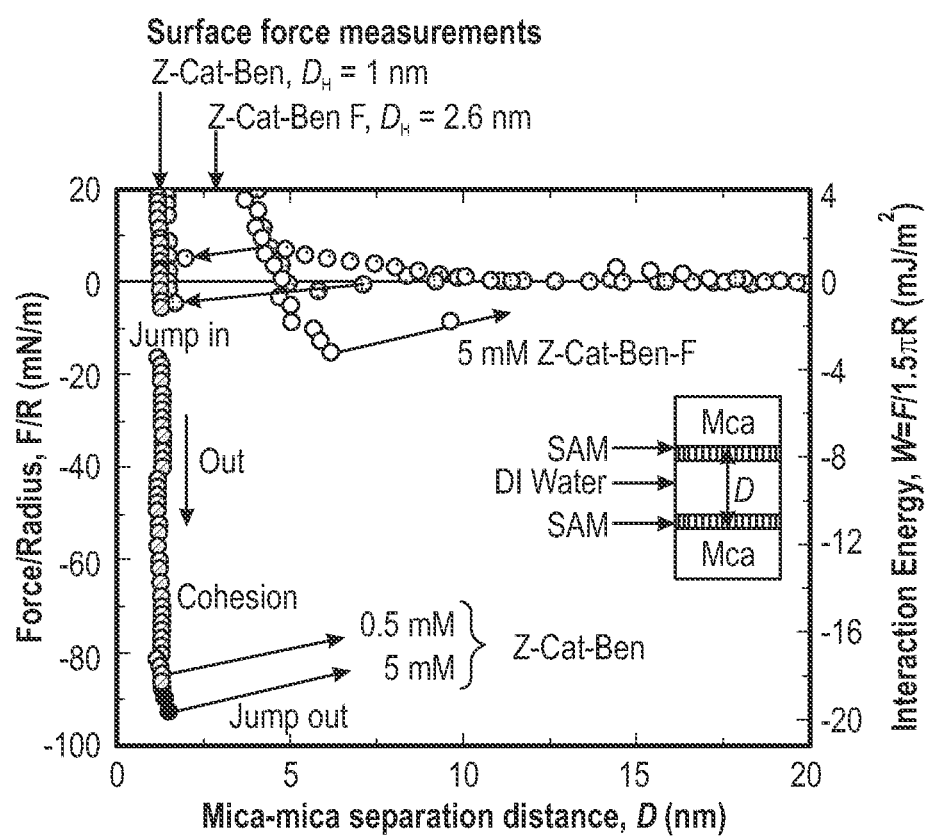
Figure 33C:
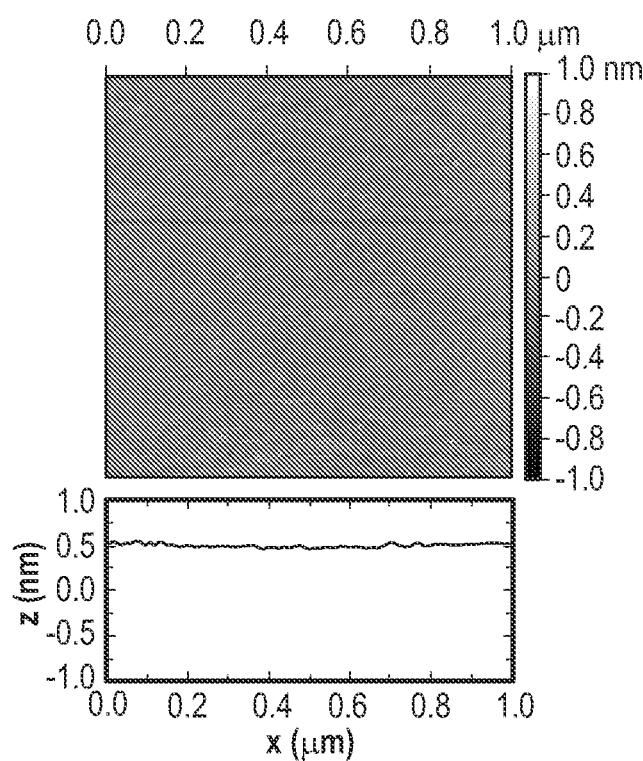
Figure 33D:
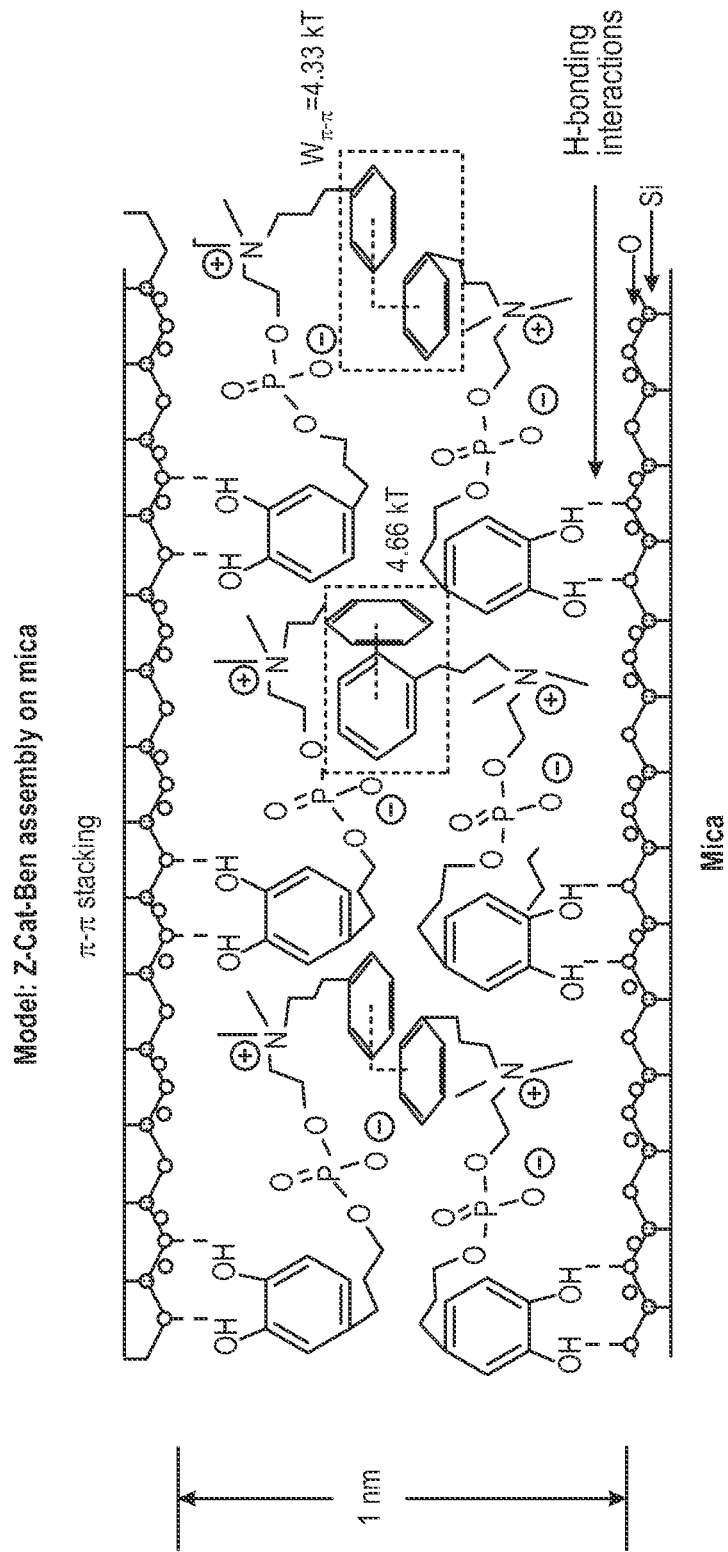
Figure 34:
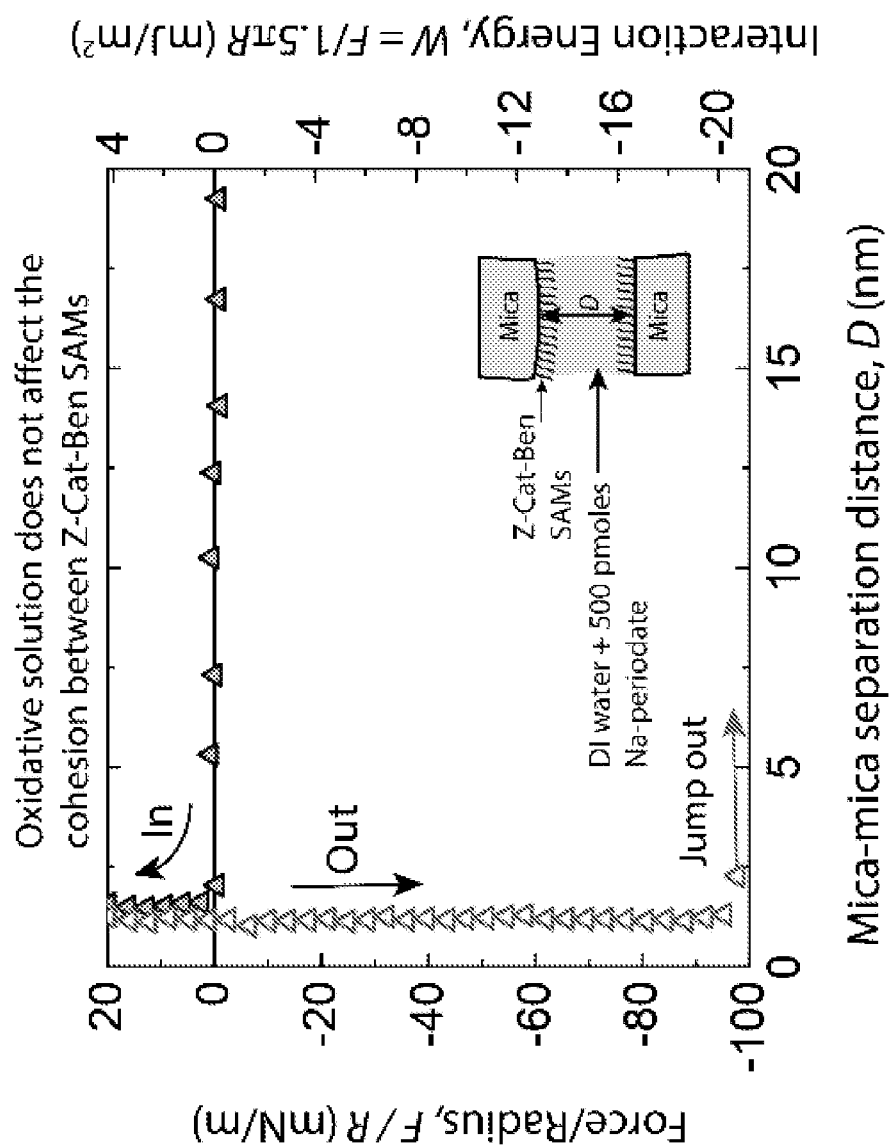
FIG. 34 is graph showing Representative force vs. distance plots between Z-Cat-Ben monolayers deposited onto mica at 5 mM concentration in DI water.
Figure 35A:
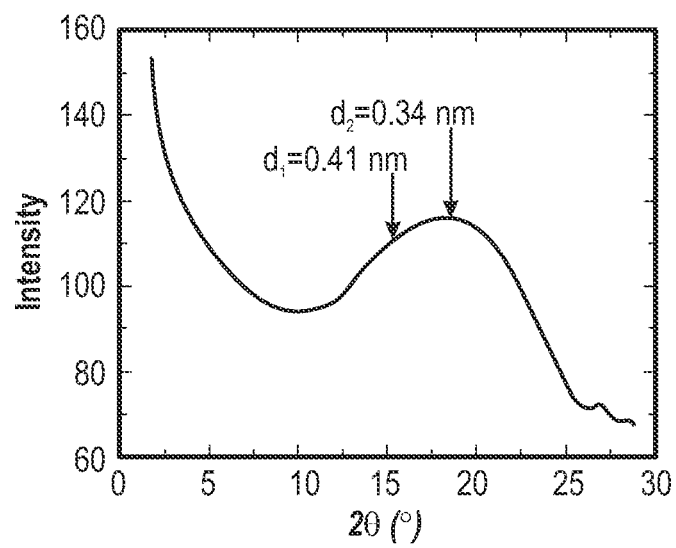

The structure-function relationship for the zwitterionic SAMs was investigated to understand the effects of electronegative residues on the benzyl group by adding electron withdrawing —$CF_3$ groups in the 3 and 5 positions on the benzyl tail of Z-Cat-Ben-F (FIG. 31). The change in the electron density of the aromatic residue due to —$CF_3$ flanking in the meta positions did not alter the monolayer assembly of the molecules and, Z-Cat-Ben-F also formed an uniform monolayer (the AFM images were same as Z-Cat-Ben shown in FIG. 33C). Z-Cat-Ben-F exhibits a repulsion between the electronegative —$CF_3$ residues (significantly weaker cohesive interaction of $W_c$, =3.3±1.0 $mJ/m^2$ compared to Z-Cat-Ben), which in turn result in a thicker hard-wall (the limiting distance between the mica surfaces during the approach run in the SFA) of 2.6±0.4 nm (FIG. 33B). The same cohesion energy ($W_c$~20 $mJ/m^2$) and hard-wall thickness (~1 nm) measured between the SAMs (~0.5 nm thick SAM on each mica surface) before and after (a) periodate (FIG. 33B) and (b) stoichiometric iron treatments (see FIG. 34) in SFA suggests that all the catechol moieties in the SAM are recruited to the mica surface whereas all the benzyl groups in the SAM are exposed to the aqueous interface (FIG. 33D in agreement with the simulation results in FIG. 35C-35G). Hence, the interaction energy measured between Z-Cat-Ben SAM surfaces (W=19±3 mJ/m$^2$) across the surfaces can be primarily attributed to π-π interaction between the benzyl groups (FIGS. 33B and 33D) as the contributions from other interactions such as electrostatic and van der Waals forces are much weaker under these conditions. Two favorable possibilities for the π-π interaction between the aromatic groups are (a) parallel displaced stacking with $W_{π-π}$=10.79 kJ/mol or 4.33 kT and (b) T-shaped stacking with $W_{π-π}$=11.62 kJ/mol or 4.66 kT (FIG. 33D, in agreement with X-ray scattering results shown in FIGS. 35a and 35b). This can be translated into a molecular density of one Z-Cat-Ben molecule per four crystal lattice (1 nm spacing) binding to the mica surface or $1.07×10^{18}$ molecules per m$^2$ (FIG. 33D). The cohesive energy measured across the SAM films in the SFA is in agreement with the theoretical predictions for π-π interactions between the films within 2% error. Each adsorbed Z-Cat-Ben and Z-Cat-Ben-F molecule causes a steric radius of influence (varying between ca. 0.3 and 0.6 nm, as shown from the simulations, see FIG. 35D) preventing other molecules from adsorbing to the immediate lattice site at the mineral-water interface.

Figure 36:
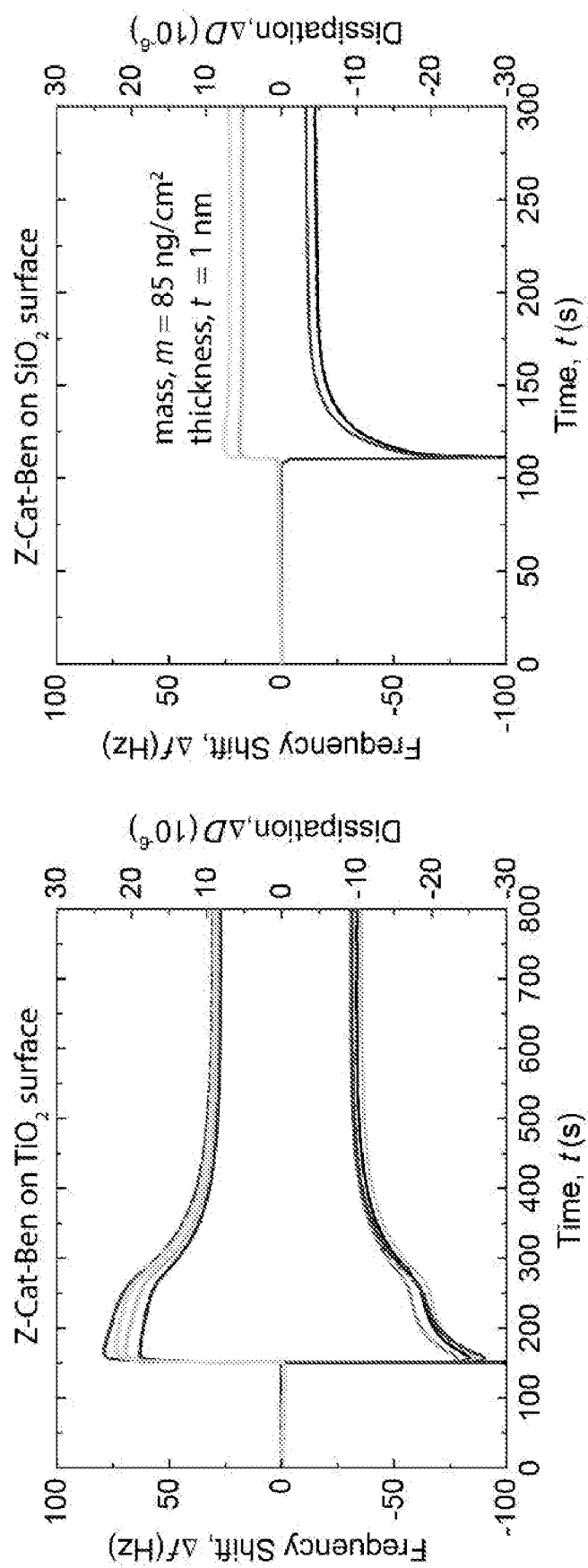
FIG. 36 shows two graphs of QCM-D experiments showing the adsorption of all molecules onto a $TiO_2$ and $SiO_2$ surfaces.

Quartz crystal microbalance with dissipation (QCM-D) also showed that the zwitterionic molecules adsorbed strongly on silica surface (mass, m=85 ng/cm$^2$, thickness, t=1 nm) under zero externally applied pressures. As shown in FIG. 36, QCM-D experiments showing the adsorption of all molecules onto a TiO$_2$ and SiO$_2$ surfaces. The 100 μL of 5 mM solution of the molecule was deposited onto a titania or silica surface in DI H$_2$O using a static cell. Frequency and dissipation change upon adsorption of the Z-Cat-Ben molecules to a titania and silica surface was measured and modeled using QTools data analysis Software® (Voigt model) from QSense®. It should be noted that the calculations and approximations are accurate for small change in dissipation ($<5×10^{-6}$).

Figure 38:
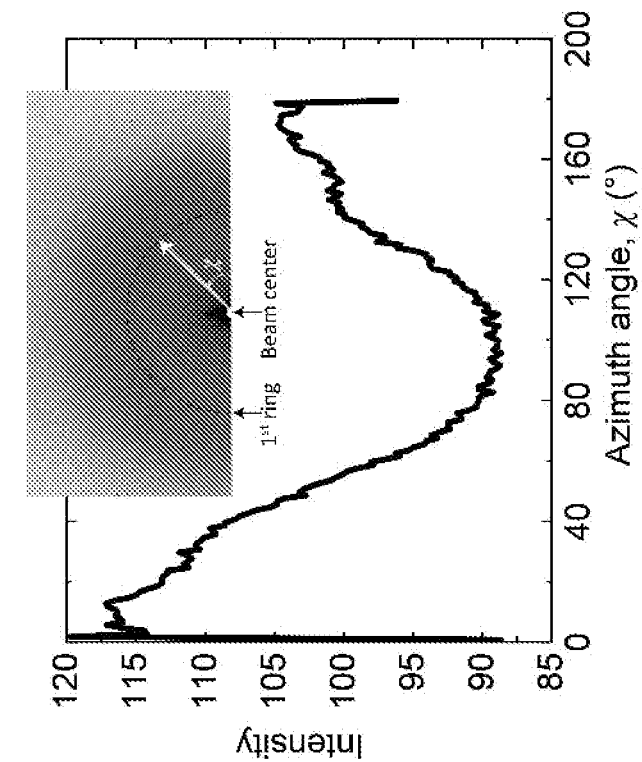
FIG. 38 is a graph showing overall the first peak χ profile shows the same trend as the second peak, with highest intensity near χ=0 or 180°. This confirms preferred orientation parallel to the surface. However, there are also two secondary peaks at χ~400 and 140°, respectively. This suggests that there is also preferred orientation at tilt angle of ~40° above the surface.
Figure 37:
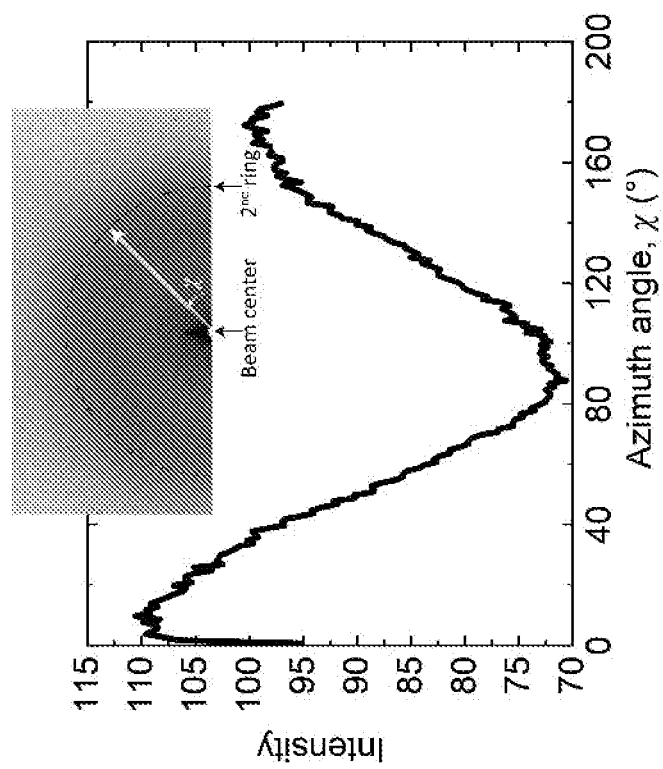
FIG. 37 is a graph showing Azimuthal angle, χ, scan data for second peak shows clear preferred orientation (higher intensity) on the equatorial (approximate χ~0° or 180°) direction, whereas the intensity is lower (but non-zero) on the meridian (χ~90°). This suggests that the stacking direction lies in plane predominantly.

Surface orientation of SAM was investigated with a custom-built 2D grazing incidence small- and wide angle X-ray Scattering (GISAXS and GIWAXS) instrument equipped a Cu target microfocusing X-ray source (Genix by Xenos SA), scatterless slit collimator and a hybrid pixel X-ray 2D photo counting detector (Piatus100K by Dectris) (FIGS. 35A, 35B and FIGS. 37 and 38). Two broad peaks were observed in the scattering data, which correspond to characteristic spacing of 0.34 nm and 0.41 nm. These spacings are consistent with parallel displaced stacking of π-π interaction (FIGS. 35A and 35B) in plane (projected perpendicularly onto a reference plane). Azimuthal intensity profiles (χ scan; the angle between the projected vector and a reference vector in the reference plane) at the two peak positions show pronounced intensity increase in the in-plane direction (χ~0° or 180°), suggesting that preferred direction of stacking is parallel to the substrate (FIGS. 37 and 38).

Figure 35B:
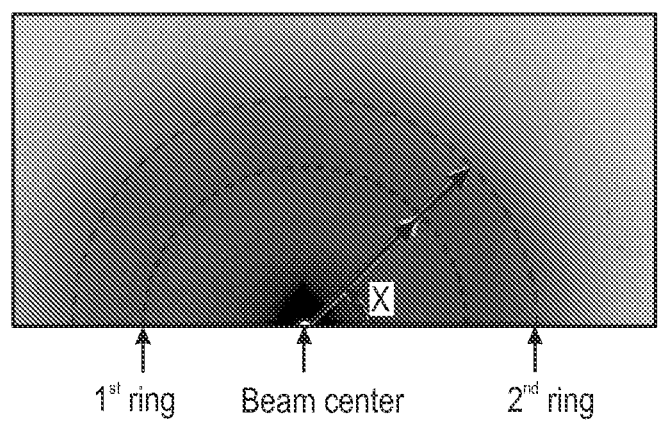
Figure 35C:
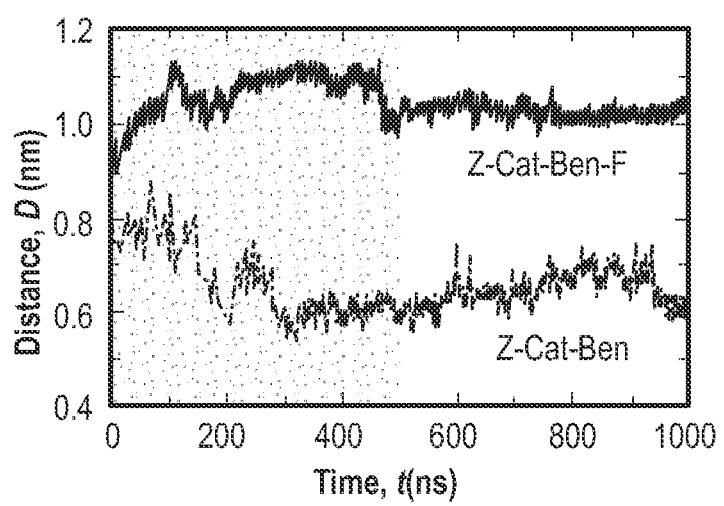
Figure 35E:
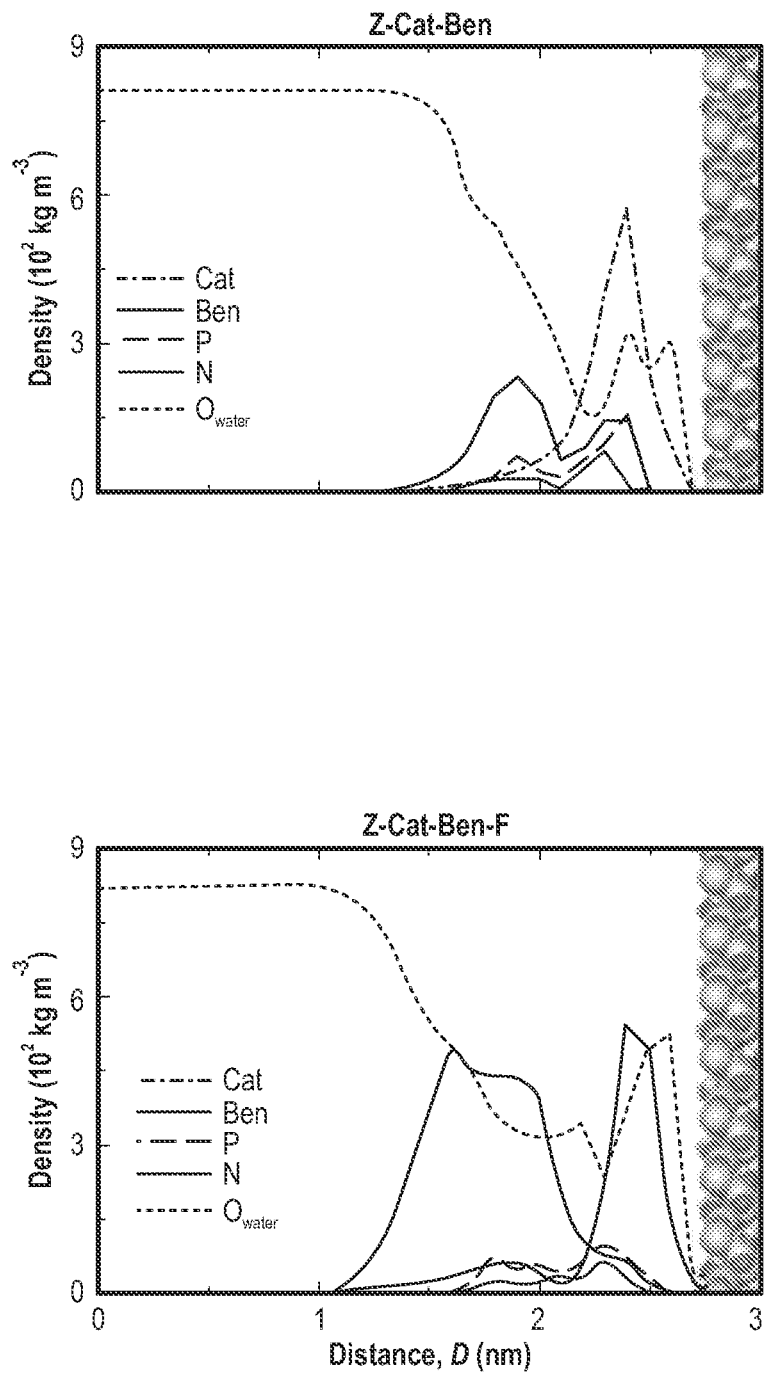
Figure 35F:
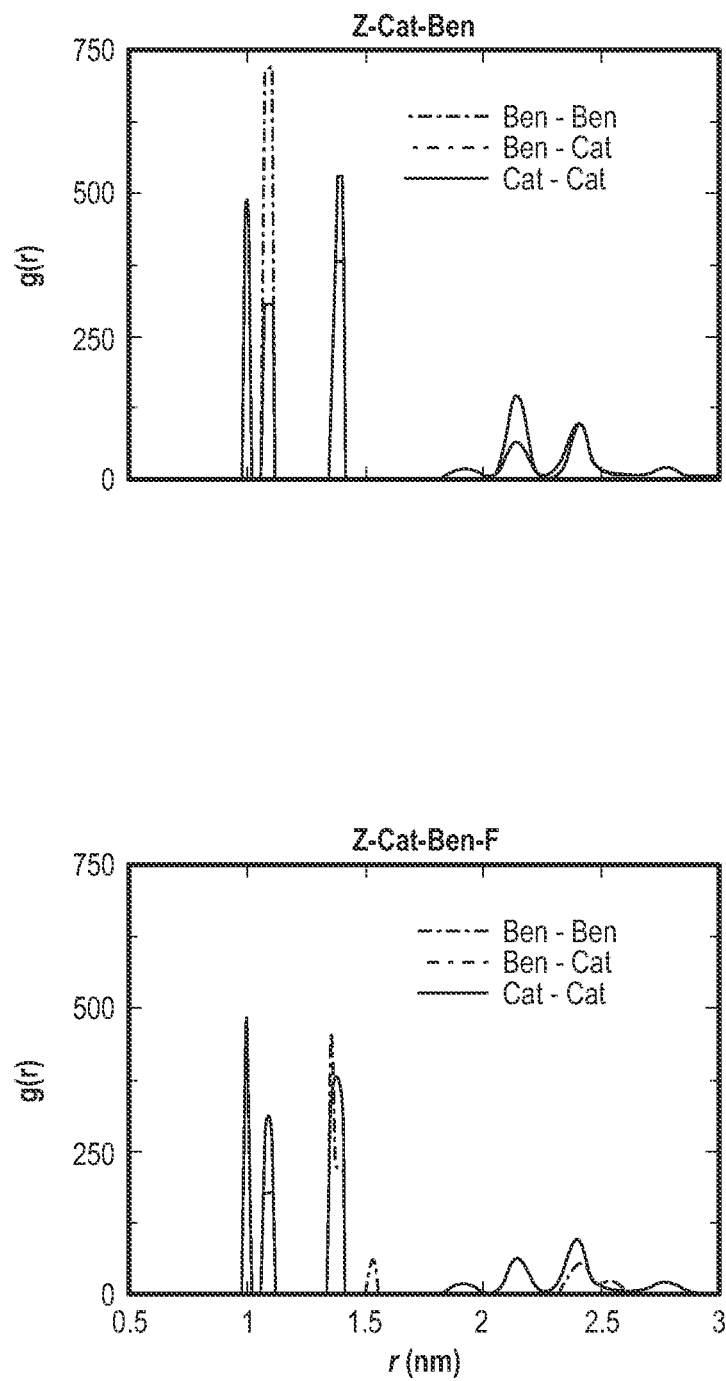

In addition, MD simulations was carried out to characterize the molecular adsorption and the configuration of the Z-Cat-Ben and Z-Cat-Ben-F molecules on a model crystalline silica surface. At a density of $1.0×10^{18}$ molecules per m$^2$, after 1 μs of simulation, Z-Cat-Ben and Z-Cat-Ben-F molecules are shown to be densely packed at the mineral surface and the results from the simulations corroborate the experimental findings: (a) the thickness of the monomolecular layer was ca. 0.65 and 1.05 nm for Z-Cat-Ben and Z-Cat-Ben-F molecules, respectively (see FIG. 33B, in close agreement with the SFA estimates of for DH of ca. 0.5 and 1.3 nm, as shown in FIG. 33B; (b) steric radius of influence compatible with X-ray Scattering experiments (see FIG. 35D): (c) catechol groups are recruited to silica surface through interactions involving their hydroxyl groups (see FIGS. 39A-39B), whereas (d) benzene groups are away from the mineral surface (FIG. 35E). Such arrangement results in catechol-catechol and benzene-benzene interactions, but not catechol-benzene interactions (FIG. 35F). Simulations reveal that molecular adhesion to silica surfaces is more energetically favorable compared to the dimerization of two adjacent catecholic molecules (see FIGS. 40A-40B). The simulation data also shows that catechol groups are mostly shielded from water (see FIGS. 41A-41B). Binding of the solute takes place at the expense of a significant desolvation of the mineral surface (FIG. 35eE). It can also be seen that the desolvation level is more pronounced for Z-Cat-Ben than Z-Cat-Ben-F. This is consistent with Cyclic Voltammetry (CV) measurements that showed that both Z-Cat-Ben and Z-Cat-Ben-F molecules are stable (shelf life) in water to oxidation (see FIG. 42) due to the shielding of the catechol residues by neighboring hydrophobic or electrophilic groups.

The two-dimensional average radius of gyration for Z-Cat-Ben shows two peaks at 0.31 and 0.47 nm for Z-Cat-Ben (FIG. 35D, top), which corresponds to the molecular spacing perpendicular to the mineral surface. The same quantity for Z-Cat-Ben-F is shifted towards higher values, with three peaks at 0.37, 0.43 and 0.54 nm (FIG. 35D, bottom), indicating less confined packing upon addition of the two extra —CF$_3$ groups and therefore higher solvation at the mineral surface (FIG. 35E).

Figure 35G:
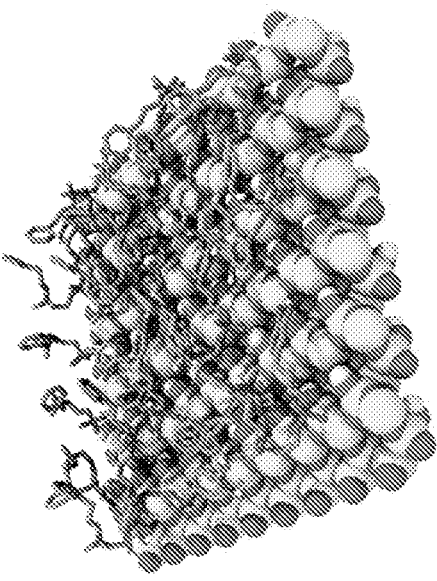

The combination of experimental (SFA, AFM, QCM-D, X-ray scattering) and computational (MD simulations) studies establishes the monomolecular self-assembly on a mineral surface as illustrated in FIG. 35G.

A molecularly smooth and thin SAM on gate dielectric surface is an essential component in nanofabrications for the next generation of electronic devices, e.g., organic field-effect transistors (OFETs). Especially for bottom-gated FETs, defect-free SAM is required to prevent undesired charge trapping by surface states on metal oxide (most often SiO$_2$) or polymer gate dielectrics upon carrier transport and to control carrier injection at metal/organic interface, thereby leading to high carrier mobility and reliable device properties. For the sake of an industrially, environmentally and economically viable fabrication perspective, a short processing time (here, <1 min) and green solvents (here, water) are imperative to form SAMs on a dielectric surface, only such SAMs will allow low-cost and high-throughput printing technologies. Although efforts to form uniform SAM through instant spin casting of alkoxysilanes have been reported previously, they require 10-17 hours of post solvent treatment using strong acid or base after spin casting and specific toxic solvents for uniform formation of SAM onto SiO$_2$ substrates. Capillary action of polymer solution on n-decyltrichlorosilane (n-DTS)-modified nano-grooved SiO$_2$ substrates enhances polymer alignment through directed self-assembly of polymer chains, thereby resulting in high saturation hole mobilities, 23-58 cm$^2$ V$^{-1}$ s$^{-1}$. Despite such high mobility, however, the surface modification using n-DTS inevitably requires toxic chemical-mediated long treatment time (>10 h) and/or high temperature (>80° C.) for effective surface coverage, which cannot be considered in practical applications such as high-throughput printing technologies, one of the most important operating assets of organic electronics. Therefore, the present molecularly smooth SAMs formed in <1 min through a facile aqueous solution treatment method (e.g., drop or dip coating) is indeed a breakthrough for a variety of "printed" electronics applications.

To evaluate performance of the Z-Cat-Ben and Z-Cat-Ben-F SAMs in OFETs, bottom-gate bottom-contact devices was fabricated by casting a regioregular polymer, poly[4-(4,4-dihexadecyl-4H-cyclopenta[1,2-b:5,4-b']dithiophen-2-yl)-alt-[1,2,5]thiadiazolo-[3,4-c]pyridine](PCDTPT), on nano-grooved SiO$_2$ substrates modified with Z-Cat-Ben or Z-Cat-Ben-F SAMs as the gate dielectric in the sandwich casting system (see FIGS. 43A-B and 43D-E).

The enhanced oleophilicity of the nano-grooved SiO$_2$ substrates modified with Z-Cat-Ben or Z-Cat-Ben-F was confirmed by contact angle measurements (FIG. 43C). The SAM-modified substrates produced lower contact angles ($\theta \approx 1°$ for Z-Cat-Ben and $\theta < 10°$ for Z-Cat-Ben-F) of a chlorobenzene droplet (solvent for PCDTPT solution used in OFET fabrication), compared with that ($\theta \approx 31°$) of a droplet on the n-DTS-modified substrate. These results imply that SiO$_2$ substrates modified with the present SAMs are more favorable to be wetted by organic (PCDTPT) solution during the film-forming process, which is crucial for achieving uniform thin films and high performance. More interestingly, the SAMs are not only oleophilic but also hydrophilic, i.e., omniphilic with <30° contact angle of water droplet, so as to easily allow water (or alcohol)-mediate fabrications.

The transistor characteristics show typical unipolar p-type transistor behavior and clear saturation in the output curves (FIGS. 43d, 43e, 43f and 44). It is noted that saturation mobility is gate voltage dependent and the focus was on high mobility regime ($\leq$-10 V) needed for digital electronics. The Z-Cat-Ben and Z-Cat-Ben-F devices with Au source and drain electrodes yielded high saturation hole mobilities, μ, of 22±4 cm$^2$ V$^{-1}$ s$^{-1}$ (n=5) and 26±5 cm$^2$ V$^{-1}$ s$^{-1}$ (n=3), respectively (FIG. 43D). To assess broader applicability of the SAM molecules, the Z-Cat-Ben-F SAM (slightly higher saturation hole mobility than the Z-Cat-Ben SAM) in OFETs with Ni source and drain electrodes was further investigated, which is known to reduce contact resistance for efficient hole injection. The Z-Cat-Ben-F SAM device exhibited an enhanced saturation hole mobility of 46±4 cm$^2$ V$^{-1}$ s$^{-1}$ (n=3) (FIGS. 43E and 43F), reaching the highest range value for OFETs reported to date.

In summary, the Z-Cat-Ben and Z-Cat-Ben-F molecules are remarkable in demonstrating the rapid formation of a robust and defect-free SAM on various mineral and metal oxide surfaces through simple water-mediated procedure. This study presents not only paramount progress for solution-processed transistors with high performance in the nanofabrication of dielectric interfaces, but also provides molecular design guidelines of SAM on various oxide surfaces. The structural integrity of the molecules on a substrate due to (a) strong bonding of the catechol groups to oxide surfaces and b) uniformly dense in-plane packing of the benzyl groups results in a robust functional interface, and can be exploited for nanosensing devices, organic solar cells, opto-electronic devices, hetero-junctions, and electron tunneling junctions.

Methods

Synthesis of the Molecules

All synthetic manipulations were carried out under an atmosphere of Argon unless otherwise noted, and no attempt was made to optimize reaction yields. TLC plates (UV 254 indicator, glass backed, thickness 200 mm) and silica gel (standard grade, 230-400 mesh) were purchased from Merck. Bonded C2 reverse phase silica was prepared as previously described[1] or purchased from Analtech (Catalog number 08010). Normal phase flash chromatography was performed manually in glass columns. Reverse phase flash chromatography was performed with bonded C2 reverse phase silica hand packed in plastic columns and performed on a Biotage SP4 chromatography system. Diethyl ether, THF, ethyl acetate, and hexanes were purchased from Fisher Scientific. Diethyl ether and THF was taken from Innovative Technologies Solvent Purification System (SPS) and used immediately. Dimethylformamide (DMF) and Acetonitrile (MeCN) were purchased pre-dried from Spectrum and stored over activated 4 Å or 3 Å molecular sieves respectively after opening. Et$_3$N was distilled and stored on activated 4 Å molecular sieves under argon. NMR solvents were purchased from Cambridge Isotopes Laboratories. NMR spectra were recorded at 23° C. on Varian Unity INOVA (500 and/or 600 MHz) spectrometers. NMR spectra were processed using the MestreNova software package and processed with automatic phase correction, and automatic baseline correction using Bernstein Polynomial fitting. Reported chemical shifts are referenced to residual solvent peaks[2]. Reported chemical shifts for multiplets are reported corresponding to the most downfield peak of the multiplet, where s=singlet, d=doublet, t=triplet, q=quartet, p=pentet, sex=sextet, sept=septet, m=multiplet, br=broad. IR spectra were acquired on a FTIR Perkin Elmer Spectrum Two: UATR Two spectrometer using 1 cm$^{-1}$ resolution. High resolution mass analyses were obtained using a 5975C Mass Selective Detector, coupled with a 7890A Gas Chromatograph (Agilent Technologies) as capillary column a HP-5MS cross-linked 5% phenylmethyl-polysiloxanediphenyl column (30 m×0.250 mm, 0.25 micron, Agilent Technologies) was employed. Helium was used as carrier gas at a constant flow of 1 mL/min.

Synthesis of Small-Molecule Zwitteronic Adhesives:

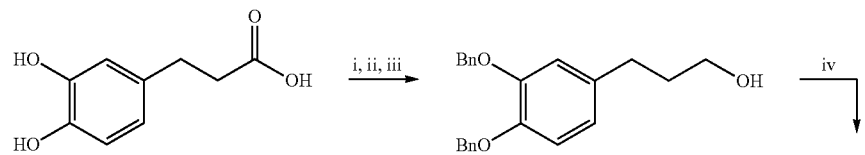

53 / 54

-continued

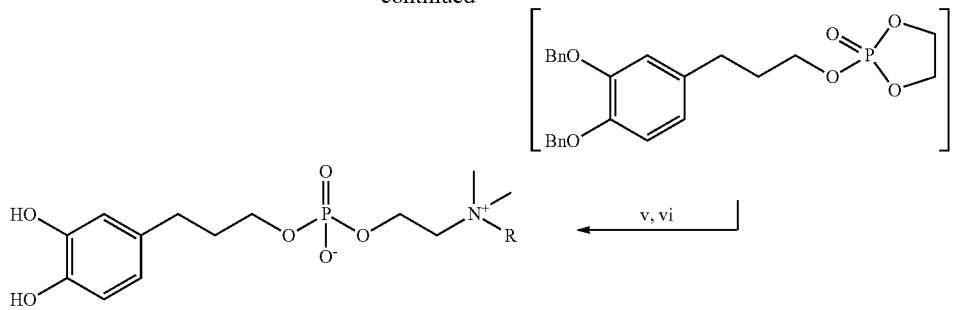

i) BnBr, DMF, K$_2$CO$_3$, 80° C., 24 h
ii) NaOH, MeOH 100° C. 4 h
iii) LiAlH$_4$, THF, overnight
iv) Ethylene chlorophospate, Et$_3$N, Et$_2$O, 0°, 4 h
v) RNMe$_2$, MeCN, 80° C. 2 days
vi) H$_2$ (1 atm), Pd/C, CH$_2$Cl$_2$/MeOH 2-4 days Synthesis of Starting Materials:

Benzyl 3-(3,4-bis(benzyloxy)phenyl)propanoate (2)

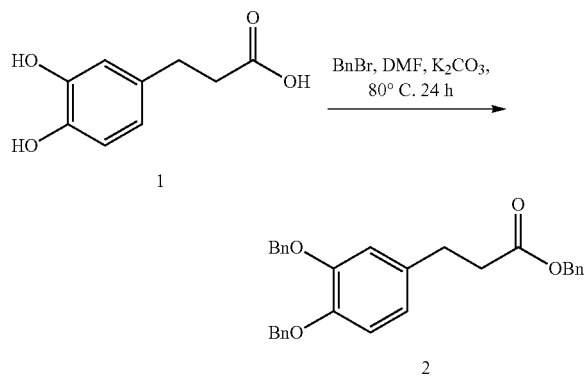

Benzyl 3-(3,4-bis(benzyloxy)phenyl)propanoate 2 was synthesized from 3-(3,4-dihydroxyphenyl)propanoic acid 1, purchased from Alfa Aesar, according to a previously described procedure[3] with slight modifications. As the carboxylic acid contains potentially air sensitive catechol moieties, after opening, the bottle of carboxylic acid was purged with argon, and the cap tightly wrapped with parafilm until subsequent use. While the previously published procedure was observed to work well on scales <5 grams, adequate stirring became problematic on the scales required for this work, and it is recommended that the procedure be performed with the largest possible football shaped stir bar that can fit into the flask. If stirring is observed to cease during the procedure due to caking of the base, one septa can be briefly removed while under positive Argon flow, and the solidified mass of K$_2$CO$_3$ at the bottom of the flask broken up gently with a dry metal spatula until stirring resumes, whereupon a fresh septa is added to the flask and the vessel stirred until completion on the reaction.

A flame dried 500 mL 3-necked round bottom flask was fitted with rubber septa and a large football shaped stir-bar and allowed to cool to ambient temperature under positive argon flow. Subsequently, 20 grams (1 equiv., 109.8 mmol) of 3-(3,4-dihydroxyphenyl)propanoic acid was added, followed by 200 ml of anhydrous DMF with stirring. Once dissolved, 90.9 grams of anhydrous K$_2$CO$_3$ (6 equiv., 658.7 mmol) was added with stirring. Then, 58.678 ml, of fresh benzyl bromide (4.5 equiv., 494 mmol) was added via syringe. The solution was placed in an oil bath set to 80° C. and stirred for 1 day at this temperature. After this time, no further reaction was observed by TLC, which also indicated the reaction was incomplete, and contained in addition to the desired product, a mixture of mono- and di-benzylated products. The reaction vessel was allowed to cool to room temperature. The reaction mixture was then poured through a large fritted glass funnel into a 2 L round bottom flask to remove solids, and the reaction vessel was rinsed 3×300 ml EtOAc through the frit. The solvent was then removed under reduced pressure with a rotary evaporator. To assist subsequent extraction, residual DMF was removed by 4 cycles of evaporation with toluene (500 ml). The crude residue was then redissolved in 1.5 L of Et$_2$O and washed 5×100 ml ice cold water, 1×500 mL Brine, dried over Na$_2$SO$_4$, and concentrated under reduced pressure. The crude residue was then dry-loaded onto silica gel and purified by flash chromatography gradient elution 10-40% Et$_2$O/hexanes in a large (18 inch tall) glass column. Fractions containing the only desired product were identified by TLC at R$_f$=0.31 (20:80 Et$_2$O:Hexanes, Stain=UV/Seebach's stain), pooled, and concentrated under reduced pressure to yield 17.42 grams of desired product. Fractions containing the two regioisomeric dibenzylated products, in which the carboxylic acid and either the 3- or 4-hydroxyl was benzylated, were identified by TLC at R$_f$=0.15 and 0.19 (20:80 Et$_2$O: Hexanes Stain=UV/Seebach's stain), pooled, concentrated under reduced pressure, and then resubjected to the reaction conditions to give an additional 20.56 grams of product, bringing the total amount of product to 37.98 grams in 76% isolated yield. The material was quickly checked for purity by $^1$H-NMR and then carried on immediately to the next step. If the yield of the initial reaction is not deemed objectionable, after removal of solvent, rather than collecting partially benzylated material and resubjecting it to the reaction conditions, the product can be more rapidly purified by 2 successive filtrations over a 6-8 inch tall pad of basic Al$_2$O$_3$ (Acros, 50-200 μm) eluting with 20% Et$_2$O/Hexanes.

$^1$H NMR (500 MHz, CDCl$_3$) δ (ppm): 7.45-7.41 (m, 4H) 7.38-7.27 (m, 11H), 6.85 (d, J=8.5 Hz, 1H), 6.80 (d, J=2 Hz, 1H), 6.70 (dd, J=2, 8.5 Hz, 1H) 5.12 (s, 2H), 5.10 (s, 2H), 5.09 (s, 2H), 2.88 (t, J=7.5 Hz, 2H), 2.63 (t, J=7.5 Hz, 2H)

3-(3,4-bis(benzyloxy)phenyl)propanoic acid (3)

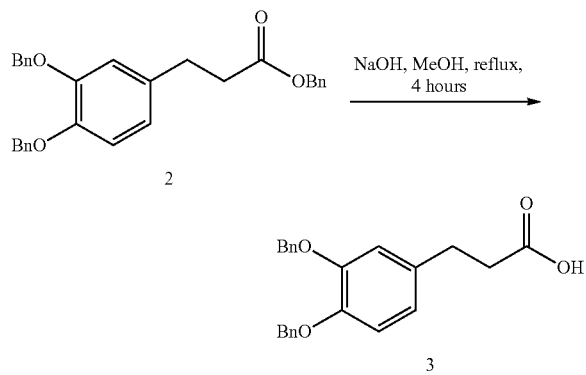

3-(3,4-bis(benzyloxy)phenyl)propanoic acid 3 was synthesized in 88% isolated yield by saponification of 2 as previously described. Spectral data matches that of previously reported. $^1$H NMR (500 MHz, CDCl$_3$) δ (ppm): 9.19 (s, 1H), 7.46-7.41 (m, 4H), 7.38-7.33 (m, 4H), 7.32-7.27 (m, 2H), 6.87 (d, J=8.5 Hz, 1H), 6.80 (d, J=2 Hz, 1H), 6.73 (dd, J=2, 8 Hz, 1H), 5.14, (s, 2H), 5.13 (s, 2H), 2.87 (t, J=7.5 Hz, 2H), 2.62 (t, J=7.5 Hz)

3-(3,4-bis(benzyloxy)phenyl)propan-1-ol (4)

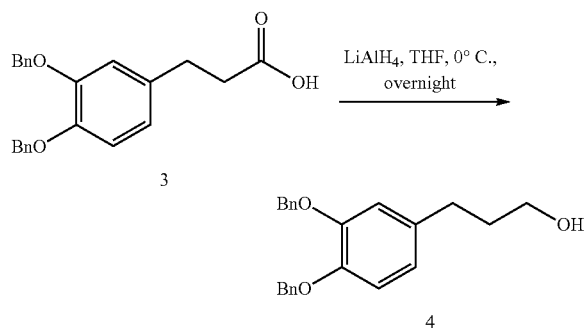

3-(3,4-bis(benzyloxy)phenyl)propan-1-ol 4 was synthesized from 3 in 89% isolated yield by reduction with LiAlH$_4$. 7.24 grams of acid 3 (20 mmol, 1 equiv.) were dissolved in 100 ml of anhydrous THF and cooled to 0° C. in an ice bath. 3.04 grams of LiAlH$_4$ (80 mmol, 4 equiv.) was then added carefully in 4 portions. The reaction was left to stir overnight under argon while warming to ambient temperature. The reaction was then quenched cautiously according to the Feiser workup, diluted with 100 ml of Et$_2$O and the aluminum solids were filtered off. The solution was then transferred to a separatory funnel, washed once with saturated NaHCO$_3$, dried over Na$_2$SO$_4$, filtered, and evaporated under reduced pressure to afford crude material. The crude material was subsequently purified on a pad of silica eluting with Et$_2$O. The compound was isolated as a clear viscous oil which gradually solidified over one week under high vacuum to a white wax. Over time, a slight pink coloration developed on the surface of the wax but this did not adversely purity as determined by $^1$H-NMR or negatively affect subsequent steps. Attempts to prepare this compound directly from the reduction of the corresponding benzyl ester led to unsatisfactory levels of purity, as benzyl alcohol co eluted with product in flash chromatography, while bulb to bulb distillation was inefficient and took extended times to reach a satisfactory level of purity.

Spectral data matches that of previously reported.

$^1$H NMR (600 MHz, CDCl$_3$) δ (ppm): 7.47-7.42 (m, 4H), 7.40-7.33 (m, 4H), 7.32-7.28 (m, 2H), 6.87 (d, J=7.8 Hz, 1H), 6.79 (d, J=1.8 Hz, 1H), 6.71 (dd, J=1.5, 8.1 Hz, 1H), 5.15 (s, 2H), 5.13 (s, 2H), 3.62 (q, J=6 Hz, 2H), 2.62 (t, J=7.5 Hz, 2H), 1.84 (p, J=7.2 Hz, 2H), 1.18 (t, J=5.7 Hz, 1H).

General Procedure for Preparation of Dimethylamides 5a-6a

Dimethylamides 5a-6a were conveniently prepared with 1-1' carbonyldiimidazole as peptide coupling reagent. A flame dried flask was fitted with a PTFE coated stir bar, rubber septa, and let cool to ambient temperature under positive argon flow. 1 equiv. of the corresponding carboxylic acid, 4 equiv. of anhydrous Et$_3$N, and anhydrous CH$_2$Cl$_2$ [0.5M] were added to the flask successively. The flask was cooled to 0° C. in an ice bath and stirred briefly, whereupon 1-1' carbonyldiimidazole (1.1 equiv.) was added portionwise, (gas evolution) the cooling bath was then removed, and the solution was stirred for an additional 30 minutes while warming to ambient temperature. Finally Dimethylamine as the hydrochloride salt, (2 equiv.), was added in one portion and the solution was stirred until TLC indicated completion. Upon completion the contents of the reaction vessel were transferred to a separatory funnel, diluted with CH$_2$Cl$_2$, and the organic layer was washed 2×1N HCl, 2×sat. NaHCO$_3$, and dried over Na$_2$SO$_4$. The organic layer was filtered, evaporated under reduced pressure, and the crude residue was filtered once over a pad of basic Al$_2$O$_3$ eluting with EtOAc, evaporated again, and purified by flash chromatography gradient elution with 50-100% EtOAc/Hexanes. Dimethylamides were obtained in high purity as determined by TLC, and not fully characterized at this stage as they were carried immediately on to the next step. Yields were not optimized.

N,N-dimethyl-3-phenylpropanamide (5a)

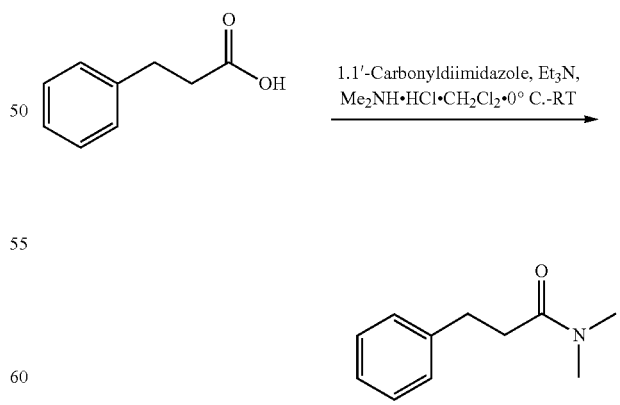

5a was prepared in 84% isolated yield according to the general procedure from hydrocinnamic acid and carried immediately on to the next step.

3-(3,5-bis(trifluoromethyl)phenyl)-N,N-dimethylpropanamide (6a)

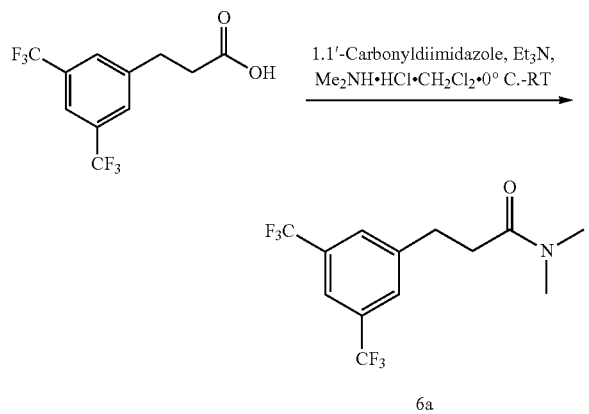

6a was prepared according to the general procedure in 77% isolated yield from 3,5-bis(trifluoromethyl)-hydrocinnamic acid (Aldrich) and carried immediately on to the next step.

General Procedure for Preparation of Dimethylamines 20-21

Dimethylamines 20-21 were prepared by reduction of dimethylamides 5a-6a with LiAlH$_4$. A flame dried flask was fitted with a PTFE coated stir bar, rubber septa, and let cool to ambient temperature under positive argon flow. 1 equiv. dimethylamide, anhydrous THF [0.2 M] was added, and the flask was placed in an ice bath and stirred for 10 minutes. LiAlH$_4$ (4 equiv.) was then cautiously added to the flask portionwise, and the solution was left to stir under argon overnight with warming to ambient temperature. The reaction was quenched cautiously according to the Feiser workup, diluted with Et$_2$O, and the aluminum solids were filtered off. The solution was then transferred to a separatory funnel, washed once with saturated NaHCO$_3$, dried over Na$_2$SO$_4$, filtered, and evaporated under reduced pressure to afford crude material. The crude residue was filtered over a short pad of basic Al$_2$O$_3$ eluting with Et$_2$O affording pure dimethylamines 20-21. Yields were not optimized.

N,N-dimethyl-3-phenylpropan-1-amine (20)

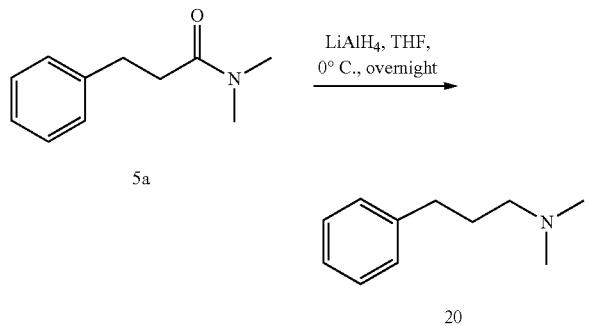

20 was obtained in 98% isolated yield from 5a according to the general procedure. Spectral data matches that of previously reported.

$^1$H NMR (600 MHz, CDCl$_3$) δ (ppm): 7.30-7.26 (m, 2H), 7.20-7.17 (m, 3H), 2.65 (t, J=7.8 Hz, 2H), 2.31 (t, J=7.8 Hz, 2H), 2.23 (s, 6H), 1.82 (p, J=7.8 Hz, 2H)

3-(3,5-bis(trifluoromethyl)phenyl)-N,N-dimethylpropan-1-amine (21)

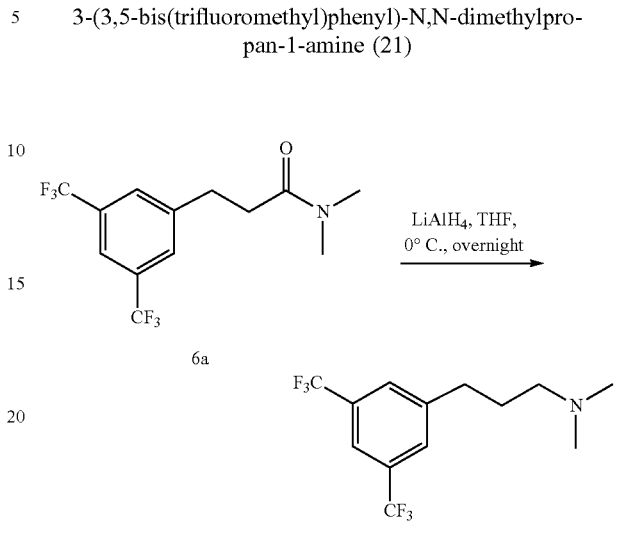

21 was obtained 95% isolated yield from 6a according to the general procedure.

$^1$H NMR (600 MHz, CDCl$_3$) δ (ppm): 7.70 (s, 1H), 7.65 (s, 2H), 2.80 (t, J=7.8 Hz, 2H), 2.29 (t, J=7.2 Hz, 2H), 2.23 (s, 6H), 1.84 (p, J=7.2 Hz, 2H); $^{13}$C NMR (150 MHz, CDCl$_3$) δ (ppm): 144.81, 131.73, 131.51, 128.79, 58.60, 45.56, 33.23, 33.23, 29.13; FTIR (cm$^{-1}$): 2947, 2862, 2820, 2770, 1622, 1463, 1377, 1346, 1275, 1227, 1167, 1125, 1039, 971, 863, 843, 729, 706, 682, 517, 460; ESI-HRMS: Calculated for C$_{13}$H$_{16}$F$_6$N$^+$: 300.1181. Found: 300.1174 (M+H)$^+$ General Procedure for the Synthesis of Benzyl-Protected Molecules by the Chabrier Reaction 22-23.

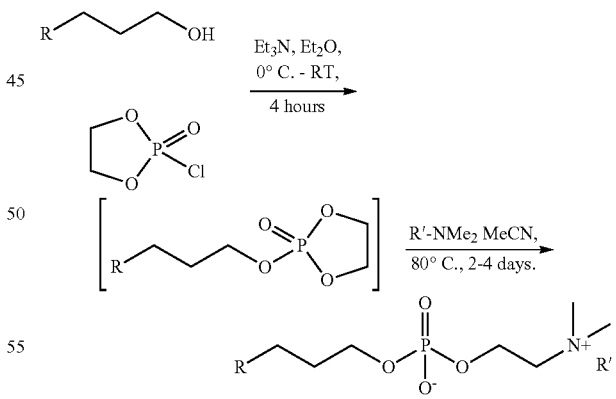

Benzyl-protected zwitterionic coacervates 22-23 were prepared via the Chabrier-Reaction, according to a previously described procedure, with certain modifications, and no attempt was made to optimize yields. Ethylene chlorophosphate was purchased from Aesar, stored in a freezer, and used as received. In a typical procedure, a flame dried flask was fitted with a PTFE coated stir bar, rubber septa, and cooled under positive argon flow. Freshly prepared alcohol was added to the flask followed by anhydrous Et$_2$O [0.4 M], 1.15 equiv. Et₃N, and stirred under argon in an ice bath. 1.15 equiv. ethylene chlorophosphate was then added semi-dropwise via syringe whereupon precipitation of the amine hydrochloride salt was observed to begin, and the flask was stirred for 10 minutes at 0° C. The ice bath was then removed and the flask was allowed to warm to ambient temperature with stirring for 4 hours. Hexanes equal to the volume of Et₂O in the flask, was then added to assist in precipitation of the amine hydrochloride salt, and the contents of the flask were filtered quickly over a pad of basic celite into a fresh round bottom flask. The contents of the reaction vessel was then rinsed once with hexanes, and once with Et₂O through the pad of basic celite, and volatiles were then removed under reduced pressure, and stored briefly in the round bottom flask under high vacuum while a second reaction vessel was prepared.

A schlenk-bomb type flask was fitted with a PTFE-coated stir bar, flame dried, fitted with two rubber septa, and allowed to cool to ambient temperature under positive argon flow. While the schlenk flask was cooling, the flask containing the phosphate ester was back-filled with argon, removed from the vacuum manifold, fitted with a rubber septa, and an argon needle was inserted into the septum. The appropriate amount of anhydrous MeCN (2-4 ml/mmol alcohol) was then added to this flask via syringe, and swirled gently by hand until completely dissolved. At this paint, the MeCN solution containing the phosphonate ester was transferred via syringe into the schlenk flask, and the round bottom was rinsed once with a minimal amount of MeCN into the schlenk flask. 2-4 equiv. of the appropriate amine was then added to the schlenk flask, and the rubber septa was replaced with a schlenk valve coated with high-vacuum grease. The schlenk valve was closed, whereupon the second rubber septa containing an argon needle was replaced with a glass adaptor connected to the high vacuum manifold and placed under high vacuum. The schlenk valve was then cautiously opened and atmosphere was removed from the flask for 10 seconds to remove atmosphere from the flask, the schlenk valve was then closed tightly, and the flask was refluxed under vacuum with stirring for 2-4 days at 80° C. in an oil bath (Note 1).

When the indicated time had been reached the flask was removed from the oil bath and allowed to cool to ambient temperature. The flask was then backfilled with argon, removed from the vacuum manifold and the schlenk valve was removed. As the inside neck of the flask contained residual vacuum grease from the schlenk valve, to avoid contamination with this potential impurity, rather than pouring, the reaction mixture was transferred via syringe into a round bottom flask and the reaction vessel was washed twice with CH₂Cl₂ into the round bottom flask. Volatiles were removed under reduced pressure and traces of solvents were removed by several rounds of evaporation with pentanes to give the crude, protected coacervates. The residue was then dissolved in a minimum amount of CH₂Cl₂ and loaded on top of a plastic column packed with bonded C2 reverse phase silica (Note 2). The column containing the crude residue w as then capped and purified on a Biotage SP4 column chromatography system with gradient elution from 0-35% MeOH/CH₂Cl₂ (Note 3) collecting the set of UV active fractions (254 nm, 10 mAu threshold) eluting last. Concentration of these fractions afforded pure benzyl protected coacervates which were characterized by HRMS, FTIR, ¹H—, and ¹³C-NMR prior to deprotection.

Note 1: A high quality schlenk valve is essential, as the vacuum manifold is active during the reaction even though the schlenk valve is closed, and a faulty valve will lead to evaporation of solvent over the course of the reaction.

Note 2: Although Menger's procedure documents the use of washing, and recrystallization to purify these compounds, the present recrystallization under the reported conditions led to only modest increases in purity, gave diminished yields and was highly dependent on the molecule being purified. As the last step of the synthesis (catalytic hydrogenolysis) was chosen to avoid the necessity of additional purification and introduction of additional impurities, and considering that catechols in their unprotected state are highly polar, and prone to oxidation/polymerization, an additional purification step following catechol-deprotection was deemed undesirable and considerably more difficult. Key to the success of this work was ensuring a high level of purity prior to deprotection of the catechols and thus it is recommended that purification of benzylated catechol intermediates be performed with C2-bonded reverse phase silica gel.

Note 3: "Reverse phase" C2 silica is technically a misnomer in this case as compounds of low polarity displayed low retention times eluting first, and compounds of high polarity displayed high retention times, eluting last. Gradient elution was performed starting with 0% MeOH/100% CH₂Cl₂ and the % of MeOH was increased over 10-25CV's to 35% MeOH/65% CH₂Cl₂. If cost of the reverse phase silica gel is of consideration, then C2 silica could be prepared readily by reacting the appropriate amount of ethyltrichlorosilane with standard grade silica gel (230-400 mesh) according to a previously described procedure. However C₂ silica prepared by this route was considerably more polar than the commercial material obtained from Analtech, and required longer and larger, 0-100% MeOH/CH₂Cl₂ gradients to allow the desired product to elute. Both sources of C2 silica gel were used in this work and no substantial difference in the purity was observed with material purified with either source of C2 silica. To further reduce cost, the C2 silica from either source could be reused several times after use by flushing with 10-20 volumes of MeOH and storing the sealed columns wet with MeOH in a refrigerator. Before reuse, the columns were then flushed with 5-10 volumes of CH₂Cl₂ prior to loading crude compound. Without exception, in all cases the desired product was observed to elute last on the column, although on occasion the first few fractions of those that contained desired material also contained unidentified yellow-colored impurities, and these fractions were either discarded or separated, concentrated, and repurified according to the procedure.

Z-Cat-Ben-Bn (22):

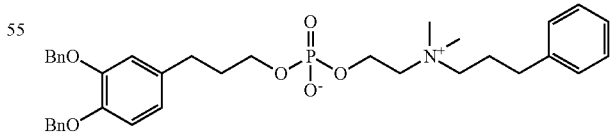

22

65% isolated yield.

¹H NMR (600 MHz, CDCl₃) δ (ppm): 7.40 (t, J=7.8 Hz, 4H), 7.32-7.18 (m, 8H), 7.15-7.10 (m, 3H), 6.80-6.76 (m, 2H), 6.65 (dd, J=1.2, 8.4 Hz, 1H), 5.05 (s, 2H), 5.03 (s, 2H), 4.19 (m, 2H), 4.00 (m, 2H), 3.82 (q, J=6 Hz, 2H), 3.64 (m, 2H), 3.42 (m, 2H), 3.16 (s, 6H), 2.61 (t, J=7.2 Hz, 2H), 2.56 (t, J=7.8 Hz, 2H), 1.97 (p, J=7.8 Hz, 2H), 1.84 (p, J=7.2 Hz, 2H) $^{13}$C NMR (150 MHz, CDCl$_3$) δ (ppm): 148.95, 147.28, 139.80, 137.57, 137.47, 135.63, 128.80, 128.51, 128.47, 127.81, 127.58, 127.43, 121.46, 116.06, 114.48, 71.58, 65.10, 64.85, 64.81, 64.18, 58.89, 51.77, 32.70, 32.17, 31.69, 24.60; FTIR (cm$^{-1}$): 3062, 3030, 2942, 2887, 1661, 1603, 1588, 1510, 1497, 1454, 1424, 1380, 1228, 1158, 1135, 1083, 1029, 1025, 968, 807, 733, 695, 621, 571, 534, 486. ESI-HRMS: C$_{36}$H$_{44}$NNaO$_6$P$^+$: 640.2798. Found: 640.2794 (M+Na)$^+$ Z-Cat-(3,5-CF$_3$-Ph)-Bn (23):

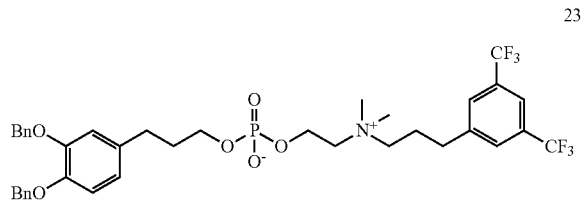 [SMILES: C[N+](C)(CCCc1cc(C(F)(F)F)cc(C(F)(F)F)c1)CCOP(=O)([O-])OCCCc1ccc(OCc2ccccc2)c(OCc2ccccc2)c1]

23

29% isolated yield.

$^1$H NMR (600 MHz, CDCl$_3$) δ (ppm): 7.71-7.62 (m, 3H), 7.40-7.32 (m, 4H) 7.31-7.20 (m, 6H), 6.79-6.75 (m, 2H), 6.61 (dd, J=1.2, 7.8 Hz, 1H), 5.03 (s, 2H), 5.02 (s, 2H), 4.22 (m, 2H), 3.78 (m, 2H), 3.64 (m, 2H), 3.59 (m, 2H), 3.17 (s, 6H), 2.74 (t, J=7.8 Hz, 2H), 2.52 (t, J=7.2 Hz, 2H), 1.99 (m, 2H), 1.81 (p, J=7.2 Hz, 2H); $^{13}$C NMR (150 MHz, CDCl$_3$) δ (ppm): 148.94, 147.44, 142.77, 137.52, 137.47, 135.56, 131.81, 128.85, 128.57, 127.97, 127.92, 127.68, 127.51, 121.63, 116.45, 115.52, 71.82, 71.67, 64.95, 64.85, 51.84, 34.05, 32.05, 32.59, 32.54, 31.82, 31.58, 24.70; FTIR (cm$^-$$_1$): 3071, 3034, 2944, 1588, 1510, 1455, 1425, 1381, 1277, 1228, 1169, 1126, 1080, 1039, 969, 896, 839, 807, 735, 696, 682, 536, 488, 461; ESI-HRMS: Calculated for C$_{38}$H$_{42}$F$_6$NNaO$_6$P$^+$: 776.2546. Found: 776.2557 (M+Na)$^+$ General Procedure for Deprotection of Catechols by Hydrogenolysis 24-25:

General Remarks: The oxidative stability of each of the zwitterionic coacervates containing unprotected catechols, either in the solid state, a solution in D$_6$-DMSO, or as a colloidal dispersion in water, was not known prior to undertaking this study and thus every effort was made to exclude atmospheric oxygen during all manipulations at all points after the catechols had been deprotected. Likewise, as purification of unprotected catechols was envisaged to be difficult and require application of purification techniques under inert atmosphere, every effort was made to increase the purity of the intermediates immediately preceding the deprotection step and the final products were all obtained in satisfactory purity as determined by FTIR, $^1$H—, and $^{13}$C-NMR Spectroscopy.

In a typical procedure, A Schlenk-bomb type flask was fitted with a PTFE coated stir bar, flame dried, fitted with two rubber septa and allowed to cool to ambient temperature under positive argon flow. One septa was briefly removed, 10-20 wt % of Pd/C (5% Pd, Type 87L, dry, Aesar) relative to mass of substrate was added to the flask and the septa was resealed. A small quantity of CH$_2$Cl$_2$ (4-8 ml) was added via syringe through the septa to rinse residual Pd on the sides of the flask to the bottom. A separate round bottom flask containing the desired amount of substrate was fitted with a rubber septa and argon needle, and vented briefly to purge air out. The vent needle was then removed, and the appropriate volume of a 1:1 v/v mixture of CH$_2$Cl$_2$/MeOH was added through the septa via syringe. The flask was then swirled by hand until the benzyl-protected coacervate had dissolved, and this solution containing the substrate was transferred via syringe to the schlenk flask. The interior of the round bottom flask was then rinsed with a small quantity of MeOH (4-8 ml), and transferred via syringe to the schlenk flask. The first septa over the threaded part of the flask was quickly removed and replaced with a schlenk valve coated with vacuum grease. The schlenk valve was closed, whereupon the second rubber septa was replaced with a glass adaptor connected to the high vacuum manifold and placed under high vacuum, which placed the antechamber before the schlenk valve under vacuum, and the flask was stirred gently. The schlenk valve was then cautiously opened placing the contents of the flask under vacuum and the atmosphere was removed under vacuum for 2-3 minutes. Once this time had elapsed the schlenk valve was closed, the antechamber before the valve was backfilled with argon and the glass adaptor connecting the flask to the vacuum manifold was quickly replaced with a rubber septa. A hydrogen balloon (double ballooned) connected to a needle was placed through the septa and then a vent needle was placed though the septa to purge argon from the antechamber for 30 seconds whereupon it was subsequently removed. Then the schlenk valve was opened slowly to allow hydrogen into the reaction vessel. Stirring was continued for 2-4 days, with periodic replacement of the hydrogen balloon (fresh balloons were used with every replacement). (Note 4)

Once the indicated time had elapsed the schlenk valve was closed, and the remaining septa was replaced with a vacuum adaptor connected to a vacuum manifold and the antechamber before the schlenk valve was placed under vacuum. The schlenk valve was then cautiously opened placing the contents of the flask under vacuum and hydrogen gas was removed from the system in this manner for 5-10 minutes with stirring, whereupon there was concomitant bubbling and cooling of the flask due to slight solvent evaporation (Caution: opening the schlenk valve too quickly in this step will lead to solvent "bumping" into the vacuum manifold). During this time a separate round bottom flask was flame dried, fitted with a rubber septa, tared, and allowed to cool to ambient temperature under positive argon flow. The schlenk flask was then backfilled with argon, and while under positive argon flow the schlenk valve was removed and quickly replaced with a rubber septa. A 30 mL, luer lock, PTFE coated syringe was fitted with a long metal needle, and the syringe was filled and purged with argon 3×, whereupon it was inserted through the septa of the reaction vessel. The Pd/C was then separated from the reaction mixture as follows: (Note 5)

With the outlet of the syringe facing down, 25 ml of the reaction mixture was pulled slowly up into the syringe, whereupon the needle was gently bent and the syringe was inverted so that the outlet of the syringe was now facing up. The needle was pulled above the level of solvent in the reaction mixture and a 5 mL blanket of argon pulled into the syringe. Then, very quickly, the needle was removed from the flask with the syringe still inverted, and the metal needle was removed from the luer lock and quickly replaced with an Acrodisc 0.45 μm PTFE membrane filter fitted with a fresh 18 gauge needle at the outlet. The empty round bottom flask, still fitted with septa and argon needle, was then inverted so that the neck of the flask was facing downward, and the needle attached to the membrane filter and syringe was placed though the septa of the inverted flask. The whole apparatus was inverted once more, so that the outlet of the syringe was facing down and the neck of the flask was facing up, and the solution was gently forced through the filter into the flask, removing the Pd/C from the solution. If more than 25 mL of solution were present in the schlenk flask, then the procedure was repeated with fresh syringes, needles, and filters, until no more liquid remained in the flask. The septa was then quickly removed from round bottom flask containing product, and immediately placed on a rotavap to remove volatiles. Several subsequent rounds of evaporation first with $CH_2Cl_2$, then with pentanes helped to remove trace solvents from the products, and the flask was immediately placed under high vacuum afforded pure deprotected coacervates which were subject to further analysis and study. (Note 6) Pure coacervates were either stored in round bottom flasks under high vacuum, or in vials under an argon atmosphere and tightly wrapped with several layers of parafilm, until further study. Unfortunately the final products were not sufficiently stable under conditions of EI- or ESI-MS for accurate mass determination. However they were all characterized by $^1$H-NMR, $^{13}$C-NMR, and IR spectroscopy, which confirmed that the anticipated products had been produced in high purity. The benzyl-protected coacervates were all sufficiently stable under conditions of ESI-HRMS for accurate mass determination and were characterized including this descriptor prior to hydrogenolysis.

Note 4: As the high polarity of the products precluded the use of TLC or GC to monitor the progress of the reaction, reaction progress was monitored at 24 h intervals by removal of a 0.5-1.0 ml aliquot of the reaction mixture which was worked up by filtration according to the procedure and analyzed by NMR to determine completion of the reaction. In general, most reactions were incomplete after one day, and showed full conversion after two full days, although on occasion, up to 4 days were necessary for certain substrates.

Note 5: This procedure was devised on the basis of the expected high polarity of the products which would preclude removal of Pd/C by the usual filtration over celite, silica, or alumina, and thus a relatively inert and nonpolar PTFE filter was chosen to remove the Pd/C. The choice of the benzyl protecting group for catechols in this context is particularly noteworthy, as the only byproduct is toluene which can be removed by simple evaporation. Use of an acetonide or silicon based protecting group for the catechol, and subsequent removal with acid or fluoride respectively, was deliberately avoided as they would introduce other organic, or highly polar water-soluble impurities which would be difficult to remove from the desired product with conventional techniques. However this procedure gave variable isolated yields, presumably due to adsorption of the products onto the charcoal surface, and no attempt was made to optimize yields, although on occasion, additional washing of the reaction flask and PTFE filter with degassed MeOH was performed to assist in product recovery.

Note 6: Although azeotropic removal with pentanes, and gentle heating under high vacuum were successful at removing the majority of trace solvents from the pure coacervates, NMR spectra invariably contained some slight traces of solvents owing to the high propensity of the product molecules to self aggregate, trapping some residual solvents in the material.

Z-Cat-Ben (24):

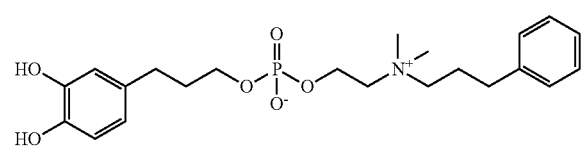

24

Reaction time=2 days (48 hours) 74% isolated yield.

$^1$H NMR (600 MHz, $D_6$-DMSO) δ (ppm): 9.37-9.10 (s, 1H), 9.01-8.76 (s, 1H), 7.34-7.17 (m, 5H), 6.67-6.58 (m, 2H), 6.40 (dd, J=1.8, 7.8 Hz, 1H), 4.05 (m, 2H), 3.67 (q, J=6 Hz, 2H), 3.52, (m, 2H), 3.41 (m, 2H), 3.08 (s, 6H), 2.59 (t, J=7.8 Hz, 2H), 2.43 (t, J=7.8 Hz, 2H), 2.03-1.95 (m, 2H), 1.74 (p, J==7.2 Hz, 2H); $^{13}$C NMR (150 MHz, $D_6$-DMSO) δ (ppm): 145.17, 143.28, 140.46, 132.26, 128.35, 126.11, 118.62, 115.81, 115.76, 115.51, 115.47, 63.77, 63.72, 63.06, 50.91, 32.54, 32.49, 31.68, 30.95, 23.86; FTIR ($cm^{-1}$): 3027, 2950, 1600, 1513, 1454, 1382, 1286, 1202, 1155, 1117, 1067, 1034, 968, 813, 753, 701, 634, 571, 533, 491

Z-Cat-(3,5-$CF_3$-Ph) (25):

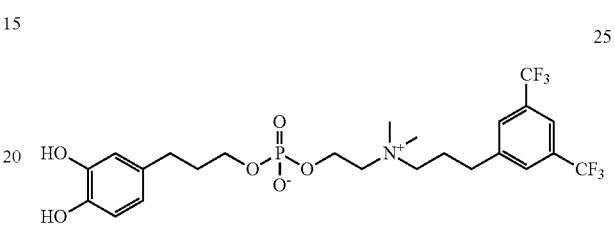

25

Reaction time=3 days (72 hours) 39% isolated yield $^1$H NMR (500 MHz, $D_6$-DMSO) δ (ppm): 9.62-8.69 (br, s, 1H), 9.62-8.69 (br, s, 1H) (overlapping), 8.06 (s, 2H), 7.93 (s, 1H), 6.67-6.56 (m, 2H), 3.39 (dd, J=2, 8 Hz, 1H), 4.08 (m, 2H), 3.69 (q, J=6.5 Hz, 2H), 3.56 (m, 2H), 3.45 (m, 2H), 3.09 (s, 6H), 2.80 (t, J=8 Hz, 2H), 2.42 (t, J=7.5 Hz, 2H), 2.12-1.98 (m, 2H), 1.74 (p, J=7 Hz, 2H); $^{13}$C NMR (125 MHz, $D_6$-DMSO) δ (ppm): 145.15, 144.34, 143.26, 132.33, 130.30, 130.04, 129.78, 129.78, 129.49, 124.52, 122.35, 119.92, 118.60, 115.78, 115.49, 63.82, 62.77, 63.42, 62.98, 62.93, 58.22, 58.19, 51.01, 32.49, 32.43, 31.04, 30.90, 23.68

Critical Aggregation Concentration:

The measurement of critical aggregation concentration (CAC) is important for surfactant systems in order to determine the deposition concentration of the molecules onto a substrate. Aqueous colloidal dispersions of each homolog were prepared in deoxygenated deionized (DI) water. The CAC was determined from the solution surface tension of varying homolog concentrations in deionized (DI) water by Wilhelmy plate tensiometry. CAC was used instead of CMC here to accommodate the uncertainty about whether micelles or other soluble aggregates were forming.

Quartz Crystal Microbalance with Dissipation (QCM-D):

Quartz crystal microbalance with dissipation (QCM-D): A "static cell" (often called "Open Model") QCM-D (Q-Sense, Biolin Scientific) was employed to qualitatively show the adsorption of the zwitterionic molecules onto mineral and metal oxide surfaces. 100 μl of 5 mM zwitterionic solution was deposited onto $TiO_2$ and $SiO_2$ surface, respectively, in DI $H_2O$ (100 l) using a static cell. The zwitterionic molecules adsorb onto both $TiO_2$ and $SiO_2$ (using quartz sensors with the corresponding top-layer, see FIG. 36). Frequency and dissipation change upon addition of 5 mM solution of each zwitterionic molecule to $TiO_2$ and $SiO_2$ surface, respectively (See FIG. 36). The results are in contrast to all the studied mussel foot proteins, which adsorb onto $TiO_2$ but not to $SiO_2$ according to previous QCM-D experiments (less than 10 ng/$cm^2$). The results emphasize qualitatively that the zwitterionic molecules adsorb onto both $TiO_2$ and $SiO_2$, which is in agreement with the SFA and AFM results. A quantitative discussion regarding the adsorbed mass (frequency shift) and the viscoelastic properties (dissipation) of the adsorbed "soft" layers is challenging because the mass of the zwitterionic molecules cannot be separated from the mass of adsorbed water. The following paragraph briefly explains the general interpretation of the QCM-D data to demonstrate the adsorption of the zwitterionic molecules onto both titania and silica surfaces.

Quartz crystal microbalance (QCM) is a surface sensitive technique that measures the change in resonant frequency of a vibrating quartz crystal upon adsorption of material to a surface. The quartz crystal is vibrated by applying a periodic voltage signal across it at its resonant frequency. The resonant frequency of the crystal decreases when the mass of the chip increases (due to adsorption of molecules on its surface), which can be converted to adsorbed mass $\Delta m$ using the Sauerbrey equation:

$$\Delta m = -\frac{A_c \Delta f \sqrt{\rho_q \mu_q}}{2 f_0^2} \quad (1)$$

where $A_c$ is the area of the crystal, $\Delta f$ is the change in frequency, $\rho_q$ is the density of quartz (2.648 g/cm$^3$), $\mu_q$ is the shear modulus of quartz (2.947×10$^{11}$ g/cm·s$^2$) and $f_0$ is the resonant frequency of the crystal. The Sauerbrey equation assumes the adsorbed mass is rigid, uniformly distributed across the crystal and the frequency shift is less than 2% of the resonant frequency.

Quartz crystal microbalance with dissipation (QCM-D) is an extension to the QCM technique developed by Q-Sense® and can be used to determine the rigidity/softness and the viscoelastic properties of the adsorbed material. The QCM quartz crystal was coated with different rigid materials (e.g., metals, polymers, dielectrics) and the adsorption kinetics can be monitored on these materials in liquid environment. Modeling of the $\Delta f$ and $\Delta D$ at different overtones also allows for the calculation of thin film viscosities, shear modulus, thicknesses, hydrations etc. of the adsorbed layers. It should be noted that the calculations and approximations are accurate for small change in dissipation (<5×10$^{-6}$).

Molecule adsorption experiments in a Quartz Crystal Microbalance with Dissipation (QCM-D) indicate that the molecules adsorbed ($\Delta F$) to TiO$_2$ and SiO$_2$ surfaces in DI H$_2$O. The change in dissipation ($\Delta D$) of the adsorbed film shows the degree viscoelasticity for each film. The film thickness and the mass of the adsorbed molecules were calculated using QTools data analysis Software®.

The molecular density of Z-Cat-Ben on silica surface calculated from the QCM-D measurement corroborates the simulation calculations (1.0×10$^{14}$ per cm$^2$) where:

$$\text{Molecules per cm}^2 = \frac{QCM \text{ surface coverage}\left(\frac{ng}{cm^2}\right) \times 6.02 \times 10^{23}\left(\frac{\text{molecules}}{\text{mole}}\right) \times 10^{-9}\left(\frac{g}{ng}\right)}{\text{Mol. Wt.}\left(\frac{g}{\text{mole}}\right)}$$

Figure 42:
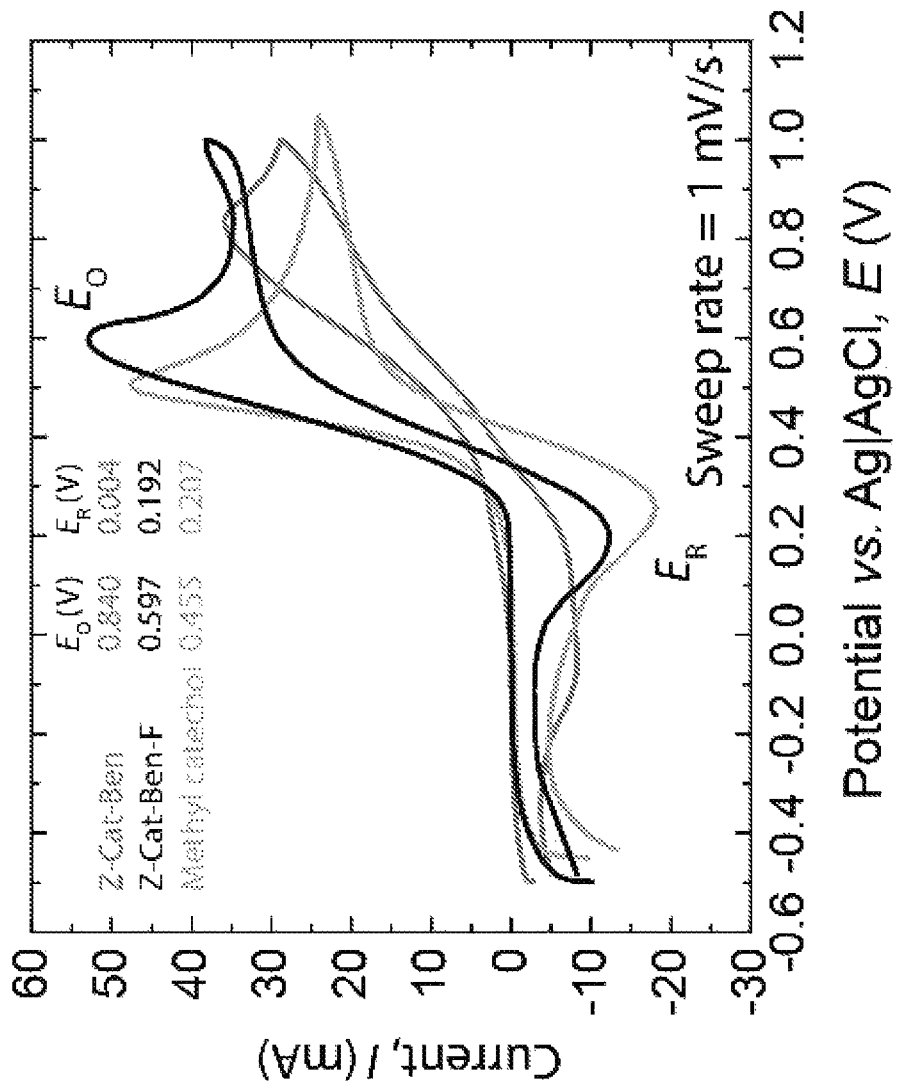
FIG. 42 is graph showing Cyclic voltammetry measurements for 5 mM solution of the small molecules in DI water.
Figure 44:
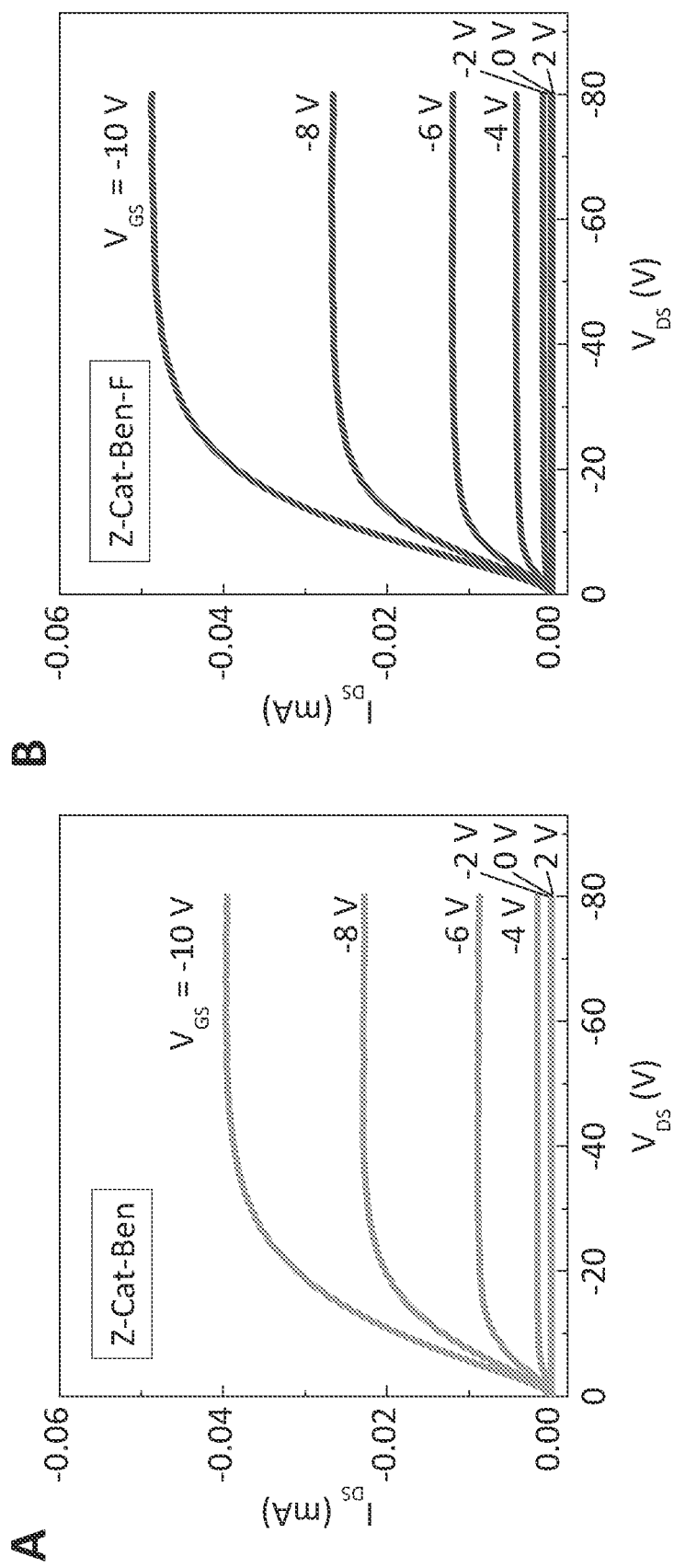
FIGS. 44A-44B are graphs showing output curves of the OFETs with Z-Cat-Ben (A) and Z-Cat-Ben-F (B) SAMs.

Cyclic Voltammetry:

Cyclic voltammetry was performed on a Versastat 3 potentiostat from Ametek Co. These analyses were carried out using a three-electrode cell: a Pt wire as the counter electrode, an Ag/AgCl reference electrode, and a Carbon paste electrode (CPE) served as the working electrode. CPE is the best choice for adhesive materials because of its ability to be completely polished before each experiment. Catechol auto-oxidation was avoided by performing all electrochemical experiments with degassed deionized water in a glove bag under argon. Scan rate 1 mV s$^{-1}$ was used for all experiments. CV of 5 mM synthesized molecules and 5 mM methyl catechol, a simple catechol-containing compound, were compared. Oxidation of Catechol carrying molecules occurred at more positive potentials than methyl catechol, indicating the unique structure of the dispersions provide shielding effects that stabilized catechol groups. Z-Cat-Ben with an oxidation peak at 840 mV is more resistant to oxidation than the other species (FIG. 42). Z-Cat-Ben also showed a redox stability, superior (Z-Cat-Ben, $E_{1/2}$=0.418 V) compared to methyl catechol ($E_{1/2}$=0.124 V) as determined by cyclic voltammetry measurements (FIG. 42) due to shielding of the catechol moieties by neighboring hydrophobic or electrophilic groups making it less vulnerable to oxidation.

Measuring Normal Forces in the Surface Forces Apparatus (SFA):

In a typical SFA experiment (FIG. 33B), the distance and the force between the surfaces are measured simultaneously. To begin with, the instrument is calibrated at large separation distances. When the two surfaces are not interacting, i.e., they are separated by large distances, the change in the separation between them is equal to the distance through which the motor moves the lower surface towards or away from the upper surface (or the upper surface driven by the piezo-tube moves towards the lower surface). However, once the surfaces are close enough to start interacting with each other, the measured separation distance deviates from the expected separation calibrated when there is no force between the surfaces. This deviation is due to the deflection of the double cantilever spring and is directly proportional to the force acting normally between the two opposing surfaces. Thus the normal force can be measured using Hooke's law, F=k$\Delta$x, where k is the spring constant of the double-cantilever spring and $\Delta x = D_{actual} - D_{applied}$ is the deflection of the spring, determined by taking the difference between the applied change in position of one of the surfaces $D_{applied}$ and the actual change in distance measured between the surfaces $D_{actual}$. The actual distance, $D_{actual}$, between the surfaces can be measured by multiple beam interferometry (MBI) and will be discussed below.

Measuring Distance: Multiple Beam Interferometry (MBI)

The distance between the surfaces, shape of the interface and the refractive index of the media between the surfaces can be accurately determined by MBI technique. In this technique, white light is directed through two back-silvered mica surfaces (or uniform and same thickness). As a white light passes between the mica surfaces, it undergoes interference due to the optical trap set up by the back silver on each of these surfaces giving rise to discrete wavelengths of light (FIG. 33B). These wavelengths of light are resolved in a spectrometer creating interference fringes known as 'fringes of equal chromatic order' (FECO). Since mica is birefringent, the FECO appears as doublets and termed as $\beta$ and $\gamma$. Alternate fringes are termed as odd and even fringes with odd fringes having nodes at the center and even fringes with anti-nodes in the center. The FECO is then recorded on a camera and analyzed to determine the distance between the surfaces using the following equations:

$$\tan\left(\frac{2\pi\mu_2 D}{\lambda_n^D}\right) = \frac{2\bar{\mu}\sin\left(\frac{1-\lambda_n^0/\lambda_n^D}{1-\lambda_n^0/\lambda_{n-1}^0}\pi\right)}{(1+\bar{\mu}^2)\cos\left(\frac{1-\lambda_n^0/\lambda_n^D}{1-\lambda_n^0/\lambda_{n-1}^0}\pi\right) \pm (\bar{\mu}^2-1)} \quad (2)$$

-continued $$T = n\lambda_n^0 / 4\mu_1 \quad (3)$$

$$n = \frac{\lambda_{n-1}^0}{F_n(\lambda_{n-1}^0 - \lambda_n^0)} \quad (4)$$

where D is the separation distance between the surfaces, n is the fringe order (n=1, 2, 3, . . . ) $A_n^0$ is the wavelength of the $n^{th}$ order fringe (0 refers to the distance between the mica, D=0, or mica-mica contact reference), T is the thickness of each of the mica surfaces, $\mu_1$ is the refractive index of mica, $\mu_2$ is the refractive index of the medium, $\bar{\mu}=\mu_1/\mu_2$, and the − is used for odd fringes and the + is used for the even fringes, $F_n$ is a correction factor that depends on the phase changes at the mica-silver interface and dispersion effects that can be estimated as $F_n \approx 1.024 + 1/n$ for odd fringes measured near $\lambda \sim 550$ nm².

For small separation distance (D<30 nm) between the surfaces, eq. 2.5 can be approximated as $$D = \frac{\lambda_{n-1}^0 (\lambda_n^D - \lambda_n^0)}{2\mu_1(\lambda_{n-1}^0 - \lambda_n^0)}, \text{ for } n \text{ odd} \quad (5)$$

$$D = \frac{\mu_1 \lambda_{n-1}^0 (\lambda_n^D - \lambda_n^0)}{2\mu_2^2(\lambda_{n-1}^0 - \lambda_n^0)}, \text{ for } n \text{ even} \quad (6)$$

It should be noted that the distance calculated with the equation for the odd fringes (eq. 5) is independent of the refractive index between the two surfaces whereas that calculated with even (eq. 6) is not. This allows for simultaneous measurement of refractive index along with the force and separation distance between the surfaces.

Interfacial Interaction Study Using Surface Forces Apparatus (SFA):

The hard-wall thickness (approximately, the sum of the hydrodynamic diameters of the films on the upper and lower mica surfaces in SFA) of each homolog was measured as the limiting distance between the mica surfaces during the approach run in the SFA. The adhesive strength of interaction of the synthetic zwitterionic molecules was investigated in SFA. The interaction between two surfaces can be measured with nano-Newton level force resolution and Angstrom level resolution in the separation distance between the surfaces. The details of the SFA techniques have been describe in a work by Israelachvili et al. Briefly, two molecularly smooth freshly cleaved back silvered mica surfaces glued on cylindrical silica discs of radius of curvature, R~2 cm, were mounted in the SFA and 50 μL of a colloidal dispersion of the synthetic molecules in DI water were injected between the surfaces at different concentrations to determine the effect of deposition above and below the CAC of the molecules (C=0.5-5 mM) (FIG. 32). In the SFA experiments, the surfaces were allowed to equilibrate for 30 mins (after injecting the solution between the surfaces) before bringing them into contact for force measurements. During a typical approach-separation force measurement cycle, the surfaces were first moved towards each other (approach) until reaching a "hard-wall" and then separated. The hard-wall distance is the separation distance between the two mica surfaces upon compression that does not change with increased compression. The energy of interaction between two crossed-cylinder geometry, roughly corresponds to a sphere of radius R approaching a flat surface based on the Derjaguin approximation, $W(D)=F(D)/2\pi R$ where, W(D) is the energy of interaction per unit area between two flat surfaces and F(D) is the measured force of interaction in the SFA. The measured adhesion, $F_{ad}$, (or cohesion, $F_c$) force (minimum of the potential well of the F/R vs. D curves obtained from SFA measurements) is related to the adhesion (or cohesion) energy per unit area by $W_c=F_c/2\pi R$ for rigid surfaces with weak adhesive interactions, and by $W_c=F_c/1.5\pi R$ (used in this study) for soft deformable surfaces with strong adhesion or cohesion. It should be noted that in SFA measurements, $W_{ad}$ or $W_c \rightarrow -E_{ad}$ or $-E_c$ respectively, where E is the energy of interaction between the surfaces. This convention was used because the measured adhesive or cohesive forces between the surfaces are attractive. It should also be noted that adhesion is referred to as the interaction between two asymmetric surfaces and cohesion as the interaction between two symmetric surfaces.

Z-Cat-Ben Oxidation Study:

Adhesive energies ($W_{ad}$) was measured between the SAMs with and without periodate treatment, which mediates a stoichiometric −2H⁺ and −2e⁻ oxidation of exposed catechol to o-quinone, in the SFA. Interestingly, the cohesion or self interaction energy ($W_c=18.7\pm2.8$ mJ/m²) between the Z-Cat-Ben SAMs (FIG. 33B) was same before and after aqueous solution (500 pmoles) of sodium periodate treatment (see FIG. 34) unlike any previously reported catechol-containing molecule which has exposed catechol residues at the water-molecule interface that undergo oxidation, resulted in significant decrease or increase in adhesion. Similarly, the cohesion between the Z-Cat-Ben SAMs was not affected by aqueous $Fe^{3+}$ Cl⁻ solution ($C_{Fe3+}=10$ M) unlike the previously reported catechol residues in a mussel foot proteins that increase cohesion by bridging between opposing films via metal coordination. In addition, the same hard-wall thickness (the limiting distance between the surfaces during the approach run followed by compression in the SFA) and $W_c$ measured in the SFA during multiple force runs at different contacts between the SAM surfaces before and after periodate and iron treatments demonstrate that the reversible cohesive failure always occurred between the benzene groups of the two SAM surfaces rather than adhesive failure (irreversible after periodate or iron treatment) between the SAM and mica surface.

Figure 45:
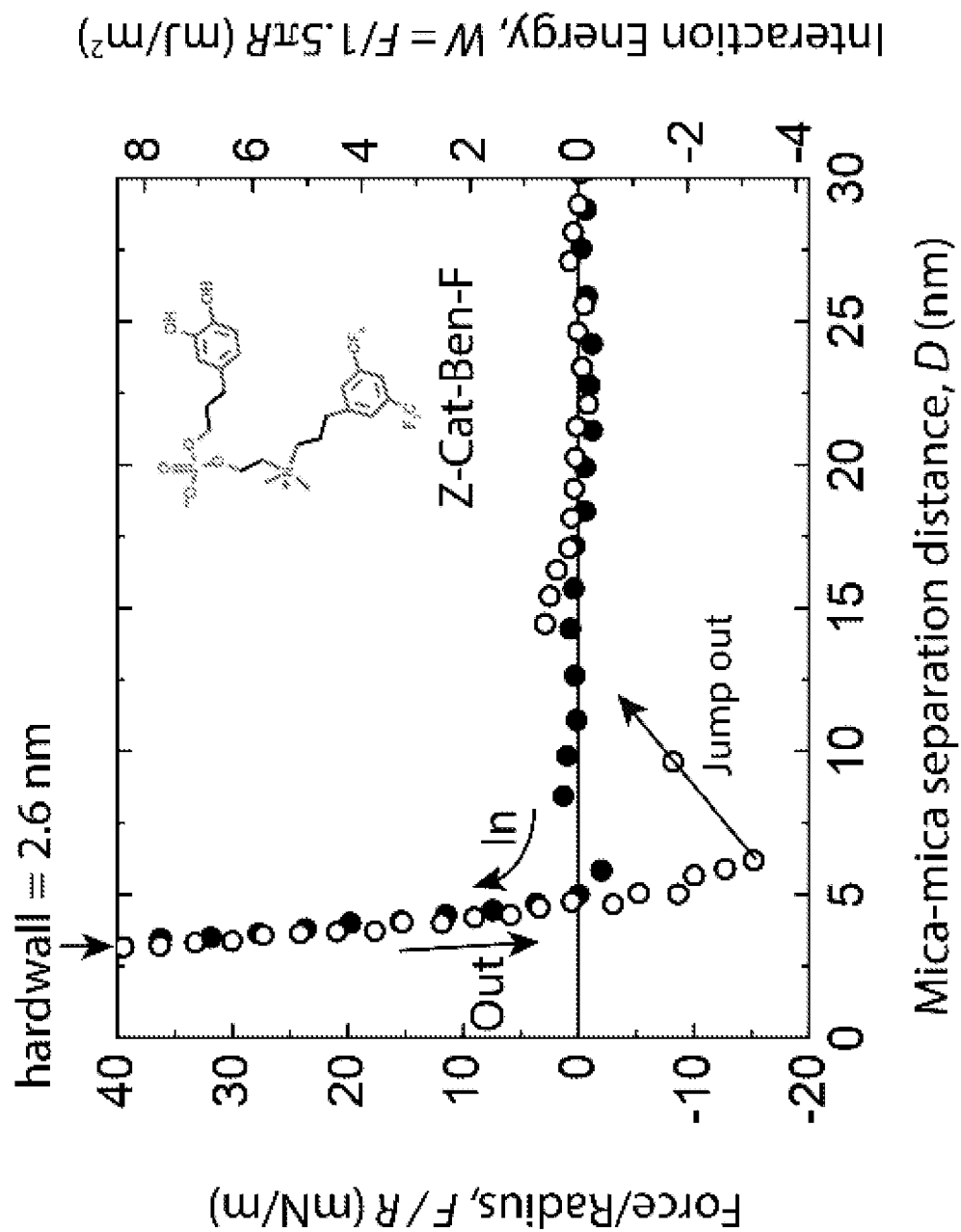
FIG. 45 is a graph showing Representative force vs. distance plots between Z-Cat-Ben-F (inset) SAMs deposited onto mica at 5 mM concentration in DI water. The cohesive forces and the force profiles have been compared with Z-Cat-Ben in FIG. 2b in the main article.
Figures 46A, 46B:
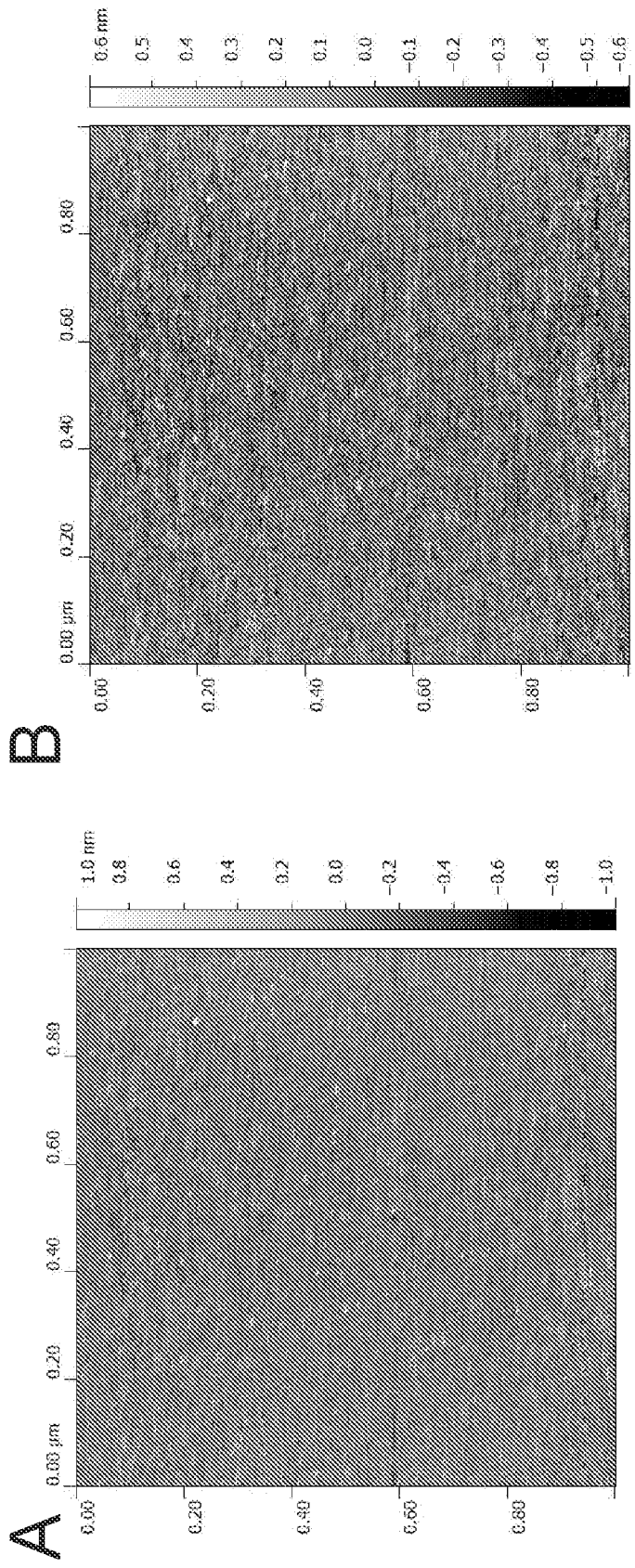
FIGS. 46A-46B show AFM images of Z-Cat-Ben absorbed on mica and silica surfaces.

Z-Cat-Ben-F Force Measurements in the SFA:

The structure-function relationship for the zwitterionic surfactants was investigated to understand the effect of electronegative residues on the benzyl group. This homologous molecule was labeled as Z-Cat-Ben-F (FIG. 45) by adding electron withdrawing —CF₃ groups in the 3 and 5 positions on the benzyl tail. This subtle change in the electron density of the aromatics significantly altered the assembly of the molecules on mica. Whereas Z-Cat-Ben formed uniform SAMs with a thickness of ~0.5 nm (FIGS. 33B and 33D), Z-Cat-Ben-F formed non-uniformly coated films (a AFM image shown in FIG. 33C) with a hardwall thickness of 2.6±0.4 nm, which translates to a thickness of 1.3 nm on each mica surface (FIG. 33B). The Z-Cat-Ben-F showed extensive defects (FIG. 33C) similar to surfactant bilayers on mica which significantly decreased the cohesive strength of interaction ($W_c=3.3\pm1.0$ mJ/m²) between the Z-Cat-Ben-F films (FIGS. 33B and 45).

Atomic Force Microscopy (AFM):

AFM scans of a mica and silica surface adsorbed with Z-Cat-Ben from a solution in DI water of varying concentrations (0.5-5 mM). Z-Cat-Ben forms a defect free atomically smooth bilayer on mica and silica.

Figure 47:
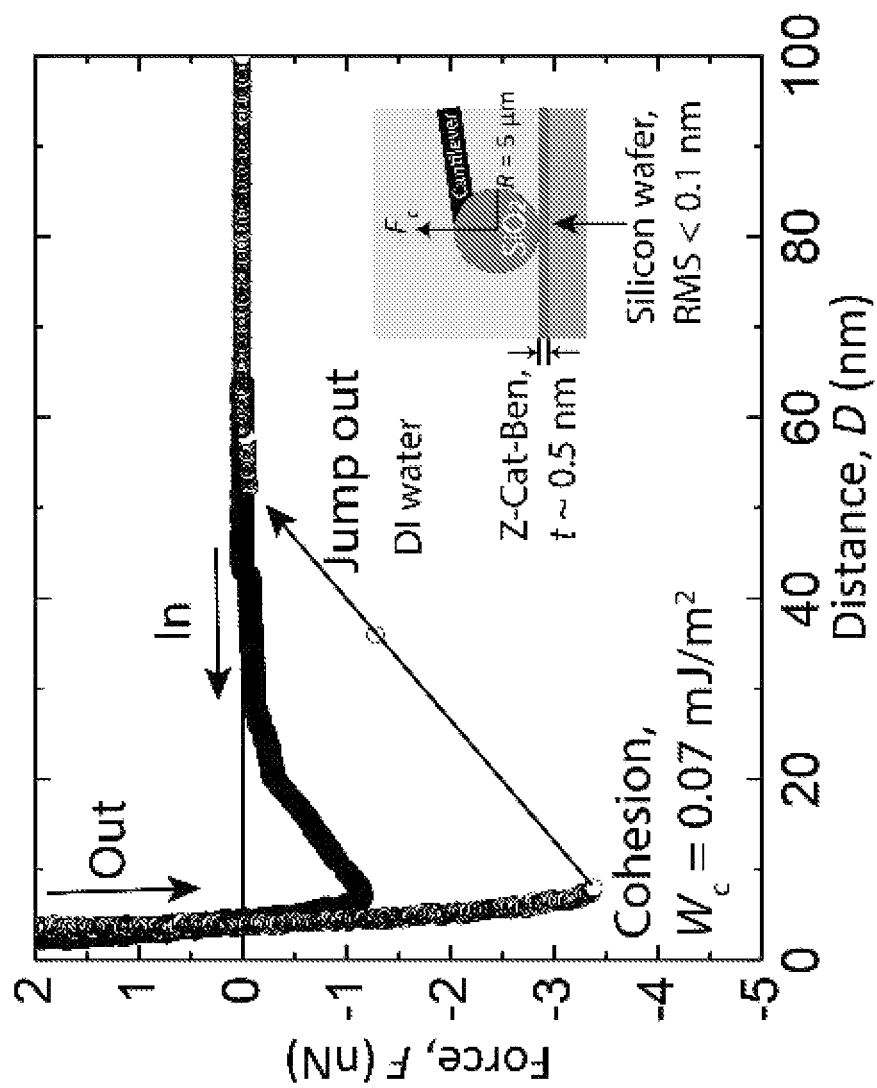
FIG. 47 is a graph showing Representative force vs. distance plots between the Z-Cat-Ben SAM deposited onto silica (at 5 mM concentration from a solution in DI water) and a silica bead (Diameter, φ=10 µm) on silicon wafer.

The pristine self-assemble of the Z-Cat-Ben molecules on silica surface exposed the aromatic residues to the air-water interface resulting in a low interfacial energy between a silica bead and the SAM surface as measured with the AFM technique ($W_{ad}$~0.07 mJ/m$^2$, see FIG. 47). This is unlike the strong adhesion of SAMs exposing catechol residues to the air water interface that bind to silica surface through hydrogen bonding interactions ($W_{ad}$~7.7 mJ/m$^2$).

X-Ray Diffraction (XRD) on Silicon Coated with Z-Cat-Ben SAM:

2D GIWAXS Pattern

Data was collected on a custom-built 2D small angle/wide angle X-ray scattering (SAXS/WAXS) instrument with a microfocusing x-ray source, scatter-less slit collimator and hybrid pixel area detector. Full 2D data was formed by stitching together 9 exposures in a 3×3 grid. The effective exposure time was ~3.5 hrs (FIG. 35B). The scattering showed two broad rings (weak inner ring and a stronger outer ring) indicating two characteristic spacings. Although on first glance the intensity on the two diffuse scattering rings appear to be isotropic, close examination reveals that there is azimuthal variation indicating existence of preferred orientation.

To check for orientation anisotropy, the intensity data were plotted as a function of azimuthal angle χ as shown in FIG. 35B. The two semi-circles define the range of scattering vector q over which the intensity is integrated. The image in FIG. 35B shows a q range corresponding to the second, more prominent peak in the data (stacked spacing 0.34 nm, FIG. 35A).

Organic Field Effect Transistor (OFET) Fabrication:

The OFETs were fabricated onto nano-grooved SiO$_2$ substrates prepared by rubbing n$^{++}$Si (500 μm)/SiO$_2$ (300 nm) substrate (International Wafer Services Co.) with a diamond lapping disc with particle sizes of 100 nm (Allied High Tech Products Inc.) as described in detail in the previous reports. The Ni (5 nm)/Au (50 nm) source and drain electrodes were patterned on the SiO$_2$ dielectrics through a conventional photolithography process. For OFETs with Ni source and drain electrodes, an additional Ni (10 nm) layer was deposited on top of the pre-deposited Au electrodes. All metal electrodes were deposited by electron beam evaporation at 7×10$^{-7}$ Torr. Then, the substrates were sonicated in acetone and isopropanol for cleaning, and were kept in an oven at >100° C. for overnight. After ultraviolet/ozone treatment of pre-cleaned nano-grooved SiO$_2$ substrates for 10 min, the substrates were passivated with the Z-Cat-Ben or Z-Cat-Ben-F SAM by dropping SAM water solution (5 mM) onto the substrates for ~1 min. The substrates were subsequently rinsed with deionized water for ~1 min, and were kept in a low vacuum for 10 min to remove residual water. The PCDTPT (1-Material Inc.) was then cast from a chlorobenzene solution (0.25 mg mL$^{-1}$) through the sandwich casting in a nitrogen-filled glove box. The devices were then cured at 200° C. for 1 min prior to measurements, and were tested using a probe station (Signatone Co.) in a nitrogen-filled glove box. Data were collected by a Keithley 4200 system.

OFET Characterization:

The field-effect mobilities in the saturation regime were extracted using the following equation, $$I_{DS}=(W/2L)C\mu(V_{GS}-V_T)^2 \tag{7}$$

where, W is the channel width, L is the channel length, C is the gate dielectric capacitance per unit area, μ is the carrier mobility in the saturation regime, $I_{DS}$ is the drain-source current, and $V_{GS}$ is the gate-source voltage. Channel width/length is 1000/200 μm for the devices used in this study.

Transistor Characteristics of OFETs with Z-Cat-Ben and Z-Cat-Ben-F:

Contact Angle Measurements:

The nano-grooved SiO$_2$ substrates passivated with Z-Cat-Ben or Z-Cat-Ben-F SAMs were prepared with the same procedure described above. For the reference substrate, the pre-cleaned and ultraviolet/ozone-treated (for 10 min) nano-grooved SiO$_2$ substrate was passivated with n-decyltrichlorosilane (Gelest Inc.) in toluene solution (1% by volume) at 80° C. for 20 min in ambient air. Then, the substrate was subsequently sonicated in toluene and rinsed with additional toluene several times. Anhydrous chlorobenzene (50 μL) was used as a droplet dropping on the substrates. All contact angle images were taken at the direction perpendicular to nano-grooves in the substrates using Dataphysics OCA 15EC goniometer.

Molecular Dynamics Simulations

The starting structural framework for the molecular dynamics simulations consists of a crystalline silica monolayer model and 18 units of Z-Cat-Ben or Z-Cat-Ben-F in water. In this model, the mineral surface was fully hydroxylated and treated as periodic, in an exact multiple of the silica cell unit in two axis, as an infinite crystal. To ensure integrity of the crystalline parameters, silica atoms were constrained in x, y and z dimensions during the simulations. Starting from a structure of a single Z-Cat-Ben molecule from a previous 300-ns long simulation, multiples Z-Cat-Ben or Z-Cat-Ben-F molecules were randomly placed onto the silica surface at a distance of 0.5 nm with half of hydroxyl groups oriented up and down. The systems were placed in a rectangular simulation box (5.0000, 4.48020, 4.16880 nm) and solvated with SPC water model molecules. The silica model was comprised of 756 atoms and a total of 2,252 and 2,232 solvent molecules were added to the simulations of Z-Cat-Ben and Z-Cat-Ben-F, respectively.

The systems were initially energy optimized using 10,000 steps of the steepest descent algorithm. Simulations were performed for 1 s using the GROMOS 53A6 force field. Atomic point charges for the catechol hydroxyl groups and a crystalline silica unit cell were estimated by a RESP fitting from calculations using MP2/6-31G** within NWChem 6.1. The obtained charges were not significantly different from the ones available in previous versions of the force field. The following atomic charges were used for the silica: bulk Si: 0.90 e, bulk O: −0.45 e, surface Si: 0.717 e, surface O: −0.675 e and H: 0.408 e, while point charges of −0.626 e and 0.423 e were assigned the oxygen and hydrogen atoms of hydroxyl groups in catechol, respectively. Periodic boundary conditions were used in the x, y and z directions along with the NVT ensemble. The LINCS method was used to constrain bonds involving all atoms. Integration was carried out by the leapfrog algorithm using a 2-fs integration time step. Short-range electrostatics and van der Waals interactions were computed within the cutoff radii of 1.4 nm and updated every step. Long-range electrostatic interactions were treated using the reaction field method with ε=66 outside of the 1.4 nm cutoff sphere. The temperature was kept at 300 K using the velocity rescale scheme with relaxation time of 1.0 ps. Center of mass motion was removed at every step. The simulations were performed using the GROMACS 4.6.7 simulation package. Umbrella sampling MD simulation to generate potential of mean force profiles were carried out across a 4 nm reaction coordinate in 0.1 nm bins, for 60 ns/coordinate. Free energy error bars were interpolated using a bootstrapping technique.

Figure 39:
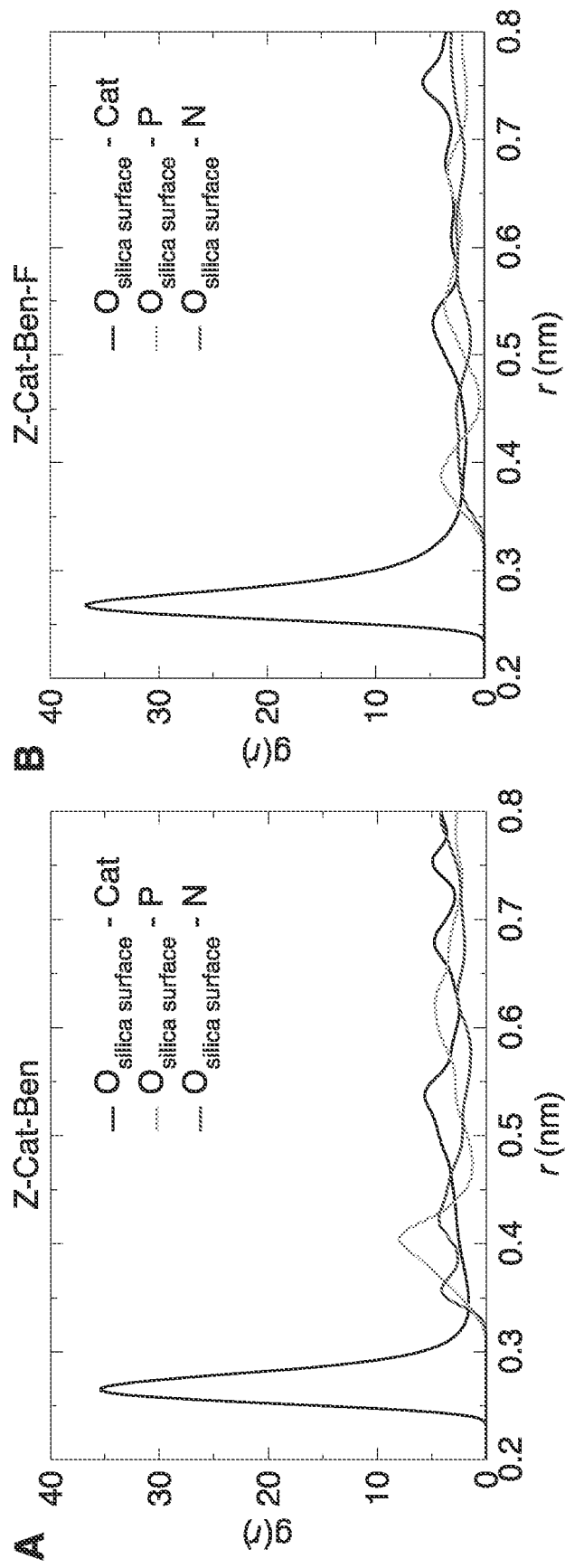
FIGS. 39A-39B are graphs showing Radial distribution functions between the oxygen atoms of the hydroxyl groups on the silica surface and selected groups: oxygen atoms of the catechol hydroxyl groups (Cat), phosphorous (P) and nitrogen (N) atoms, over the last 200 ns of simulation for Z-Cat-Ben (A) and Z-Cat-Ben-F (B); (r is the distance between two defined groups).
Figure 40:
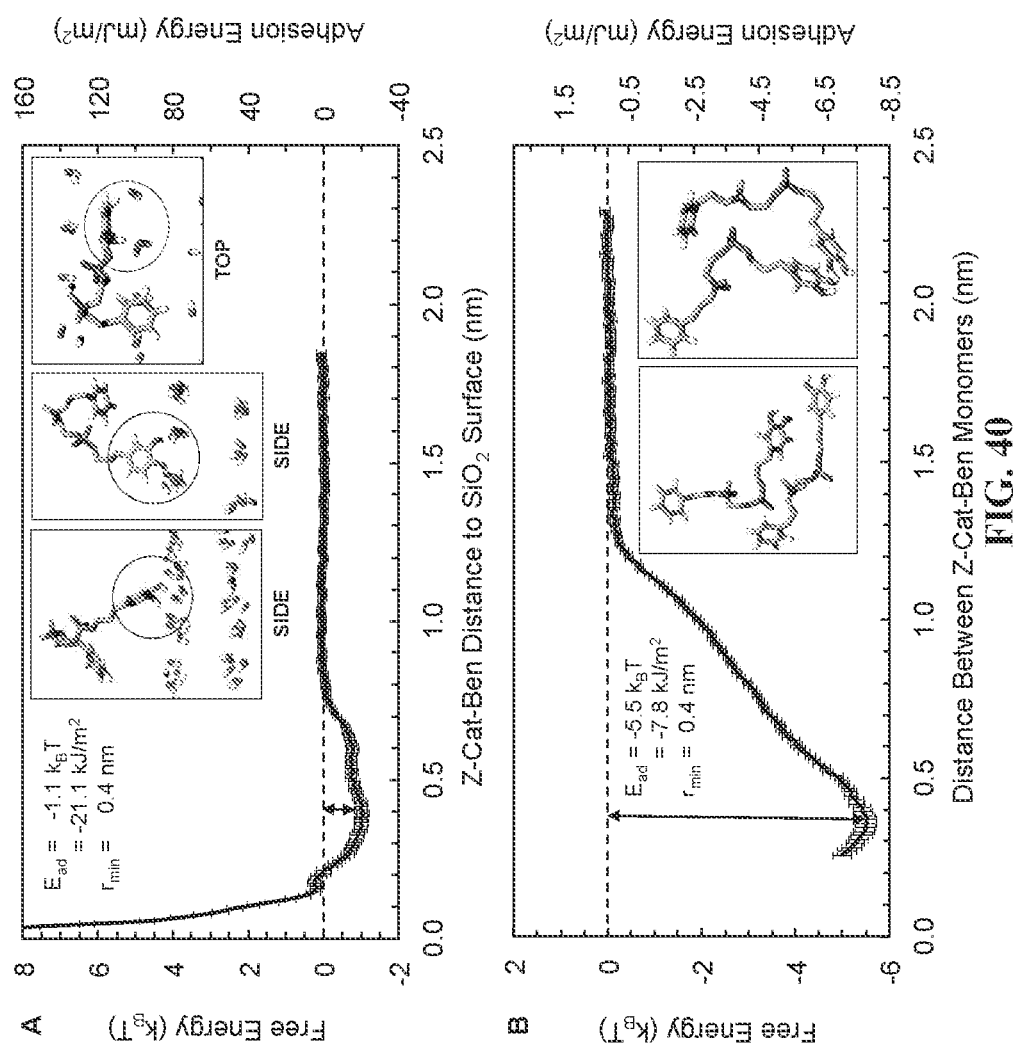
FIGS. 40A-40B are graphs showing Potentials of mean force between Z-Cat-Ben and (A) a silica surface, or (B) a neighboring Z-Cat-Ben molecule. Simulations reveal a strong preference for molecular adhesion to surfaces with adhesion energy of −21.1 mJ/m², whereas the adhesion energy between Z-Cat-Ben monomers is only −7.8 mJ/m². While the absolute energy value for the dimer (−5.5 $k_BT$) is higher than in the Z-Cat-Ben/SiO₂ case (−1.1 $k_BT$), the higher contact area in the former case leads to an overall lower adhesion energy per area.

In support to the results outlined in the main text, additional analyses are presented below for the Z-Cat-Ben and Z-Cat-Ben-F simulations. FIGS. 39A-39B show that catechol binding to silica is mediated by its hydroxyl groups and that phosphate and amine groups do not contribute significantly to the binding.

Figures 41A, 41B:
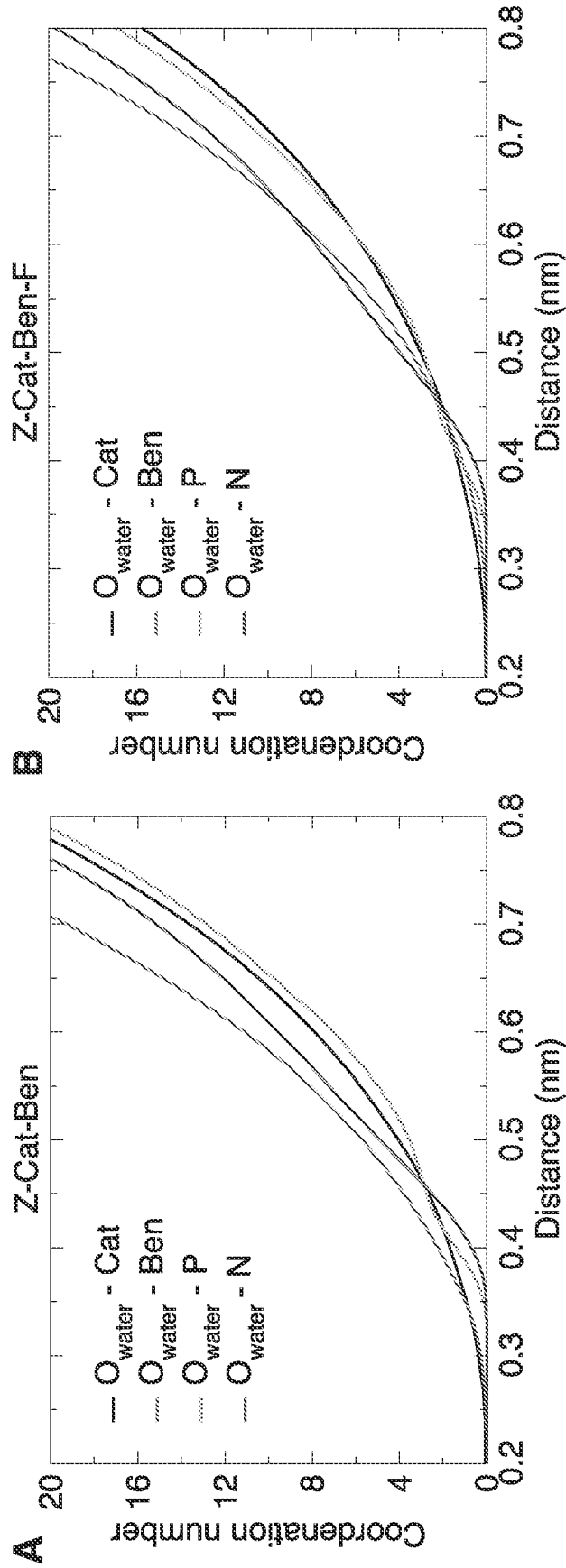
FIGS. 41A-41B are graphs showing Average amount of water (represented by its oxygen atoms) around selected groups of the solute as a function of the distance, over the last 200 ns of simulation ($O_{water}$: water oxygen atoms; Cat: all atoms of the catechol groups; Ben: all atoms of the aromatic rings; P: phosphorous atoms; N: nitrogen atoms).

Although from the density profiles (FIG. 35 in the main text) some water content can be seen at the silica surface at the same region occupied by catechol groups, the radial distribution functions for catechol hydroxyl groups and silica oxygen atoms (FIGS. 39A-39B) shows the interaction peak at ca. 0.275 nm. At this distance the total amount of water molecules nearby any atom of the catechol group is negligible (FIGS. 41A-41B). At larger distances, the catechol (Cat) and phosphate groups (P) remain less solvated than the amine groups (N) and aromatic rings (Ben). It is worth noting that catechol groups are also considerably more shielded from water, despite of being more hydrophilic than the Ben groups (FIGS. 35E and 41A-41B). These results are supported by the potential of mean force profiles (FIGS. 41A-41B), which show a high affinity between DOPA and silica hydroxyl groups.

Significant Performance Enhancement of Polymer Resins by Bioinspired Dynamic Bonding Marine mussels use catechol-rich interfacial mussel foot proteins (mfps) as surface primers that adhere/bind to mineral surfaces via hydrogen-, coordination, electrostatic, ionic or hydrophobic bonds and to create a secondary surface that promotes bonding with the bulk mfps. Inspired by this biological mechanism, it is shown here that a ~1 nm thick catecholic single-molecule priming layer increases the adhesion strength of crosslinked polymethacrylate (PMA) resin on mineral surfaces by up to an order of magnitude compared with conventional primers such as non-catecholic silane- and phosphate-based grafts. Molecular dynamics simulations confirm that catechol groups anchor to different mineral surfaces and shed light on the binding mode of each molecule. Here the ~50% toughness enhancement is achieved in a stiff load-bearing polymer network, demonstrating the utility of mussel-inspired bonding for processing a wide range of polymeric interfaces.

Marine mussels (FIG. 48A) attach strongly to rocks using a holdfast called the byssus, in which seven different proteins, i.e., mussel foot protein (mfp) 1-6 and collagen, have been identified to date. Of these, mfp-3 and -5 are located at the interface between the byssal plaque, the disk-shaped adhesive pad which connects to the mussel via a long thin thread, and the rock surface (FIG. 48B). These are used as surface primers, creating a thin coating to improve bonding performance of adhesives.

These interfacial mfps have unusually high abundance (28-34 mol %) of aromatic residues including tyrosine (Y), 3,4-dihydroxyphenyl-L-alanine (Dopa, Y'), a post-translationally modified form of tyrosine, and tryptophan (W). In particular, Dopa in the interfacial mfps is now accepted as one of the key functional groups for wet-adhesion due to its strong, bidentate binding to oxide mineral surfaces. Inspired by the natural Dopa chemistry, catechol functionalization has been utilized in the translation of the bio-adhesion to numerous synthetic systems. Although previous studies using catechol-functionalized polymers have demonstrated improvements in adhesion, the adhesive performance of such manmade polymers, native mussel and engineered proteins is still far lower than that of natural mussel plaques, in terms of total energy required to dislodge the plaque from a surface. These differences may arise from the lack of consideration of the heterogeneous nature of the mussel plaque structures, and its impact on load transfer within the material, in previous biomimetic approaches using catechol-decorated polymers. For example, although catechol residues are highly enriched (20-28 mol %) in interfacial mfps they are much less abundant in bulk mfps (2-5 mol %). Nonetheless, the majority of efforts in mussel-inspired wet-adhesion have focused on applying catechol functionalities, which promote nanoscale interfacial adhesion, into the bulk phase of synthetic polymers to enhance performance in lap-shear tests, which involves not only a combination of micro/macroscopic adhesion, but also cohesive failure and friction. By a simple paradigm shift of translation, in which the discovery of catechol-rich biological priming was applied to synthetic catecholic priming at the same nanoscopic length scales, here it is shown a significant, i.e., an order of magnitude, adhesion enhancement of a conventional polymethacrylate (PMA) resin.

Noteworthily, mussels construct their plaques and threads in incremental instalments from priming surfaces to the bulk plaque components and solidification (e.g., crosslinking). This processing of surface priming prior to applying bulk resins is already well known in the field of adhesive technologies, and strong catecholic bonding to a metal surface has been demonstrated and utilized. However, hydrated mineral surfaces still remain as the most challenging surfaces for current synthetic adhesives. Increasing reliance on hydrophilic priming chemistry to wet the surfaces can also create an interfacial "sponge" with water trees that continues to draw in water thereby weakening bonds over time. Silane-based coupling agents are widely used to treat mineral surfaces, but replacing silane-based surface grafting is urgently required since it involves the toxic and difficult process. In this work, it was tested whether mimicking the priming strategy of mussels with a very simplified analog can provide performance enhancement of a conventional PMA resin. First, acrylate primers (small bifunctional molecules containing, respectively, aromatic and acrylic groups at opposite ends) were prepared to mimic catecholic interfacial interactions to mineral surfaces and cohesive crosslinking interaction to the bulk PMA resin. Rather than synthesizing perfectly matching homologs with exactly same linkers, the primers were prepared using commercially available, cheap, and naturally abundant compounds (e.g., eugenol and dihydrocaffeic acid derivatives) for a more practical and versatile synthetic system. Four different acrylic surface primers functionalized with benzene ($P_1$), phenol ($P_2$), and catechol ($P_3$ and $P_4$) were synthesized as analogs of W, Y, and Y', respectively (FIG. 48B). $P_4$ differs from $P_3$ its longer alkyl spacer (additional 8 hydrocarbons) between the catechol and acrylate groups.

Each primer solution (1 wt. % in methanol or DMSO) was applied onto a mica and glass surface, respectively. After a 30 second incubation, the excess of each primer was rinsed away, and the height profile of each surface was investigated by Atomic Force Microscopy (AFM). Whereas non-catecholic primers showed no adsorption or aggregate formation, catecholic primers $P_3$ and $P_4$ densely primed the mica (FIG. 48C) and glass surfaces (FIG. 49), respectively. The quantitative adsorption of the primers to $SiO_2$ surfaces evaluated by Quartz Crystal Microbalance with Dissipation (QCM-D) confirms the adsorption of monolayers of the catecholic primers on mica and glass surfaces (Data shown in FIG. 50A and FIGS. 51A-51B). The experimental methods are fully described in the Supplementary information.

Molecular dynamics (MD) simulations were carried out to characterize the molecular adsorption of the primers (P molecules) on model crystalline silica and mica surfaces.

Figures 50A, 50B, 50C, 50D, 50E, 50F:
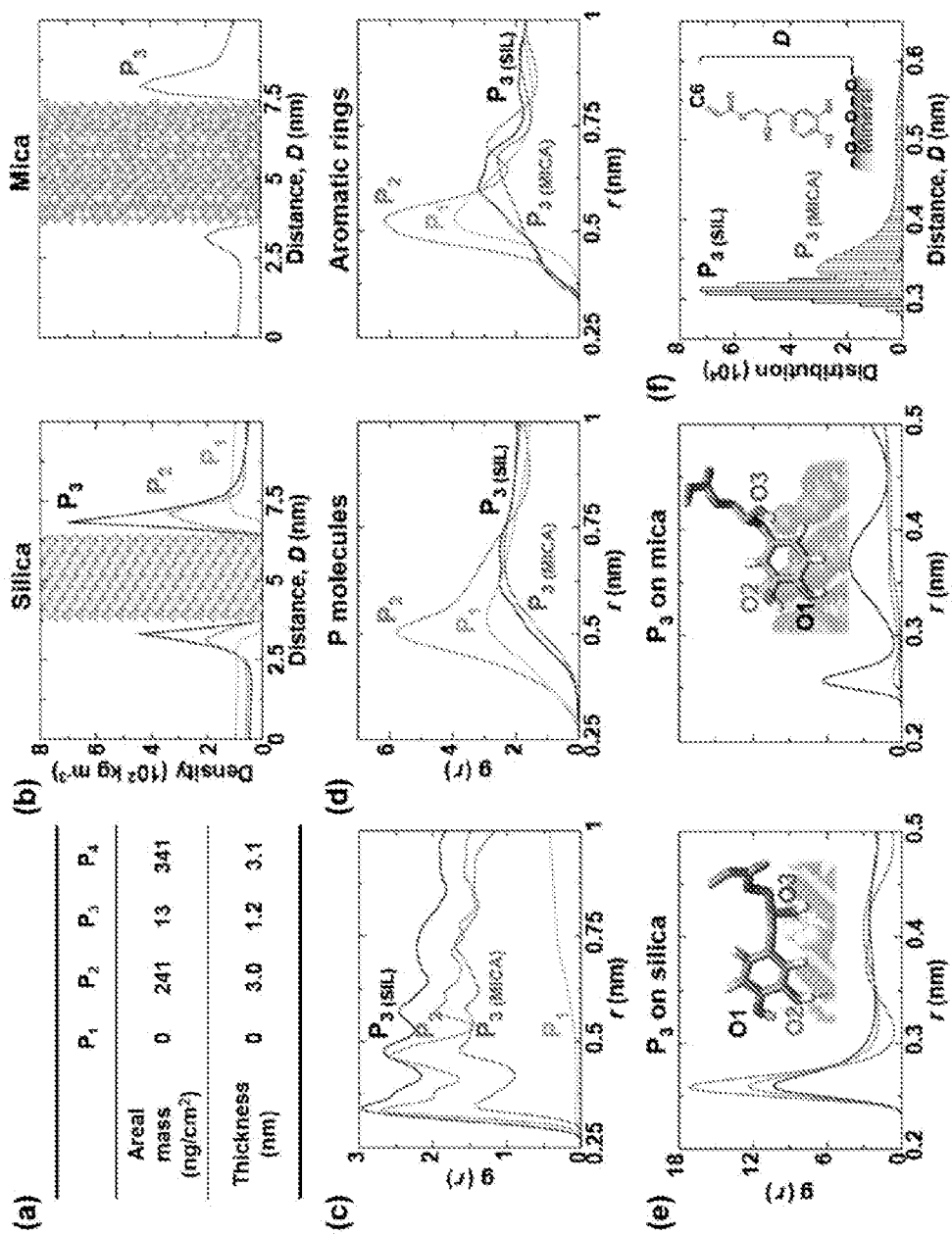
FIGS. 50A-50F show Computational modelling of primer adsorption onto silica and mica surfaces.
Figures 51A, 51B:
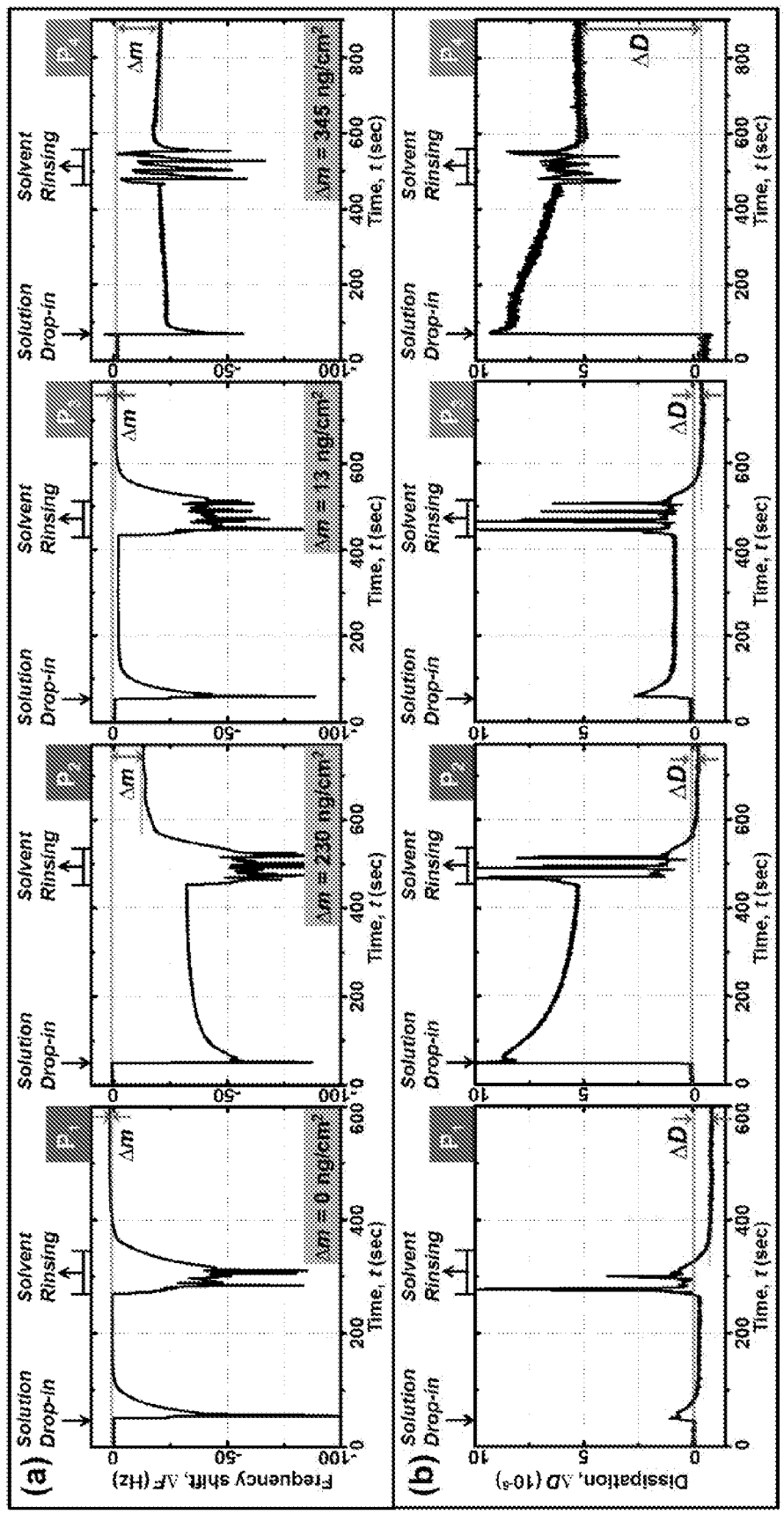
FIGS. 51A and 51B show graphs showing (51a) Frequency change (ΔF) and (55b) dissipation change (ΔD) upon addition of each primer solution to a SiO$_2$ surface.
Figures 52A, 52B:
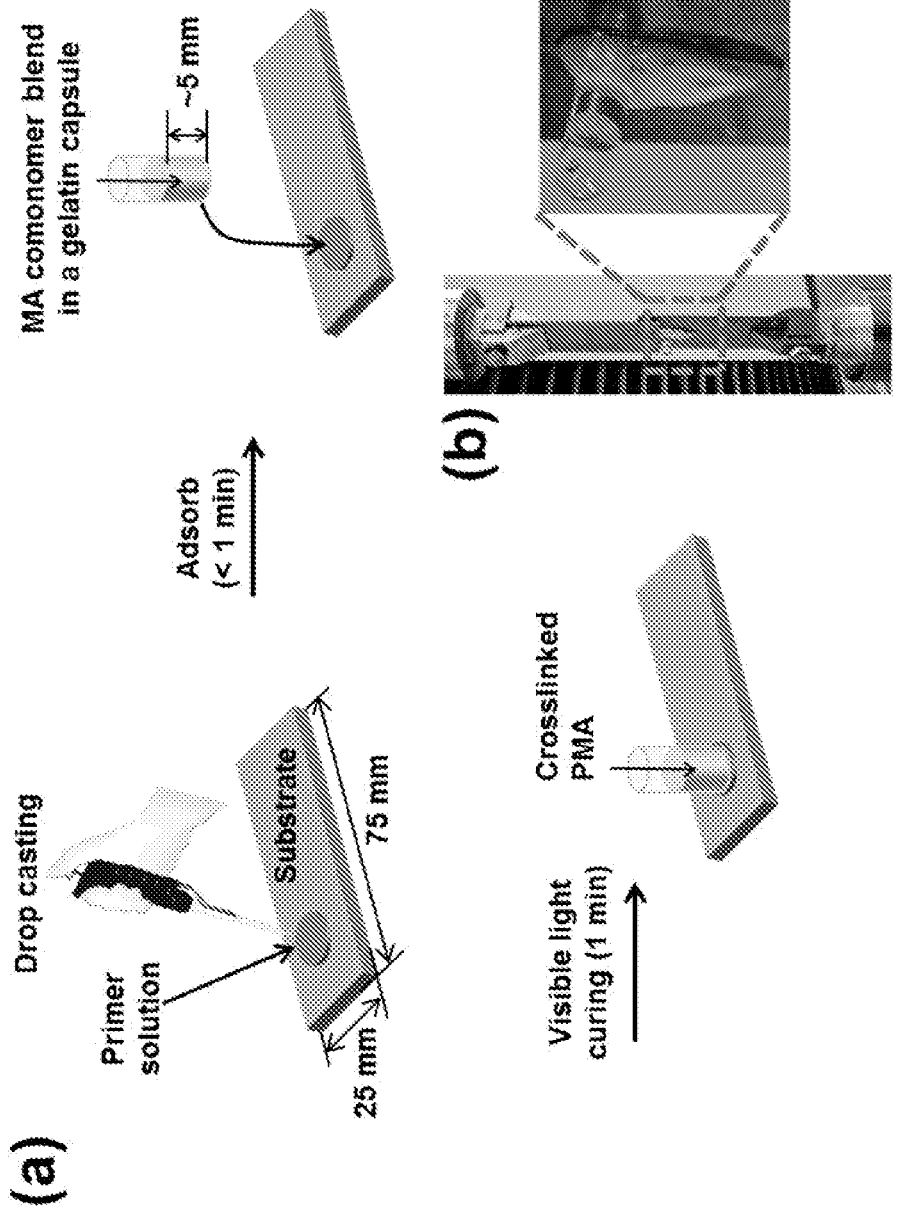
FIG. 52A is Schematic of sample preparation for the lap shear test.
FIG. 52B is a photograph of experimental setup for the lap shear measurement of crosslinked PMA on the surface treated tooth enamel.
Figures 53A, 53B:
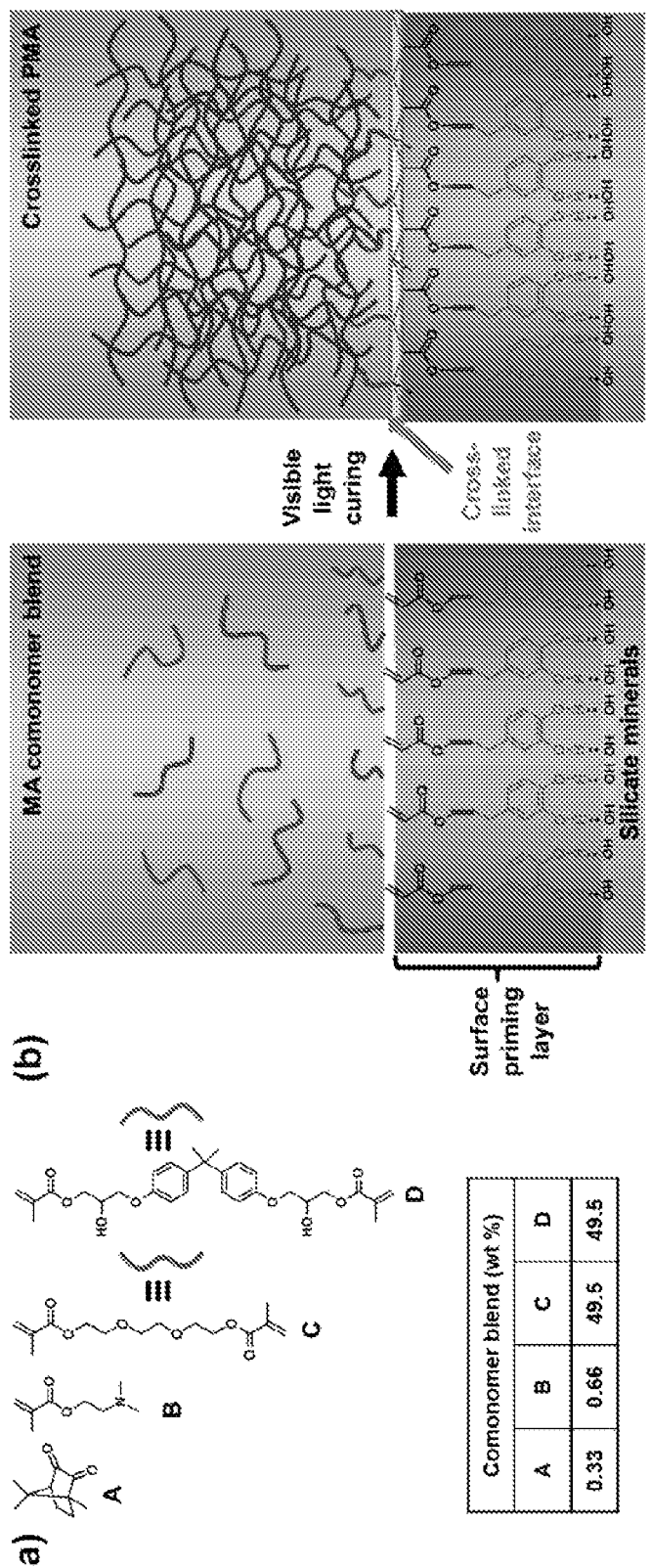
FIG. 53A shows comonomer composition of a visible light-curable methacrylic adhesive blend—camphorquinone, comonomer A, 2-(dimethylamino)ethyl methacrylate, comonomer B, triethylene glycol dimethacrylate, comonomer C, and bisphenol A glycerolate dimethacrylate, comonomer D.
FIG. 53B shows schematic drawing showing the polymerization and crosslinking of the PMA onto a catechol-primed surface.

This modelling of adsorption of each molecules via MD simulation can elucidate how small changes in molecular structure and surface characteristics can affect the adsorption. The computational methods are fully described in the Supplemental Information. $P_1$, $P_2$ and $P_3$ were selected to assess the influence of their aromatic groups (W, Y and Y') on mineral surface adsorption as their similar structure and contour length accommodate more convenient comparisons in MD simulations. The simulations were initiated with a dense layer of the primers, about 2.5 molecules per nm$^2$, placed above the mineral surfaces, and run for 200 nanoseconds. The results of the MD simulations agreed with those of the AFM and QCM-D studies: the catecholic moieties in $P_3$ were densely packed at both mica and silica surfaces, while $P_1$ did not adsorb (FIGS. 50A and 50B) as experimentally shown in FIG. 48C. In addition, the MD simulations allow a more detailed assessment of the differences between the catechol and phenol groups of the $P_3$ and $P_2$ molecules, respectively. It was found that both $P_2$ and $P_3$ are recruited to oxide surfaces via hydrogen bond formation; however, although the $P_2$ hydroxyl groups showed a well-defined interaction with silica surface, the molecules possessed a higher diffusion coefficient in the normal plane to the mineral surface. This behaviour indicates multiple binding and unbinding events that, in the case of $P_2$, resulted in significantly less dense priming pattern than $P_3$, in agreement with experimental observations. This finding agreed with previous studies that showed that vicinal two or more hydroxyl groups are crucial for the effective adsorption in a bidentate fashion. $P_2$ molecules also show the strongest interaction between aromatics rings leading to the formation of aggregates (FIG. 50C), which agreed with AFM and QCM-D studies. Notably, all three hydroxyl groups of $P_3$ molecules significantly contributed to hydrogen bonding to the silica surface, whereas only the catecholic hydroxyl groups of $P_3$ effectively interact with mica surface (FIG. 50D). As a result, it was observed that a greater contact surface of $P_3$ to silica and consequently, a smaller thickness of the $P_3$ molecular layer than on mica (FIG. 50E).

To explore the effects of a mussel-inspired single molecular priming layer (1-5 nm) on adhesion enhancement, the performance of a crosslinked PMA resin, a common crosslinked copolymer resin used in dental restoration and medical bone cement applications was investigated (FIGS. 52A-52B and 53A-53B). The resin was prepared by a photo-initiated radical polymerization of four comonomers: triethylene glycol dimethacrylate, bisphenol A glycerolate dimethacrylate, 2-dimethylaminoethyl methacrylate, camphorquinone. Each primer was applied onto various mineral substrates prior to applying the PMA resin. Two conventional priming layers were used as comparisons for the new mussel-inspired priming system: a phosphate-based primer (10-methacryloyloxydecyl dihydrogen phosphate, herein called 'MDP') and a silane-based primer (3-trimethoxysilylpropyl acrylate, herein called 'Silane').

Figures 54A, 54B, 54C, 54D, 54E, 54F:
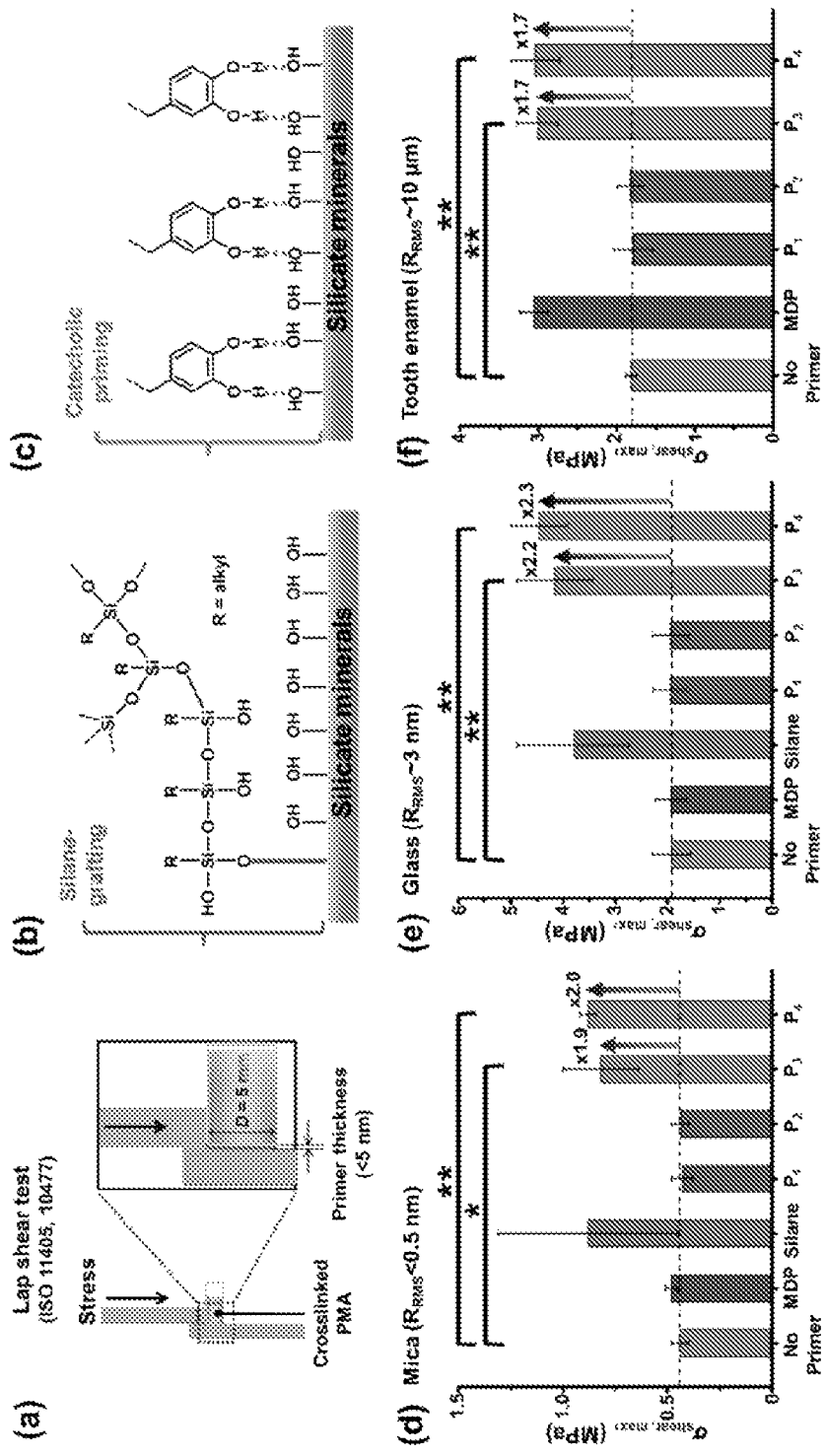
FIGS. 54A-54H show effects of surface priming on adhesion of a crosslinked PMA resin.
Figure 55:
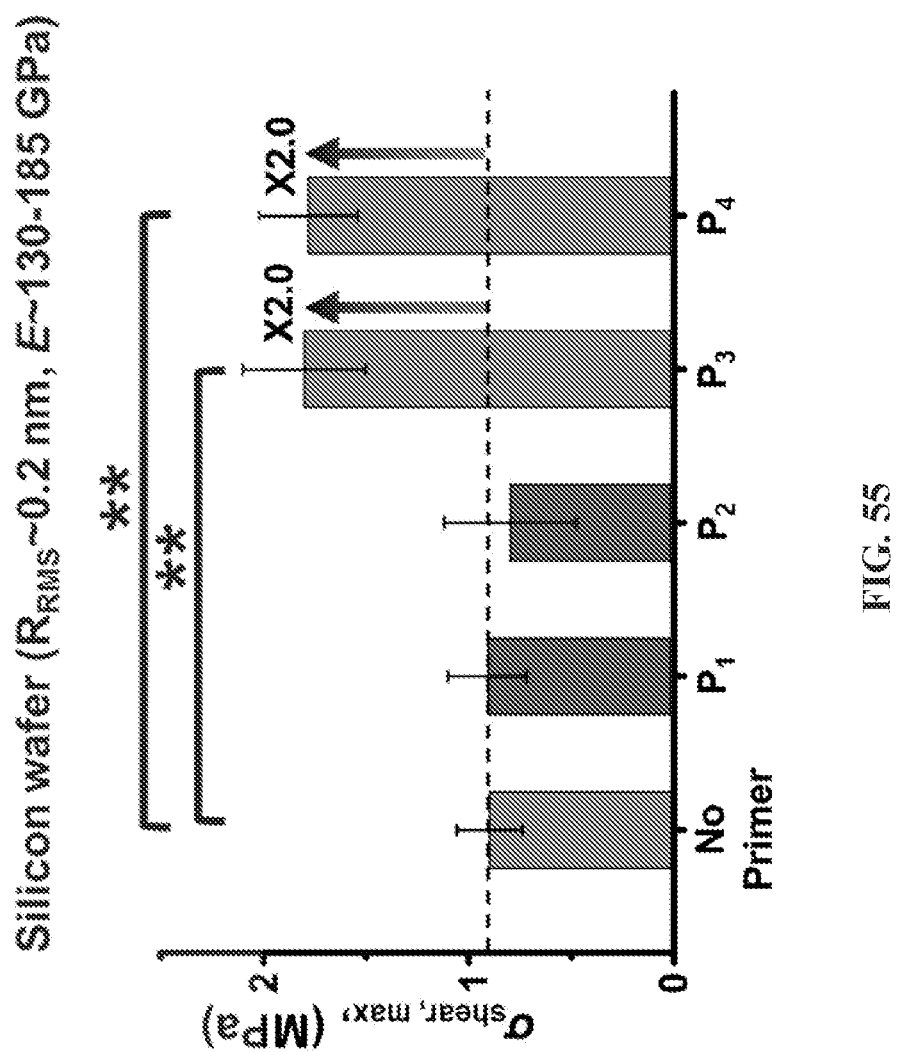
FIG. 55 is graph showing lap shear strength of cured PMA on silicon wafer surfaces treated with different primers (P$_1$, P$_2$, P$_3$ and P$_4$). P-value was calculated using the Student's t-test; **p<0.001.

First, the effect of mussel-inspired priming on the lap shear strength of the PMA resin bonded to mica, glass, silicon wafer, and tooth enamel (consisting of >90% hydroxyapatite, the chief mineral component of human bone), respectively, was investigated. The Student's t-test was performed and the compared values in all mechanical testing results in this paper showed statistically significant difference (p<0.05). Primer adsorption was performed as described, then the PMA resin was cured on the primed substrates (FIG. 54A). The measured maximum lap shear force, Fmax, was converted to shear strength, $\sigma_{shear,\ max}$=Fmax/$\pi R^2$, where R is the radius of the glued surface. Microscopic adhesive failure between polymer and substrate was confirmed with optical microscopy. On silicate materials (e.g., mica and silica), the lap shear strength of cured PMA using $P_1$, $P_2$ and MDP primers ($\sigma_{shear,\ max}$=0.4~0.5 MPa and 1.9~2.3 MPa) was similar to that of PMA cured with no primer at all. By contrast, the use of the catecholic primers $P_3$ ($\sigma_{shear,\ max}$=0.8±0.2 MPa and 4.2±0.7 MPa, n=5; the +/−value is standard deviation and the n is number of experiments), $P_4$ ($\sigma_{shear,\ max}$=0.9±0.1 MPa and 4.5±0.5 MPa, n=5) doubled the lap shear strength compared to the no-primer case, to a value similar to that of a silane-primed surface ($\sigma_{shear,\ max}$=0.9±0.4 MPa and 3.8±1.1 MPa, n=5), which is used as the industry standard despite of its low surface coverage, high energy consumption and toxic chemical usage (FIGS. 54D, 54E, and 55). On tooth enamel (FIG. 54F), the lap shear strength measured using surfaces primed with $P_3$ ($\sigma_{shear,\ max}$=3.0±0.3 MPa), and $P_4$ ($\sigma_{shear,\ max}$=3.0±0.3 MPa, n=5) was twice as great as the no primer case ($\sigma_{shear,\ max}$=1.8±0.1 MPa, n=5), and resembled MDP ($\sigma_{shear,\ max}$=3.1±0.2 MPa, n=5), which is used as the dental industry standard despite pH dependency of phosphate-calcium binding. By contrast, surfaces primed with $P_1$, $P_2$ and silane showed no increase in the lap shear strength as compared to the no primer control. Most importantly, the catecholic primer shows a universal increase in lap shear strength on both silicate and human mineral surfaces, in contrast to current treatments which are optimized to a specific surface chemistry.

Figures 54G, 54H:
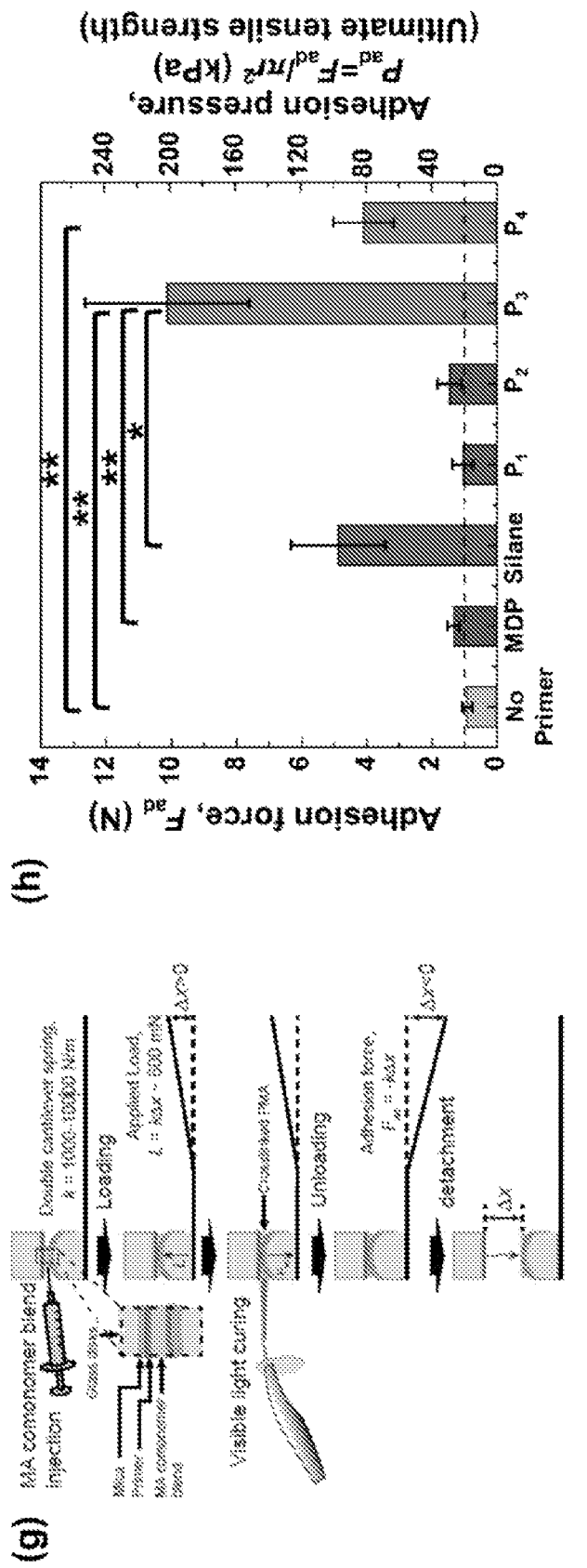

To further investigate the effects of primers, a Surface Forces Apparatus (SFA) (see FIG. 54G) was used which allows for measurement of pure adhesion. To eliminate surface roughness that can contribute to mechanical interlocking, each primer was applied onto an atomically-smooth mica surface before the PMA resin was applied. The measured adhesion force, $F_{ad}$, was converted to adhesion pressure ($P_{ad}=F_{ad}/\pi r^2$), where r is the radius of the surface area at adhesive contacts. It was confirmed that the adhesive failure occurs almost always between the resin and mica, but never occurred in bulk phase of the cured PMA resin. Occasionally, with surfaces primed with $P_3$, adhesion between mica and PMA resin exceeded adhesion between mica and epoxy resin, which used to fix the mica substrate to the glass cylinder in SFA, and hence the adhesive failure occurred between mica and epoxy resin (the values obtained from mica-epoxy resin failure were excluded). As shown in FIG. 54H, as compared with plain mica (with no primer), surfaces primed with $P_1$ and $P_2$ showed no increase in adhesion, whereas $P_3$ ($P_{ad}$=201.5±50.2 kPa, n=5) and $P_4$ ($P_{ad}$=81.7±18.5 kPa, n=5) exhibited a ~10-fold and ~4-fold increase in adhesion, respectively. Importantly, the adhesion pressure ($P_{ad}$) measured with $P_3$ was ~8 and ~2 times higher than that of the conventional MDP and Silane primers, respectively. This enhancement was attributed to the higher surface physicochemical binding density of the catecholic bidentate hydrogen bonding compared with silane-based coupling agents that typically provide only 10-20% binding efficiency during covalent bonding (as shown schematically in FIGS. 54B and 54C). Moreover, the measured adhesion of $P_3$ (~200 kPa) is comparable with the estimated interfacial stress achieved just before adhesive failure of actual mussel plaques ($P_{ad}$~270 kPa).

Figures 59A, 59B:
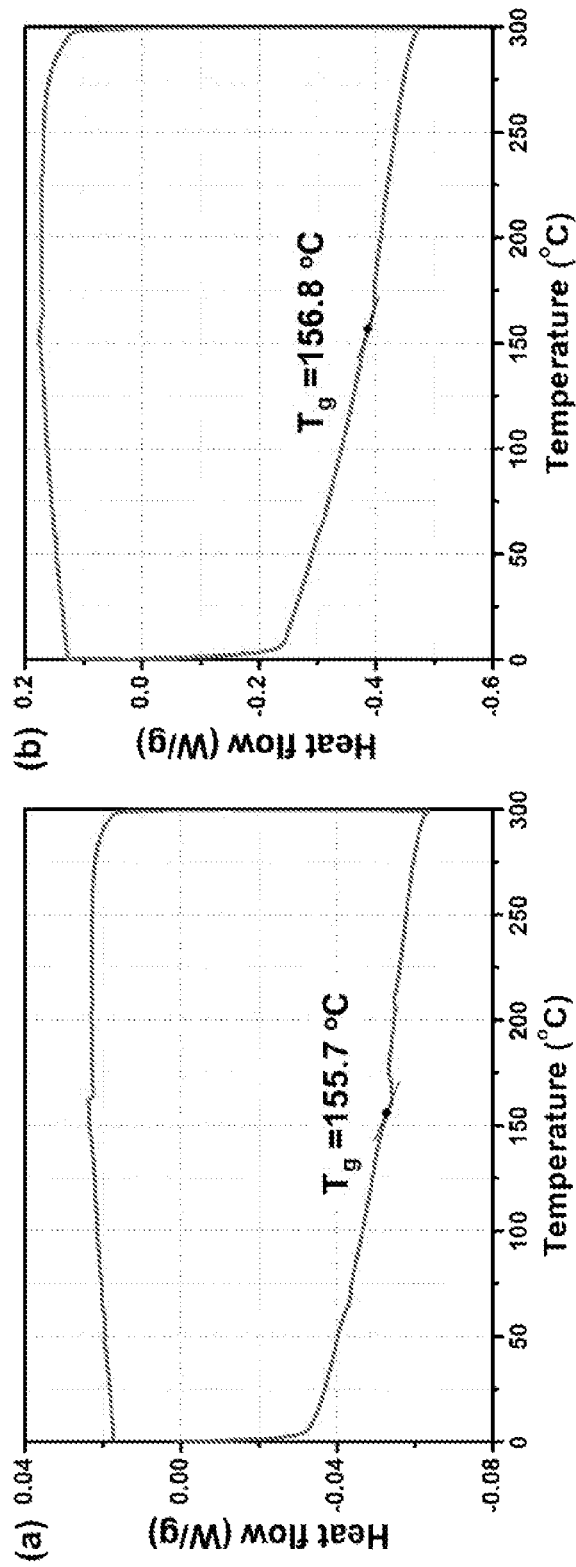
FIGS. 59A-59B are graphs showing differential scanning calorimetry curves of (a) Silane-treated glass-filled composite and (b) Catechol-treated glass-filled composite.
Figure 60:
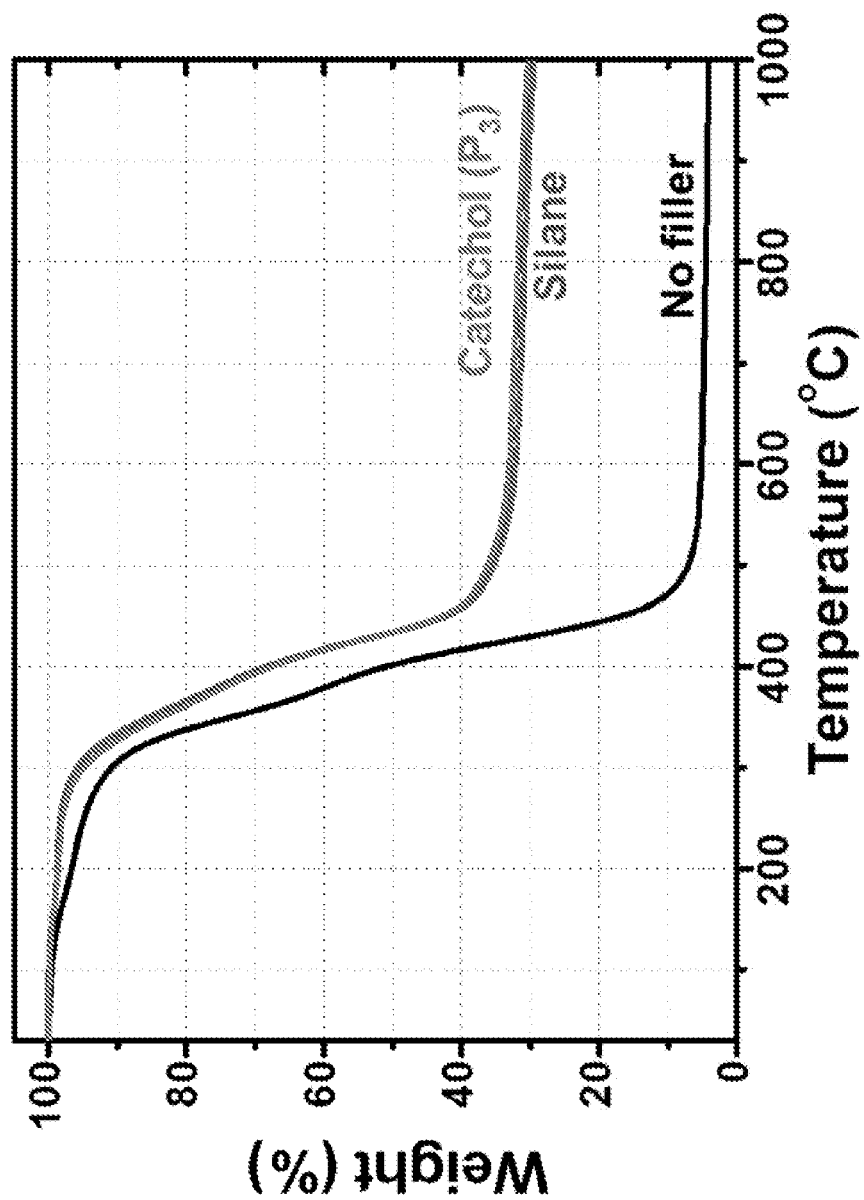
FIG. 60 is a graph showing thermogravimetric curves of the unfilled PMA resin and primer-treated glass-filled PMA composites.

PMA resins are widely used in various applications and in particular in medical and dental restorative materials and adhesives. For dental applications, the PMA resins are typically formed with glass fillers that are treated by silane-grafting to increase the rigidity and hardness of PMA resin composites. Next, the use of the catecholic primers was tested, which are less toxic than silane-based covalent coupling agents, and offer the promise of dynamic, self-repairing bonds. Catecholic primer $P_3$, which exhibited higher adsorption and adhesion performance compared $P_4$, was chosen for further scrutiny. To rule out contact cytotoxicity a $P_3$-primed glass surface was prepared, and non-toxicity was confirmed in a cell viability assay based on ISO 10993 (FIGS. 56A-56B), suggesting high potential for biomedical and dental applications. The mechanical properties of PMA resin composites containing $P_3$ primed glass fillers were tested in compressive loading and compared to those of composites either containing conventional Silane-primed fillers or without fillers (FIGS. 57A-57C), respectively. To rule out the possible contributions of changes in the filler distribution under various treatments to the observed mechanical properties, the topology and thermal properties of the composites were investigated. Scanning electron microscopy (SEM) shows the glass fillers to be densely packed in all the composites (FIG. 57A), and no obvious differences in packing were observed between the Silane- and $P_3$-treated samples. Unfortunately, the non-uniformity of the crushed glass fillers and the highly irregular surfaces of the fracture debris after compressive failure did not allow us to distinguish whether failure occurs cohesively within the bulk of the resin, or at the glass-polymer interface (FIGS. 58A-58D). However, similar glass transition temperatures ($T_g$~156° C., FIGS. 59A-59B) was observed for all three composites using Differential Scanning Calorimetry (DSC) and similar thermal decomposition patterns for the glass-filled composites through ThermoGravimetric Analysis (TGA) (FIG. 60). These results suggest that the mechanical and thermal properties of the PMA composites are not strongly affected by fillers, but rather dominated by bulk polymer network.

Figures 57A, 57B, 57C:
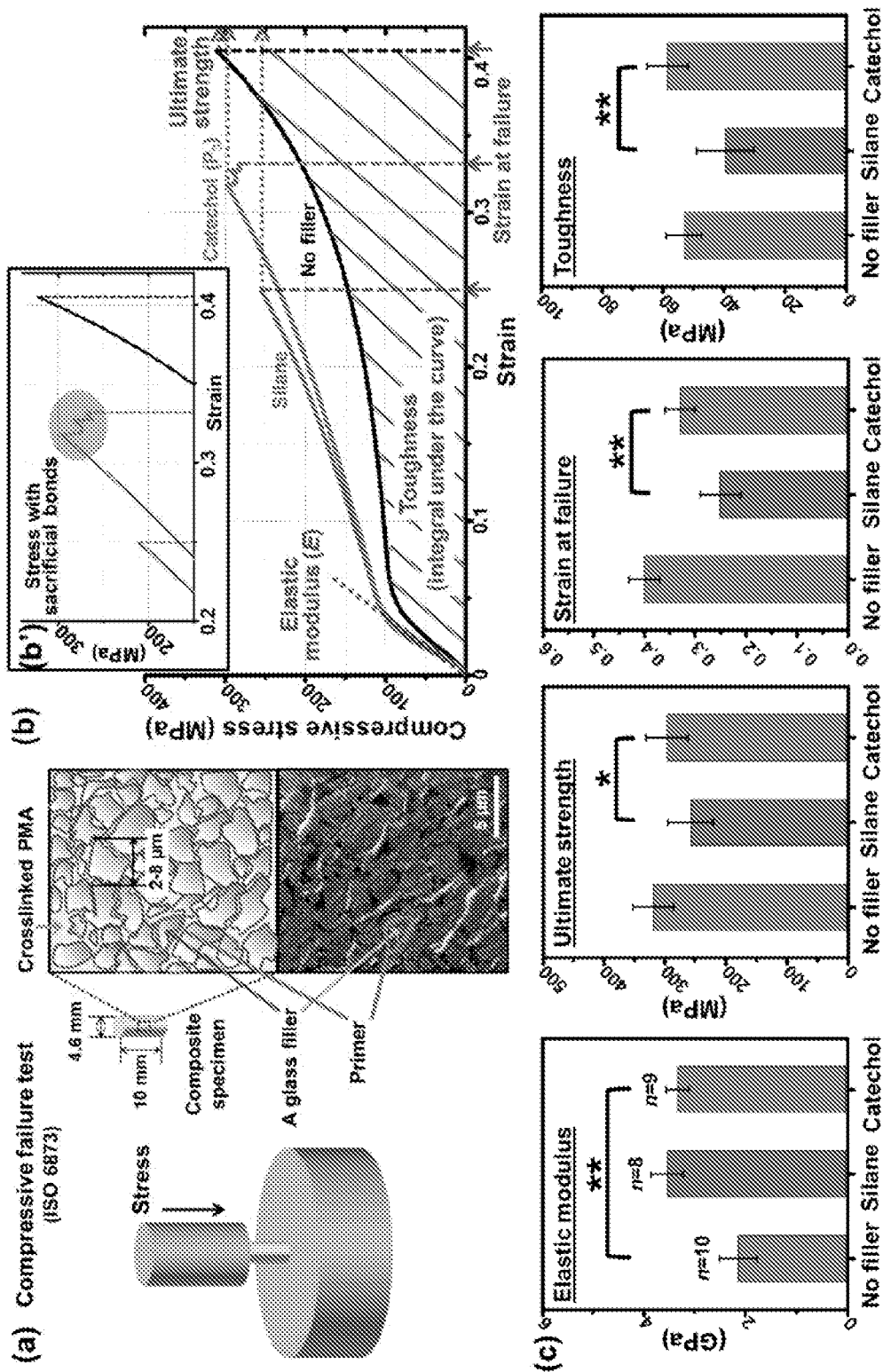
FIGS. 57A-57C show effects of surface priming on the mechanical properties of rigid glass-filled PMA resin composites.
Figures 58A, 58B, 58C, 58D:
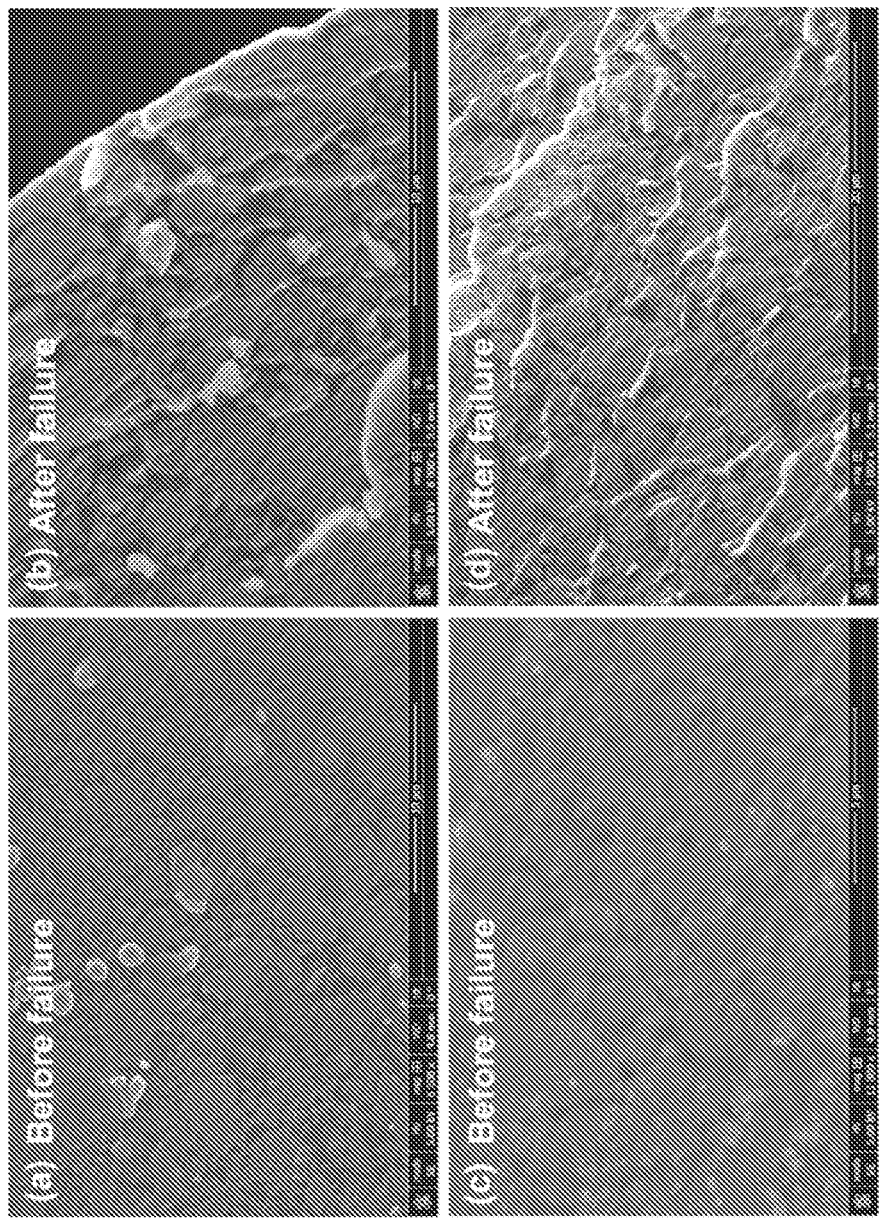
FIGS. 58A-58D show SEM images of (a, b) Silane-treated glass-filled composite (c, d) Catechol-treated glass-filled containing composite before (left column) and after (right column) compressive failure.

In the mechanical testing, although tensile failure mode is more popular and often more comprehensible, the PMA composites was chosen in compressive failure mode since in general such rigid composites are used in medical and dental load bearing systems to resist compressive strain. FIG. 57B shows a representative stress-strain curve for each of the three composite samples. As expected, the Silane-treated glass-filled PMA composite exhibited ~50% increase in elastic modulus as compared to the no-filler PMA sample; this E enhancement is the rationale for adding fillers into PMA composites. However, in such rigid synthetic polymer composites, this increase in modulus always results in reduction in extensibility (as determined by the strain at failure) and the resultant brittleness often leads to reduction in ultimate strength, as shown here in the Silane-filler-containing samples (~20% decrease in ultimate strength and ~40% decrease of strain at failure). By contrast, the catechol-treated glass-filled PMA composites exhibited the same enhancement in modulus but with negligible reduction in the ultimate strength and only ~15% decrease of strain at failure, leading to a significant ~50% enhancement in toughness compared to the brittle Silane-filler-containing PMA composites (FIG. 57C). Thus, with the ductile catechol-based priming system, the requisite increase in resin stiffness was achieved while better maintaining the energy dispersive properties of the PMA. Cyclic loading and rheology test at above $T_g$ were conducted to further investigate the catecholic dynamic bonding (see Supplementary Information for more details). However, difference between Silane and Catechol samples was negligible due to the high modulus of the samples (FIGS. 61A-61B and 62A-62C).

Interestingly, the stress-strain curve for the $P_3$-coated glass-filled exhibited a noticeable pattern of jagged stress decreases after reaching its ultimate strength value (FIG. 57B) in 8 out of 9 samples whereas the Silane-treated and no-filler samples did not show such pattern in all samples, rather exhibiting abrupt and immediate fracture. In other biomaterials (i.e. bone) and in soft polymer networks such features are attributed to the nanoscale rupture of sacrificial bonds which dissipate energy and provide hidden length and thus ductility. The inventors hypothesized that macroscopic saltatory pattern of stress decrease in the $P_3$-treated samples might be correlated to sacrificial bond failure between the catechol and mineral surfaces, given its obvious difference when compared to the other samples, the excessively strong and rigid nature of the PMA resin composites, and the dynamic bonding nature of the catecholic primers observed via MD simulation and in previous studies of Dopa-containing polymers. Importantly, and in contrast to previous reports of toughening with sacrificial networks in soft hydrogels (E=1-100 kPa) or elastomers (E=0.5-4.5 MPa), the primed, glass-filled PMA composites demonstrated here possess the strength and rigidity needed for a practical load bearing system, for example in medical and dental applications (E>3.5 GPa: a million fold stiffer than those hydrogels in literature).

In summary, the catecholic surface priming mechanism of mussels was successfully translated to a synthetic priming system. The bioinspired primer forms a ~1 nm thick self-assembled single molecular layer within 30 s. The binding mechanism dependence with different mineral surfaces was revealed by MD simulations, in combination with AFM and QCM-D. Building on this fundamental understanding of molecular adsorption and adhesion of newly designed catecholic primers, the adhesion performance of a PMA resin was enhanced by up to an order of magnitude on mica, glass, silica and tooth enamel. The strong and dynamic catecholic binding also led to significant toughness enhancement (~50%) of a highly rigid (E~3.5 GPa) polymer resin composite, providing particular promise for use as structural materials, including biomedical applications. Finally, this study suggests the enormous potential of the next generation of bioinspired surface primers that can replace the toxic, time and energy consuming silane-based coupling agents currently in use.

Methods

Materials

All reactions were carried out under argon unless otherwise noted. All glassware was pre-dried in an oven at 150° C. for 30 min. 1,8-Octanediol, acryloyl chloride, triethylamine, 3,4-dihydroxyhydrocinnamic acid, N,N'-dicyclohexylcarbodiimide (DCC), 4-(dimethylamino)pyridine (DMAP), tetrabutylammonium fluoride solution—1 M in THF (TBAF), 3-(trimethoxysilyl)propyl acrylate, triethylene glycol dimethacrylate (TEGDMA), bisphenol A glycerolate dimethacrylate (Bis-GMA), 2-(dimethylamino)ethyl methacrylate (DMAEMA) and camphorquinone (CQ) were purchased from Sigma-Aldrich. Benzyl acrylate ($P_1$), 4-hydroxybenzyl alcohol, 10-methacryloyloxydecyl dihydrogen phosphate (MDP) and glass filler (2-8 μm) were purchased from Alfa Aesar, Chem-Impex International, Kuraray Medical Inc., and Youth Tech Co., respectively. Triethylsilane-protected eugenol acrylate was provided by Osaka Chemical.

Synthesis of Compounds

Figures 63A, 63B, 63C:
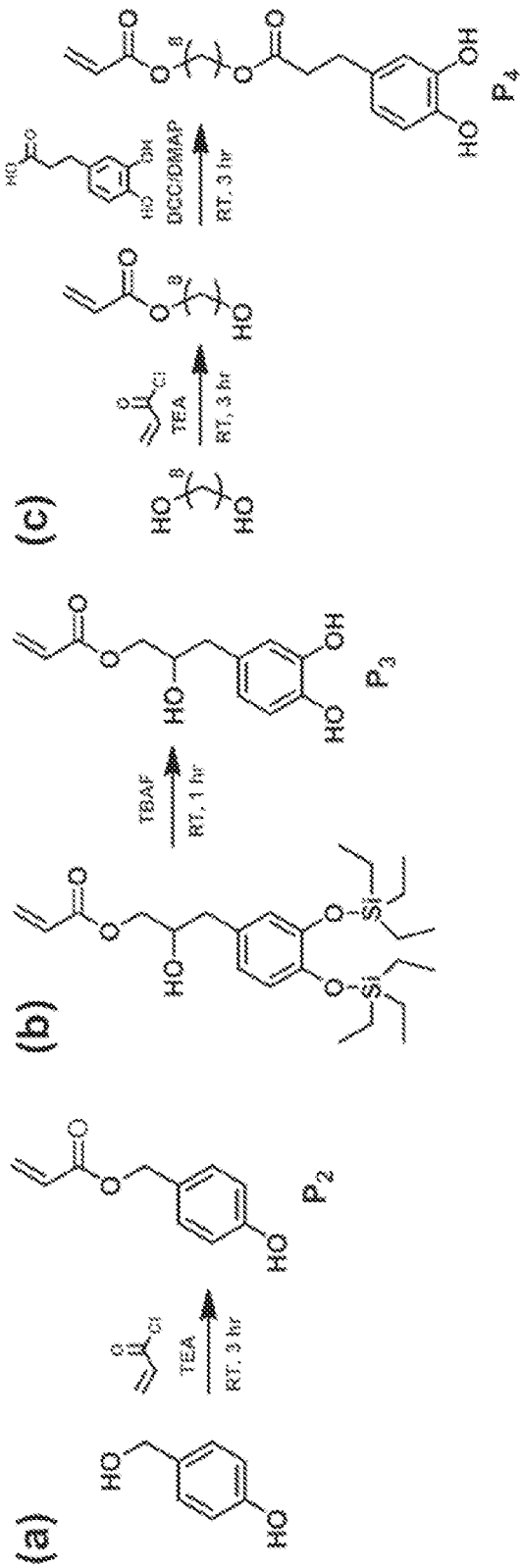
FIGS. 63A-63C show synthetic schemes of (a) 4-hydroxybenzyl acrylate ($P_2$), (b) 3-(3,4-dihydroxyphenyl)-2-hydroxypropyl acrylate ($P_3$), and (c) 8-((3-(3,4-dihydroxyphenyl)propanoyl)oxy)octyl acrylate ($P_4$).

Bioinspired primer molecules ($P_2$-$P_4$) were synthesized (FIGS. 63A-63C). The chemical structure and mass was confirmed by $^1$H NMR and Mass spectrometry.

4-Hydroxybenzyl acrylate ($P_2$). 4-Hydroxybenzyl alcohol (5 g, 40.28 mmol, 1.0 equiv) and triethylamine (6.7 ml, 48.33 mmol, 1.2 equiv) were agitated in THF (30 ml) at room temperature for 1 min. Subsequently, acryloyl chloride (3.27 ml, 40.28 mmol, 1.0 equiv) was added dropwise into the reaction mixture, and the reaction continued for 3 hours. The THF solvent was removed using a rotary vacuum evaporator. The crude material was extracted with 150 ml diethyl ether and the solution washed with 1N HCl. After purification by Biotage Isolera™ Prime automatic column chromatography (Biotage SNAP 50 g silica column; hexane/diethyl ether 100:0 to 75:25 gradient; flow rate 40 ml/min), 3 g (42% yield) of a transparent oil was obtained.

Figure 64:
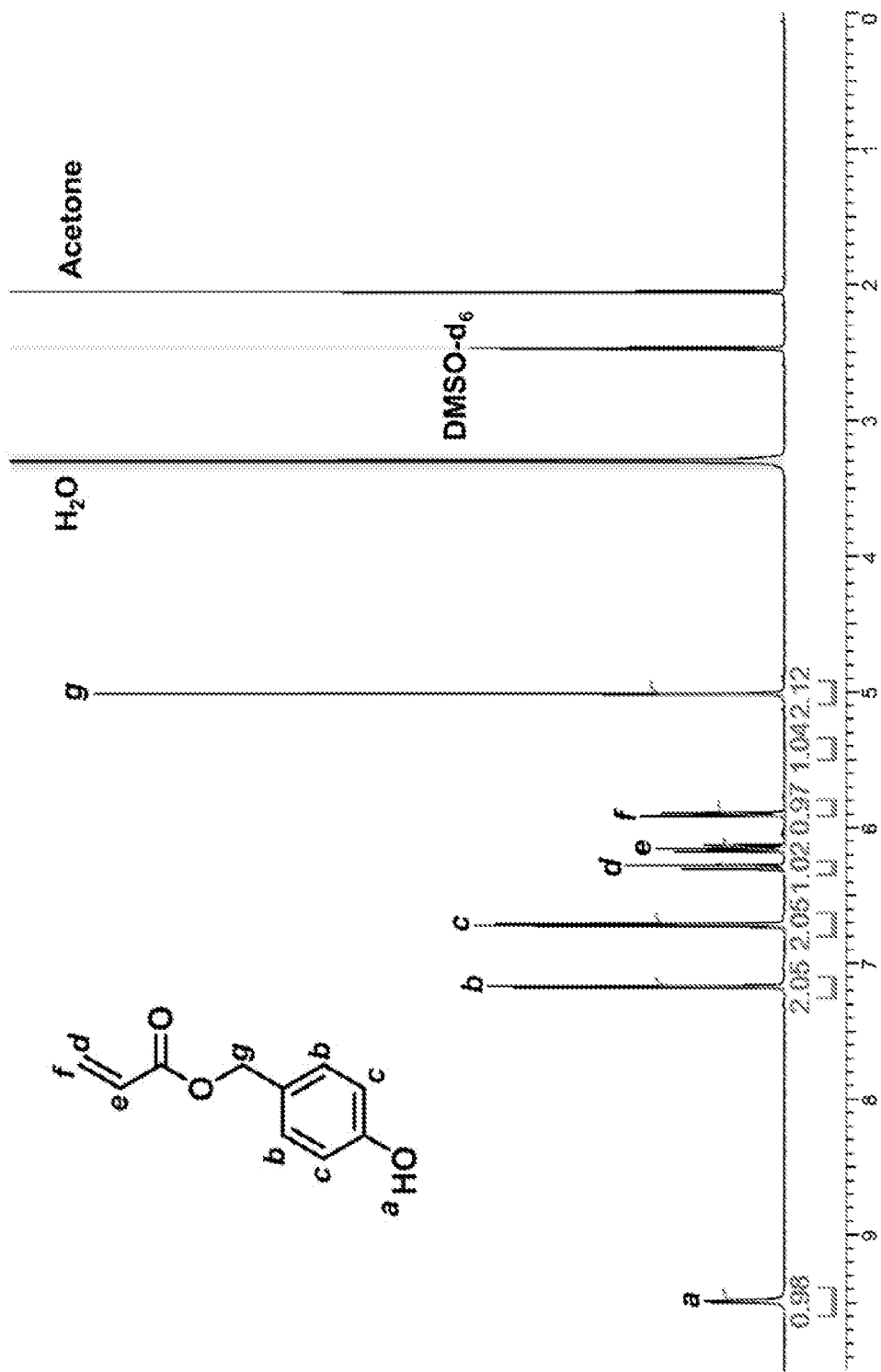
FIG. 64 is a $^1$H NMR spectrum of $P_2$ in DMSO-$d_6$.

$^1$H NMR (600 MHz, DMSO-$d_6$): =9.49 (s, 1H, Ar—OH), 7.18 (d, 2H, Ar—H), 6.72 (d, 2H, Ar—H), 6.28 (d, 1H, —CH=CH$_2$), 6.16 (q, 1H, —CH=CH$_2$), 5.91 (d, 1H, —CH=CH$_2$), 5.01 (s, 2H, —CH$_2$CH(OH)—) (FIG. 64). EI-MS, m/z=179.05 [M+Na$^+$].

3-(3,4-dihydroxyphenyl)-2-hydroxypropyl acrylate ($P_3$). Triethylsilane-protected eugenol acrylate was synthesized, as described[1]. TBAF (1.71 ml, 1.71 mmol, 0.8 equiv) was added dropwise to a solution of the triethylsilane-protected eugenol acrylate (1 g, 2.14 mmol, 1.0 equiv) in THF (40 ml). After 1 hour stirring at room temperature, the crude material was purified via a silica gel flash column chromatography using methanol to remove triethylfluorosilane. Subsequently, the product was further purified by silica gel using 50:50 hexane/diethyl ether to provide 367 mg (90% yield) of slightly brownish liquid.

Figure 65:
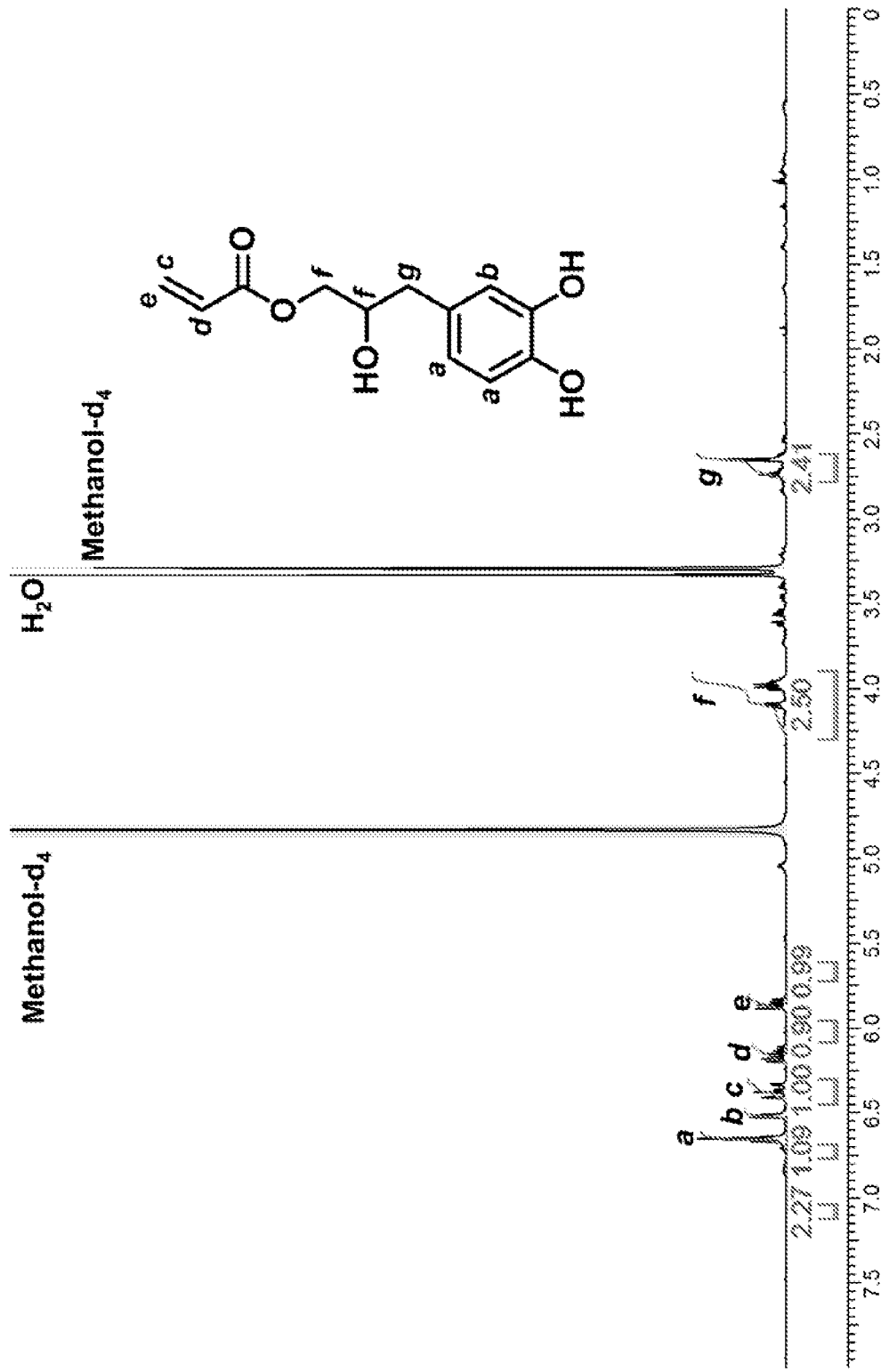
FIG. 65 is a $^1$H NMR spectrum of $P_3$ in methanol-$d_4$.

$^1$H NMR (600 MHz, methanol-$d_4$): =6.65 (d, 2H, Ar—H), 6.52 (q, 1H, Ar—H), 6.38 (d, 1H, —CH=CH$_2$), 6.15 (q, 1H, —CH=CH$_2$), 5.85 (d, 1H, —CH=CH$_2$) 4.09 (m, 3H, —CH(OH)CH$_2$OOC—), 2.75 (m, 2H, —CH$_2$CH(OH)—) (FIG. 65). EI-MS, m/z=238.08 [M+Na$^+$].

8-((3-(3,4-dihydroxyphenyl)propanoyl)oxy)octyl acrylate ($P_4$). 1,8-Octanediol (16.7 g, 114.20 mmol, 2.5 equiv) and trimethylamine (7.6 ml, 54.71 mmol, 1.2 equiv) were agitated in THF (200 ml) at room temperature for 1 min. Subsequently, acryloyl chloride (3.7 ml, 45.59 mmol, 1.0 equiv) was added dropwise into the reaction mixture, and the reaction continued for 3 hours. The THF solvent was removed using a rotary vacuum evaporator. The crude material was extracted with 150 ml ethyl acetate and the solution washed with 1N HCl. After purification by Biotage Isolera™ Prime automatic column chromatography (Biotage SNAP 50 g silica column; hexane/ethyl acetate 100:0 to 75:25 gradient; flow rate 40 ml/min), 4.03 g (44% yield) of a transparent liquid (8-hydroxyoctyl acrylate) was obtained (Data not shown).

$^1$H NMR (600 MHz, CDCl$_3$): =6.38 (d, 1H, —CH$_2$CH=CH$_2$), 6.10 (q, 1H, —CH$_2$CH=CH$_2$), 5.80 (d, 1H, —CH$_2$CH=CH$_2$), 4.13 (t, 2H, —CH$_2$CH$^2$OOC—), 4.07 (q, 2H, —CH(OH)CH$_2$OOC—), 3.63 (q, 2H, HO—CH$_2$CH$_2$—), 2.16 (s, 2H, HO—CH$_2$), 1.45 (m, 12H, —CH$_2$CH$_2$CH$_2$CH$_2$CH$_2$CH$_2$CH$_2$—).

3,4-Dihydroxyhydrocinnamic acid (2.75 g, 15.09 mmol, 0.75 equiv), DCC (4.15 g, 20.12 mmol, 1.0 equiv) and DMAP (2.46 g, 20.12 mmol, 1.0 equiv) were agitated in THF (200 ml) at room temperature for 1 hour. Subsequently, the 8-hydroxyoctyl acrylate (4.03 g, 20.12 mmol, 1.0 equiv) added into the reaction mixture, and the reaction continued for 3 hours. The THF solvent was removed using a rotary vacuum evaporator. The crude material was extracted with 150 ml ethyl acetate and the solution washed with 1N HCl. After purification by Biotage Isolera™ Prime automatic column chromatography (Biotage SNAP 50 g silica column; hexane/ethyl acetate 100:0 to 50:50 gradient; flow rate 40 ml/min), 1.72 g (31% yield) of a white crystal was obtained.

Figure 66:
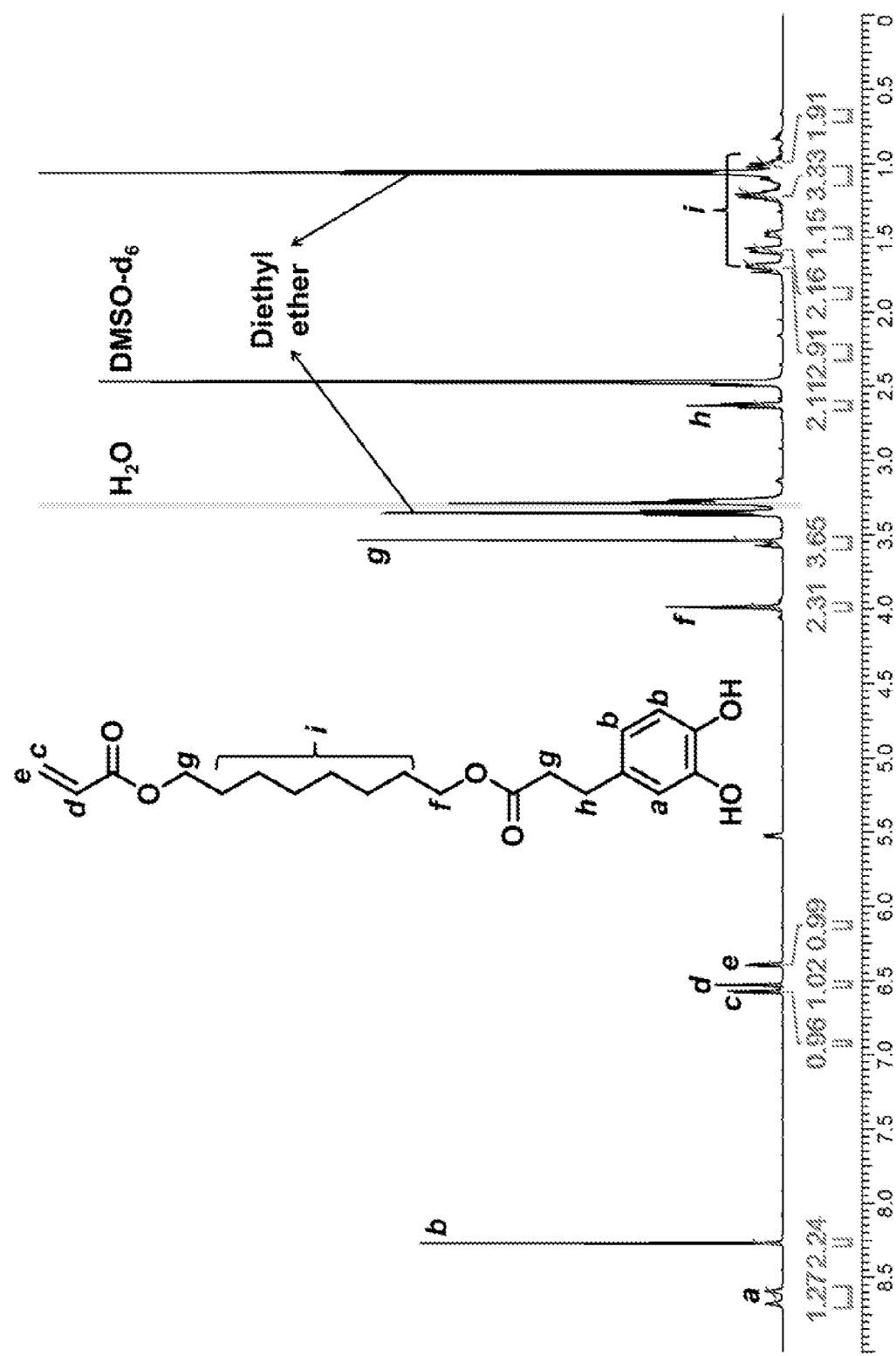
FIG. 66 is a $^1$H NMR spectrum of $P_4$ in DMSO-$d_6$.

$^1$H NMR (600 MHz, DMSO-$d_6$): =8.64 (q, 1H, Ar—H), 8.27 (d, 2H, Ar—H), 6.58 (d, 1H, —CH$_2$CH=CH$_2$), 6.53 (q, 1H, —CH$_2$CH=CH$_2$), 6.40 (d, 1H, —CH$_2$CH=CH$_2$), 3.98 (t, 2H, —COO—CH$_2$CH$_2$—), 3.55 (m, 4H, —CH$_2$CH$_2$OOC—, —CH$_2$—CH$_2$—OOC—), 2.62 (q, 2H, —ArCH$_2$CH$_2$—), 1.76-0.96 (m, 12H, —CH$_2$CH$_2$CH$_2$CH$_2$CH$_2$CH$_2$CH$_2$CH$_2$—) (FIG. 66). EI-MS, m/z=364.21 [M+Na$^+$].

All solvents used in these studies were degassed and filled with argon unless otherwise noted.

Atomic Force Microscopy (AFM) Experiments

Figure 49:
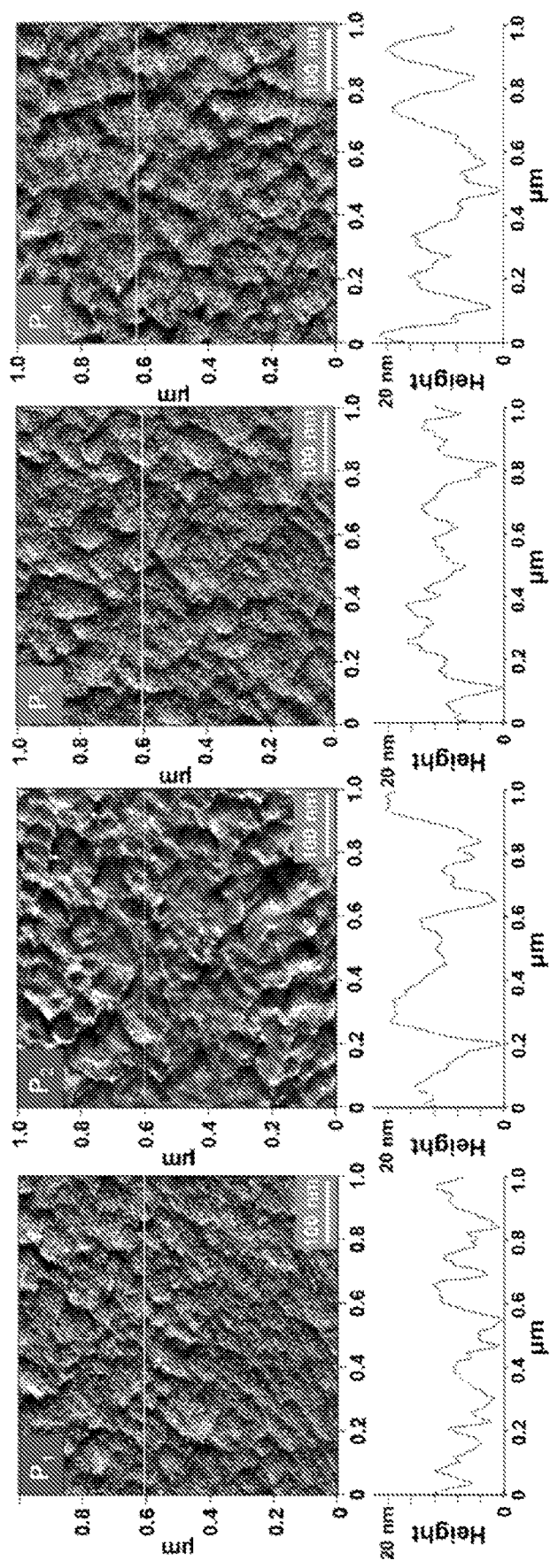
FIG. 49 shows AFM images and height profiles of adsorbed primers onto glass surfaces. The root mean square (RMS) roughness R of the glass is ~5 nm, making a quantitative comparison of the height profiles of the various primer-treated surfaces difficult, whereas atomically smooth mica surfaces in the main text exhibit clear comparison between the primed surfaces. However, the general trends appear to follow those observed on the low-roughness mica substrates.

Each primer solution (1 wt %) was prepared in methanol (for $P_1$-$P_3$) or DMSO (for $P_4$). The primer solution was drop cast onto a freshly cleaved mica or glass surface, and kept at room temperature for 1 min. Subsequently, the surfaces were thoroughly rinsed with the respective solvents and dried with argon. All images, surface profiles and surfaces roughnesses were collected using an Asylum MFP-3D standard system (Asylum Research, Santa Barbara, CA) using silicon cantilevers (FORTGG-50, Applied NanoStructures, Santa Clara, CA) (FIGS. 48C and 49).

Quartz Crystal Microbalance with Dissipation (QCM-D) Experiments

A 'static cell' (often called 'Open Module') QCM-D (Q-Sense, Biolin Scientific) was employed to quantitatively evaluate the adsorption of each primer onto SiO$_2$ surface using a quartz sensor (QSX 303, Biolin Scientific). Changes in resonance frequency ($\Delta F$) and dissipation ($\Delta D$) of the SiO$_2$ were recorded and used to measure the adsorbed mass and layer viscoelasticity, respectively, of the primer deposited on the sensor. In detail, pure solvent (100 µl) was dropped onto the sensor and equilibrated for ~20-30 min. Then, 2 wt % primer solution (100 µl) was dropped onto the sensor (this is labeled "Solution Drop-in" in FIG. 51) and equilibrated until the frequency and dissipation signals stabilized. To remove unbound primers, the sensor was rinsed with solvents (this is labeled "Solvent Rinsing" in FIG. 51) and equilibrated until frequency and dissipation signals stabilized.

Given that the frequency change ($\Delta F$) is proportional to the mass change ($\Delta m$) using Sauerbrey equation[2], $P_1$, $P_2$, $P_3$, and $P_4$ adsorbed layers showed surfaces concentrations of 0, 230, 13, and 345 ng/cm$^2$, respectively. Calculated thickness of $P_3$ is ~1.6 nm which agrees with height profile (~1-2 nm) of the AFM image ($P_3$, FIG. 48C) and the contour length of $P_3$, demonstrating a conformal $P_3$ monolayer on surfaces. Mass loss of $P_3$ and $P_4$ during the rinsing was negligible compared to $P_2$ which lost 60% of initial mass, indicating outstanding adsorption efficiency of catechol-containing primers on SiO$_2$ surfaces even compared to mussel foot protein adsorption (~30% loss of mfp-3s[3]). The priming thickness of $P_4$ estimated by QCM-D is ~3.1 nm which agrees with the average height of AFM images (~3.5 nm), assuming that QCM-D measures the average thickness of a uniform layer. The smaller average thickness of $P_4$ (~3.1 nm) compared to the molecular contour length (~4.8 nm) may be attributed to the flexible alkyl spacer in $P_4$. The possibility of a softer, more flexible layer with $P_4$ is supported by a higher change in dissipation ($\Delta D$) compared to other primers.

Molecular Dynamics Simulations

The models simulated by molecular dynamics (MD) consisted of a crystalline silica or mica slab and a layer of P molecules embedded in a methanol box. The composition of each system and the final box size is shown in the Table 1.

TABLE 1

Description of simulated systems

| Primer molecules | | Mineral surface | | Solvent | | Box size (nm) | | |
|---|---|---|---|---|---|---|---|---|
| Type | # | Type | # atoms | type | # molecules | x | y | z |
| $P_1$ | 180 | Silica | 17820 | Methanol | 6990 | 8.10780 | 8.84410 | 10.46244 |
| $P_2$ | 180 | Silica | 17820 | Methanol | 6996 | 8.10780 | 8.84410 | 10.44390 |
| $P_3$ | 180 | Silica | 17820 | Methanol | 6786 | 8.10780 | 8.84410 | 10.37626 |
| $P_3$ | 151 | Mica | 21504 | Methanol | 5675 | 8.32320 | 7.21920 | 11.29101 |

All simulations were performed using the GROMOS 53A6 force field. Parameters for primer molecules were derived from existing parameters for peptides and DPPC in the GROMOS 53A6 force field[7]. The charges for the catechol hydroxyl groups were estimated by a RESP fitting from quantum level MP2/6-31G** within NWChem 6.1. The obtained charges, 0.203 e for carbon; −0.626 e for oxygen and 0.423 e for hydrogen atoms were very similar to the ones already present for tyrosine in the above-mentioned force field.

To build the crystalline silica model, a unit cell was replicated filling a cube with approximate size of (8.1×8.8×3.1 nm). The silica surface was fully hydroxylated. The following atomic charges were used for the silica: Si: 2.1 e, bulk O: −1.05 e, surface O: −0.950 e and H: 0.425 e.

The mica model used is a muscovite-$2M_1$ with formula $KAl_2(Si_3Al)O_{10}(OH)_2$. The muscovite unit cell was replicated 16, 8 and 2 times along the a, b and c vectors, respectively. The crystal size was approximately (8.3×7.2×4.0 nm). Each mica surface contained a layer with one-half of adhered $K^+$ ions. The parameters used for this crystal model were obtained from the CLAYFF force field, which has been parameterized for the SPC water model, like the entire GROMOS 53A6 force field.

Starting structural framework. To obtain an appropriated density for the simulated systems, a box containing primer molecules and solvent was equilibrated by 1 ns of MD simulation. Then, the resulting system was placed onto the mineral surface to obtain the initial configuration for the molecular dynamics simulations.

The protocol to build the box with solvent and primer molecules is described below. Multiples primer molecules were randomly distributed as a dense layer along the x-y plane. These molecules were built in an extended configuration with their phenyl groups along the mineral normal plane, so that they would be oriented towards the mineral surface upon building the initial system. The systems were placed in a rectangular simulation box about 1.5 nm away from the mineral surfaces. The box lengths were the same size of mineral surfaces in x and y directions and z-axis length was 7.8 nm. The solute boxes were solvated using a methanol[4] solvent model, and the number of primer molecules and solvent molecules added, as shown in Table 1.

An initial energy optimization was obtained using 10,000 steps of the steepest descent algorithm. Simulations were performed for 1 ns in a NPT ensemble using semi-isotropic conditions. Reference pressure used was 1 bar coupling each 0.5 ps via a Berendsen's barostat. The pressure coupling was isotropic in the x and y directions with compressibility set to zero, while in z direction the compressibility was set to 7.5 $10^{-4}$ bar$^{-1}$. The LINCS algorithm was used to constrain all bonds in methanol systems with a 2 fs integration time step. Integrations were carried out by the leapfrog algorithm.

Periodic boundary conditions in the x, y and z directions was applied to all systems. A cutoff radius of 1.4 nm was used to compute the short-range electrostatics and van der Waals interactions, updating the neighbor list each 5th step. Electrostatic interactions outside of the 1.4 nm cutoff sphere were treated using the reaction field method with ε=32.63 for methanol. Velocity rescale scheme kept the temperature at 300 K with time coupling of 0.1 ps. The initial velocities were generated randomly according to a Maxwell distribution at 300 K. Center of mass translation was removed at every step. The simulations were performed using the GROMACS 4.6.x simulation package.

After each simulation of solvent and primer molecules the resulting systems were placed onto their respective mineral surface, the final boxes size were shown in Table 1. A new energy optimization was carried using the steepest descent algorithm of 10,000 steps.

Production. Simulations were performed for 50 ns with the NVT ensemble. Periodic boundary conditions were used in all directions. The position for the mineral bulk atoms was constrained in x, y and z dimensions during the simulations. The aforementioned constraint was not applied to hydrogen atoms from the hydroxyl groups and $K^+$ ions in the mica surface. LINCS method was used to constrain all bonds and a 2-fs time step integration used. Integrations were carried out by the leapfrog algorithm. A cutoff radius of 1.4 nm was used to compute the short-range electrostatics and van der Waals interactions, updating the neighbor list each 5th step. Electrostatic interactions outside of the 1.4 nm cutoff sphere were treated using Particle-mesh Ewald (PME) method. Velocity rescale scheme kept the temperature at 300 K with a coupling time of 1 ps. The velocities were generated randomly according to a Maxwell distribution at 300 K. Center of mass translational was removed at every step. The simulations were performed using the 4th versions of GROMACS simulation package.

In support to the results outlined in the main text, additional analyses are presented below for the primer molecule simulations. $P_2$ molecules showed strong interaction with silica surface, however the higher diffusion coefficient along the z direction (perpendicular axis to the mineral surface) indicated the lower propensity for efficient adhesion (Table 2). In addition, $P_2$ molecules also showed higher diffusion coefficient in the x-y plane compared to $P_3$ molecules. $P_1$ molecules showed high translational mobility on x-y plane, but lowest mobility in the z direction (normal to the mineral)

as a consequence the confinement between surfaces on which they presented weak affinity.

TABLE 2

Diffusion coefficient along the z axis and in the xy plane

| | z axis($10^{-7}$ cm$^2$ s$^{-1}$) | xy plane ($10^{-5}$ cm$^2$ s$^{-1}$) |
|---|---|---|
| $P_1$ | 0.01855 | 1.7497 |
| $P_2$ | 2.19 | 0.6463 |
| $P_{3silica}$ | 1.74 | 0.0174 |
| $P_{3mica}$ | 1.63 | 0.3374 |

Preparation of Silane-Grafted Substrates

Freshly cleaved mica and clean glass slides were placed in a desiccator (Pyrex nalge Sybron Corp) with a small dish of 3-(trimethoxysilyl)propyl acrylate (200 μl). The desiccator was evacuated for 30 min and then sealed to allow the silane deposition to occur for overnight at room temperature. The surfaces were then rinsed with ethanol and dried with argon.

7. Statistical Analysis

All data of the adhesion and mechanical testing results in this article exhibited as the mean±standard error of the mean. The Student's t-test was used to confirm the significant difference of a comparison. P value of less than 0.05 indicates significance difference.

Lap Shear Tests 1 wt % primer solution was spread on mica, glass, tooth enamel, or a silicon wafer and incubated for 1 min, followed by thorough washing with methanol (for MDP, $P_1$-$P_3$) or DMSO (for $P_4$) and drying by flowing nitrogen. The surfaces were exposed to a basic aqueous solution (pH 9, using sodium hydroxide), incubated for 1 min, and drying by flowing nitrogen (see FIG. 52). The methacrylic comonomer blend (Bis-GMA, TEGDMA, DMAEMA and CQ) was packed in a gelatin capsule (size #4, 5-mm diameter, Torpac Inc.) and placed up on top of the primer-treated substrates. The comonomer blend was cured (or crosslinked) for 1 min using a portable dental curing lamp (Foshan Liang Ya Dental Co., LY-A180, 420-480 nm, 1200-2000 mW·cm$^{-2}$) (see FIG. 53). Uniaxial compression was applied to the capsule at a rate of 0.05 inch min$^{-1}$ using a materials testing system (MTS Bionix 200) until the capsules are separated from the substrate. The lap shear fracture measurements were repeated at least 10 times for each condition.

Surface Forces Apparatus (SFA) Experiments

Figures 67A, 67B:
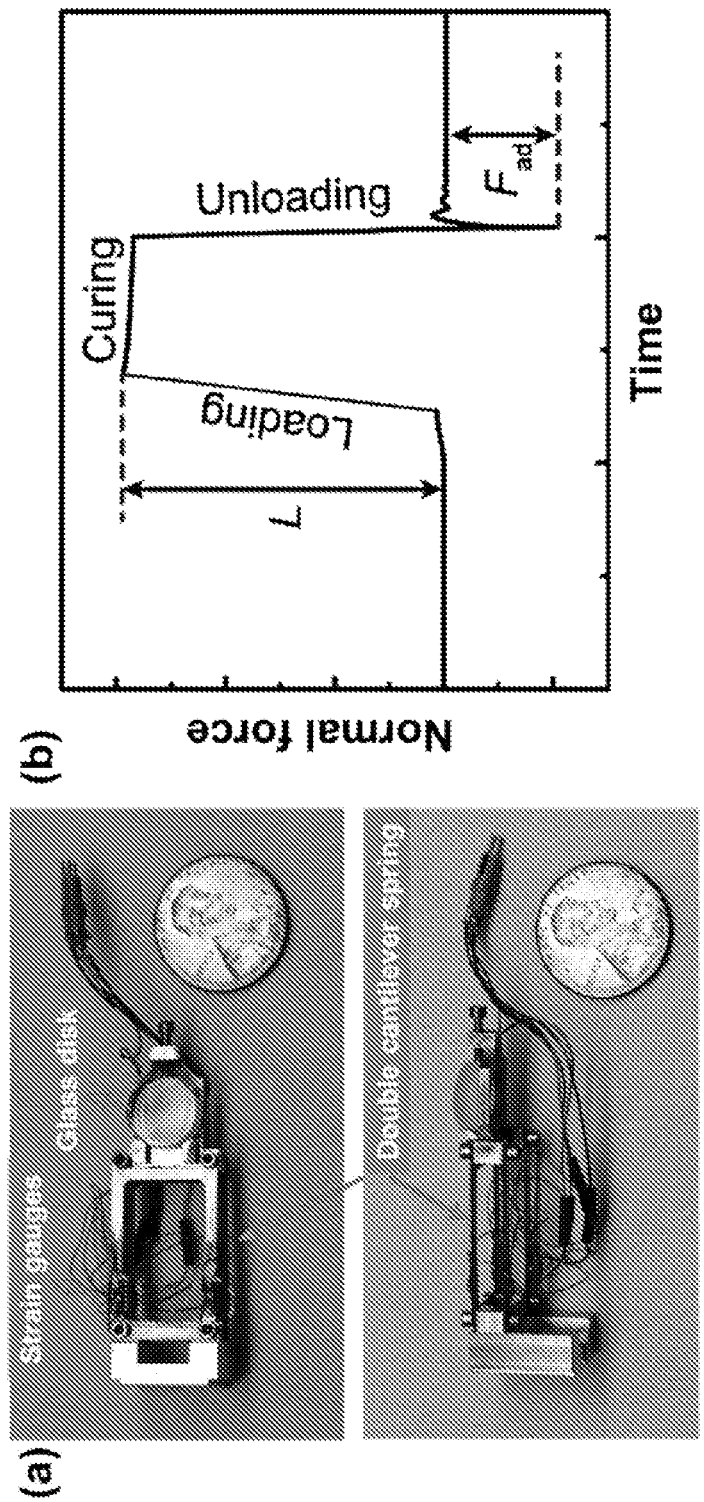
FIG. 67A shows two photographs of strain gauge attached double cantilever spring, which allows direct measurement of forces in the SFA.
FIG. 67B is an example of the measured normal force signal during loading and adhesion force measurement.

Atomically-smooth muscovite mica sheets were freshly cleaved (thickness of 2-5 μm) and attached on another large freshly cleaved mica backing sheet under a laminar flow hood and placed in a desiccator for clean storage. To ensure use of a fresh surface for each experiment, mica was peeled away from the backing sheet and glued on cylindrical disks using an epoxy glue (EPON 1004 F® from Exxon Chemicals). In each experiment, the mica surfaces were treated with one of the primer solutions, as described for the lap shear experiments, and then mounted in the SFA in a cross cylindrical geometry. In contrast to typical SFA experiments, which use an interferometric method to calculate the disk-disk separation distances and thus the interaction forces, in the SFA used here for adhesion testing, the disk separations were directly measured using semiconductor strain-gauged double cantilever springs (k=1000-10000 N/m)(see FIG. 67). After separating the surfaces, 100 □1 of comonomer blend was injected between the two surfaces. Then, ~600 mN of load was applied, followed by visible light curing for 1 min using the portable dental curing lamp (see FIG. 54G). Adhesion strength of cured polymer toward the mica was measured by detaching (unloading) two surfaces. All loading and unloading were performed using a coarse micrometer at the velocity of ~2 mm s$^{-1}$. The SFA measurements were repeated at least 5 times for each condition.

To enable comparison of the SFA data with measurements of native mussel adhesives, the adhesion pressure of the actual mussel plaques was calculated as follows. The critical force for detachment of a ~3-mm diameter plaque under conditions of purely adhesive failure was measured to be ~2 N[24]. The adhesive pressure can be roughly estimated by dividing this critical force by the adhesive area ~π (1.5 mm)$^2$)=282 kPa.

Cell Viability Assays on Surface Treated Glasses

Figures 56A, 56B:
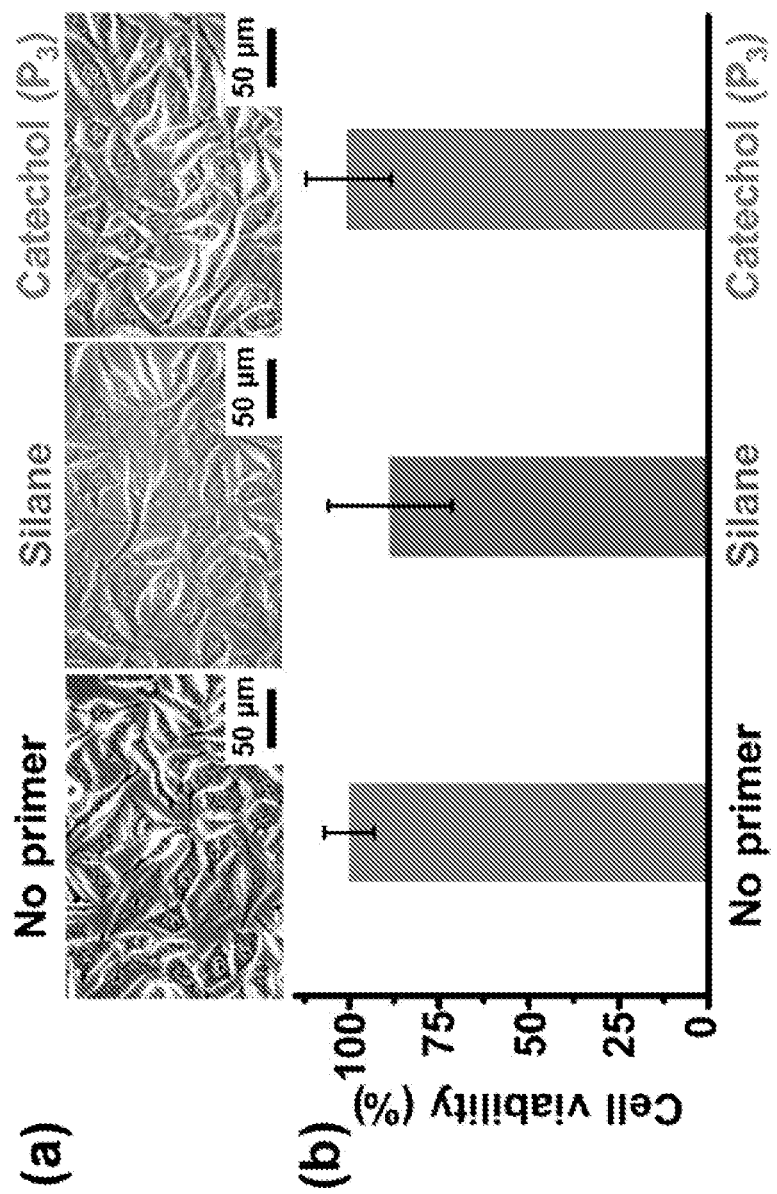
FIG. 56A shows phase-contrast microscopy images and FIG. 56B shows cell viability results of L929 mammalian fibroblast cells grown on untreated glass slides ('no primer') or glass slides treated with Silane or Catechol (P$_3$) primer. Each bar represent the average cell viability from 9 different glass slides, and the error bars indicate standard deviation.

L929 mammalian fibroblast cells were purchased from the Korean Cell Line Bank (Seoul, Korea) and cultured in Roswell Park Memorial Institute (RPMI) 1640 media (Life Technologies) with 10% fetal bovine serum, 25 mM sodium bicarbonate and 1% penicillin-streptomycin. Silane-grafted and Catechol ($P_3$) primed glass slides were prepared by following procedures described in section 6 and 3, respectively. Each glass substrate was placed on the 100π cell culture plate and sterilized by 70% ethanol solution. After equilibrated in phosphate buffered saline (PBS) and media for 5 min each, L929 cells were seeded onto the glass substrates at a density of 1×10$^6$ cells per plate. Cells were incubated for 3 days in 5% $CO_2$ at 37° C. After 3 days, the substrates were transferred to new culture plates and washed extensively with PBS. Cells were then detached by 0.05% trypsin-EDTA and stained with trypan blue solution to assess cell viability. Living cells are impermeable to the stain, whereas dead cells with compromised membranes turn blue. The number of live cells was counted using a standard hemocytometer. The bare glass slide without any modification served as a control (FIGS. 56A-56B).

Preparation of Surface Treated Glass Fillers

Silane grafted glass filler. To a solution of deionized water (70 ml) and ethanol (30 ml), 3-(trimethoxysilyl)propyl acrylate (0.5 g) and 1N acetic acid (0.125 ml) was added sequentially. The mixture was vigorously stirred for 1 hour at room temperature. The non-treated glass filler (5 g) was gradually added to the solution and vigorously stirred for 2 hours. The slurry was precipitated (or rinsed) by a centrifuge at 10,000 rpm for 5 min. The rinsing procedure was repeated three times. The precipitate was dried in a freeze drier for 48 hours. The dried filler was placed in a drying oven at 120° C. for 2 hours to complete the silane grafting reaction.

Catecholic primer ($P_3$) treated glass filler. To a 1 wt % $P_3$ solution in methanol (25 ml), the non-treated glass filler (5 g) was gradually added and vigorously stirred for 10 min at room temperature. The slurry was rinsed by a centrifuge at 10,000 rpm for 5 min. The rinsing procedure was repeated three times. The precipitate was dried in a freeze drier for overnight. The dried filler was gradually added to pH 9 aqueous solution and vigorously stirred for 10 min. The slurry was rinsed three times by a centrifuge at 10,000 rpm for 5 min. The precipitate was dried in a freeze drier for 48 hours.

Compression Tests of Composites

To the comonomer blend in agate mortar (Walter Stem Inc.), the surface-treated glass fillers were thoroughly mixed using a pestle at 80° C. (Note: the glass fillers were filtered with a 60 standard mesh using a Mini-Sieve™ micro sieve set (Sigma-Aldrich) prior to mixing with the comonomer blend). The mixture was drawn into a 1-ml syringe (BD), completely filling it, then cured for 3 min using the portable dental curing lamp. The cured PMA composites were then cut into cylindrical specimens (4.6 mm diameter, 10 mm height). Uniaxial compression was applied to the specimen at a rate of 1 mm min$^{-1}$ using a materials testing system (Instron 8871) at room temperature.

Steady-state failure tests. The composite specimens were compressed until the specimens are fragmented. The compressive failure measurements were evaluated for at least 8 specimens. In stress-strain curve (FIG. 57B), zero strain value was found by linear extrapolation in elastic regime. The toughness values were determined using an 8' order polynomial fit to smooth and approximate the data. The fit curve was then integrated to avoid the complications of non-uniform and non-monotonic strain values. The ultimate strength was given as the maximum stress recorded for each sample. The strain at failure is given by the strain value at which the maximal stress occurred.

Recovery tests. Cycle 1 probed the linear elastic regime: loading to 40 MPa stress, then fully unloading; Cycle 2 probed the nonlinear regime after yield was observed: loading to 140 MPa stress, then fully unloading. Although cycle 1 was constrained to the linear regime, a waiting time of 9 hours was included between cycles 1 and 2 to test for recovery of the glass-filled PMA composite.

Figures 61A, 61B:
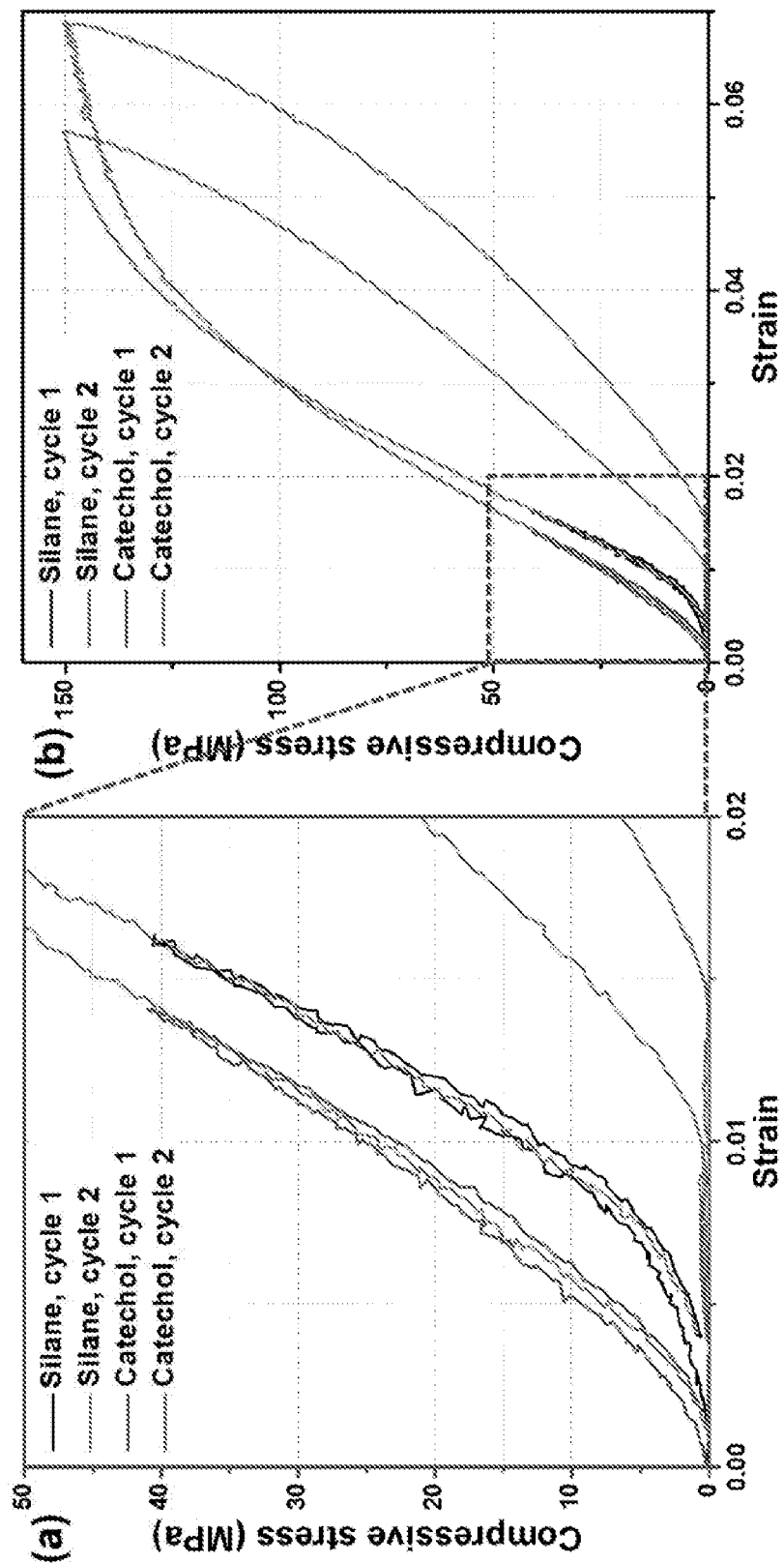
FIGS. 61A-61B are graphs showing cyclic compression testing of the primer-coated glass-filled PMA composites (a) in the low-strain range (x-axis: 0-0.02, y-axis: 0-50 MPa) to highlight the linear regime and clarify Cycle 1 and (b) in the full strain range (x-axis: 0-0.07, y-axis: 0-160 MPa). Cycle 1, linear regime: load to 40 MPa stress, then fully unload; Cycle 2, yield regime: load to 140 MPa stress, then fully unload.

The Cycle 1 was performed in the elastic regime. The lowest proportional limit stress reported (for the "No filler" sample) was 50 MPa, so the 40 MPa stress was proposed with 25% safety factor. Both the Silane-coated and Catechol-coated glass-filled composites completed recovery in the elastic regime. The maximum stress in Cycle 2 was chosen to exceed the largest yield strength (83 MPa—for Silane-coated glass-filled composites) but to be substantially smaller than the lowest measured ultimate compressive strength (294 MPa—for the "No filler" sample) (FIGS. 61A-61B).

Dynamic Thermo-Mechanical Tests

The mineral-PMA composites were prepared by curing the mixture (comonomer blend and glass fillers) within a Teflon mold (8 mm diameter, 0.5 mm thickness). The mechanical properties were measured using an ARES rheometer (Rheometric Scientific) in a 8-mm-diameter parallel plate geometry at 175° C. Strain sweeps were conducted at $\omega=0.1$ Hz. Frequency sweeps were performed from $\omega=10$ Hz to 0.1 Hz at strain amplitude of $\gamma_0=0.1\%$ and 1%, which lie within the linear viscoelastic region of the materials.

Figures 62A, 62B, 62C:
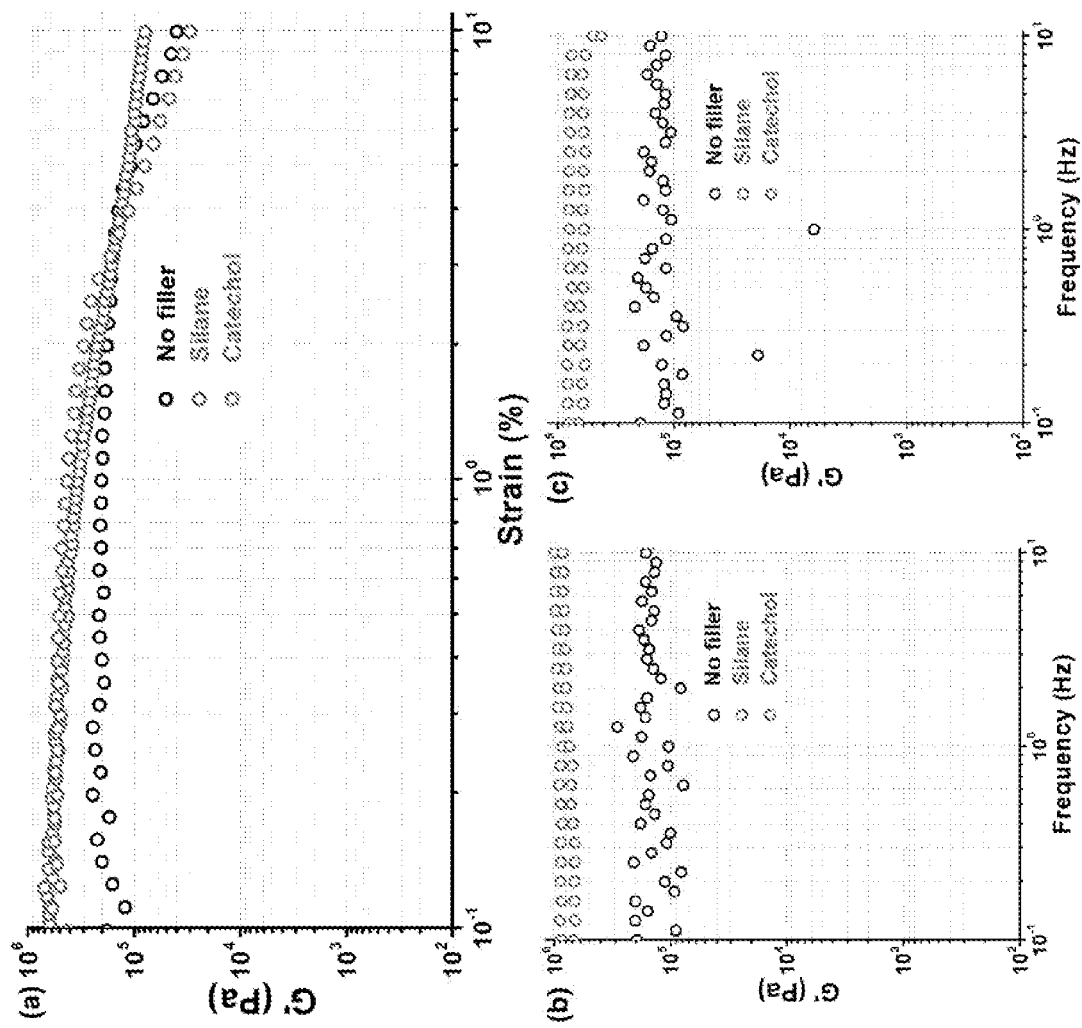
FIGS. 62A-62C are three graphs showing (FIG. 62A) Storage moduli (G') as a function of strain amplitude for the unfilled PMA resin and primer-treated glass-filled PMA composites. Frequency sweep of the composites at (FIG. 62B) 0.1% and (FIG. 62C) 1% strain (both within the linear range). The loss modulus was too small to be reliably measured.

To further examine the energy dissipation, dynamic thermo-mechanical properties of the composites were measured at 175° C. (above their glass transition temperature, $T_g \sim 156°$ C.) using a strain-controlled ARES-LC rheometer. The measured trends for the storage shear moduli (G') of the composites ($G'_{Silane} \approx G'_{Catechol} > G'_{no\ fillers}$) generally agreed with the elastic modulus (E) measured in the compressive failure test (FIGS. 62A-62C). Note: Strain sweep experiments determined the linear viscoelastic region (0.1-1% strain) before running the frequency sweep. The loss moduli (G") measurements were unreliable due to extremely high stiffness of the composites, and are not reported.

Scanning Electron Microscope (SEM)

For imaging of samples before compressive failure, samples were polished using a 1-μm diamond slurry to allow for analysis of the filler distribution and identify any voids that might exist within the composite. After compressive failure, pieces of the fracture debris were directly imaged without any treatment to enable identification of the location of failures. In all cases, the samples were sputter coated with gold/palladium 60/40, 99.99% (Hummer 6.2, Anatech) for 90 s and imaged in secondary electron mode with a scanning electron microscope (FEI XL30 Sirion FEG) (FIGS. 58A-58D).

Thermal Analysis

Thermogravimetric analysis (TGA) and Differential Scanning Calorimetry (DSC) of the composites were performed using a Discovery TGA (TA instruments) and Q2000 DSC (TA instruments), respectively, with nitrogen as purging gas. In the both experiments, the heating rate was 10° C./min. Silane- and Catechol-coated glass-filled PMA composites showed very similar thermogravimetric curves (FIGS. 59A-59B).

After complete thermal decomposition of organic compounds, TGA curves exhibits ~30 wt % of inorganic compounds, the glass transition temperatures ($T_g$) shown in TGA (no filler—~155° C., Silane—~156° C., Catechol—~156° C.) is similar to DSC results (FIG. 64).

6. REFERENCES

Lee, B. P., Messersmith, P. B., Israelachvili, J. N. & Waite, J. H. Mussel-Inspired Adhesives and Coatings. *Annual Review of Materials Research* 41, 99-132 (2011).

Seo, S. et al. Microphase Behavior and Enhanced Wet-Cohesion of Synthetic Copolyampholytes Inspired by a Mussel Foot Protein. *J. Am. Chem. Soc.* 137, 9214-9217 (2015).

Ahn, B. K. et al. High-performance mussel-inspired adhesives of reduced complexity. *Nat Commun* 6, 8663 (2015).

Hwang, D. S. et al. Protein- and Metal-dependent Interactions of a Prominent Protein in Mussel Adhesive Plaques. *Journal of Biological Chemistry* 285, 25850-25858 (2010).

Lee, H., Lee, B. P. & Messersmith, P. B. A reversible wet/dry adhesive inspired by mussels and geckos. *Nature* 448, 338-341 (2007).

Ye, Q., Zhou, F. & Liu, W. Bioinspired catecholic chemistry for surface modification. *Chemical Society Reviews* 40, 4244-4258 (2011).

Faure, E. et al. Catechols as versatile platforms in polymer chemistry. *Progress in Polymer Science* 38, 236-270 (2013).

Zhong, C. et al. Strong underwater adhesives made by self-assembling multi-protein nanofibres. *Nat Nano* 9, 858-866 (2014).

Desmond, K. W., Zacchia, N. A., Waite, J. H. & Valentine, M. T. Dynamics of mussel plaque detachment. *Soft Matter* 11, 6832-6839 (2015).

Filippidi, E. et al. The microscopic network structure of mussel (Mytilus) adhesive plaques. *Journal of The Royal Society Interface* 12 (2015).

Matos-Pérez, C. R., White, J. D. & Wilker, J. J. Polymer Composition and Substrate Influences on the Adhesive Bonding of a Biomimetic, Cross-Linking Polymer. *Journal of the American Chemical Society* 134, 9498-9505 (2012).

Lee, H., Scherer, N. F. & Messersmith, P. B. Single-molecule mechanics of mussel adhesion. *Proceedings of the National Academy of Sciences* 103, 12999-13003 (2006).

Stepuk, A., Halter, J. G., Schaetz, A., Grass, R. N. & Stark, W. J. Mussel-inspired load bearing metal-polymer glues. *Chemical Communications* 48, 6238-6240 (2012).

Tay, F. R. & Pashley, D. H. Have Dentin Adhesives Become Too Hydrophilic?*Journal of the Canadian Dental Association* 69, 726-731 (2003).

Gooding, J. J. & Ciampi, S. The molecular level modification of surfaces: from self-assembled monolayers to complex molecular assemblies. *Chemical Society Reviews* 40, 2704-2718 (2011).

Ahn, B. K., Lee, D. W., Israelachvili, J. N. & Waite, J. H. Surface-initiated self-healing of polymers in aqueous media. *Nat Mater* 13, 867-872 (2014).

Dupraz, A. M. P., v. d. Meer, S. A. T., De Wijn, J. R. & Goedemoed, J. H. Biocompatibility screening of silane-treated hydroxyapatite powders, for use as filler in resorbable composites. *J Mater Sci: Mater Med* 7, 731-738, doi:10.1007/bf00121408 (1996).

Emmett, M. A comparison of clinically useful phosphorus binders for patients with chronic kidney failure. *Kidney International* 66, S25-S32 (2004).

Van Landuyt, K. L. et al. Systematic review of the chemical composition of contemporary dental adhesives. *Biomaterials* 28, 3757-3785 (2007).

Yu, J. et al. Adaptive hydrophobic and hydrophilic interactions of mussel foot proteins with organic thin films. *Proceedings of the National Academy of Sciences* 110, 15680-15685 (2013).

Huheey, J. E., Keiter, E. A., Keiter, R. L. *Inorganic Chemistry, Principles of Structure and Reactivity.* 4th edn, (1993).

Naik, V. V., Crobu, M., Venkataraman, N. V. & Spencer, N. D. Multiple Transmission-Reflection IR Spectroscopy Shows that Surface Hydroxyls Play Only a Minor Role in Alkylsilane Monolayer Formation on Silica. *The Journal of Physical Chemistry Letters* 4, 2745-2751 (2013).

Kuehn, K.-D., Ege, W. & Gopp, U. Acrylic bone cements: composition and properties. *Orthopedic Clinics* 36, 17-28 (2005).

Roeters, J. J. M., Shortall, A. C. C. & Opdam, N. J. M. Can a single composite resin serve all purposes? *Br Dent J* 199, 73-79 (2005).

Pu, Z., Mark, J. E., Jethmalani, J. M. & Ford, W. T. Effects of Dispersion and Aggregation of Silica in the Reinforcement of Poly(methyl acrylate) Elastomers. *Chemistry of Materials* 9, 2442-2447 (1997).

Vaca, C., Shlomovitz, R., Yang, Y., Valentine, M. T. & Levine, A. J. Bond breaking dynamics in semiflexible networks under load. *Soft Matter* 11, 4899-4911 (2015).

Fantner, G. E. et al. Sacrificial bonds and hidden length dissipate energy as mineralized fibrils separate during bone fracture. *Nat Mater* 4, 612-616 (2005).

Lieou, C. K. C., Elbanna, A. E. & Carlson, J. M. Sacrificial bonds and hidden length in biomaterials: A kinetic constitutive description of strength and toughness in bone. *Physical Review* E 88, 012703 (2013).

Holten-Andersen, N. et al. pH-induced metal-ligand crosslinks inspired by mussel yield self-healing polymer networks with near-covalent elastic moduli. *Proceedings of the National Academy of Sciences*, (2011).

Menyo, M. S., Hawker, C. J. & Waite, J. H. Versatile tuning of supramolecular hydrogels through metal complexation of oxidation-resistant catechol-inspired ligands. *Soft Matter* 9, 10314-10323 (2013).

Sun, J.-Y. et al. Highly stretchable and tough hydrogels. *Nature* 489, 133-136 (2012).

Ducrot, E., Chen, Y., Bulters, M., Sijbesma, R. P. & Creton, C. Toughening Elastomers with Sacrificial Bonds and Watching Them Break. *Science* 344, 186-189 (2014).

Sauerbrey, G. Verwendung von Schwingquarzen zur Wägung dünner Schichten und zur Mikrowägung. *Z. Physik* 155, 206-222 (1959).

Wei, W. et al. A mussel-derived one component adhesive coacervate. *Acta Biomaterialia* 10, 1663-1670 (2014).

Walser, R., Mark, A., van Gunsteren, W., Lauterbach, M. & Wipff, G. The effect of force-field parameters on properties of liquids: Parametrization of a simple three-site model for methanol. *Journal of Chemical Physics* 112, 10450-10459 (2000).

Dequidt, A., Devemy, J. & Malfreyt, P. Confined KCl Solution between Two Mica Surfaces: Equilibrium and Frictional Properties. *Journal of Physical Chemistry C* 119, 22080-22085 (2015).

Cygan, R., Liang, J. & Kalinichev, A. Molecular models of hydroxide, oxyhydroxide, and clay phases and the development of a general force field. *Journal of Physical Chemistry B* 108, 1255-1266 (2004).

Oostenbrink, C., Villa. A., Mark, A. E. & Van Gunsteren, W. F. A biomolecular force field based on the free enthalpy of hydration and solvation: The GROMOS force-field parameter sets 53A5 and 53A6. *Journal of Computational Chemistry* 25, 1656-1676 (2004).

Bayly, C. I., Cieplak, P., Cornell, W. & Koliman, P. A. A well-behaved electrostatic potential based method using charge restraints for deriving atomic charges: the RESP model. *The Journal of Physical Chemistry* 97, 10269-10280 (1993).

Valiev, M. et al. NWChem: A comprehensive and scalable open-source solution for large scale molecular simulations. *Computer Physics Communications* 181, 1477-1489 (2010).

Berendsen, H. J. C., Postma, J. P. M., van Gunsteren, W. F. & Hermans, J. Intermolecular Forces. *Pullman, B., Ed.; Reidel Publishing Company: Dordrecht,* 331-342 (1981).

Berendsen, H. J. C., Postma, J. P. M., Van Gunsteren, W. F., Dinola, A. & Haak, J. R. Molecular-Dynamics with Coupling to an External Bath. *Journal of Chemical Physics* 81, 3684-3690 (1984).

Hess, B., Bekker, H., Berendsen, H. J. C. & Fraaije, J. G. E. M. LINCS: A linear constraint solver for molecular simulations. *J. Comput. Chem.* 18, 1463-1472, (1997).

Hockney, R. W. in Methods in Computational Physics Vol. 9 (eds B. Alder, S. Fernbach, & M. Rotenberg) (Academic Press, 1970).

Tironi, I. G., Sperb, R., Smith, P. E. & van Gunsteren, W. F. A generalized reaction field method for molecular dynamics simulations. *The Journal of Chemical Physics* 102, 5451-5459 (1995).

Bussi, G., Donadio, D. & Parrinello, M. Canonical sampling through velocity rescaling. *The Journal of chemical physics* 126, 014101-014107 (2007).

Hess, B., Kutzner, C., van der Spoel, D. & Lindahl, E. GROMACS 4: Algorithms for Highly Efficient, Load-Balanced, and Scalable Molecular Simulation. *Journal of Chemical Theory and Computation* 4, 435-447(2008).

Essmann, U. et al. A SMOOTH PARTICLE MESH EWALD METHOD. *Journal of Chemical Physics* 103, 8577-8593 (1995).

Pick, C., Argento, C., Drazer, G. & Frechette, J. Micropatterned Charge Heterogeneities via Vapor Deposition of Aminosilanes. *Langmuir* 31, 10725-10733 (2015).

Glass, N. R., Tjeung, R., Chan, P., Yeo, L. Y. & Friend, J. R. Organosilane deposition for microfluidic applications. *Biomicrofluidics* 5, 036501-036501-036507 (2011).

Israelachvili, J. et al. Recent advances in the surface forces apparatus (SFA) technique. *Reports on Progress in Physics* 73, 036601 (2010).

Israelachvili, J. N. *Intermolecular and Surface Forces,* 3rd edition. 227-230 (2010).

Lee, D. W. et al. Lipid domains control myelin basic protein adsorption and membrane interactions between model myelin lipid bilayers. Proceedings of the National Academy of Sciences 111, E768-E775 (2014).

Lee, D. W., Banquy, X. & Israelachvili, J. N. Stick-slip friction and wear of articular joints. Proceedings of the National Academy of Sciences 110, E567-E574 (2013).

Biological evaluation of medical devices—Part 1: Evaluation and testing within a risk management process. ISO 10993-1:2009.

Lee, J.-H., Um, C.-M. & Lee, I.-b. Rheological properties of resin composites according to variations in monomer and filler composition. Dental Materials 22, 515-526 (2006).

Grindy, S. C. et al. Control of hierarchical polymer mechanics with bioinspired metal-coordination dynamics. Nat Mater 14, 1210-1216 (2015).

Holten-Andersen, N. et al. pH-induced metal-ligand cross-links inspired by mussel yield self-healing polymer networks with near-covalent elastic moduli. Proceedings of the National Academy of Sciences 108, 2651-2655 (2011).

Shafiq, Z. et al. Bioinspired underwater bonding and debonding on demand. *Angew. Chem., Int. Ed.* 51, 4332-4335 (2012).

Krogsgaard, M., Behrens, M. A., Pedersen, J. S. & Birkedal, H. Self-Healing Mussel-Inspired Multi-pH-Responsive Hydrogels. *Biomacromolecules* 14, 297-301 (2013).

Rodriguez, N. R. M. et al. Mussel adhesive protein provides cohesive matrix for collagen type-1α. *Biomaterials* 51, 51-57 (2015).

Wang, J. et al. Influence of Binding-Site Density in Wet Bioadhesion. *Adv. Mater.* 20, 3872-3876 (2008).

Hwang, D. S. et al. Viscosity and interfacial properties in a mussel-inspired adhesive coacervate. *Soft Matter* 6, 3232-3236 (2010).

Stewart, R. J., Wang, C. S. & Shao, H. Complex coacervates as a foundation for synthetic underwater adhesives. *Adv. Colloid Interface Sci.* 167, 85-93 (2011).

Skeist, I. *Handbook of adhesives*. (Van Nostrand Reinhold Co, 1977).

Wei, W., Yu, J., Broomell, C., Israelachvili, J. N. & Waite, J. H. Hydrophobic Enhancement of Dopa-Mediated Adhesion in a Mussel Foot Protein. *J. Am. Chem. Soc.* 135, 377-383 (2013).

Yamamoto, H. Synthesis and adhesive studies of marine polypeptides. *J. Chem. Soc., Perkin Trans.* 1, 613-618 (1987).

Deming, T. Mussel byssus and biomolecular materials. *Curr. Opin. Chem. Biol.* 3, 100-105 (1999).

Winslow, B. D., Shao, H., Stewart, R. J. & Tresco, P. A. Biocompatibility of adhesive complex coacervates modeled after the sandcastle glue of *Phragmatopoma californica* for craniofacial reconstruction. *Biomaterials* 31, 9373-9381 (2010).

Liu, B., Burdine, L. & Kodadek, T. Chemistry of periodate-mediated cross-linking of 3,4-dihydroxylphenylalanine-containing molecules to proteins. *J. Am. Chem. Soc.* 128, 15228-15235 (2006).

Yu, M. & Deming, T. J. Synthetic Polypeptide Mimics of Marine Adhesives. *Macromolecules* 31, 4739-4745 (1998).

Martinez Rodriguez, N. R., Das, S., Kaufman, Y., Israelachvili, J. N. & Waite, J. H. Interfacial pH during mussel adhesive plaque formation. *Biofouling* 31, 221-227 (2015).

Danner, E. W., Kan, Y. J., Hammer, M. U., Israelachvili, J. N. & Waite, J. H. Adhesion of mussel foot protein mefp-5 to mica: an underwater superglue. *Biochemistry* 51, 6511-6518 (2012).

Peresypkin, A. V. & Menger, F. M. Zwitterionic geminis. coacervate formation from a single organic compound. *Org. Lett.* 1, 1347-1350 (1999).

Gandhi, D. D. et al. Annealing-induced interfacial toughening using a molecular nanolayer. *Nature* 447, 299-302 (2007).

Magasinski, A. et al. High-performance lithium-ion anodes using a hierarchical bottom-up approach. *Nat. Mater.* 9, 353-358 (2010).

Hirakata, H., Kitamura, T. & Yamamoto, Y. Direct Measurement of Interface Strength between Copper Submicron-Dot and Silicon Dioxide Substrate. *JSME Int. J., Ser. A* 47, 324-330 (2004).

Jeong, J. W. et al. High-resolution nanotransfer printing applicable to diverse surfaces via interface-targeted adhesion switching. *Nat Commun* 5, (2014).

Israelachvili, J. N. *Intermolecular and surface forces: revised third edition*. (Academic press, 2011).

Das, S. et al. JKR theory for the stick-slip peeling and adhesion hysteresis of gecko mimetic patterned surfaces with a smooth glass surface. *Langmuir* 29, 15006-15012 (2013).

Heo, J. et al. Improved Performance of Protected Catecholic Polysiloxanes for Bioinspired Wet Adhesion to Surface Oxides. *J. Am. Chem. Soc.* 134, 20139-20145 (2012).

Meyer, E. E., Rosenberg, K. J. & Israelachvili, J. Recent progress in understanding hydrophobic interactions. *Proc. Natl. Acad. Sci. U.S.A* 103, 15739-15746 (2006).

Tamarin, A., Lewis, P. & Askey, J. The structure and formation of the byssus attachment plaque in Mytilus. *J. Morphol.* 149, 199-221 (1976).

Betancourt, T. & Brannon-Peppas, L. Micro- and nanofabrication methods in nanotechnological medical and pharmaceutical devices. *Int. J. Nanomed.* 1, 483-495 (2006).

Das, S., Donaldson Jr, S. H., Kaufman, Y. & Israelachvili, J. N. Interaction of adsorbed polymers with supported cationic bilayers. *RSC Adv.* 3, 20405-20411 (2013).

Israelachvili, J. Thin-Film Studies Using Multiple-Beam Interferometry. *J. Colloid Interf Sci.* 44, 259-272 (1973).

Talmon, Y. Transmission electron microscopy of complex fluids: the state of the art. *Ber. Bunsenges. Phys. Chem.* 100, 364-372 (1996).

Panne, P. & Fox, J. M. Rh-catalyzed intermolecular reactions of alkynes with α-diazoesters that possess β-hydrogens: ligand-based control over divergent pathways. J. Am. Chem. Soc. 129, 22-23 (2007).

Fulmer, G. R. et al. NMR chemical shifts of trace impurities: common laboratory solvents, organics, and gases in deuterated solvents relevant to the organometallic chemist. Organometallics 29, 2176-2179 (2010).

Garcia, G. et al. Losartan-antioxidant hybrids: novel molecules for the prevention of hypertension-induced cardiovascular damage. J. Med. Chem. 52, 7220-7227 (2009).

Garcia, G. et al. New losartan-hydrocaffeic acid hybrids as antihypertensive-antioxidant dual drugs: Ester, amide and amine linkers. Eur. J. Med. Chem. 50, 90-101 (2012).

Thanh, T. & Chabrier, P. New method of preparation for phosphorylcholine, phosphorylhomocholine and their derivatives. Bull. Soc. Chem. Fr. 3, 667-671 (1974).

Akdogan, Y. et al. Intrinsic Surface-Drying Properties of Bioadhesive Proteins. Angew. Chem., Int. Ed. 53, 11253-11256 (2014).

Q. Lin, D. Gourdon, C. Sun, N. Holten-Andersen, T. H. Anderson, J. H. Waite, J. N. Israelachvili, Proceedings of the National Academy of Sciences 2007, 104, 3782-3786.

T. H. Anderson, J. Yu, A. Estrada, M. U. Hammer, J. H. Waite, J. N. Israelachvili, Advanced Functional Materials 2010, 20, 4196-4205.

J. Yu, W. Wei, E. Danner, R. K. Ashley, J. N. Israelachvili, J. H. Waite, Nat Chem Biol 2011, 7, 588-590.

H. Shao, K. N. Bachus, R. J. Stewart, Macromolecular Bioscience 2009, 9, 464-471.

J. J. Wilker, Current Opinion in Chemical Biology 2010, 14, 276-283.

H. Lee, S. M. Dellatore, W. M. Miller, P. B. Messersmith, Science 2007, 318, 426-430.

S. M. Kang, I. You, W. K. Cho, H. K. Shon, T. G. Lee, I. S. Choi, J. M. Karp, H. Lee, Angewandte Chemie International Edition 2010, 49, 9401-9404.

Q. Wei, K. Achazi, H. Liebe, A. Schulz, P.-L. M. Noeske, I. Grunwald, R. Haag, Angewandte Chemie International Edition 2014, 53, 11650-11655.

F. Schreiber, Progress in Surface Science 2000, 65, 151-257.

H. Lee, Y. Lee, A. R. Statz, J. Rho, T. G. Park, P. B. Messersmith, Advanced Materials 2008, 20, 1619-1623.

R. B. Martin, The Journal of Physical Chemistry 1971, 75, 2657-2661.

M. B. McBride, L. G. Wesselink, Environmental Science & Technology 1988, 22, 703-708.

J. Yu, W. Wei, M. S. Menyo, A. Masic, J. H. Waite, J. N. Israelachvili, Biomacromolecules 2013, 14, 1072-1077.

M. Valtiner, S. H. Donaldson, M. A. Gebbie, J. N. Israelachvili, Journal of the American Chemical Society 2012, 134, 1746-1753.

Ulman, A. Formation and structure of self-assembled monolayers. Chem. Rev. 96, 1533-1554 (1996).

Feller, D. & Feyereisen, M. W. Ab initio study of hydrogen bonding in the phenol-water system. J. Comput. Chem. 14, 1027-1035 (1993).

Luo, C. et al. General strategy for self-assembly of highly oriented nanocrystalline semiconducting polymers with high mobility. Nano Lett. 14, 2764-2771 (2014).

Love, J. C., Estroff, L. A., Kriebel, J. K., Nuzzo, R. G. & Whitesides, G. M. Self-assembled monolayers of thiolates on metals as a form of nanotechnology. Chem. Rev. 105, 1103-1169 (2005).

Sugawara, T. & Matsushita, M. M. Spintronics in organic n-electronic systems. J. Mater. Chem. 19, 1738-1753 (2009).

Levicky, R., Herne, T. M., Tarlov, M. J. & Satija, S. K. Using self-assembly to control the structure of DNA ronolayers on gold: a neutron reflectivity study. J. Am. Chem. Soc. 120, 9787-9792 (1998).

Abbott, N. L., Gorman, C. B. & Whitesides, G. M. Active control of wetting using applied electrical potentials and self-assembled monolayers. Langmuir 11, 16-18 (1995).

Sarikaya, M., Tamerler, C., Jen, A. K.-Y., Schulten, K. & Baneyx, F. Molecular biomimetics: nanotechnology through biology. Nat. Mater. 2, 577-585 (2003).

Vericat, C., Vela, M. E., Benitez, G., Carro, P. & Salvarezza, R. C. Self-assembled monolayers of thiols and dithiols on gold: new challenges for a well-known system. Chem. Soc. Rev. 39, 1805-1834 (2010).

Li, S.-C. et al. Correlation between Bonding Geometry and Band Gap States at Organic-Inorganic Interfaces: Catechol on Rutile TiO2 (110). J. Am. Chem. Soc. 131, 980-984 (2009).

Hanson, E. L., Schwartz, J., Nickel, B., Koch, N. & Danisman, M. F. Bonding self-assembled, compact organophosphonate monolayers to the native oxide surface of silicon. J. Am. Chem. Soc. 125, 16074-16080 (2003).

Klauk, H., Zschieschang, U., Pflaum, J. & Halik, M. Ultralow-power organic complementary circuits. Nature 445, 745-748 (2007).

Yip, H. L., Hau, S. K., Baek, N. S., Ma, H. & Jen, A. K. Y. Polymer solar cells that use self-assembled-monolayer-modified ZnO/Metals as cathodes. Adv. Mater. 20, 2376-2382 (2008).

Ito, Y. et al. Crystalline ultrasmooth self-assembled monolayers of alkylsilanes for organic field-effect transistors. J. Am. Chem. Soc. 131, 9396-9404 (2009).

Ikawa, M. et al. Simple push coating of polymer thin-film transistors. Nat. Comm. 3, 1176 (2012).

Das, S., Rodriguez, N. R. M., Wei, W., Waite, J. H. & Israelachvili, J. N. Peptide Length and Dopa Determine Iron-Mediated Cohesion of Mussel Foot Proteins. Adv. Funct. Mater. 25, 5840-5847 (2015).

Grimme, S. Do special noncovalent $\pi$-$\pi$ stacking interactions really exist?Angew. Chem., Int. Ed. 47, 3430-3434 (2008).

Headen, T. F. et al. Structure of $\pi$-$\pi$ Interactions in Aromatic Liquids. J. Am. Chem. Soc. 132, 5735-5742 (2010).

Kobayashi, S. et al. Control of carrier density by self-assembled monolayers in organic field-effect transistors. Nat. Mater. 3, 317-322 (2004).

Lee, B. H., Bazan, G. C. & Heeger, A. J. Doping-Induced Carrier Density Modulation in Polymer Field-Effect Transistors. Advanced Materials 28, 57-62 (2016).

Lee, B. H. et al. Flexible organic transistors with controlled nanomorphology. Nano Lett. 16, 314-319 (2015).

Hulea, I. N., Russo, S., Molinari, A. & Morpurgo, A. F. Reproducible low contact resistance in rubrene single-crystal field-effect transistors with nickel electrodes. Applied physics letters 88, 113512 (2006).

Kim, G. et al. A Thienoisoindigo-Naphthalene Polymer with Ultrahigh Mobility of 14.4 $cm^2$/V·s That Substantially Exceeds Benchmark Values for Amorphous Silicon Semiconductors. J. Am. Chem. Soc. 136, 9477-9483 (2014).

Hanada, S.; Tsutsumi, E.; Motoyama, Y.; Nagashima H. J. Am. Chem. Soc. 2009, 131, 15032-15040.

Das, S. et al. Tough coating proteins: subtle sequence variation modulates cohesion. Biomacromolecules 16, 1002-1008 (2015).

Li, Y., Beck, R., Huang, T., Choi, M. C. & Divinagracia, M. Scatterless hybrid metal-single-crystal slit for small-angle X-ray scattering and high-resolution X-ray diffraction. Appl. Crystallogr. 41, 1134-1139 (2008).

Tseng, H.-R. et al. High-mobility field-effect transistors fabricated with macroscopic aligned semiconducting polymers. Adv. Mater. 26, 2993-2998 (2014).

Gilles, H. in Organic Field-Effect TransistorsOptical Science and Engineering 73-101 (CRC Press, 2007).

Marinkovic, M., Belaineh, D., Wagner, V. & Knipp, D. On the Origin of Contact Resistances of Organic Thin Film Transistors. Adv. Mater. 24, 4005-4009 (2012).

We claim:
1. A compound, comprising:
an end group attached to a spacer group, wherein
the spacer group is -$L_3$-Q-$L_2$-M-$L_1$; and
the end group is E;
wherein the spacer group is selected from the group consisting of alkyl, non-polar, zwitterionic, cationic, anionic, and non-charged polar moiety;
wherein each of $L_2$ and $L_1$ is $C_1$-$C_{15}$ alkyl, or optionally substituted $C_2$-$C_{15}$ alkenyl;

wherein $L_3$, when present, is a bond, $C_1$-$C_{15}$ alkyl, or optionally substituted $C_2$-$C_{15}$ alkenyl;

wherein M comprises a first anionic moiety or first cationic moiety and Q comprises a second anionic moiety or second cationic moiety;

wherein E is selected from the group consisting of acrylate, methacrylate, epoxy, amine, substituted phenyl, unsubstituted phenyl, catechol, alkyl, alkylenyl, cationic, anionic, non-charged polar, and non-polar moiety;

wherein the compound is capable of adhering to at least one of a bone surface, a tooth enamel surface, a silicon surface, a $SiO_2$ surface, a glass surface, or a metal containing surface such that the spacer group is between the surface and the end group, and wherein the compound further comprises a catechol group attached to the end group through the spacer group.

2. The compound of claim 1, wherein E is selected from a group consisting of $C_2$-$C_6$ alkenyl, $C_1$-$C_6$ alkyl, and optionally substituted or unsubstituted phenyl.

3. The compound of claim 2, wherein the substituted phenyl is an aromatic moiety selected from a group consisting of dihydroxyphenyl, catechol, and di(trifluoromethyl)phenyl.

4. The compound of claim 1, wherein the end group comprises a polymer.

5. The compound of claim 1, comprising a surfactant.

6. The compound of claim 1, wherein M is NRR' or $PO_{4-}$, Q is NRR' or $PO_{4-}$, R is H or $C_1$-C5 alkyl, and R' is H or $C_1$-C5 alkyl.

7. The compound of claim 1, wherein the compound is capable of adhering to at least one of the glass surface, the metal containing surface, or a hydroxyapatite surface.

8. An adhesive system comprising the compound of claim 1 and a monomer:
wherein the monomer is polymerizable in a presence of the end group to form a dental cement or a bone cement attached to the catechol group, the spacer group between the cement and the catechol group.

9. A nano-adhesive and surface primer comprising the compound of claim 1.

10. A compound, comprising a catechol group attached to an end group E through a spacer group, wherein the catechol group, the end group E and spacer group satisfy Formula:

Formula (II)

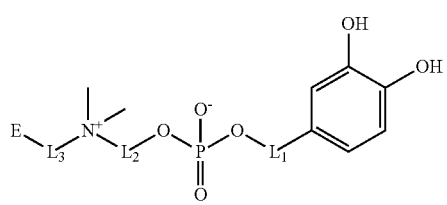

wherein:
each of $L_1$ and $L_2$ is $C_2$-$C_6$ alkyl;
$L_3$ is a bond or $C_2$-$C_{15}$ alkyl;
E is selected from a group consisting of $C_4$-$C_{12}$ alkyl, phenyl, dihydroxyphenyl, catechol, and 3,5-di(trifluoromethyl)phenyl.

11. The compound of claim 10 selected from a group consisting of:

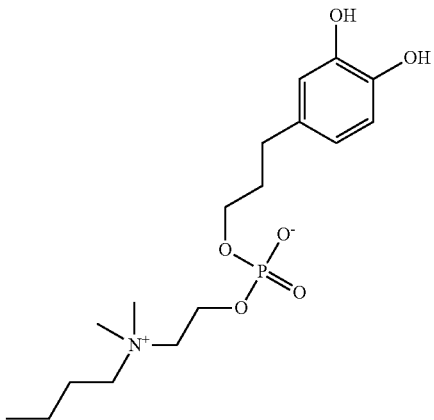

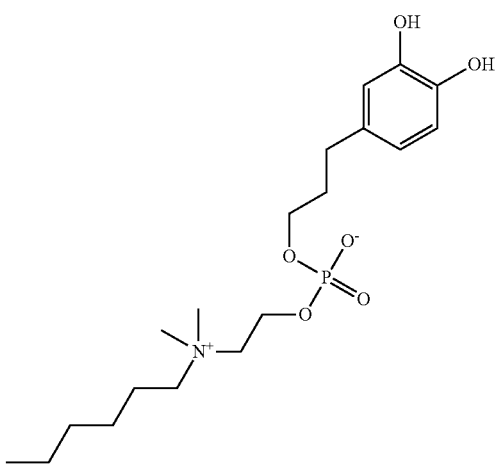

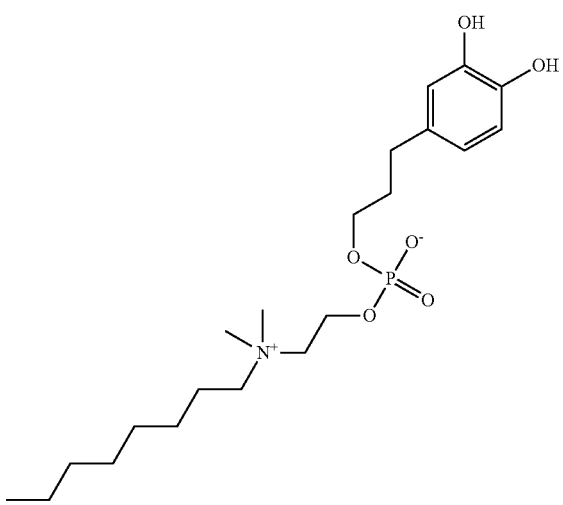

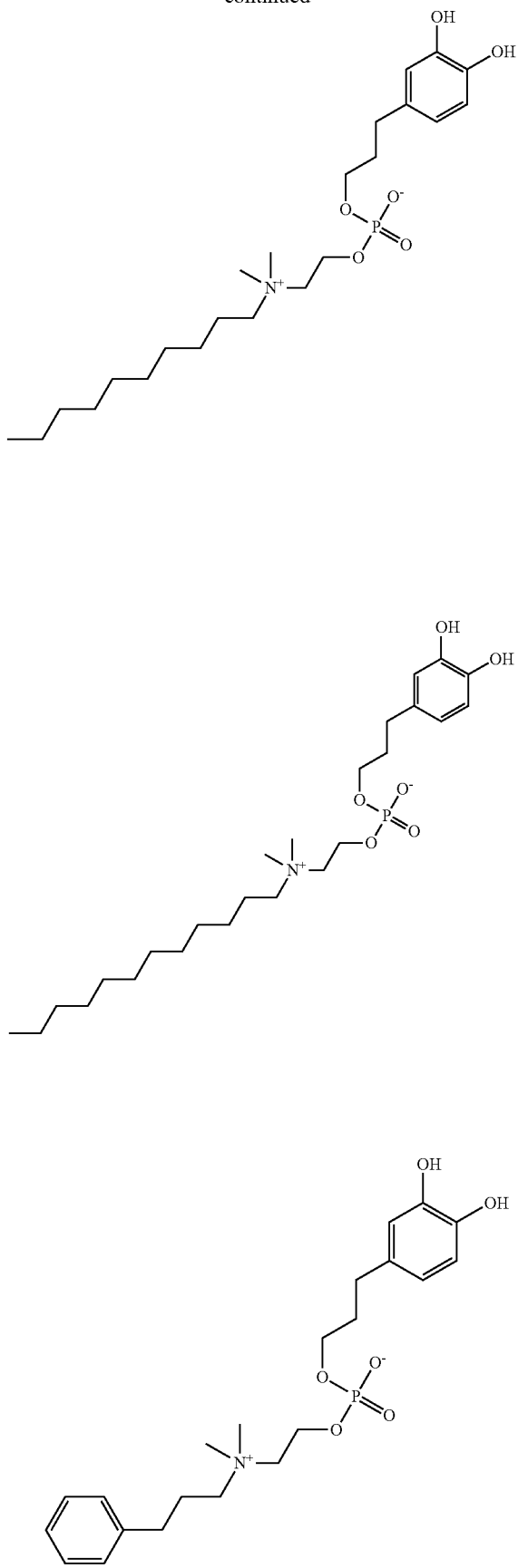

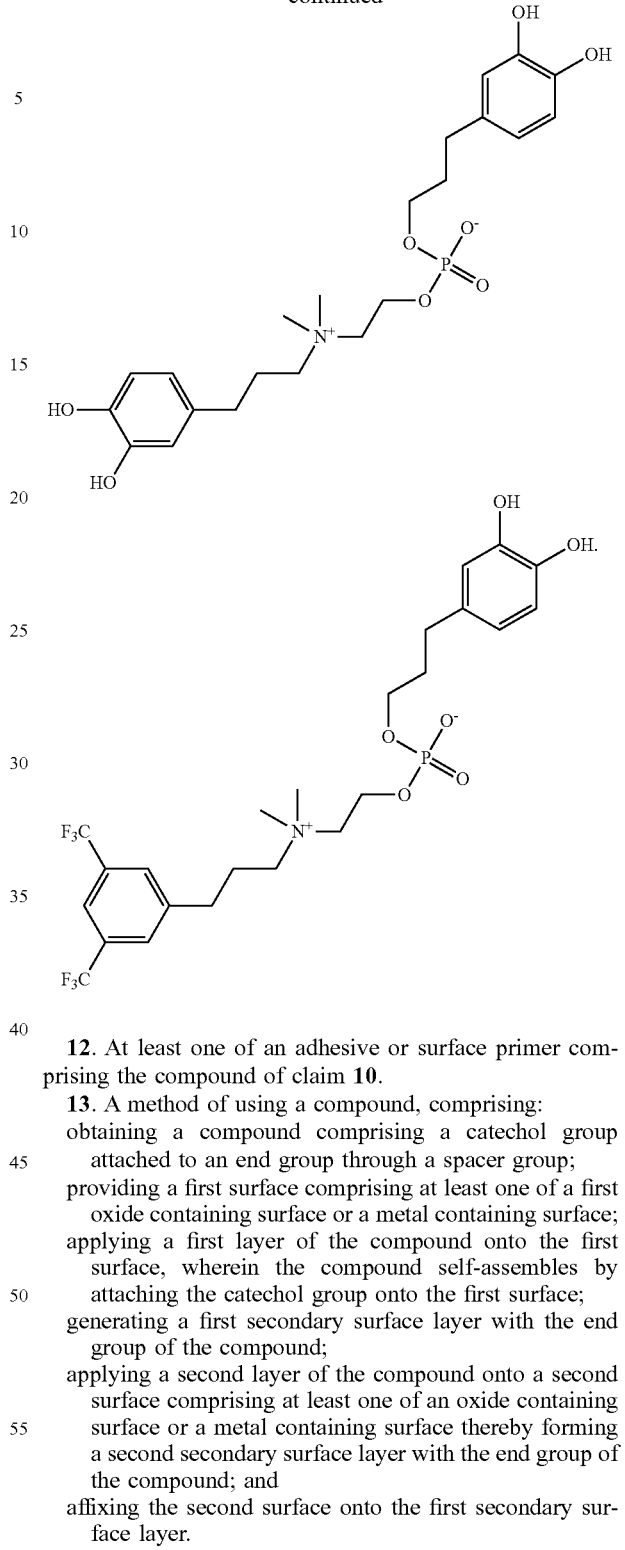

12. At least one of an adhesive or surface primer comprising the compound of claim 10.

13. A method of using a compound, comprising:
obtaining a compound comprising a catechol group attached to an end group through a spacer group;
providing a first surface comprising at least one of a first oxide containing surface or a metal containing surface;
applying a first layer of the compound onto the first surface, wherein the compound self-assembles by attaching the catechol group onto the first surface;
generating a first secondary surface layer with the end group of the compound;
applying a second layer of the compound onto a second surface comprising at least one of an oxide containing surface or a metal containing surface thereby forming a second secondary surface layer with the end group of the compound; and
affixing the second surface onto the first secondary surface layer.

14. The method of claim 13, wherein the first surface is an oxide containing surface and the catechol group of the compound forms an H-bond with the oxide containing surface.

15. The method of claim 13, wherein the first surface is a metal containing surface and the catechol group of the compound forms a chelating-bond with the metal containing surface.

16. The method of claim 13, wherein the oxide containing surface is selected from the group consisting of mica, silica, kaolin, zirconia, aluminum, copper, chrome, chrome-cobalt, silicon, calcium, aluminum oxide, copper oxide, titanium oxide, zinc oxide, calcium oxide, tin oxide, indium-tin oxide, steal, and hydroxylapatite.

17. The method of claim 13, wherein the first layer has a thickness between 0.1 to 10 nm.

18. The method of claim 13, wherein the compound is treated with an oxidizing agent.

19. The method of claim 18, wherein the oxidizing agent is periodate.

20. The method of claim 13, wherein the compound is used as a dental/bone adhesive, a surface primer for a dental/medical implant, a surface primer for a polymer composite including dental and bone cement, or for a battery anode/binder, electro circuit, a semiconductor device, a nanosensing device, an organic solar cell, an opto-electronic device, a hetero-junction, or an electron tunneling junction.

21. The method of claim 13, wherein the end group of the compound of the first secondary surface layer interacts with the end group of the compound of the second secondary surface layer.

22. The method of claim 21, wherein an interaction between the first secondary surface layer and the second secondary surface layer includes a hydrophobic interaction or π-π stacking.

23. The method of claim 13, wherein a third and a fourth layer of the compound are applied onto the first secondary surface layer and the second secondary surface layer, wherein the compound self-assembles onto the first secondary surface layer and the second secondary surface layer creating a third and a fourth secondary surface layer with the catechol group of the compound.

24. The method of claim 23, wherein the catechol group of the third secondary surface layer interacts with the fourth secondary surface layer.

25. The method of claim 24, wherein an interaction of the third secondary surface layer and the fourth secondary surface layer is crosslinking or H-bonding.

26. The method of claim 13, wherein the catechol group, the end group and spacer group satisfy Formula (II):

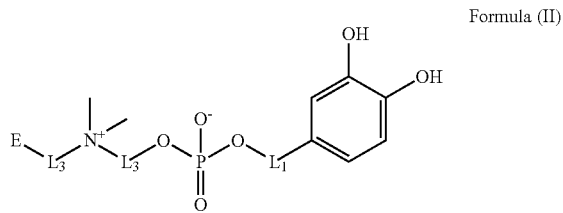

Formula (II)

wherein:
each of $L_1$ and $L_2$ is $C_2$-$C_6$ alkyl;
$L_3$ is a bond or $C_2$-$C_{15}$ alkyl;
E is selected from a group consisting of $C_4$-$C_{12}$ alkyl, phenyl, dihydroxyphenyl, catechol, and 3,5-di(trifluoromethyl)phenyl, or the compound satisfies the formula:
Formula (I):

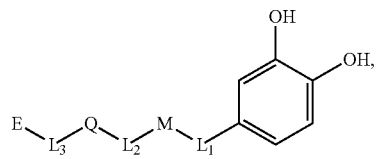

Formula (I)

or
wherein:
the catechol group is

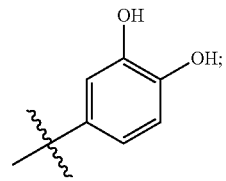 [SMILES: *c1ccc(O)c(O)c1]

the spacer group is -$L_3$-Q-$L_2$-M-$L_1$; and
the end group is E;
wherein the spacer group is selected from the group consisting of alkyl, non-polar, zwitterionic, cationic, anionic, and non-charged polar moiety;
wherein each of $L_2$ and $L_1$ is $C_1$-$C_{15}$ alkyl, or optionally substituted $C_2$-$C_{15}$ alkenyl;
wherein $L_3$, when present, is a bond, $C_1$-$C_{15}$ alkyl, or optionally substituted $C_2$-$C_{15}$ alkenyl;
wherein M, when present, is —($CO_2$)—, NRR', —RCOH or $PO_4$, wherein Q, when present, is —($CO_2$)—, NRR', —RCOH or $PO_4$, wherein R is H or $C_1$-C5 alkyl; wherein R' is H or $C_1$-C5 alkyl; and
wherein E is selected from the group consisting of acrylate, methacrylate, epoxy, amine, substituted phenyl, unsubstituted phenyl, catechol, alkyl, alkylenyl, cationic, anionic, non-charged polar, and non-polar moiety.

27. A composition of matter useful as an adhesive, comprising:
a first layer of compound on a first surface, the compound comprising a catechol group attached to an end group through a spacer group, wherein the catechol group is:

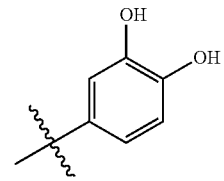 [SMILES: *c1ccc(O)c(O)c1]

wherein:
the spacer group is -$L_3$-Q-$L_2$-M-$L_1$; and
the end group is E;
wherein the spacer group is selected from the group consisting of alkyl, non-polar, zwitterionic, cationic, anionic, and non-charged polar moiety;
wherein each of $L_2$ and $L_1$ is $C_1$-$C_{15}$ alkyl, or optionally substituted $C_2$-$C_{15}$ alkenyl;

wherein $L_3$, when present, is a bond, $C_1$-$C_{15}$ alkyl, or optionally substituted $C_2$-$C_{15}$ alkenyl;

wherein M is optional and when present is —($CO_2$)—, NRR', —RCOH or $PO_4$, wherein Q is optional and when present is —($CO_2$)—, NRR', —RCOH or $PO_4$, wherein R is H or $C_1$-C5 alkyl; wherein R' is H or $C_1$-C5 alkyl; and wherein:

E is selected from the group consisting of acrylate, methacrylate, epoxy, amine, substituted phenyl, unsubstituted phenyl, and catechol;

the first layer comprises a first secondary surface layer with the end group;

a second layer of the compound is on the first secondary surface; and the end group of the first layer interacts with the end group of the second layer to affix the first layer to the second layer.

28. The composition of matter of claim 27 comprising a bioadhesive.

29. The compound of claim 27, wherein E comprises a dihydroxyphenyl.

\* \* \* \* \*